US011433065B2

(12) United States Patent
Ren et al.

(10) Patent No.: US 11,433,065 B2
(45) Date of Patent: Sep. 6, 2022

(54) CERTAIN CHEMICAL ENTITIES, COMPOSITIONS AND METHODS

(71) Applicant: Intellikine LLC, La Jolla, CA (US)

(72) Inventors: Pingda Ren, San Diego, CA (US); Yi Liu, San Diego, CA (US); Troy Edward Wilson, San Marino, CA (US); Liansheng Li, San Diego, CA (US); Katrina Chan, Fremont, CA (US); Christian Rommel, La Jolla, CA (US)

(73) Assignee: Intellikine LLC, La Jolla, CA (US)

( * ) Notice: Subject to any disclaimer, the term of this patent is extended or adjusted under 35 U.S.C. 154(b) by 0 days.

(21) Appl. No.: 16/556,048

(22) Filed: Aug. 29, 2019

(65) Prior Publication Data
US 2020/0222384 A1 Jul. 16, 2020

Related U.S. Application Data

(60) Continuation of application No. 15/599,378, filed on May 18, 2017, now abandoned, which is a continuation of application No. 14/938,647, filed on Nov. 11, 2015, now Pat. No. 9,655,892, which is a continuation of application No. 14/296,953, filed on Jun. 5, 2014, now Pat. No. 9,216,982, which is a continuation of application No. 13/403,394, filed on Feb. 23, 2012, now Pat. No. 8,785,456, which is a division of application No. 12/503,776, filed on Jul. 15, 2009, now Pat. No. 8,193,182, which is a continuation-in-part of application No. PCT/US2009/000042, filed on Jan. 5, 2009, and a continuation-in-part of application No. PCT/US2009/000038, filed on Jan. 5, 2009.

(60) Provisional application No. 61/201,146, filed on Dec. 5, 2008, provisional application No. 61/194,294, filed on Sep. 26, 2008, provisional application No. 61/009,971, filed on Jan. 4, 2008.

(51) Int. Cl.
| | | |
|---|---|---|
| C07D 487/04 | (2006.01) |
| A61K 31/4725 | (2006.01) |
| A61K 31/506 | (2006.01) |
| A61K 31/52 | (2006.01) |
| A61K 31/5377 | (2006.01) |
| A61K 45/06 | (2006.01) |
| C07D 473/34 | (2006.01) |
| A61K 31/131 | (2006.01) |
| A61K 31/196 | (2006.01) |
| A61K 39/395 | (2006.01) |
| A61N 5/10 | (2006.01) |

(52) U.S. Cl.
CPC ........ *A61K 31/4725* (2013.01); *A61K 31/131* (2013.01); *A61K 31/196* (2013.01); *A61K 31/506* (2013.01); *A61K 31/52* (2013.01); *A61K 31/5377* (2013.01); *A61K 39/3955* (2013.01); *A61K 39/39558* (2013.01); *A61K 45/06* (2013.01); *A61N 5/10* (2013.01); *C07D 473/34* (2013.01); *C07D 487/04* (2013.01); *A61N 5/1007* (2013.01); *A61N 2005/109* (2013.01); *Y02A 50/30* (2018.01); *Y02P 20/55* (2015.11)

(58) Field of Classification Search
CPC ............... A61K 31/131; A61K 31/196; A61K 31/4725; A61K 31/506; A61K 31/52; A61K 31/5377; A61K 39/3955; A61K 39/39558; A61N 2005/109; A61N 5/10; A61N 5/1007; C07D 473/34; C07D 487/04; Y02A 50/30; Y02P 20/55; A61P 1/00; A61P 5/00; A61P 7/00; A61P 7/02; A61P 9/00; A61P 11/00; A61P 11/06; A61P 13/00; A61P 17/00; A61P 17/06; A61P 19/00; A61P 19/02; A61P 19/08; A61P 25/00; A61P 27/00; A61P 29/00; A61P 35/00; A61P 35/02; A61P 37/02; A61P 37/06; A61P 37/08; A61P 37/00; A61P 43/00

See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,657,744 A | 4/1972 | Ersek |
| 3,845,770 A | 11/1974 | Theeuwes et al. |
| 3,916,899 A | 11/1975 | Theeuwes et al. |
| 3,939,161 A | 2/1976 | Ratajczyk et al. |
| 4,008,719 A | 2/1977 | Theeuwes et al. |
| 4,270,537 A | 6/1981 | Romaine |
| 4,547,508 A | 10/1985 | Konz et al. |
| 4,596,556 A | 6/1986 | Morrow et al. |
| 4,656,159 A | 4/1987 | McPherson et al. |
| 4,704,381 A | 11/1987 | Schaumann et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Abdel-Mohsen, "Synthesis, Reactions and Antimicrobial Activity of 2-Amino-4-(8-quinolinol-5-yl)-1-(p-tolyl)-pyrrole-3-carbonitrile," *Bull. Korean Chem. Soc.* 26(5):719-728 (2005).

(Continued)

*Primary Examiner* — Sarah Pihonak
(74) *Attorney, Agent, or Firm* — Cooley LLP

(57) ABSTRACT

Chemical entities that modulate PI3 kinase activity, pharmaceutical compositions containing the chemical entities, and methods of using these chemical entities for treating diseases and conditions associated with PI3 kinase activity are described herein.

16 Claims, 11 Drawing Sheets

Specification includes a Sequence Listing.

(56) References Cited

U.S. PATENT DOCUMENTS

| | | |
|---|---|---|
| 4,739,762 A | 4/1988 | Palmaz |
| 4,790,824 A | 12/1988 | Morrow et al. |
| 4,795,627 A | 1/1989 | Fisher et al. |
| 4,886,499 A | 12/1989 | Cirelli et al. |
| 4,940,460 A | 7/1990 | Casey et al. |
| 4,941,880 A | 7/1990 | Bums |
| 4,992,445 A | 2/1991 | Lawter et al. |
| 5,001,139 A | 3/1991 | Lawter et al. |
| 5,015,235 A | 5/1991 | Crossman |
| 5,023,252 A | 6/1991 | Hseih |
| 5,040,548 A | 8/1991 | Yock |
| 5,059,595 A | 10/1991 | Le Grazie |
| 5,061,273 A | 10/1991 | Yock |
| 5,064,413 A | 11/1991 | McKinnon et al. |
| 5,073,543 A | 12/1991 | Marshall et al. |
| 5,120,548 A | 6/1992 | McClelland et al. |
| 5,141,496 A | 8/1992 | Daito et al. |
| 5,190,521 A | 3/1993 | Hubbard et al. |
| 5,195,984 A | 3/1993 | Schatz |
| 5,240,941 A | 8/1993 | Bruneau |
| 5,292,331 A | 3/1994 | Boneau |
| 5,294,612 A | 3/1994 | Bacon et al. |
| 5,310,731 A | 5/1994 | Olsson et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,354,556 A | 10/1994 | Sparks et al. |
| 5,364,862 A | 11/1994 | Spada et al. |
| 5,383,851 A | 1/1995 | McKinnon et al. |
| 5,409,930 A | 4/1995 | Spada et al. |
| 5,417,662 A | 5/1995 | Hjertman et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,451,233 A | 9/1995 | Yock |
| 5,466,220 A | 11/1995 | Brenneman |
| 5,480,381 A | 1/1996 | Weston |
| 5,480,883 A | 1/1996 | Spada et al. |
| 5,496,346 A | 3/1996 | Horzewski et al. |
| 5,503,627 A | 4/1996 | McKinnon et al. |
| 5,504,103 A | 4/1996 | Bonjouklian et al. |
| 5,506,347 A | 4/1996 | Erion et al. |
| 5,520,639 A | 5/1996 | Peterson et al. |
| 5,527,288 A | 6/1996 | Gross et al. |
| 5,561,134 A | 10/1996 | Spada et al. |
| 5,563,257 A | 10/1996 | Zilch et al. |
| 5,569,189 A | 10/1996 | Parsons |
| 5,591,767 A | 1/1997 | Mohr et al. |
| 5,593,997 A | 1/1997 | Dow et al. |
| 5,599,302 A | 2/1997 | Lilley et al. |
| 5,639,476 A | 6/1997 | Oshlack et al. |
| 5,639,480 A | 6/1997 | Bodmer et al. |
| 5,646,128 A | 7/1997 | Firestein et al. |
| 5,646,153 A | 7/1997 | Spada et al. |
| 5,649,912 A | 7/1997 | Peterson |
| 5,652,366 A | 7/1997 | Spada et al. |
| 5,654,307 A | 8/1997 | Bridges et al. |
| 5,656,643 A | 8/1997 | Spada et al. |
| 5,665,721 A | 9/1997 | Bhagwat et al. |
| 5,674,278 A | 10/1997 | Boneau |
| 5,674,533 A | 10/1997 | Santus et al. |
| 5,674,998 A | 10/1997 | Boyer et al. |
| 5,686,455 A | 11/1997 | Adams et al. |
| 5,704,911 A | 1/1998 | Parsons |
| 5,710,158 A | 1/1998 | Spada et al. |
| 5,714,493 A | 2/1998 | Spada et al. |
| 5,721,237 A | 2/1998 | Spada et al. |
| 5,733,566 A | 3/1998 | Lewis |
| 5,736,554 A | 4/1998 | Spada et al. |
| 5,739,108 A | 4/1998 | Mitchell |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,861,510 A | 1/1999 | Piscopio et al. |
| 5,863,949 A | 1/1999 | Robinson et al. |
| 5,879,382 A | 3/1999 | Boneau |
| 5,891,474 A | 4/1999 | Busetti et al. |
| 5,893,397 A | 4/1999 | Peterson et al. |
| 5,914,488 A | 6/1999 | Sone |
| RE36,256 E | 7/1999 | Spada et al. |
| 5,919,808 A | 7/1999 | Petrie et al. |
| 5,922,356 A | 7/1999 | Koseki et al. |
| 5,922,753 A | 7/1999 | Petrie et al. |
| 5,948,776 A | 9/1999 | Petrie et al. |
| 5,962,457 A | 10/1999 | Chenard et al. |
| 5,965,573 A | 10/1999 | Petrie et al. |
| 5,972,891 A | 10/1999 | Kamei et al. |
| 5,977,061 A | 11/1999 | Holy et al. |
| 5,980,945 A | 11/1999 | Ruiz |
| 5,981,533 A | 11/1999 | Traxler et al. |
| 5,985,589 A | 11/1999 | Chantry et al. |
| 5,990,109 A | 11/1999 | Chen et al. |
| 5,990,169 A | 11/1999 | Petrie et al. |
| 5,993,412 A | 11/1999 | Deily et al. |
| 5,993,855 A | 11/1999 | Yoshimoto et al. |
| 5,994,358 A | 11/1999 | Petrie et al. |
| 6,001,839 A | 12/1999 | Calderwood et al. |
| 6,045,830 A | 4/2000 | Igari et al. |
| 6,057,305 A | 5/2000 | Holy et al. |
| 6,057,320 A | 5/2000 | Spada et al. |
| 6,057,371 A | 5/2000 | Glennon |
| 6,084,095 A | 7/2000 | Bridges et al. |
| 6,087,324 A | 7/2000 | Igari et al. |
| 6,093,737 A | 7/2000 | Anthony et al. |
| 6,113,943 A | 9/2000 | Okada et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,197,350 B1 | 3/2001 | Yamagata et al. |
| 6,242,453 B1 | 6/2001 | Cirillo et al. |
| 6,248,363 B1 | 6/2001 | Patel et al. |
| 6,251,901 B1 | 6/2001 | Petrie et al. |
| 6,264,970 B1 | 7/2001 | Hata et al. |
| 6,265,410 B1 | 7/2001 | Bridges et al. |
| 6,267,981 B1 | 7/2001 | Okamoto et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,344,053 B1 | 2/2002 | Boneau |
| 6,350,741 B1 | 2/2002 | Golec et al. |
| 6,358,945 B1 | 3/2002 | Breitfelder et al. |
| 6,362,216 B1 | 3/2002 | Burgess et al. |
| RE37,650 E | 4/2002 | Spada et al. |
| 6,376,461 B1 | 4/2002 | Igari et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,419,961 B1 | 7/2002 | Igari et al. |
| 6,455,534 B2 | 9/2002 | Bridges et al. |
| 6,472,153 B1 | 10/2002 | Dempcy et al. |
| 6,472,562 B1 | 10/2002 | Klingler et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,589,548 B1 | 7/2003 | Oh et al. |

(56) References Cited

U.S. PATENT DOCUMENTS

| | | |
|---|---|---|
| 6,613,358 B2 | 9/2003 | Randolph et al. |
| 6,613,798 B1 | 9/2003 | Porter et al. |
| 6,630,495 B1 | 10/2003 | Cooke et al. |
| 6,632,789 B1 | 10/2003 | June |
| 6,645,969 B1 | 11/2003 | Spada et al. |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,664,393 B2 | 12/2003 | Klingler et al. |
| 6,667,300 B2 | 12/2003 | Sadhu et al. |
| 6,667,398 B2 | 12/2003 | Dunn et al. |
| 6,690,583 B1 | 2/2004 | Bergstedt et al. |
| 6,699,500 B2 | 3/2004 | Okada et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,825,219 B2 | 11/2004 | Cywin et al. |
| 6,849,420 B2 | 2/2005 | Vanhasebroeck et al. |
| 6,849,637 B2 | 2/2005 | Andrianjara et al. |
| 6,849,713 B2 | 2/2005 | Zhang et al. |
| 6,852,727 B2 | 2/2005 | Goulet et al. |
| 6,858,756 B2 | 2/2005 | Rampf et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,005,520 B2 | 2/2006 | Dunn et al. |
| 7,026,461 B1 | 4/2006 | Shokat |
| 7,030,242 B2 | 4/2006 | Noe et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,597 B1 | 8/2006 | Miwa et al. |
| 7,102,046 B2 | 9/2006 | Rampf et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,493 B2 | 4/2007 | Wrasidlo et al. |
| 7,208,601 B2 | 4/2007 | Mjalli et al. |
| 7,217,794 B2 | 5/2007 | Abdel-Meguid et al. |
| 7,223,780 B2 | 5/2007 | Nazare et al. |
| 7,230,004 B2 | 6/2007 | Adams et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,317,027 B2 | 1/2008 | Nazare et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,088 B2 | 4/2008 | Nazare et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,465,806 B2 | 12/2008 | Bauer et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,642,272 B2 | 1/2010 | Shankar et al. |
| 7,678,803 B2 | 3/2010 | Huang et al. |
| 7,700,552 B2 | 4/2010 | Waehling et al. |
| 7,700,607 B2 | 4/2010 | Hu et al. |
| 7,705,018 B2 | 4/2010 | Chen et al. |
| 7,745,485 B2 | 6/2010 | Durden |
| 7,812,164 B2 | 10/2010 | Austad et al. |
| 7,829,590 B2 | 11/2010 | Brenchley et al. |
| 7,919,046 B2 | 4/2011 | Delapierre et al. |
| 7,932,260 B2 | 4/2011 | Fowler et al. |
| 8,053,445 B2 | 11/2011 | Yamamori et al. |
| 8,053,603 B2 | 11/2011 | Shao et al. |
| 8,088,385 B2 | 1/2012 | Tapolsky et al. |
| 8,101,637 B2 | 1/2012 | Bessis et al. |
| 8,106,146 B2 | 1/2012 | Benz et al. |
| 8,124,625 B2 | 2/2012 | Yamamori et al. |
| 8,188,134 B2 | 5/2012 | Brenchley et al. |
| 8,193,182 B2 | 6/2012 | Ren et al. |
| 8,399,483 B2 | 3/2013 | Allen et al. |
| 8,557,823 B2 | 10/2013 | Tapolsky et al. |
| 8,785,456 B2 | 7/2014 | Ren et al. |
| 9,326,505 B2 | 5/2016 | Sisler et al. |
| 9,605,003 B2 | 3/2017 | Castro et al. |
| 9,790,228 B2 | 10/2017 | Ren et al. |
| 10,675,286 B2 | 6/2020 | Kutok et al. |
| 10,759,806 B2 | 9/2020 | Evans |
| 2001/0019829 A1 | 9/2001 | Nelson et al. |
| 2001/0027197 A1 | 10/2001 | Bridges et al. |
| 2002/0006931 A1 | 1/2002 | Beachy et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |

(56) References Cited

U.S. PATENT DOCUMENTS

| | | |
|---|---|---|
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Guicherit et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0060546 A1 | 3/2007 | Ruat et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0032980 A1 | 2/2008 | Fraley et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287420 A1 | 11/2008 | Castro et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0293754 A1 | 11/2008 | Austad et al. |
| 2008/0293755 A1 | 11/2008 | Castro et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312310 A1 | 12/2009 | Kawato et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |
| 2010/0009963 A1 | 1/2010 | Knight et al. |
| 2010/0022531 A1 | 1/2010 | Kincaid et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0202963 A1 | 8/2010 | Gallatin et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0286114 A1 | 11/2010 | Thomas et al. |
| 2010/0298290 A1 | 11/2010 | Anand et al. |
| 2010/0305084 A1 | 12/2010 | Castanedo et al. |
| 2010/0305096 A1 | 12/2010 | Castanedo et al. |
| 2011/0009378 A1 | 1/2011 | Lange et al. |
| 2011/0046165 A1 | 2/2011 | Ren et al. |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |

(56) References Cited

U.S. PATENT DOCUMENTS

| | | |
|---|---|---|
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0190157 A1 | 8/2011 | Kipps et al. |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2011/0306622 A1 | 12/2011 | Lannutti et al. |
| 2012/0004198 A1 | 1/2012 | Liao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Yu et al. |
| 2012/0177749 A1 | 7/2012 | Tapolsky et al. |
| 2012/0183535 A1 | 7/2012 | Buggy et al. |
| 2012/0184568 A1 | 7/2012 | Ren et al. |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1 | 9/2012 | Baldwin et al. |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |
| 2013/0045229 A1 | 2/2013 | Iadonato et al. |
| 2013/0053362 A1 | 2/2013 | Castro et al. |
| 2013/0064812 A1 | 3/2013 | Gallatin et al. |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2013/0267521 A1 | 10/2013 | Castro et al. |
| 2013/0344061 A1 | 12/2013 | Palombella et al. |
| 2013/0345216 A1 | 12/2013 | Ren et al. |
| 2014/0024637 A1 | 1/2014 | Rice |
| 2014/0031547 A1 | 1/2014 | Sheridan et al. |
| 2014/0037622 A1 | 2/2014 | Boshoff et al. |
| 2014/0088099 A1 | 3/2014 | Ren et al. |
| 2014/0100214 A1 | 4/2014 | Castro et al. |
| 2014/0120060 A1 | 5/2014 | Palombella et al. |
| 2014/0120083 A1 | 5/2014 | Stem et al. |
| 2014/0206685 A1 | 7/2014 | Ren et al. |
| 2014/0275135 A1 | 9/2014 | Genov et al. |
| 2014/0288048 A1 | 9/2014 | Castro et al. |
| 2014/0296207 A1 | 10/2014 | Ren et al. |
| 2014/0341894 A1 | 11/2014 | Ren et al. |
| 2014/0343057 A1 | 11/2014 | Palombella et al. |
| 2014/0371246 A1 | 12/2014 | Evarts et al. |
| 2014/0371450 A1 | 12/2014 | Ren et al. |
| 2014/0377258 A1 | 12/2014 | Stem et al. |
| 2015/0031672 A1 | 1/2015 | Ren et al. |
| 2015/0065431 A1 | 3/2015 | Xu et al. |
| 2015/0105385 A1 | 4/2015 | Castro et al. |
| 2015/0111874 A1 | 4/2015 | Castro et al. |
| 2015/0126506 A1 | 5/2015 | Castro et al. |
| 2015/0184249 A1 | 7/2015 | Chang et al. |
| 2015/0225410 A1 | 8/2015 | Castro et al. |
| 2015/0290207 A1 | 10/2015 | Kutok et al. |
| 2016/0016957 A1 | 1/2016 | Ren et al. |
| 2016/0031886 A1 | 2/2016 | Ren et al. |
| 2016/0113932 A1 | 4/2016 | Stem et al. |
| 2016/0122365 A1 | 5/2016 | Castro et al. |
| 2016/0152619 A1 | 6/2016 | Ren et al. |
| 2016/0158239 A1 | 6/2016 | Ren et al. |
| 2016/0168157 A1 | 6/2016 | Ren et al. |
| 2016/0185800 A1 | 6/2016 | Ren et al. |
| 2016/0222016 A1 | 8/2016 | Castro et al. |
| 2016/0244452 A1 | 8/2016 | Castro et al. |
| 2017/0088553 A1 | 3/2017 | Grenier et al. |
| 2017/0137407 A1 | 5/2017 | Castro et al. |
| 2017/0369511 A1 | 12/2017 | Castro et al. |
| 2018/0044346 A1 | 2/2018 | Castro et al. |
| 2018/0098983 A1 | 4/2018 | Ren et al. |
| 2019/0330240 A1 | 10/2019 | Castro et al. |
| 2019/0367521 A1 | 12/2019 | Castro et al. |
| 2020/0222384 A1 | 7/2020 | Ren et al. |

FOREIGN PATENT DOCUMENTS

| | | |
|---|---|---|
| CN | 102206172 | 10/2011 |
| CN | 102731492 | 10/2012 |
| DE | 2139107 A1 | 2/1973 |
| EP | 0110372 B1 | 9/1986 |
| EP | 773023 A1 | 5/1997 |
| EP | 606046 | 8/1997 |
| EP | 0818442 | 1/1998 |
| EP | 0945864 | 9/1999 |
| EP | 1004578 | 5/2000 |
| EP | 780386 | 2/2002 |
| EP | 1 262 176 A1 | 4/2002 |
| EP | 931788 | 6/2002 |
| EP | 1020445 B1 | 8/2008 |
| GB | 812366 A | 4/1959 |
| GB | 937725 A | 9/1963 |
| JP | 61-109797 A | 5/1986 |
| JP | H04211063 | 8/1992 |
| JP | 05-256693 A | 10/1993 |
| JP | 8295667 | 11/1996 |
| JP | 08295667 A | 11/1996 |
| JP | 9143163 | 6/1997 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 1983/001446 A1 | 4/1983 |
| WO | WO 1990/005719 A1 | 5/1990 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/019774 | 7/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/027583 A1 | 9/1996 |
| WO | WO 1996/033172 A1 | 10/1996 |
| WO | WO 1996/040706 A1 | 12/1996 |
| WO | WO 1997/013537 A1 | 4/1997 |
| WO | WO 1997/028133 A1 | 8/1997 |
| WO | WO 1997/028161 A1 | 8/1997 |
| WO | WO 1997/037705 A1 | 10/1997 |
| WO | WO 1998/003516 A1 | 1/1998 |
| WO | WO 1998/007697 A1 | 2/1998 |
| WO | WO 1998/030566 A1 | 7/1998 |
| WO | WO 1998/033768 A1 | 8/1998 |
| WO | WO 1998/034915 A1 | 8/1998 |
| WO | WO 1998/034918 A1 | 8/1998 |
| WO | WO 1998/041525 A1 | 9/1998 |

(56) References Cited

FOREIGN PATENT DOCUMENTS

| | | |
|---|---|---|
| WO | WO 1998/052611 A1 | 11/1998 |
| WO | WO 1998/057952 A1 | 12/1998 |
| WO | WO 1999/007675 A1 | 2/1999 |
| WO | WO 1999/029667 A1 | 6/1999 |
| WO | WO 1999/034850 A1 | 7/1999 |
| WO | WO 1999/052889 A1 | 10/1999 |
| WO | WO 1999/052910 A1 | 10/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019800 A2 | 3/2001 |
| WO | WO 2001/019829 A2 | 3/2001 |
| WO | WO 2001/021160 | 3/2001 |
| WO | WO 2001/025238 A2 | 4/2001 |
| WO | WO 2001/026664 A2 | 4/2001 |
| WO | WO 2001/027135 A2 | 4/2001 |
| WO | WO 2001/031063 A1 | 5/2001 |
| WO | WO 2001/038584 A2 | 5/2001 |
| WO | WO 2001/049279 A2 | 7/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/060824 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/074344 A2 | 10/2001 |
| WO | WO 2001/081346 A2 | 11/2001 |
| WO | WO 2002/006192 A1 | 1/2002 |
| WO | WO 2001/081346 A3 | 3/2002 |
| WO | WO 2001/002369 A3 | 4/2002 |
| WO | WO 2002/030944 A2 | 4/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/028853 A1 | 11/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/011219 A2 | 2/2003 |
| WO | WO 2003/016275 A1 | 2/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/059884 A1 | 7/2003 |
| WO | WO 2003/020880 A3 | 10/2003 |
| WO | WO 2003/082341 A1 | 10/2003 |
| WO | WO 2003/088970 A2 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/020599 A2 | 3/2004 |
| WO | WO 2004/031177 A1 | 4/2004 |
| WO | WO 2004/039774 A2 | 5/2004 |
| WO | WO 2004/046128 | 6/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/075917 A1 | 9/2004 |
| WO | WO 2004/087053 A2 | 10/2004 |
| WO | WO 2004/087679 | 10/2004 |
| WO | WO 2004/089877 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/013800 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/032343 A2 | 4/2005 |
| WO | WO 2005/033288 A2 | 4/2005 |
| WO | WO 2005/012323 A3 | 5/2005 |
| WO | WO 2005/016528 A3 | 5/2005 |
| WO | WO 2005/042700 A2 | 5/2005 |
| WO | WO 2005/044181 A2 | 5/2005 |
| WO | WO 2005/047289 A1 | 5/2005 |
| WO | WO 2005054202 A1 | 6/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/074606 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/015279 | 2/2006 |
| WO | WO 2005/044181 A3 | 3/2006 |
| WO | WO 2006/028958 A2 | 3/2006 |
| WO | WO 2006/030032 A1 | 3/2006 |
| WO | WO 2006/038865 A1 | 4/2006 |
| WO | WO 2006/050351 A2 | 5/2006 |
| WO | WO 2006/050501 A2 | 5/2006 |
| WO | WO 2006/050946 A1 | 5/2006 |
| WO | WO 2006/068760 A2 | 6/2006 |
| WO | WO 2006/078283 A2 | 7/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2007/029121 | 3/2007 |
| WO | WO 2006/050501 A3 | 5/2007 |
| WO | WO 2007/054623 A2 | 5/2007 |
| WO | WO 2007/059157 A1 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/120827 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/131201 A2 | 11/2007 |
| WO | WO 2007/134828 A1 | 11/2007 |
| WO | WO 2007/135380 A1 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |

(56) References Cited

FOREIGN PATENT DOCUMENTS

| | | |
|---|---|---|
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/063625 A2 | 5/2008 |
| WO | WO 2008/064018 A1 | 5/2008 |
| WO | WO 2008/070357 A2 | 6/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/110611 A1 | 9/2008 |
| WO | WO 2008/112715 A2 | 9/2008 |
| WO | WO 2008/112913 A1 | 9/2008 |
| WO | WO 2007/114926 A3 | 10/2008 |
| WO | WO 2008/117050 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2008/131354 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/019531 A2 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/103022 | 8/2009 |
| WO | WO 2009/114870 A2 | 9/2009 |
| WO | WO 2009/117157 A1 | 9/2009 |
| WO | WO 2009/118765 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/053998 | 5/2010 |
| WO | WO 2010/057048 A1 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/133836 A1 | 11/2010 |
| WO | WO 2011/008302 A1 | 1/2011 |
| WO | WO 2011/041399 A2 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/094890 | 8/2011 |
| WO | WO 2011/111880 | 9/2011 |
| WO | WO 2011/146882 A1 | 11/2011 |
| WO | WO 2012/009452 | 1/2012 |
| WO | WO 2012/032334 A1 | 3/2012 |
| WO | WO 2012/037204 | 3/2012 |
| WO | WO 2012/052540 | 4/2012 |
| WO | WO 2012/061696 A1 | 5/2012 |
| WO | WO 2012/064973 A2 | 5/2012 |
| WO | WO 2012/068096 | 5/2012 |
| WO | WO 2012/068106 | 5/2012 |
| WO | WO 2012/071519 | 5/2012 |
| WO | WO 2012/097000 A1 | 7/2012 |
| WO | WO 2012/121953 A1 | 9/2012 |
| WO | WO 2012/129562 | 9/2012 |
| WO | WO 2012/135750 | 10/2012 |
| WO | WO 2012/136549 | 10/2012 |
| WO | WO 2013/006532 | 1/2013 |
| WO | WO 2013/012915 A1 | 1/2013 |
| WO | WO 2013/013504 | 1/2013 |
| WO | WO 2013/013505 | 1/2013 |
| WO | WO 2013/025498 | 2/2013 |
| WO | WO 2013/044169 | 3/2013 |
| WO | WO 2013/059738 A2 | 4/2013 |
| WO | WO 2013/066483 | 5/2013 |
| WO | WO 2013/074583 | 5/2013 |
| WO | WO 2013/074583 A1 | 5/2013 |
| WO | WO 2013/086131 | 6/2013 |
| WO | WO 2013/090725 | 6/2013 |
| WO | WO 2013/113838 | 8/2013 |
| WO | WO 2013/113841 | 8/2013 |
| WO | WO 2013/188763 | 12/2013 |
| WO | WO 2014/004470 | 1/2014 |
| WO | WO 2014/018567 A1 | 1/2014 |
| WO | WO 2014/046617 | 3/2014 |
| WO | WO 2014/071105 | 5/2014 |
| WO | WO 2014/071109 A1 | 5/2014 |
| WO | WO 2014/071125 A1 | 5/2014 |
| WO | WO 2014/072937 A1 | 5/2014 |
| WO | WO 2014/075393 | 5/2014 |
| WO | WO 2014/124458 | 8/2014 |
| WO | WO 2014/141165 | 9/2014 |
| WO | WO 2014/168975 | 10/2014 |
| WO | WO 2014/175267 | 10/2014 |
| WO | WO 2014/194254 A1 | 12/2014 |
| WO | WO 2014/203959 | 12/2014 |
| WO | WO 2015/002729 | 1/2015 |
| WO | WO 2015/010641 A1 | 1/2015 |
| WO | WO 2015/037005 | 3/2015 |
| WO | WO 2015/051252 | 4/2015 |
| WO | WO 2015/054099 | 4/2015 |
| WO | WO 2015/054355 | 4/2015 |
| WO | WO 2015/081127 | 6/2015 |
| WO | WO 2015/083008 | 6/2015 |
| WO | WO 2015/095807 | 6/2015 |
| WO | WO 2015/095819 | 6/2015 |
| WO | WO 2015/095825 | 6/2015 |
| WO | WO 2015/095829 | 6/2015 |
| WO | WO 2015/095831 | 6/2015 |
| WO | WO 2015/095834 | 6/2015 |
| WO | WO 2015/095838 | 6/2015 |
| WO | WO 2015/095840 | 6/2015 |
| WO | WO 2015/095842 | 6/2015 |
| WO | WO 2015/109286 | 7/2015 |
| WO | WO 2015/143382 | 9/2015 |
| WO | WO 2015/160975 | 10/2015 |
| WO | WO 2015/160986 | 10/2015 |
| WO | WO 2015/175966 | 11/2015 |
| WO | WO 2015/179772 | 11/2015 |
| WO | WO 2015/181053 | 12/2015 |
| WO | WO 2015/181055 | 12/2015 |
| WO | WO 2015/188119 | 12/2015 |
| WO | WO 2016/054555 | 4/2016 |

OTHER PUBLICATIONS

Abe et al., "T cell receptor-mediated recognition of self-ligand induces signaling in immature thymocytes before negative selection," *J. Exp. Med.* 176(2):459-468 (1992).

Abrahamian et al., "Immunological and Clinical Profile of Adult Patients with Selective Immunoglobulin Subclass deficiency: response

(56) References Cited

OTHER PUBLICATIONS to intravenous immunoglobulin therapy," *Clin. Exp. Immunol.* 159(3):344-350 (2010).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).
Anderson et al., "Paradoxical inhibition of T-cell function in response to CTLA-4 blockade; heterogeneity within the human T-cell population," *Nat. Med.* 6(2):211-214 (2000).
Andrews et al., "Effects of the 11β-hydroxy steroid dehydrogenase inhibitor carbenoxolone on insulin sensitive in men with type 2 diabetes," *J. Clin. Endocrinol. Metab.* 88(1):285-291 (2003).
Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).
Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).
Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).
Baggiolini et al., "Inhibition of the phagocytosis-induced respiratory burst by the fungal metabolite wortmannin and some analogues," *Exp. Cell. Res.* 169(2): 408-418 (1987).
Ballell et al. "New Thiopyrazolo[3,4-d] pyrimidine derivatives as anti-mycobacterial agents," *Bioorg. Med. Chem. Lett.* 17(6):1736-1740 (2007).
Banker et al., Modern Pharmaceutics, pp. 451, 596, 3$^{rd}$ ed, Marcel Dekker, New York (1996).
Bansal et al., "The Molecular Biology of Endometrial Cancers and the Implications for Pathogenesis, Classification, and Targeted Therapies," *Cancer Control* 16(1):8-13 (2009).
Barber et al., "PI3Kgamma inhibition blocks glomerulonephritis and extends lifespan in a mouse model of systemic lupus," *Nat. Med.* 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxy steroid dehydrogenase Type 1," *J. Med. Chem.* 45(18):3813-3815 (2002).
Barnes et al., "Efficacy and Safety of Inhaled Corticosteroids in Asthma—Report of A Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
Basotest®, Test Kit for the Quantitative Determination of the Degranulation of Basophilic Granulocytes in Heparinized Human Whole Blood, version Apr. 2002, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).

Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells." *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).

(56) References Cited

OTHER PUBLICATIONS

Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.(Tokyo)* 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxy steroid-dehydrogenases (11βHSDs): chenodeoxycholic acid selectively inhibits 11β-HSD-I," *Eur. J. Endocrinol.* 142(2):200-207 (2000).
Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C-C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines,"*Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from Fusarium oxysporum," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226(1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).

(56) References Cited

OTHER PUBLICATIONS

Hasselblom et al., "High immunohistochemical expression of p-AKT predicts inferior survival in patients with diffuse large B-cell lymphoma treated with immunochemotherapy," *Brit. J. Haematol.* 149:560-568 (2010).

Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).

Hell Winkel et al., "Heterocyclensynthesen mit MF/A1203-basensystemen; 2-arylbenzofurane and 2,3-diarylisochinolin-1(2H)-one," *Synthesis* 1995( 9):1135-1141 (1995).

Herishanu et al., "The lymph node microenvironment promotes B-cell receptor signaling, NF-κB activation, and tumor proliferation in chronic lymphocytic leukemia," *Blood* 117(2):563-574 (2011).

Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).

Herman et al., "The role of phosphatidylinositol 3-kinase-δ in the immunomodulatory effects of lenalidomide in chronic lymphocytic leukemia," *Blood* 117(16):4323-4327 (2011).

Herrera et al., "The dual PI3K/mTOR inhibitor BEZ235 is effective in lung cancer cell lines," *Anticancer Res.* 31:849-854 (2011).

Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).

Hirsch et al., "CALming Down T Cell Acute Leukemia," *Cancer Cell* 21:449-450 (2012).

Hirsch et al., "Central Role for G Protein-Coupled Phosphoinositide 3-Kinase γ in Inflammation," *Science* 287:1049-1053 (2000).

Hoellenriegel and Burger, "Phosphoinositide 3'-kinase delta: turning off BCR signaling in Chronic Lymphocytic Leukemia," *Oncotarget* 2(10):737-738 (2011).

Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).

Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (Ash Annual Meeting 2010).

Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).

Ikeda et al., "PI3K/p110δ is a novel therapeutic target in multiple myeloma," *Blood* 116(9):1460-1468 (2010).

International Preliminary Report on Patentability and Written Opinion for PCT/US2005/042524 dated May 22, 2007.

International Preliminary Report on Patentability and Written Opinion for PCT/US2007/008355 dated Nov. 4, 2008.

International Preliminary Report on Patentability and Written Opinion for PCT/US2007/008395 dated Oct. 8, 2008.

International Preliminary Report on Patentability and Written Opinion for PCT/US2009/049969 dated Jan. 11, 2011.

International Preliminary Report on Patentability and Written Opinion for PCT/US2009/060985 dated Apr. 19, 2011.

International Preliminary Report on Patentability for PCT/US2009/000038 dated Jul. 6, 2010.

International Preliminary Report on Patentability for PCT/US2009/005380 dated Apr. 7, 2011.

International Preliminary Report on Patentability for PCT/US2010/002020 dated Jan. 26, 2012.

International Preliminary Report on Patentability for PCT/US2009/000042 dated Jul. 6, 2010.

International Search Report & Written Opinion for PCT/US2011/060212 dated Jun. 1, 2012.

International Search Report & Written Opinion issued after Submission of Request for Additional Search for PCT/US2011/060212 dated Jul. 6, 2012.

International Search Report and Written Opinion for PCT/US2009/005380 dated Nov. 20, 2009.

International Search Report and Written Opinion for PCT/US2009/049969 dated Mar. 15, 2010.

International Search Report and Written Opinion for PCT/US2010/033939, dated Nov. 5, 2010.

International Search Report and Written Opinion for PCT/US2012/047190 dated Oct. 2, 2012.

International Search Report and Written Opinion for PCT/US2012/020831 dated May 2, 2012.

International Search Report for PCT/US2011/037412 dated Aug. 22, 2011.

International Search Report for PCT/US1995/005213 dated Aug. 21, 1995.

International Search Report for PCT/US2007/008395 (4 pages) dated Aug. 27, 2008.

International Search Report for PCT/US2009/000038 dated Mar. 11, 2009.

International Search Report for PCT/US2009/000042 dated Mar. 23, 2009.

International Search Report for PCT/US2005/042524 (7 pages) dated Oct. 2, 2006.

International Search Report for PCT/US2007/008355 dated Sep. 25, 2008.

International Search Report for PCT/US2009/060985 dated Jun. 28, 2010.

International Search Report for PCT/US2010/002020 dated Nov. 2, 2010.

Ishiyama et al., "A stoichiometric aromatic C-H borylation catalyzed by iridium(I)/2,2'-bipyridine complexes at room temperature," *Angew. Chem. Int. Ed. Engl.* 41(16):3056-3058 (2002).

Ishiyama et al., "Mild iridium-catalyzed borylation of arenes. High turnover numbers room temperature reactions, and isolation of a potential intermediate," *J. Am. Chem. Soc.* 124(3):390-391 (2002).

Jackson et al., "PI 3-kinase p110β: a new target for antithrombotic therapy," *Nat. Med.* 11:507-514 (2005).

Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).

Johnson et al., "Accessory cell-derived signals required for T cell activation," *Immunol. Res.* 48-64 (1993).

Jou et al., "Essential, nonredundant role for the phosphoinositide 3-kinase p110delta in signaling by the B-cell receptor complex," *Mol. Cell. Biol.* 22:8580-8591 (2002).

June et al., "Evidence for the involvement of three distinct signals in the induction of IL-2 gene expression in human T lymphocytes," *J. Immunol.* 143(1):153-161 (1989).

June et al., "Inhibition of tyrosine phosphorylation prevents T-cell receptor mediated signal transduction," *Proc. Natl. Acad. Sci. U.S.A.* 87:7722-7726 (1990).

June et al., "Role of CD28 receptor in T-cell activation." *Immunol. Today* 11(6):211-216 (1990).

June, C.H., "Signaling transduction in T cells," *Curr. Opin. Immunol.* 3(3):287-293 (1991).

Kajita et al., "Nickel-catalyzed decarbonylative addition of phthalimides to alkynes," *J. Am. Chem. Soc.* 130(19):6058-6059 (2008).

Kallberg et al., "Short-chain dehydrogenase/reductase (SDR) relationships: a large family with eight clusters common to human, animal, and plant genomes," *Protein Sci.* 11(3):636-641 (2002).

Kallberg et al., "Short-Chain Dehydrogenases/Reductases (SDRs)—Coenzyme-Based Functional Assignments in Completed Genomes," *Eur. J. Biochem.* 269(18):4409-4417 (2002).

Kang et al., "Oncogenic transformation induced by the p110β, -γ, and -δ isoforms of class I phosphoinositide 3-kinase," *PNAS* 103(5):1289-1294 (2006).

Karpeiskii et al., "Pyridoxal-5'-Derivatives of Nucleobases," *Bioorganicheskaya Khimiya* 11(8): 1097-1104 (1985).

Khwaja, A., "PI3K as a Target for Therapy in Haematological Malignancies," *Curr. Top. Microbiol. Immunol.* 347:169-188 (2010).

Kim et al., "Activation and Function of the mTORC1 Pathway in Mast Cells," *J. Immunol.* 180(7):4586-4595 (2008).

Knight et al., "A Pharmacological Map of the PI3-K Family Defines a Role for p110α in Insulin Signaling," *Cell* 125(4):733-747 (2006).

(56) References Cited

OTHER PUBLICATIONS

Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio-and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotypebased screen," *Science* 286(5441):971-974 (1999).
Mazzoletti and Broggini, "PI3K/AKT/mTOR inhibitors in ovarian cancer," *Curr. Med. Chem.* 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," *Blood* (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV—synthesis of methyl, 3-formyl & other 3-substituted N-arylisoquinolones." *Indian J. Chem.* 18B:304-306 (1979).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxy steroid dehydrogenases with retained oxidoreductase activities," *Protein Expr. Purif.* 26(3):349-356 (2002).
Norman, "Selective PI3K-delta Inhibitors, A Review of the Patent Literature," *Expert Opinion on Therapeutic Patents,* 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).

(56) References Cited

OTHER PUBLICATIONS

Patel et al., "Immunopathological aspects of age-related macular degeneration," *Semin. Immunopathol.* 30(2):97-110 (2008).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).
Romero et al., "Cloning and expression of the bovine 11b-hydroxysteroid dehydrogenase type-2," *J. Steroid Biochem. Mol. Biol.* 72(5):231-237 (2000).
Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 (Pt 1):227-231 (1993).
Sinclair et al., "Phosphatidylinositol-3 Kinase Delta (PI3K5) Inhibitor AMG 319 Is a Potent, Selective and Orally Bioavailable Small Molecule Inhibitor That Suppresses PI3K-Mediated Signaling and Viability in Neoplastic B Cells," *Blood* (*ASH Annual Meeting Abstracts*). 118:Abstract 4964 (2011).
Soldan et al., "Induction of daunorubicin carbonyl reducing enzymes by daunombicin in sensitive and resistant pancreas carcinoma cells," *Biochem. Pharmacol.* 51(2):117-123 (1996).
Soond et al., "PI3K p100δ regulates T-cell cytokine production during primary and secondary immune responses in mice and humans," *Blood* 115(11):2203-2213 (2010).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Vara et al., "PI3K/Akt Signalling Pathway and Cancer," *Cancer Treat. Rev.* 30(2):193-204 (2004).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
American Cancer Society. Non-Hodgkin's Lymphoma. Last Revised Mar. 11, 2015, Retrieved online: <http://www.cancer.org/cancer/nonhodgkinlymphoma/detailedguide/non-hodgkin-lymphoma-types-of-non-hodgkin-lymphoma>.
Ameriks et al., "Small Molecule Inhibitors of Phosphoinositide 3-Kinase (PI3K) δ and γ", Curr Top Med Chern, 2009, vol. 9, pp. 738-753.
Barnes et al., "Glucocortiod resistance in inflammatory diseases," *The Lancet*, 373:1905-1917 (2009).
Bouska et al.,"Genome-wide copy-number analyses reveal genomic abnormalities involved in transformation of follicular lymphoma", *Blood*, Mar. 13, 2014, vol. 123, N. 11, pp. 1681-1690.

Boyle et al., "Efficacy of the potent PI3K-δ,γ inhibitor IPI-145 in rat adjuvant arthritis," *Arthritis & Rheumatism*, 64:S879 (2012).
Brown et al. "Phase I Trial of SAR245408 (S08), a Pan-Phosphatidylinositol 3 Kinase (PI3K) Inhibitor, in Patients with Chronic Lymphocytic Leukemia (CLL) and Lymphoma", Blood (ASH Annual Meeting Abstracts) 2011 118: Abstract 2683, Downloaded from the Internet.
Brown et al., "Idelalisib, an inhibitor of phosphatidylinositol 3-kinase p110d, for relapsed/refractory chronic lymphocytic leukemia", *Blood*, May 29, 2014, vol. 123, No. 22, pp. 3390-3397.
Caira, M., "Crystalline Polymorphism of Organic Compounds," Topics in Current Chemistry, Springer, Berlin, DE, v. 198 (Jan. 1, 1998), p. 163-208.
Calin et al., "A MicroRNA Signature Associated with Prognosis and Progression in Chronic Lymphocytic Leukemia", *N Engl J Med.* 353:1793-801 (2005).
Castor et al., "PI$_3$Kγ controls leukocyte recruitment, tissue injury, and lethality in a model of graft-versus-host disease in mice," *J. Leukoc. Biol.*, 89:955-964 (2011).
Cheson et al., "Novel Targeted Agents and the Need to Refine Clinical End Points in Chronic Lymphocytic Leukemia", Journal of Clinical Oncology, vol. 30, No. 23 (Aug. 10), 2012, pp. 2820-2822.
Cheung et al., "Genome-wide profiling of follicular lymphoma by array comparative genomic hybridization reveals prognostically significant DNAcopy number imbalances", Blood, Jan. 1, 2009, ,vol. 113, No. 1,pp. 137-148.
Cheung et al., "High Resolution Analysis of Follicular Lymphoma Genomes Reveals Somatic Recurrent Sites of Copy-Neutral Loss of Heterozygosity and Copy Number Alterations that Target Single Genes", Genes, Chromosomes & Cancer 49; 669-681 (2010), DOI 10.1002/gcc.
Chiron et al., "Cell-Cycle Reprogramming for PI3K Inhibition Overrides a Relapse-Specific C481S BTK Mutation Revealed by Longitudinal Functional Genomics in Mantle Cell Lymphoma", Cancer Discovery, (Sep. 2014), vol. 4, pp. 1022-1035, Published OnlineFirst Jul. 31, 2014; DOI 10.1158/2159-8290.CD-14-0098.
ClinicalTrials.gov, "Dose Escalation Study of CAL-101 in Select Relapsed or Refractory Hematologic Malignancies" [online] (2008) [Retrieved on Jul. 23, 2014] Retrieved from <http://clinicaltrials.gov/ct2/show/NCT00710528>.
ClinicalTrials.gov, NCT01476657 Study, "A Phase 1 Study of IPI-145 in Patients with Advanced Hematologic Malignancies", Nov. 17, 2011.
Conte et al., "Inhibition of PI3K Prevent the Proliferation and Differentiation of Human Lung Fibroblasts into Myofibroblasts: The Role of Class I P110 Isoforms," Plos One (2011), 6(10):e24663, pp. 1-10.
Cui et al., "MicroRNA-155 influences B-cell receptor signaling and associates with aggressive disease in chronic lymphocytic leukemia", *Blood*, 124(4):546-554 (2014).
D'Amore et al., "Clonal Evolution in t(14;18)—Positive Follicular Lymphoma, Evidence for Multiple Common Pathways, and Frequent Parallel Clonal Evolution", Clin Cancer Res 2008;14(22) Nov. 15, 2008, pp. 7180-7187.
D'Cruz et al. "Novel Bruton's tyrosine kinase inhibitors currently in development," OncoTargets and Therapy, Mar. 5, 2013, vol. 6, pp. 161-176,.
De Frias et al., "Akt inhibitors induce apoptosis in chronic lynphocytic leukemia cells", Haematologica (2009), vol. 94, pp. 1698-1707.
De Vos et al., "A Phase 1 Study of the Selective Phosphatidylinositol 3-Kinase-Delta (PI3K delta) Inhibitor, Cal-101 (GS1101), in Combination with Rituximab and/or Bendamustine in Patients with Previously Treated, Indolent Non-Hodgkin Lymphoma (iNHL)", Blood, ASH, US, vol. 118, No. 21, Dec. 13, 2011, p. 1160, XP008152289, ISSN: 0006-4971.
Engelman, J. "Targeting PI3K signalling in cancer: opportunities, challenges and limitations", *Nature Reviews: Cancer*, 9:550-562 (2009).
Flinn et al., "Clinical Safety and Activity in a Phase 1 Trial of IPI-145, a Potent Inhibitor of Phosphoinositide-3-Kinase-δ, γ, in Patients with advanced Hematologic Malignancies," Blood, vol. 120, No. 21, Nov. 16, 2012, p. 3663, XP008166549, & 54th ASH Annual Meeting (Dec. 10, 2012).

(56) References Cited

OTHER PUBLICATIONS

Fruman et al., "PI3Kδ Inhibitors in Cancer: Rationale and Serendipity Merge in the Clinic," Cancer Discovery, 1:562-572 (2011).
Fulci et al., "Quantitative technologies establish a novel microRNA profile of chronic lymphocytic leukemia", Blood, 109(11):4944-4951 (2007).
Furman et al., "CAL-101, An Isoform-Selective Inhibitor of Phosphatidylinositol 3-Kinase P110 delta, Demonstrates Clinical Activity and Pharmacodynamic Effects in patients with Relapsed or Refractory Chronic Lymphocytic Leukemia," BLOOD; 52nd Annual Meeeting of ASH, Orlando, FL, USA, vol. 116, No. 21, Nov. 1, 2010, p. 31, XP008168032, ISSN: 0006-4971.
Ghigo et al., "PI3K Inhibition in Inflammation: Toward tailored therapies for specific diseases," BioEssays 32 (2010), pp. 185-196.
Graham et al., "The TAM family: phosphatidylserinesensing receptor tyrosine kinases gone awry in cancer", Nature Rev Cancer, 14:769-785 (2014).
Hall et al., "The dual PI3K/mTOR inhibitor NVP-BEZ235 enhances dexamethasone induced apoptosis in models of T-cell ALL with PTEN dysfunction and hyperactivated PI3K/Akt pathway.", Cancer Research: Apr. 15, 2013; vol. 73, Issue 8, Supplement 1, doi: 10.1158/1538-7445.AM2013-2757.
Harris et al., "PI3K isoforms as drug targets in inflammatory diseases: Lessons from pharmacological and genetic strategies", Curr. Opin. In Inv. Drugs, 2009, vol. 10(11), pp. 1151-1162.
Henderson et al., "Delineation of a Minimal Region of Deletion at 6q16.3 in Follicular Lymphoma and Construction of a Bacterial Artificial Chromosome Contig Spanning a 6-Megabase Region of 6q16-q21", Genes, Chromosomes & Cancer 40:60-65 (2004).
Herman et al., "Molecular Pathways: Targeting the Phosphoinositide 3-Kinase (PI3-Kinase) p110 delta in Chronic Lymphocytic Leukemia", Clin. Cancer Res. (2012) Aug. vol. 18, pp. 4013-4018.
Higgs et al., "Patients with systemic lupus erythematosus, myositis, rheumatoid arthritis and scleroderma share activation of a common type I interferon pathway", Ann Rheum Dis, 2011, vol. 70 pp. 2029-2036.
Hoe et al., "Drugging the p53 pathway: understanding the rout to clinical efficacy", Nature Reviews Drug Discovery, Mar. 2014, vol. 13, pp. 217-236.
Infinity Pharmaceuticals, Inc.—Press Release dated Jul. 18, 2012, "Infinity Regains Worldwide Rights to PI3K, FAAH and Early Discovery Programs," Retrieved from the Internet: URL:http://phx.corporate-.net/phoenix.zhtml?c=121941&p=irol-newsArticle_print&ID=1715695&hightlight= [retrieved on Jan. 10, 2014].
Kassern, Noreen, "Top Ten Bone Diseases," LiveStrong.com, Apr. 29, 2011. <http://www.livestrong.com/article/119479-top-ten-bone-diseases/>.
Kavanagh, et al., "Patient. Mylodysplastic syndromes. 2012," [online], Retrieved on Apr. 24, 2015, <http://www.patient.co.uk/doctor/myelodysplastic-syndromes-pro>.
Kiefer, "Lymphoma Prevention," Healthline. 2011, <http://www.healthline.com/health/lymphoma/prevention>.
Kridel et al., "Pathogenesis of follicular lymphoma", J. of Clinical Investigation, vol. 122, No. 10, Oct. 2012, pp. 3424-3431.
Kukulski et al., "The P2 receptor antagonist PPADS abrogates LPS-induced neutrophil migration in the murine air pouch via inhibition of MIP-2 and KC production," Mol. Immun., 47(4):833-839 (2010).
Macias-Perez and Flinn, "B-Cell Receptor Pathobiology and Tarteting in NHL," Curr. Oncol. Rep., 14:411-418 (2012).
Mansour et al., "Discovery of a Secreted Tumor Suppressor Provides a Promising Therapeutic Strategy for Follicular Lymphoma", Cancer Cell 20, Nov. 15, 2011, pp. 559-561.
MedicineNet.Com, Cancer Definition, http://www.medterms.com, 2004.
Medline Plus, Autoimmune Diseases, NIH, 2014. <http://www.nlm.nih.gov/medlineplus/autoimmunediseases.html>.
Mraz et al., "miR-150 influences B-cell receptor signaling in chronic lymphocytic leukemia by regulating expression of GABI and FOXP1", Blood 124(1):84-95 (2014).

National Cancer Institute, "AIDS-Related Lymphoma Treatment," 2015. <http://www.cancer.gov/cancertopics/pdq/treatment/AIDS-related-lymphoma/Patient/pagel>.
NCBI, Nutritional and Metabolic Diseases, NCBI Bookshelf, 1998. <http://www.ncbi.nlm.nih.gov/books/NBK22259/>.
NCBI, The Nervous System, NCBI Bookshelf, 1998. <http://www.ncbi.nlm.nih.gov/books/NBK22197/>.
O'Connor, "Adult T-Cell Leukemia/Lymphoma (HTLV-1)", Lymphoma Research Foundation, 2008, 1-4.
Okosun et al., "Integrated genomic analysis identifies recurrent mutations and evolution patterns driving the initiation and progression of follicular lymphoma", Nature Genetics (2014) vol. 46, No. 2, pp. 176-181.
Okosun et al., Supplementary Information "Integrated genomic analysis identifies recurrent mutations and evolution patterns driving the initiation and progression of follicular lymphoma", Nature Genetics (2014), doi:10.1038/ng.2856.
Oricchio et al., "The Eph-Receptor A7 Is a Soluble Tumor Suppressor for Follicular Lymphoma", Cell 147, 554-564, Oct. 28, 2011.
Pharmacyclics Inc. Form 8-K Filing. May 16, 2013. Article retrieved from the Internet: <http://www.sec.gov/Archives/edgar/data/949699/000092189513001115/0000921895-13-001115-index.htm> on Dec. 11, 2014.
Porter et al., "The Potent Phosphoinositide-3 -Kinase-(δ,γ) Inhibitor IPI-145 is Active in Preclinical Models of Arthritis and Well Tolerated in Healthy Adult Subjects," Arthritis & Rheumatism, 64:S147 (2012).
Ross et al., "ComprehensiveAnalysis of Copy Number and Allele Status Identifies Multiple Chromosome Defects Underlying Follicular Lymphoma Pathogenesis", Clin Cancer Res 2007; 13(16), pp. 4777-4785, Aug. 15, 2007.
Schwaenen et al., "Microarray-Based Genomic Profiling Reveals Novel Genomic Aberrations in Follicular Lymphoma Which Associate with Patient Survival and Gene Expression Status", Genes, Chromosomes & Cancer 48:39-54 (2009) DOI 10.1002/gcc.
Seda and Mraz, "B-cell receptor signalling and its crosstalk with other pathways in normal and malignant cells", European Journal of Haematology 94(3):193-205 (2015).
Sharman et al., "A Phase 1 Study of the Selective Phosphatidylinositol 3-Kinase-Delta (PI3K delta) Inhibitor, CAL-101 (GS-1101), in Combination with Rituximab and/or Bendamustine in Patients with Relapsed or Refractory Chronic Lymphocytic Leukemia (CLL)", Blood; 53rd ASH Annual Meeting, San Diego, CA, vol. 118, No. 21, Nov. 18, 2011, p. 779-780, XP008152290, ISSN: 006-4971 Retrieved from the Internet.
Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(4):471-474 (2011) (abstract only).
Stone, Richard. "Mast Cell Leukemia and Other Mast Cell Neoplasms." In: Kufe DW, Pollock RE, Weichselbaum RR, et al., editors. Holland-Frei Cancer Medicine. 6th Edition. Hamilton (ON): BC Decker, 2003, URL: <http://www.ncbi.nlm.nih.gov/books/NBK13427/>.
Suralkar et al., "In-Vivo Animal Models for Evaluationof Anti-Inflammatory Activity," Pharmainfo.net/reviews, vol. 6, Issue 2, Mar. 17, 2008; downloaded Nov. 4, 2014.
Sylvester Comprehensive Cancer Center, "Definition: Leukemia, Lymphoma and Myeloma," 2015. URL: <http://sylvester.org/cancer/leukemia-lymphoma-and-myeloma/education/definition>.
Treon et al., "A Prospective Multicenter Study of the Bruton's Tyrosine Kinase Inhibitor Ibrutinib in Patients with Relapsed or Refractory Waldenstrom's Macroglobulinemia," ASH Annual Meeting, Oral Presentation 251, Dec. 9, 2013,.
Venable et al., "Phosphoinositide 3-kinase gamma (PI3Kgamma) inhibitors for the treatment of inflammation and autoimmune disease", Recent Pat Inflamm Allergy Drug Discov (2010) 4: 1-15.
Viardot et al., "Clinicopathologic Correlations of Genomic Gains and Losses in Follicular Lymphoma", Journal of Clinical Oncology, vol. 20, No. 23 (Dec. 1), 2002: pp. 4523-4530.

(56) References Cited

OTHER PUBLICATIONS

Vora et al., "CDK 4/6 Inhibitors Sensitize PIK3CA Mutant Breast Cancer to PI3K Inhibitors", Cancer Cell (Jul. 2014), vol. 26, pp. 136-149.
WebMD, "Chronic Myeloproliferative Disorders Treatment (PDQ®): Treatment-Patient Information [NCI]—General Information About Chronic Myeloproliferative Disorders," 2014. <http://webmd.com/cancer/tc/chronic-myeloproliferative-disorders-treatment-patient-information-nci-pdq-general-information>.
WebMD, "HIV & AIDS Heath Center HTLV Type I and Type II," 2014. <http://www.webmd.com/hiv-aids/htlv-type-i-and-type-ii>.
WebMD, Leukemia-Prevention. Cancer Health Center. 2012. <http://www.webmd.com/cancer/tc/leukemia-prevention>.
WebMD, Lung Disease Overview. (2014). <http://www.webmd.com/lung/lung-diseases-overview>.
Wei et al., "A phosphoinositide 3-kinase-γ inhibitor, AS605240 prevents bleomycin-induced pulmonaiy fibrosis in rats," Biochem. Biophy. Res. Comm. 397:311-317 (2010).
Wen et al., "Current clinical development of PI3K pathway inhibitors in glioblastoma", Neuro-Oncology (2012) vol. 14, pp. 819-829.
Winkler et al., "PI3K-d and PI3K-g Inhibition by IPI-145 Abrogates Immune Responses and Suppresses Activity in Autoimmune and Inflammatory Disease Models," Chemistry & Biology (2013),://dx.doi.org/10.1016/j.chembiol.2013.09.017.
Wong et al., "Targeting the PI3K signaling pathway in Cancer," Current Opinion in Genetics & Development, vol. 20, (2010), pp. 87-90.
Woyach et al., "Resistance Mechanisms for the Bruton's Tyrosine Kinase Inhibitor Ibrutinib," N Engl J Med 2014; 370; p. 2286-2294.
Wymann et al., "Phosphoinositide 3-kinase γ: a key modulator in inflammation and allergy," *Biochem Soc. Transactions*, 31(part 1):275-280 (2003).
Zhao et al., "TNF-α promotes $LPA_1$- and $LPA_3$-mediated recruitment of leukocytes in vivo through CXCR2 ligand chemokines," *J. Lipid Res.*, 52(7):1307-1318 (2011).
Ashizawa, Kazuhide, Science of polymorphism and crystallization in pharmaceutical products:, Maruzen Planet Co., Sep. 20, 2002, pp. 3-16.
Buet et al., "Cotargeting signaling pathways driving survival and cell cycle circumvents resistance to Kit inhibitors in leukemia", Blood, 119(18):4228-4241 (2012).
Campbell, et al., "The Potent PI3K-δ,γ Inhibitor, IPI-145, Exhibits Differential Activity in Diffuse Large B-cell Lymphoma (DLBCL) Cell Lines", Dec. 7, 2013, 55th ASH Annual Meeting and Exposition, New Orleans, LA, Poster 1832.
Cao et al., "The BCL2 antagonist ABT-199 triggers apoptosis, and augments ibrutinib and idelalisib mediated cytotoxicity in CXCR4Wildtype and CXCR4WHIM mutated Watdenstram macroglabulinaemia cells", British Journal of Haematology, 170(12): 134-138 (2015).
Chang et al., "PI3-Kinase Inhibitors in Chronic Lymphocytic Leukemia", Current Hematologic Malignancy Reports, 9(1):33-43 (2014).
Chang et al., "Novel Synthesis and Reactions of 5, 7-Dialkyl-4,6-dioxo-4,5,6,7-tetrahydro-isothiazolo[3,4,-d]pyrimidine-3-carbonitrilesand6-Methyl-4-oxo-4H-1-aza-5-oxa-2-thiaindene-3-carbonitrile", Org. Lett. 5(4):507-510 (2003).
Chiron et al., "791 Induction of Early G1-Arrest by CDK4/CDK6 Inhibition Sensitizes Mantle Cell Lymphoma Cells to Selective PI3Kδ Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper52021.html.
Choudhary et al., "MCL-1 and BCL-xL-dependent resistance to the BGL-2 inhibitor ABT-199 can be overcome by preventing PI3KJ AKT/mT4R activation in lymphoid malignancies", Cell Death & Disease 2015, 6: e1593 (2015).
Equivalent Surface Area Dosage Conversion Factors (https://ncifrederick.cancer.gov/lasp/acuc/frederick/Media/Documents/ACUC42.pdf, Aug. 2007).

Flinn et al., "A Phase 1 Evaluation of Duvelisib (IPI-145), a PI3K-delta,gamma Inhibitor, in Patients with Relapsed/Refractory iNHL", American Society of Hematology Meeting, Dec. 6, 2014.
Flinn et al., "Preliminary Safety and Efficacy of IPI-145, a Potent Inhibitor of Phosphoinositide-3-Kinase-δ,γ, In Patients With Chronic Lymphocytic Leukemia", Blood, 122(21):677 (2013).
Goodman, A., "Encouraging Early Results With Novel Agents in CLL", The ASCO Post, Mar. 1, 2014, Reterieved from the internet: URL: http://www.ascopost.com/issues/march-1,-2014/encouraging-early-results-with-novel-agents-in-cll.aspx.
Harb et al., "Combined Pharmacologic Inhibition of Bcl-Xl/Bcl-2 and mTORC1/2 Survival Signals Trigger Apoptosis in BCR-ABL1+ in Vitro Models of Blast Crisis Chronic Myelogenous Leukemia (CML-BC), and Primary CD34+/CD38- Stem and CD34+ progenitor Cells From CML-BC Patients", Blood, 53rd Ash Annual Meeting and Exposition, San Diego, CA, Dec. 10-13, 2011, Retrieved from: https://ash.confex.com/ash/2011Jwebprogram/Paper44381.html.
Horwitz et al., "Duvelisib (IPI-145), a Phosphoinositide-3-Kinase-Delta,Gamma Inhibitor, Shows Activity in Patients with Relapsed/Refractory T-Cell Lymphoma", American Society of Hematology Meeting, Dec. 6, 2014.
Infinity Pharmaceuticals, Inc., "Infinity Reports Preclinical Data at ASH Annual Meeting in Diffuse Large B-Cell Lymphoma and T-Cell Acute Lymphoblastic Leukemia Suggesting Broad Potential of IPI-145 in Blood Cancers", http://businesswire.com, Dec. 7, 2013, Downloaded from: http://www.businesswire.com/news/home/20131207005015/en/Infinity-Reports-Preclinical-Data-ASH-Annual-Meeting.
Letai et al., "Antiapoptotic BCL-2 is required for maintenance of a model leukemia", Cancer Cell, 6(3):241-249 (2004).
Linhua et al., "Efficacy and Mechanisms of Apoptosis Induction by Simultaneous Inhibition of PI3K with GDC-0941 and Blockade of Bcl-2 (ABT-737) or FLT3 (Sorafenib) In AML Cells In the Hypoxic Bone Marrow Microenvironment", Blood, 116:777 (2010).
Liu et al., "Improved synthesis of α-BOC-aminoketones from α-BOC-amino-Weinreb amides using a pre-deprotonation protocol", Tetrahedron Letters, 43(46):8223-8226 (2002).
Martin-Sanchez et al., "Simultaneous inhibition of pan-phosphatidylinositol-3-kinases and MEK as a potential therapeutic strategy in peripheral T-cell lymphomas", Haematologica, 98(1):57-64 (2013).
Milella et al., 566 POSTER Anti-leukemic activity of the novel MEK inhibitor PD0325901, European Journal of Cancer Supplement, 4(12):172 (2006).
Morrison, C., "First P13k inhibitor launches info crowded hematology markets", Nature Biotechnology, 32(10):963-964 (2014).
Muranen et al., "Inhibition of P13K/mTOR Leads to Adaptive Resistance in Matrix-Attached Cancer Cells", Cancer Cell, 21(2):227-239 (2011).
Muranen et al., "Promising Rationally Derived Combination Therapy with PI3K and CDK4/6 Inhibitors", Cancer Cell, 26(1):7-9 (2014).
Nakai, Yoshinobu, et al., ed., New galenical pharmacy, Nanzando Co., Ltd., Apr. 25, 1984, pp. 102-103, 232-233.
Nishigaki, Sadao, Dispensing pharmacy (Principle and application), Nanzando Co., Ltd, Sep. 20, 1977, pp. 142-145.
Okano, Teisuke, New general remarks of practical pharmacy, 3rd ed., Nankodo Co., Ltd, Apr. 10, 1987, p. 111.
Okkenhaug, K., "Two Birds with One Stone: Dual p110δ and p110γ Inhibition", Chemistry and Biology, 20(11):1309-1310 (2013).
Patel et al., "Early Clinical Activity and Pharmacodynamic Effects of Duvelisib, a PI3K-delta,gamma Inhibitor, in Patients with Treatment-Naïve CLL", ASCO Annua Meeting May 29-Jun 2, 2015, Chicago, IL (poster).
Qian et al., "Synergy between phosphatidylinositol 3-kinase/Akt pathway and Bcl-xL in the control of apoptosis in adenocarcinoma cells of the lung", Molecular Cancer Therapeutics, 8(1):101-109 (2009).
Rahmani et al., "Dual Inhibition of Bcl-2 and Bcl-xL Strikingly Enhances PI3K Inhibition-Induced Apoptosis in Human Myeloid Leukemia Cells through a GSK3- and Bim-Dependent Mechanism", Cancer Research, 73(4):1340-1351 (2013).

(56) References Cited

OTHER PUBLICATIONS

Roberts et al., "Substantial Susceptibility of Chronic Lymphocytic Leukemia to BCL2 Inhibition: Results of a Phase I Study of Navitoclax in Patients With Relapsed or Refractory Disease", Journal of Clinical Oncology, 30(5):488-496 (2012).

Schwamb et al., "B-cell receptor triggers drug sensitivity of primary CLL cells by controlling glucosylation of ceramides", Blood, 120(19):3978-3985 (2012).

Seymour et al., "Bcl-2 Inhibitor ABT-199 (GDC-0199) Monotherapy Shows Anti-Tumor Activity Including Complete Remissions In High-Risk Relapsed/Refractory (R/R) Chronic Lymphocytic Leukemia (CLL) and Small Lymphocytic Lymphoma (SLL)", Blood, 122(21):872 (2013).

Simioni et al., "Cytotoxic activity of the novel Akt inhibitor, MK-2206, in T-cell acute lymphoblastic leukemia", Leukemia, 26(11):2336-2342 (2012).

The Chemical Society of Japan ed., Jikken kagaku kouza (zoku), 2. Bunri to seisei (Experimental chemical lecture, second series, 2. Separation and purification), Maruzen Co., Ltd., Jan. 25, 1967, pp. 159-178, 186-187.

Tong et al., "Perifosine induces protective autophagy and upregulation of ATG5 in human chronic myelogenous leukemia cells in vitro", Acta Pharmacologica Sinica, 33(4):542-550 (2012).

Vachhani et al., "Ratianal combination of dual PI3K/mTOR blockade and Bcl-2/-xl inhibition in AML", Physiological Genomics, 46(13):448-456 (2014).

Veliz et al., "Treatment of relapsed or refractory chronic lymphocytic leukemia", Cancer Control, 19:37-53 (2012).

Wullschleger et al., "Quantitative MRI Establishes the Efficacy of PI3K Inhibitor (GDC-0941) Multi-Treatments in PTEN-deficient Mice Lymphoma", Anticancer Research, 32(2):415-420 (2012).

Yu et al., "Development of a Practical Synthesis of DPP IV Inhibitor LY2497282", Organic Process Research & Development, 12(2):218-225 (2008).

Zhu et al., "PI3K inhibition potentiates Bcl-2-dependent apoptosis in renal carcinoma cells", Journal of Cellular and Molecular Medicine, 17(3):377-385 (2013).

CAL-101, PubChem CID 11625818, created date Oct. 26, 2006.

Mashkovskiy, Lekarstvennye sredstva, vol. 1, 2001, p. 11.

Akinleye et al., "Phosphatidylinositol 3-kinase (PI3K) inhibitors as cancer therapeutics", Journal of Hematology & Oncology, Nov. 2013, vol. 6:88, pp. 1-18,.

Brittain, H.G., et al. "Polymorphism in pharmaceutical solids" edited by H. G. Brittain, Marcel Dekker, D.J.W., Grant (chapter 1), p. 1-10 and J. K. Guillory (chapter 5); p. 183-226 (1999).

Byrn, S. et al. "Pharmaceutical Solids: A Strategic Approach to Regulatory Considerations"; S. Byrn et al.; Pharmaceutical research, vol. 12, No. 7, p. 945-954 (1995).

Chabner et al., "Chemotherapy and the war on cancer", Nature Reviews Cancer, 2005, Nature Publishing Group, vol. 5, pp. 65-72.

D'Cruz et al., "Protein kinase inhibitors against malignant lymphoma", Expert Opinion on Pharmacotherapy, Mar. 2013, Taylor and Francis Group, vol. 14(6), pp. 707-721.

Kakkola et al., "Anticancer compound ABT-263 accelerates apoptosis in virus-infected cells and imbalances cytokine production and lowers survival rates of infected mice", Cell Death & Disease (2013) 4, e742.

Leaf, "Why We're Losing the War on Cancer - and How to Win it", Fortune, Mar. 9, 2004, Time Inc., pp. 1-28.

Vaillant et al., "Targeting BCL-2 with the BH3 Mimetic ABT-199 in Estrogen Receptor-Positive Breast Cancer", Cancer Cell 24, pp. 120-129, Jul. 8, 2013.

Vanhaesebroek et al., "Molecules in medicine mini-review: isoforms of PI3K in biology and disease," J. Mol. Med., 94(1):5-11 (2016), e-published Dec. 10, 2015.

Stedman's Medical Dictionary Stedman's online. Autoimmune disease; <http://stedmansonline.com/content.aspx?id=mlrA2100002481&termtype=> (accessed Mar. 11, 2017).

Hirayama, Noriaki, Yuki Kagoubutsu Kessyo Sakusei Handbook—Genri to Nouhau (Handbook of organic compound crystal production—principle and know-how-), Maruzen Co., Ltd., Jul. 25, 2008, pp. 57-74.

Akira Ogata, Chemical experiment manual, Nankodo Co.,Ltd., Jun. 20, 1977, 36th edit., pp. 515-535.

Shadan-hojin Japan Chemistry Association, Kagaku Biman Ouyou Kagaku hen, 6th edit., Maruzen Co., Ltd., Jan. 30, 2003, pp. 178.

White et al., "Abstract 376: Combination of duvelisib with either ibrutinib or dexamethasone prevents mTOR-dependent feedback in aggressive B-cell lymphoma cell lines", Cancer Research, vol. 76, No. Suppl. 14, Apr. 2016, Proceedings of the 107th Annual Meeting of the American Association for Cancer Research; Apr. 16-20, 2016; New Orleans, LA, Retrieved from the Internet: URL:http://cancerres.aacrjournals.org/content/76/14_SupplemenI/376 [retrieved on Sep. 13, 2017].

Bedognetti et al., "Checkpoint Inhibitors and Their Application in Breast Cancer (supplementary information)", Breast Care, vol. 11, No. 2, Apr. 26, 2016, pp. 108-115.

De Henau et al., "Abstract 554: Checkpoint blockade therapy is improved by altering the immune suppressive microenvironment with IPI-549, a potent and selective inhibitor of PI3K-gamma, in preclinical models", Cancer Research, Apr. 2016, 107th Annual Meeting of the American Association for Cancer Research; Apr. 16-20, 2016; New Orleans, LA, Retrieved from the Internet: URL:http://cancerres.aacrjournals.org/content/76/14_Supplement/554 [retrieved on Sep. 13, 2017].

Mittendorf et al., "PD-L1 expression in triple-negative breast cancer", Cancer Immunol. Res. 2014, 2:361-370.

U.S. Appl. No. 13/552,460, filed Jul. 18, 2012, U.S. Pat. No. 8,969,363, Heterocyclic Compounds and Uses Thereof, Patented.

U.S. Appl. No. 13/552,473, filed Jul. 18, 2012, U.S. Pat. No. 9,056,877, Heterocyclic Compounds and Uses Thereof, Patented.

U.S. Appl. No. 13/552,516, filed Jul. 18, 2012, U.S. Pat. No. 8,785,470, Heterocyclic Compounds and Uses Thereof, Patented.

U.S. Appl. No. 13/841,265, filed Mar. 15, 2013, U.S. Pat. No. 8,940,742, Heterocyclic Compounds and Uses Thereof, Patented.

U.S. Appl. No. 13/839,912, filed Mar. 15, 2013, 2014-0120060, Treatment of Rheumatoid Arthritis and Asthma Using PI3 Kinase Inhibitors, Abandoned.

U.S. Appl. No. 14/209,842, filed Mar. 13, 2014, U.S. Pat. No. 9,481,667, Salts and Solid Forms of Isoquinolinones and Composition Comprising and Methods of Using the Same, Patented.

U.S. Appl. No. 13/840,822, filed Mar. 15, 2013, 2014-0120083, Treatment of Cancers Using PI3 Kinase Isoform Modulators, Published.

U.S. Appl. No. 12/811,695, filed Nov. 11, 2010, U.S. Pat. No. 8,703,777, Substituted Bicyclic Compounds and Methods of Use Thereof, Patented.

U.S. Appl. No. 12/503,776, filed Jul. 15, 2009, U.S. Pat. No. 8,193,182, Substituted Isoquinolin-1(2H)-Ones, and Methods of Use Thereof, Patented.

U.S. Appl. No. 13/403,394, filed Feb. 23, 2012, U.S. Pat. No. 8,785,456, Certain Chemical Entities, Compositions and Methods, Patented.

U.S. Appl. No. 13/350,444, filed Jan. 13, 2012, U.S. Pat. No. 8,569,323, Substituted Isoquinolin-1(2H)-One Compounds, Compositions, and Methods Thereof, Patented.

U.S. Appl. No. 13/121,157, filed Aug. 2, 2011, U.S. Pat. No. 8,703,778, Heterocyclic Kinase Inhibitors, Patented.

U.S. Appl. No. 13/289,540, filed Nov. 4, 2011, U.S. Pat. No. 8,785,454, Heterocyclic Compounds and Uses Thereof, Patented.

U.S. Appl. No. 13/293,828, filed Nov. 10, 2011, U.S. Pat. No. 8,901,133, Heterocyclic Compounds and Uses Thereof, Patented.

U.S. Appl. No. 13/112,611, filed May 20, 2011, U.S. Pat. No. 8,604,032, Chemical Compounds, Compositions and Methods for Kinase Modulation, Patented.

U.S. Appl. No. 13/347,423, filed Jan. 10, 2012, U.S. Pat. No. 8,809,349, Processes for Preparing Isoquinolinones and Solid Forms of Isoquinolinones, Patented.

(56) References Cited

OTHER PUBLICATIONS

U.S. Appl. No. 13/837,195, filed Mar. 15, 2013, U.S. Pat. No. 8,828,998, Treatment of Lupus, Fibrotic Conditions, and Inflammatory Myopathies and Other Disorders Using PI3 Kinase Inhibitors, Patented.
U.S. Appl. No. 14/222,488, filed Mar. 21, 2014, 2014-0206684, Certain Chemical Entities, Compositions and Methods, Abandoned.
U.S. Appl. No. 14/085,660, filed Nov. 20, 2013, U.S. Pat. No. 9,181,221, Chemical Compounds, Compositions and Methods for Kinase Modulation, Patented.
U.S. Appl. No. 14/099,821, filed Dec. 6, 2013, U.S. Pat. No. 9,115,141, Heterocyclic Compounds and Uses Thereof, Patented.
U.S. Appl. No. 14/776,604, filed Sep. 14, 2015, 2016-0024051, Salts and Solid Forms of Isoquinolinones and Composition Comprising and Methods of Using the Same, Abandoned.
U.S. Appl. No. 13/971,793, filed Aug. 20, 2013, U.S. Pat. No. 9,206,182, Certain Chemical Entities, Compositions and Methods, Patented.
U.S. Appl. No. 15/026,947, filed Apr. 1, 2016, U.S. Pat. No. 9,751,888, Heterocyclic Compounds and Uses Thereof, Patented.
U.S. Appl. No. 14/506,438, filed Oct. 3, 2014, U.S. Pat. No. 9,359,365, Heterocyclic Compounds and Uses Thereof, Patented.
U.S. Appl. No. 14/222,500, filed Mar. 21, 2014, U.S. Pat. No. 9,296,742, Heterocyclic Kinase Inhibitors, Patented.
U.S. Appl. No. 14/292,475, filed May 30, 2014, 2014-0377258, Treatment of Cancers Using PI3 Kinase Isoform Modulators, Published.
U.S. Appl. No. 15/030,701, filed Apr. 20, 2016, 2016-0244452, Unassigned, Heterocyclic Compounds and Uses Thereof, Abandoned.
U.S. Appl. No. 14/297,526, filed Jun. 5, 2014, U.S. Pat. No. 9,546,180, Heterocyclic Compounds and Uses Thereof, Patented.
U.S. Appl. No. 14/296,953, filed Jun. 5, 2014, U.S. Pat. No. 9,216,982, Certain Chemical Patented Entities, Compositions and Methods, Patented.
U.S. Appl. No. 14/302,340, filed Jun. 11, 2014, U.S. Pat. No. 9,315,505, Heterocyclic Compounds and Uses Thereof, Patented.
U.S. Appl. No. 14/327,499, filed Jul. 9, 2014, U.S. Pat. No. 9,290,497, Processes for Preparing Isoquinolinones and Solid Forms of Isoquinolinones, Patented.
U.S. Appl. No. 14/439,965, filed Apr. 30, 2015, 2015-0283142, Treatment of Cancers Using PI3 Kinase Isoform Modulators, Published.
U.S. Appl. No. 14/448,998, filed Jul. 31, 2014, 9,527,847, Treatment of Lupus, Fibrotic Conditions, and Inflammatory Myopathies and Other Disorders Using PI3 Kinase Inhibitors, Patented.
U.S. Appl. No. 14/512,262, filed Oct. 10, 2014, U.S. Pat. No. 9,388,183, Heterocyclic Compounds and Uses Thereof, Patented.
U.S. Appl. No. 14/573,961, filed Dec. 17, 2014, U.S. Pat. No. 9,255,108, Heterocyclic Compounds and Uses Thereof, Patented.
U.S. Appl. No. 15/059,962, filed Mar. 3, 2016, U.S. Pat. No. 9,822,131, Certain Chemical Entities, Compositions and Methods, Patented.
U.S. Appl. No. 14/661,656, filed Mar. 18, 2015, U.S. Pat. No. 9,775,844, Heterocyclic Compounds and Uses Thereof, Patented.
U.S. Appl. No. 14/592,628, filed Jan. 8, 2015, U.S. Pat. No. 9,718,815, Heterocyclic Compounds and Uses Thereof, Patented.
U.S. Appl. No. 14/687,714, filed Apr. 15, 2015, 2015-0320754, Combination Therapies, Published.
U.S. Appl. No. 14/687,768, filed Apr. 15, 2015, 2015-0320755, Combination Therapies, Published.
U.S. Appl. No. 14/695,699, filed Apr. 24, 2015, U.S. Pat. No. 9,828,377, Heterocyclic Compounds and Uses Thereof, Patented.
U.S. Appl. No. 14/710,336, filed May 12, 2015, U.S. Pat. No. 9,605,003, Heterocyclic Compounds and Uses Thereof, Patented.
U.S. Appl. No. 15/051,529, filed Feb. 23, 2016, RE46,621, Processes for Preparing Isoquinolinones and Solid Forms of Isoquinolinones, Patented.
U.S. Appl. No. 14/874,328, filed Oct. 2, 2015, U.S. Pat. No. 9,708,348, Heterocyclic Compounds and Uses Thereof, Patented.
U.S. Appl. No. 15/264,417, filed Sep. 13, 2016, U.S. Pat. No. 10,160,761, Solid Forms of Isoquinolinones, and Process of Making, Composition Comprising, and Methods of Using the Same, Patented.
U.S. Appl. No. 14/869,637, filed Sep. 29, 2015, U.S. Pat. No. 9,738,644, Chemical Compounds, Compositions and Methods for Kinase Modulation, Patented.
U.S. Appl. No. 14/876,589, filed Oct. 6, 2015, 2016-0022692, Treatment of Rheumatoid Arthritis and Asthma Using PI3 Kinase Inhibitors, Abandoned.
U.S. Appl. No. 14/884,612, filed Oct. 15, 2015, U.S. Pat. No. 9,522,146, Certain Chemical Entities, Compositions and Methods, Patented.
U.S. Appl. No. 14/894,854, filed Nov. 30, 2015, 2016-0113932, Unassigned Treatment of Cancers Using PI3 Kinase Isoform Modulators, Abandoned.
U.S. Appl. No. 14/938,647, filed Nov. 11, 2015, U.S. Pat. No. 9,655,892, Certain Chemical Entities, Compositions and Methods, Patented.
U.S. Appl. No. 14/971,954, filed Dec. 16, 2015, 2016-0207940, Heterocyclic Compounds and Uses Thereof, Abandoned.
U.S. Appl. No. 15/016,117, filed Feb. 4, 2016, U.S. Pat. No. 9,840,505, Processes for Preparing Isoquinolinones and Solid Forms of Isoquinolinones, Patented.
U.S. Appl. No. 16/085,536, filed Sep. 14, 2018, 2019-0202835, Isotopologues of Isoquinolinone and Quinazolinone Compounds and Uses Thereof as PI3K Kinase Inhibitors, Allowed.
U.S. Appl. No. 15/050,029, filed Feb. 22, 2016, U.S. Pat. No. 9,790,228, Heterocyclic Kinase Inhibitors, Patented.
U.S. Appl. No. 16/312,896, filed Dec. 21, 2018, 2019-0216816, Unassigned, Combination Therapies, Published.
U.S. Appl. No. 16/308,377, filed Dec. 7, 2018, 2019-0135833, Heterocyclic Compounds and Uses Thereof, Published.
U.S. Appl. No. 15/179,570, filed Jun. 10, 2016, Unpublished, Unassigned Heterocyclic Compounds and Uses Thereof, Abandoned.
U.S. Appl. No. 15/333,803, filed Oct. 25, 2016, 2017-0137407, Heterocyclic Compounds and Uses Thereof, Abandoned.
U.S. Appl. No. 15/347,489, filed Nov. 9, 2016, 2017-0281614, Certain Chemical Entities, Compositions and Methods, Abandoned.
U.S. Appl. No. 15/599,378, filed May 18, 2017, 2018-0098983, Certain Chemical Entities, Compositions and Methods, Abandoned.
U.S. Appl. No. 15/621,815, filed Jun. 13, 2017, U.S. Pat. No. 10,253,047, Heterocyclic Compounds and Uses Thereof, Patented.
U.S. Appl. No. 15/621,764, filed Jun. 13, 2017, Unpublished, Unassigned Chemical Compounds, Compositions and Methods for Kinase Modulation, Abandoned.
U.S. Appl. No. 15/672,964, filed Aug. 9, 2017, 2018-0055852, Heterocyclic Compounds and Uses Thereof, Allowed.
U.S. Appl. No. 15/675,185, filed Aug. 11, 2017, Unpublished, Unassigned Heterocyclic Compounds and Uses Thereof, Abandoned.
U.S. Appl. No. 15/794,816, filed Oct. 26, 2017, U.S. Pat. No. 10,329,299, Heterocyclic Compounds and Uses Thereof, Patented.
U.S. Appl. No. 15/799,612, filed Oct. 31, 2017, U.S. Pat. No. 10,550,122, Processes for Preparing Isoquinolinones and Solid Forms of Isoquinolinones, Patented.
U.S. Appl. No. 15/789,868, filed Oct. 20, 2017, 2018-0258103, Certain Chemical Entities, Compositions and Methods, Published.
U.S. Appl. No. 16/172,539, filed Oct. 26, 2018, 2019-0290636, Certain Chemical Entities, Compositions and Methods, Published.
U.S. Appl. No. 16/197,195, filed Nov. 20, 2018, 2019-0185477, Solid Forms of Isoquinolinones, and Process of Making, Composition Comprising, and Methods of Using the Same, Published.
U.S. Appl. No. 16/290,545, filed Mar. 1, 2019, 2019-0330240, Heterocyclic Compounds and Uses Therof, Published.
U.S. Appl. No. 16/417,420, filed May 20, 2019, 2019-0367521, Heterocyclic Compounds and Uses Thereof, Published.
U.S. Appl. No. 16/734,135, filed Jan. 3, 2020, Unpublished, Unassigned, Processes for Preparing Isoquinolinones and Solid Forms of Isoquinolinones, Pending.
U.S. Appl. No. 16/816,132, filed Mar. 11, 2020, Unpublished, Unassigned, Heterocyclic Compounds and Uses Thereof, Pending.

(56) References Cited

OTHER PUBLICATIONS

Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7):1953-1957 (1982).
Al-Alwan et al., "Requirement for Phosphoinositide 3-Kinase pl 108 Signaling in B Cell Antigen Receptor-Mediated Antigen Presentation," J. Immunol. 178:2328-35 (2007).
Ali et al., "Essential role for the pl 108 phosphoinositide 3-kinase in the allergic response," Nature 431:1007-11 (2004).
Ali et al., "Isoform-Specific Functions of Phosphoinositide 3-Kinases: p110δ but Not p110γ Promotes Optimal Allergic Responses In Vivo," J. Immunol. 180:2538-44 (2008).
American Cancer Society. Non-Hodgkin's Lymphoma. Last Revised Mar. 11, 2015, Retrieved online: <http://www.cancer.org/cancer/nonhodgkinlymphoma/detailedguide/non-hodgkin-lymphoma-types-of-non-hodgkin-lymphoma>, 79 pages.
Asbahr et al., "Obsessive-Compulsive and Related Symptoms in Children and Adolescents With Rheumatic Fever With and Without Chorea: A Prospective 6-Month Study," Am. J. Psychiatry 155:1122-1124 (1998).
Barber et al., "Class IB-Phosphatidylinositol 3-Kinase (PI3K) Deficiency Ameliorates IA-PI3K-Induced Systemic Lupus but Not T Cell Invasion," J. Immunol. 176(1):589-93 (2006).
Bartok et al., "Phosphoinositide 3-Kinase Delta (PI3K) Regulation and Function in RA," Arthritis Rheum. 62(Suppl 10):362 (2010).
Berge et al., "Pharmaceutical Salts," J. Phann. Sci. 66(1):1-19 (1977).
Bilancio et al., "Key role of the pll08 isoform of PI3K in B-cell antigen and IL-4 receptor signaling: comparative analysis of genetic and pharmacologic interference with pl 108 function in B cells," Blood 107(2):642-50 (2006).
Bojarczuk et al., "B-cell receptor pathway inhibitors affect CD20 levels and impair antitumor activity of anti-CD20 monoclonal antibodies," Leukemia (2014), 1-5.
Bolland et al., "Spontaneous Autoimmune Disease in FcyRIIB-Deficient Mice Results from Strain-Specific Epistasis," Immunily: 13:277-285 (2000).
Bone et al., "Phosphoinositide 3-kinase signalling regulates early development and developmental haemopoiesis," J. Cell. Sci. 120(Pt 10): 1752-1762 (2007).
Bouska et al., "Genome-wide copy-number analyses reveal genomic abnormalities involved in transformation of follicular lymphoma", Blood, Mar. 13, 2014, vol. 123, N. 11, DD. 1681-1690.
Buchwald et al., "Long-term, continuous intravenous heparin administration by an implantable infusion pump in ambulatory patients with recurrent venous thrombosis," Surgery 88(4):507-516 (1980).
Bundgaard, "Design of Prodrugs: Bioreversible derivatives for various functional groups and chemical entities," Design of Prodrugs, pp. 1-92 (Elsevier, Amsterdam, 1985).
Chiron et al., "791 Induction of Early GI-Arrest by CDK4/CDK6 Inhibition Sensitizes Mantle Cell Lymphoma Cells to Selective PI3Kδ Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper5202 I .html.
Condliffe et al., "Sequential activation of class 1B and class IA PI3K is important for the primed respiratory burst of human but not murine neutrophils," Blood 106(4):1432-1440 (2005).
Davis et al., "Chronic active B-cell-receptor signaling in diffuse large B-cell lymphoma," Nature 463:88-92 (2010).
Dil et al., "Role of phosphoinositide 3-kinase pl 108 in TLR4- and TLR9-mediated B cell cytokine production and differentiation," Mol. Immunol. 46(10):1970-1978 (2009).
Donahue et al., "Measuring Phosphorylated Akt and Other Phosphoinositide 3-kinase—Regulated Phosphoproteins in Primary Lymphocytes," Methods Enzymol. 434:131-54 (2007).
Doukas et al., "Aerosolized Phosphoinositide 3-Kinase y/8 Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," J. Pharmacol. Exp. Ther. 328(3):758-65 (2009).
Durand et al., "Phosphoinositide 3-Kinase pl 108 Regulates Natural Antibody Production, Marginal Zone and B-1 B Cell Function, and Autoantibody Responses," J. Immunol. 183:5673-84 (2009).
Extended European Search Report from European Application No. 18193879, dated Nov. 22, 2018, 6 pages.
Furman et al., "Interim results from a phase I study of CAL-101, a selective oral inhibitor of phosphatidylinositol 3-kinase pl 10d isoform, in patients with relapsed or refractory hematologic malignancies," J. Clin. Oncol. 28(15 suppl):3032 (ASH Annual Meeting 2010).
Gaestel et al., "Protein kinases as small molecule inhibitor targets in inflammation," Curr. Med. Chem. 14(21):2214-2234 (2007).
Garcon et al., "CD28 provides T-cell costimulation and enhances PI3K activity at the immune synapse independently of its capacity to interact with the p85/pl 10 heterodimer," Blood 111(3):1464-71 (2008).
Garvey et al., "PANDAS: The Search for Environmental Triggers of Pediatric Neuropsychiatric Disorders. Lessons from Rheumatic Fever," J Child Neurol. 13:413-423 (1998).
Garvey et al., "Treatment of Sydenham's Chorea With Intravenous Immunoglobulin, Plasma Exchange, or Prednisone," J. Child Neurol. 20:424-429 (2005).
Geng et al., "A Specific Antagonist of the pl 108 Catalytic Component of Phosphatidylinositol 3'-Kinase, IC486068, Enhances Radiation-Induced Tumor Vascular Destruction," Cancer Res. 64(14):4893-4899 (2004).
Goodson, "Dental Applications," Medical Applications of Controlled Release 2:115-138 (1984).
Guo et al., "The pl 108 of PI3K plays a critical role in NK cell terminal maturation and cytokine/chemokine generation," J. Exp. Med. 205(10):2419-2435 (2008).
Hirschtritt et al., "Executive and Attention Functioning Among Children in the PANDAS Subgroup," Child Neuropsychol. 15:179-194 (2009).
Hoellenriegel et al., "Spleen Tyrosine Kinase (Syk) Inhibitors Block B Cell Receptor Signaling and Survival in Chronic Lymphocytic Leukemia," Blood 116:3604 (ASH Annual Meeting Abstracts 2010).
Hoffman et al., "A Murine Model for Neuropsychiatric Disorders Associated with Group A—Hemolytic Streptococcal Infection," J. Neurosci. 24(7):1780-1791 (2004).
Hollander et al., "B Lymphocyte Antigen 08/17 and Repetitive Behaviors in Autism," Am. J. Psychia!!_y 156:317-320 (1999).
International Search Report dated Aug. 22, 2011 for PCT Application No. PCT/US2011/37412, 2 pages.
Jarmin et al., "T cell receptor-induced phosphoinositide-3-kinase pl 108 activity is required for T cell localization to antigenic tissue in mice," J. Clin. Invest. 118(3):1154-1164 (2008).
Ji et al., "Inactivation of PI3Kγ and PI3Kδ distorts T-cell development and causes multiple organ inflammation," Blood 110:2940-2947 (2007).
Kahl et al., "Clinical Safety and Activity in a Phase 1 Study of CAL-101, An Isoform-Selective Inhibitor of Phosphatidylinositol 3-Kinase Pl 108, In Patients with Relapsed or Refractory Non-Hodgkin Lymphoma," Blood 116:1777 (ASH Annual Meeting Abstracts 2010).
Karpeiskii et al., "Pyridoxal-5'-Derivatives of Nucleobases," Bioorganicheskaya Khimiya 11(8): 1097-1104(1985).
Kashishian et al., "Anti-tumor activity of CAL-101, a potent selective inhibitor of the pll08 isoform of PI3K, in models of human glioblastoma," (AACR Annual Meeting Abstracts 2011), 2 pages.
Kim et al., "The multiple roles of phosphoinositide 3-kinase in mast cell biology," Trends Immunol. 29(10):493-501 (2008).
Kim et al., "The p110delta catalytic isoform of PI3K is a key player in NK-cell development and cytokine secretion," Blood 110:3202-3208 (2007).
Kirvan et al., "Antibody-mediated neuronal cell signaling in behavior and movement disorders," J. Neuroimmunol. 179:173-179 (2006).

(56) References Cited

OTHER PUBLICATIONS

Konrad et al., "Phosphoinositide 3-Kinases γ and δ, Linkers of Coordinate C5a Receptor-Fcy Receptor Activation and Immune Complex-induced Inflammation," J. Biol. Chem. 283(48):33296-33303 (2008).
Kurlan et al., "The Pediatric Autoimmune Neuropsychiatric Disorders Associated With Streptococcal Infection (PANDAS) Etiology for Tics and Obsessive-Compulsive Symptoms: Hypothesis or Entity? Practical Considerations for the Clinician," Pediatrics 113(4):883-886 (2004).
Langer, "New Methods of Drug Delivery," Science 249:1527-1533 (1990).
Lee et al. "Phosphoinositide 3-kinase-d inhibitor reduces vascular permeability in a murine model of asthma," J. Allergy Clin. Immunol. 118:403-409 (2006).
Lee et al., "Inhibition of phosphoinositide 3-kinase δ attenuates allergic airway inflammation and hyperresponsiveness in murine asthma model," FASEB J. 20:455-465 (2006).
Lee et al., "The CD28 signal transduction pathway in T cell activation", Advances in Cell Regulation of Cell Growth, vol. 2, pp. 141-160, New York: Raven Press, Ltd. (1991).
Leslie et al., "Neuropsychiatric Disorders Associated With Streptococcal Infection: A Case-Control Study Among Privately Insured Children," J. Am. Acad. Child Adolesc. Psychiatry 47(10):1166-1172 (2008).
Liu et al., "The P110δ Isoform of Phosphatidylinositol 3-Kinase Controls the Quality of Secondary Anti-Leishmania Immunity by Regulating Expansion and Effector Function of Memory T Cell Subsets," J. Immunol. 184:3098-3105 (2010).
Lucas et al., "Design of l-piperazinyl-4-arylphthalazines as potent Smoothened antagonists," Bioorg. Med. Chem. Lett. 20:3618-3622 (2010).
Margutti et al., "Autoantibodies Associated with Psychiatric Disorders," Curr. Neurovasc. Res. 3(2):149-157 (2006).
Marwick et al., "Inhibition of PI3Kδ Restores Glucocorticoid Function in Smoking-induced Airway Inflammation in Mice," Am. J. Respir. Crit. Care Med. 179:542-548 (2009).
Moon et al., "A novel microtubule destabilizing entity from orthogonal synthesis of triazine library and zebrafish embryo screening," J. Am. Chem. Soc. 124(39):11608-11609 (2002).
Mraz and Kipps, "MicroRNAs and B cell receptor signaling in chronic lymphocytic leukemia", Leukemia & Lymphoma, 54(8):1836-1839 (2013).
Mraz et al., "MicroRNAs in chronic lymphocytic leukemia pathogenesis and disease subtypes", Leukemia & Lymphoma, 50(3):506-509 (2009).
Mraz et al., "miR-150 influences B-cell receptor signaling in chronic lymphocytic leukemia by regulating expression of GAB1 and FOXP1", Blood 124(1):84-95 (2014).
Musilova and Mraz, "MicroRNAs in B-cell lymphomas: how a complex biology gets more complex", Leukemia 1-14(2015).
NCBI, The Nervous System, NCBI Bookshelf, 1998.
Office Action issued by the European Patent Office for Application No. 19175005.8, dated Dec. 22, 2020, 3 pages.
Okkenhaug et al., "Impaired Band T Cell Antigen Receptor Signaling in p110δ PI 3-Kinase Mutant Mice," Science 297:1031-1034 (2002).
Okkenhaug et al., "The p110δ Isoform of Phosphoinositide 3-Kinase Controls Clonal Expansion and Differentiation of Th Cells," J. Immunol. 177:5122-5128 (2006).
Oltersdorf et al., "An inhibitor of Bcl-2 family proteins induces regression of solid tumours", Nature, 435:677-681 (2005).
Orpegen Pharma "Instructions for Basotest® Reagent Kit", pp. 1-8, Version Aug. 2006.
Pan et al., "Discovery of NVP-LDE225, a Potent and Selective Smoothened Antagonist," ACS Med. Chem. Lett. 1:130-134 (2010).
Perez-Blas et al., "Impaired T cell signal transduction through CD28 in a patient with idiopathic thrombocytopenia," Clin. Exp. Immunol. 85(3):424-428 (1991).

Persson, "Glucocorticoids for asthma—early contributions," Pulm. Pharmacol. 2(3):163-166 (1989).
Peterson et al., "Preliminary Findings of Antistreptococcal Antibody Titers and Basal Ganglia Volumes in Tic, Obsessive-compulsive, and Attention-Deficit/Hyperactivity Disorders," Arch. Gen. Psychiatry 57:364-372 (2000).
Petrie et al., "Novel biotinylated adenylate analogue derived from pyrazolo[3,4-d]pyrimidine for labeling DNA probes," Bioconjug. Chem. 2(6):441-446 (1991).
Pighi et al., "Phospho-proteomic analysis of mantle cell lymphoma cells suggests a pro-survival role of B-cell receptor signaling," Cell Oncol. (Dordr) 34(2):141-153 (2011).
Pinho et al., "Tissue- and Stimulus-Dependent Role of Phosphatidylinositol 3-Kinase Isoforms for Neutrophil Recruitment Induced by Chemoattractants In Vivo," J. Immunol. 179:7891-7898 (2007).
Polak et al., "The PI3K/PKB signaling module as key regulator of hematopoiesis: implications for therapeutic strategies in leukemia," Blood 119(4):911-923 (2012).
Porta and Figlin, "Phosphatidy linositol-3-kinase/Akt signaling pathway and kidney cancer, and the therapeutic potential of phosphatidylinositol-3-kinase/Akt inhibitors," J. Urol. 182(6):2569-2577 (2009).
Prasad et al., "Phosphatidylinositol (PI) 3-kinase and PI 4-kinase binding to the CD4-p56lck complex: the p56lck SH3 domain binds to PI 3-kinase but not PI 4-kinase," Mol. Cell. Biol. 13(12): 7708-7717 (1993).
Prasad et al., "Src-homology 3 domain of protein kinase p59fyn mediates binding to phosphatidylinositol 3-kinase in T cells," Proc. Natl. Acad. Sci. U.S.A. 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," Proc. Natl. Acad. Sci. U. S. A. 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," J. Med. Chem. 33(7):1984-1992 (1990).
Puri and Gold, "Selective inhibitors of phosphoinositide 3-kinase delta: modulators of B-cell function with potential for treating autoimmune inflammatory disease and B-cell malignancies," Front. Immunol. 3:256 (2012).
Quiroga et al., "B-cell antigen receptor signaling enhances chronic lymphocytic leukemia cell migration and survival: specific targeting with a novel spleen tyrosine kinase inhibitor, R406," Blood 114(5):1029-1037 (2009).
Randis et al., "Role of PI3Kδ and PI3Kγ in inflammatory arthritis and tissue localization of neutrophils," Eur. J. Immunol. 38:1215-1224 (2008).
Reif et al., "Cutting Edge: Differential Roles for Phosphoinositide 3-Kinases, p110γ and p110δ, in Lymphocyte Chemotaxis and Homing," J. Immunol. 173:2236-2240 (2004).
Reif et al., "Divergent regulation of phosphatidylinositol 3-kinase P85α and P85 isoforms upon T cell activation," J. Biol. Chem. 268(15):10780-10788 (1993).
Report of the Expert Committee on the Diagnosis and Classification of Diabetes Mellitus, Diabetes Care 2( Suppl. I):S5-SI9 (1992).
Rizzatti et al., "Gene expression profiling of mantle cell lymphoma cells reveals aberrant expression of genes from the PI3K-AKT, WNT and TGF signaling pathways," Brit. J. Haematol. 130:516-526 (2005).
Robarge et al., "GDC-0449-A potent inhibitor of the hedgehog pathway," Bioorg. Med. Chem. Lett. 19:5576-5581 (2009).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," J. Immunol. 189:4612-4620 (2012).
Romero et al., "Cloning and expression of the bovine 11β-hydroxysteroid dehydrogenase type-2," J. Steroid Biochem. Mol. Biol. 72(5):231-237 (2000).

(56) References Cited

OTHER PUBLICATIONS

Rominger et al., "Evidence for Allosteric Interactions of Antagonist Binding to the Smoothened Receptor," J. Pharmacol. Exp Ther. 329(3):995-1005 (2009).
Rommel et al., "PI3Kδ and PI3Kγ : partners in crime in inflammation in rheumatoid arthritis and beyond?" Nat. Rev. Immunol. 7:191-201 (2007).
Rott et al., "Recent developments in the use of biologies in psoriasis and autoimmune disorders. The role of autoantibodies," BMJ 330(7493):716-720 (2005).
Rudelius et al., "Constitutive activation of Akt contributes to the pathogenesis and survival of mantle cell lymphoma," Blood 108(5):1668-1676 (2006).
Rudin et al., "Treatment of Medulloblastoma with Hedgehog Pathway Inhibitor GDC-0449," N. Engl. J. Med. 361(12):1173-1178 (2009).
Rudolph et al., "Cytogenetic characterization of a BCR-ABL transduced mouse cell line," Cancer Genet. Cvtogenet. 161(1):51-56 (2005).
Sadhu et al., "Essential Role of Phosphoinositide 3-Kinase 8 in Neutrophil Directional Movement," J. Immunol. 170:2647-2654 (2003).
Saif and Chu, "Biology of colorectal cancer," Cancer J. 16(3):196-201 (2010).
Salmena et al., "Tenets of PTEN Tumor Suppression," Cell 133(3):403-414 (2008).
Sarker et al., "Targeting the PI3K/AKT pathway for the treatment of prostate cancer," Clin. Cancer Res. 15(15):4799-4805 (2009).
Sasaki et al., "Function of PI3Kγ in Thymocyte Development, T Cell Activation, and Neutrophil Migration," Science 287:1040-1046 (2000).
Saudek et al., "A Preliminary Trial of the Programmable Implantable Medication System for Insulin Delivery," N. Engl. J. Med. 321(9):574-579 (1989).
Saudemont et al., "p110γ and p110δ isoforms of phosphoinositide 3-kinase differentially regulate natural killer cell migration in health and disease," Proc. Natl. Acad. Sci. 106(14):5795-5800 (2009).
Schwartz et al., "Quercetin inhibition of the induction and function of cytotoxic T lymphocytes," Immunopharmacology 4(2):125-138 (1982).
Schwartz, "A cell culture model for T lymphocyte clonal anergy," Science 248(4961): 1349- 1356 (1990).
Sefton, "Implantable Pumps," Crit. Rev. Biomed. Eng. 14(3):201-240 (1987).
Oojima, H. Handbook of Chemistry, Applicated vol. of Chemistry I (Shadan-hojin Japan Chemistry Association, Kagaku Biman Ouyou Kagaku hen), 6th ed, MARUZEN Co., Ltd., Jan. 30, 2003, p. 178.
Shapiro et al., "Phase I Dose-Escalation Study of XL147, A PI3K Inhibitor Administered Orally to Patients with Solid Tumors," J. Clin. Oncol. 27:15s (Suppl Abstr 3500) (2009), 2 pages.
Shibasaki et al., "Different properties of monomer and heterodimer forms of phosphatidylinositol 3-kinases," Biochem. J. 289 ( 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," Blood (ASH Annual Meeting Abstracts) 118:Abstract 4964 (2011).
Singer et al., "Optimization of in situ hybridization using isotopic and non-isotopic detection methods," Biotechniques 4(3):230-250 (1986).
Singh et al., "In vitro Metabolism of a Potent HIV-protease Inhibitor (141W94) Using Rat, Monkey and Human Liver S9," Rapid Commun. Mass Spectrum. 10:1019-1026 (1996).
Siu et al., "A first-in-human, phase I study of an oral hedgehog (HH) pathway antagonist, BMS-833923 (XL139), in subjects with advanced or metastatic solid tumors," J. Clin. Oncol. 28(15_suppl):2501 (ASCO Annual Meeting Abstracts 2010).
Smith et al., "Expression of Bruton's Agammaglobulinemia Tyrosine Kinase Gene, BTK, Is Selectively Down-Regulated in T Lymphocytes and Plasma Cells," J. Immunol. 152:557-565 (1994).

Sokol et al., "D8/17 Expression on B Lymphocytes in Anorexia Nervosa," Am. J. Psychiatry 159:1430-1432 (2002).
Sokol, "Infection-Triggered Anorexia Nervosa in Children: Clinical Description of Four Cases," J. Child Adolesc. Psychopharmacol. 10(2):133-145 (2000).
Soldan et al., "Induction of daunorubicincarbonyl reducing enzymes by daunorubicin in sensitive and resistant pancreas carcinoma cells," Biochem. Pharmacol. 51(2):117-123 (1996).
Soond et al., "PI3K p110δ regulates T-cell cytokine production during primary and secondary immune responses in mice and humans," Blood 115(11):2203-2213 (2010).
Srinivasan et al., "PI3 Kinase Signals BCR-Dependent Mature B Cell Survival," Cell 139:573-586 (2009).
Stanoeva et al., "Homophthalic anhydrides and their application to the synthesis of heterocyclic compounds (review)," Chemistry of Heterocyclic Compounds 20(12):1305-1315 (1984).
Subramaniam et al., "Targeting Nonclassical Oncogenes for Therapy in T-ALL," Cancer Cell 21:459-472 (2012).
Sujobert et al., "Essential role for the p110δ isoform in phosphoinositide 3-kinase activation and cell proliferation in acute myeloid leukemia," Blood 106(3):1063-1066 (2005).
Supplementary European Examination Report EP Application No. 07754845.1 dated Sep. 20, 2011, 3 pages.
Supplementary European Search Report for EP Application No. 07754845 dated Feb. 24, 2010, 3 pages.
Supplementary European Search Report for EP Application No. 10800175.1 dated Nov. 7, 2012, 4 pages.
Sykes et al., "Treatment of severe autoimmune disease by stem-cell transplantation," Nature 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," Cancer Res. 65(8):3336-3346 (2005).
Tanaka et al., "An unbiased cell morphology-based screen for new, biologically active small molecules," PLoS Biol. 3(5):0764-0776 (2005).
Tassi et al., "p110γ and p110δ Phosphoinositide 3-Kinase Signaling Pathways Synergize to Control Development and Functions of Murine NK Cells," Immunity 27:214-227 (2007).
Thompson et al., "Identification of distinct populations of PI-3 kinase activity following T-cell activation," Oncogene 7(4):719-725 (1992).
Torbett et al., "A chemical screen in diverse breast cancer cell lines reveals genetic enhancers and suppressors of sensitivity to PI3K isoform-selective inhibition," Biochem. J. 415(1):97-110 (2008).
Torimoto et al., "CD45 molecule and T cell activation", 1990, vol. 27, pp. 63-71.
Truitt et al., "Stimulation of CD28 triggers an association between CD28 and phosphatidylinositol 3-kinasein Jurkat T cells," J. Exp. Med. 179(3):1071-1076 (1994).
Tyukavkina et al., Bioorganicheskaya Khimiya, Moskva, DROFA, pp. 83-85 (2004).
U.S. Appl. No. 15/179,570, filed Jun. 10, 2016, Heterocyclic Compounds and Uses Thereof.
U.S. Appl. No. 15/621,764, filed Jun. 13, 2017, Chemical Compounds, Compositions and Methods for Kinase Modulation.
Uddin et al., "Role of phosphatidylinositol 3'-kinase/AKT pathway in diffuse large B-cell lymphoma survival," Blood 108(13):4178-4186 (2006).
Ugarkar et al., "Adenosine kinase inhibitors. 2. Synthesis, enzyme inhibition, and antiseizure activity of diaryltubercidin analogues," J. Med. Chem. 43(15):2894-2905 (2000).
Vandenberghe et al., "Antibody and B7/BB1-mediated ligation of the CD28 receptor induces tyrosine phosphorylation in human T cells," J. Exp. Med. 175(4):951-960 (1992).
Vanhaesebroeck et al., "PI3K: from the bench to the clinic and back," Curr. Top. Microbiol. Immunol. 347:1-19 (2010).
Vanhaesebroeck et al., "Synthesis and Function of 3-phosphorylated Inositol Lipids," Annu. Rev. Biochem 70:535-602 (2001).
Vara et al., "PI3K/Akt Signalling Pathway and Cancer," Cancer Treat. Rev. 30(2):193-204 (2004).

(56) References Cited

OTHER PUBLICATIONS

Vasilevsky et al., "Study of the Heterocyclization of vic-Substituted Hydrazides of Acetylenylpyrazolecarboxylic Acids into N-Amino Pyrazolopyridinones," Journal of Heterocyclic Chemistry 39(6): 1229-1233 (2002).
Vasilevsky et al., "Unexpected results in the heterocyclization of 5-acetylenylpyrazole-4-carboxylic acid hydrazides under the influence of CuCI: formation of a diazepinone and dehydrodimerization into the corresponding bis(pyrazolo [4,3-d] [1,2] diazepinone)," Tetrahedron Lett. 46(26):4457-4459 (2005).
Vippagunta et al., "Crystalline Solids," Adv. Drug Deliv. Rev. 48(1):3-26 (2001).
Vitali et al., "Immunotherapy in rheumatoid arthritis: a review," Int. J. Artif. Organs 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," J. Biol. Chem. 269(7):5241-5248 (1994).
Vogt et al., "Phosphatidylinositol 3-kinase: the oncoprotein," Curr. Top. Microbiol. Immunol. 347:79-104 (2010).
Vogt et al., "Phosphoinositide 3-kinase: from viral oncoprotein to drug target," Virology 344(1):131-138 (2006).
Von Hoff et al., "Inhibition of the Hedgehog Pathway in Advanced Basal-Cell Carcinoma," N. Engl. J. Med. 361(12):1164-1672 (2009).
Wagner et al., "A First-in-Human Phase I Study to Evaluate the Pan-PI3K Inhibitor GDC-0941 Administered QD or BID in Patients with Advanced Solid Tumors," J. Clin. Oncol. 27:15s (Suppl, Abstr 3501) (2009), 2 pages.
Wahlstrom et al., "Aberrant MAPK and PI3K Signaling Contribute to Chemotherapy Resistance in T Cell Acute Lymphobalstic Leukemia by Altering the Balance of Apoptosis Mediators," Blood (ASH Annual Meeting Abstracts) 118: Abstract 3490 (2011).
Ward et al., "Inhibition of CD28-mediated T cell costimulation by the phosphoinositide 3-kinase inhibitor wortmannin," Eur. J. Immunol. 25(2):526-532 (1995).
Ward et al., "Ligation of CD28 receptor by B7 induces formation of D-3 phosphoinositides in T lymphocytes independently of T cell receptor/CD3 activation," Eur. J. Immunol. 23(10):2572-2577 (1993).
Ward et al., "Regulation of D-3 phosphoinositides during T cell activation via the T cell antigen receptor/CD3 complex and CD2 antigens," Eur. J. Immunol. 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," J. Biol. Chem. 267(33):23862-23869 (1992).
Ward et al., "Therapeutic potential of phosphoinositide 3-kinase inhibitors," Chem. Biol. 10(3):207-213 (2003).
Webb et al., "Clinical Pharmacokinetics of CAL-101, a p110δ Isoform-Selective PI3 Following Single- and Multiple-Dose Administration in Healthy Volunteers and Patien Hematological Malignancies," Blood 116:1774 (ASH Annual Meeting Abstracts 2010).
Webb et al., "Cutting Edge: T Cell Development Requires the Combined Activities of the pII08 Catalytic Isoforms of Phosphatidylinositol 3-Kinase," J. Immunol. 175:2783-278.

White et al., "1 1β-Hydroxysteroid Dehyrdogenase and the Syndrome of Apparent Mineralocorticoid Excess," Endocr. Rev. 18(1):135-156 (1997).
Widler et al., "7-alkyl- and 7-Cycloalkyl-5-aryl-pyrrolo [2,3-d]pyrimidines-potent inhibitors of the tyrosine kinase c-Src," Bioorg. Med. Chem. Lett. 11(6):849-852 (2001).
Wiesinger et al., "Antiinflammatory activity of the new mould metabolite 11-desacetoxy-wortmannin and of some of its derivatives," Experientia 30(2):135-136 (1974).
Wilen et al., "Strategies in Optical Resolutions," Tetrahedron 33:2725-2736 (1977).
Wilen, Tables of Resolving Agents and Optical Resolutions pp. 268-298 (Univ. of Notre Dame Press, 1972).
Williams et al., "Discovery of Dual Inhibitors of the Immune Cell PI3Ks p110δ and p110γ: a Prototype for New Anti-inflammatory Drugs," Chem. Biol. 17:123-134 (2010).
Wolff, Burger's Medicinal Chemistry, 5th ed, Part 1, pp. 975-977, John Wiley & Sons (1995).
Woscholski et al., "A comparison of demethoxyviridin and wortmannin as inhibitors of phosphatidylinositol 3-kinase," FEBS Lett. 342(2):109-114 (1994).
Wu et al., "Shared signaling networks active in B cells isolated from genetically distil mouse models oflupus," J. Clin. Invest. 117(8):2186-2196 (2007).
Wu et al., "Decreased immunological responses by wortmannin-contAIning rice culture of Fusarium oxysporum and by purified wortmannin in avian species," Immunopharmacol. Immunotoxicol. 14(4):913-923 (1992).
Wu et al., "Wortmannin (a mycotoxin) inhibited immune responses in chickens," Poultry Sci. Vo. 71, Suppl 1, pp. 13 (1992).
Yaddanapudi et al., "Passive transfer of streptococcus-induced antibodies reproduces behavioral disturbances in a mouse model of pediatric autoimmune neuropsychiatric disorders associated with streptococcal infection," Mol. Psychiatry 15:712-726 (2010).
Yaguchi et al., "Antitumor activity of ZSTK474, a new phosphatidylinositol 3-kinase inhibitor," J. Natl. Cancer Inst. 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," J. Exp. Med. 168(4):1457-1468 (1988).
Yano et al., "Inhibition of histamine secretion by wortmannin through the blockade of phosphatidylinositol 3-kinase in RBL-2H3 cells," J. Biol. Chem. 268(34):25846-25856 (1993).
Yauch et al., "Smoothened Mutation Confers Resistance to a Hedgehog Pathway Inhibitor in Medulloblastoma," Science 326:572-574 (2009).
Yoshida et al., "Quercetin arrests human leukemic T-cells in late G1 phase of the cell cycle," Cancer Res. 52(23):6676-6681 (1992).
Zhang et al., "Genetic or pharmaceutical blockade of pl 108 phosphoinositide 3-kinase enhances IgE production," J. Allergy Clin. Immunol. 122(4):811-819 (2008).
Zhao and Vogt, "Class I PI3K in oncogenic cellular transformation," Oncogene 27(41):5486-5496 (2008).

TNP-Ficoll assay description

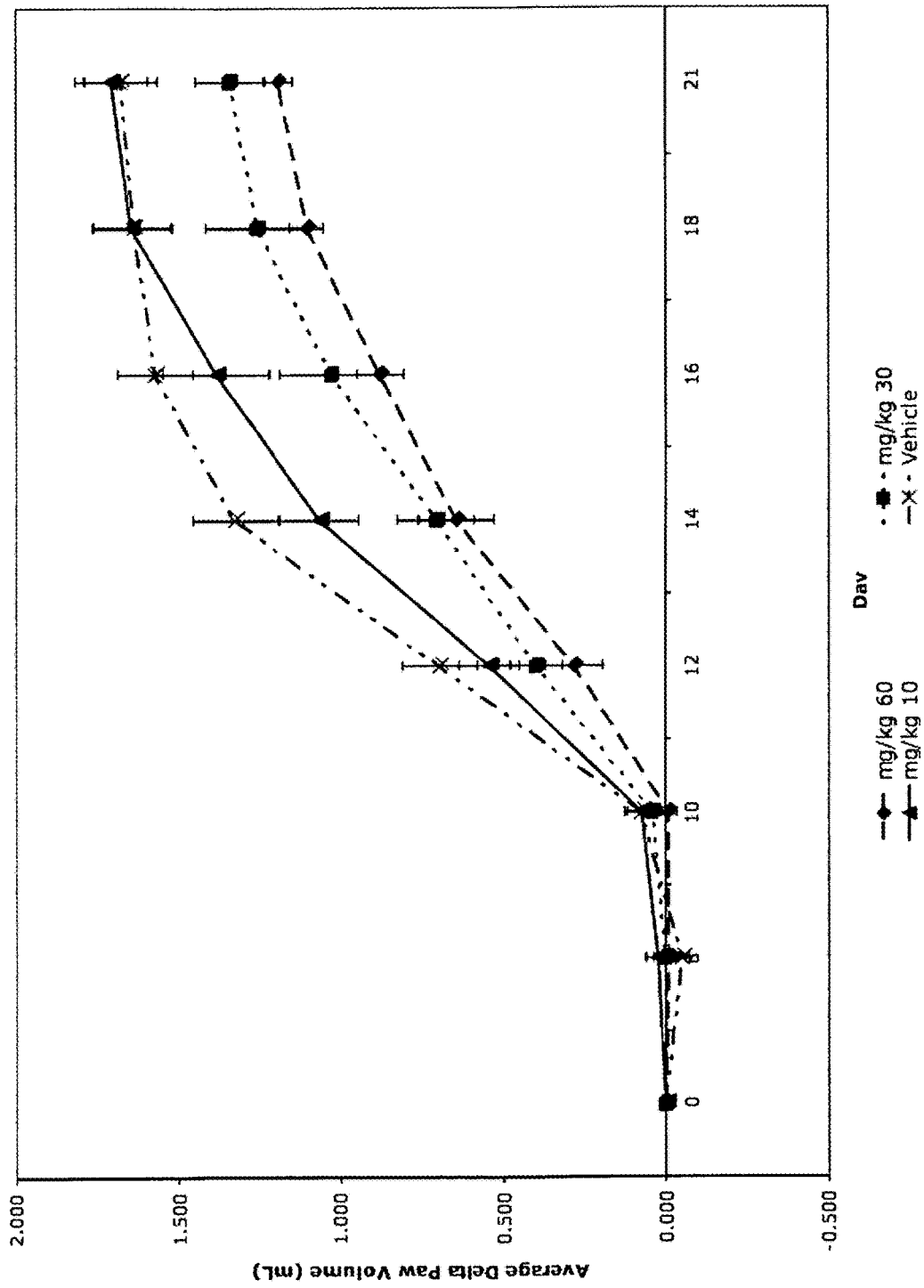

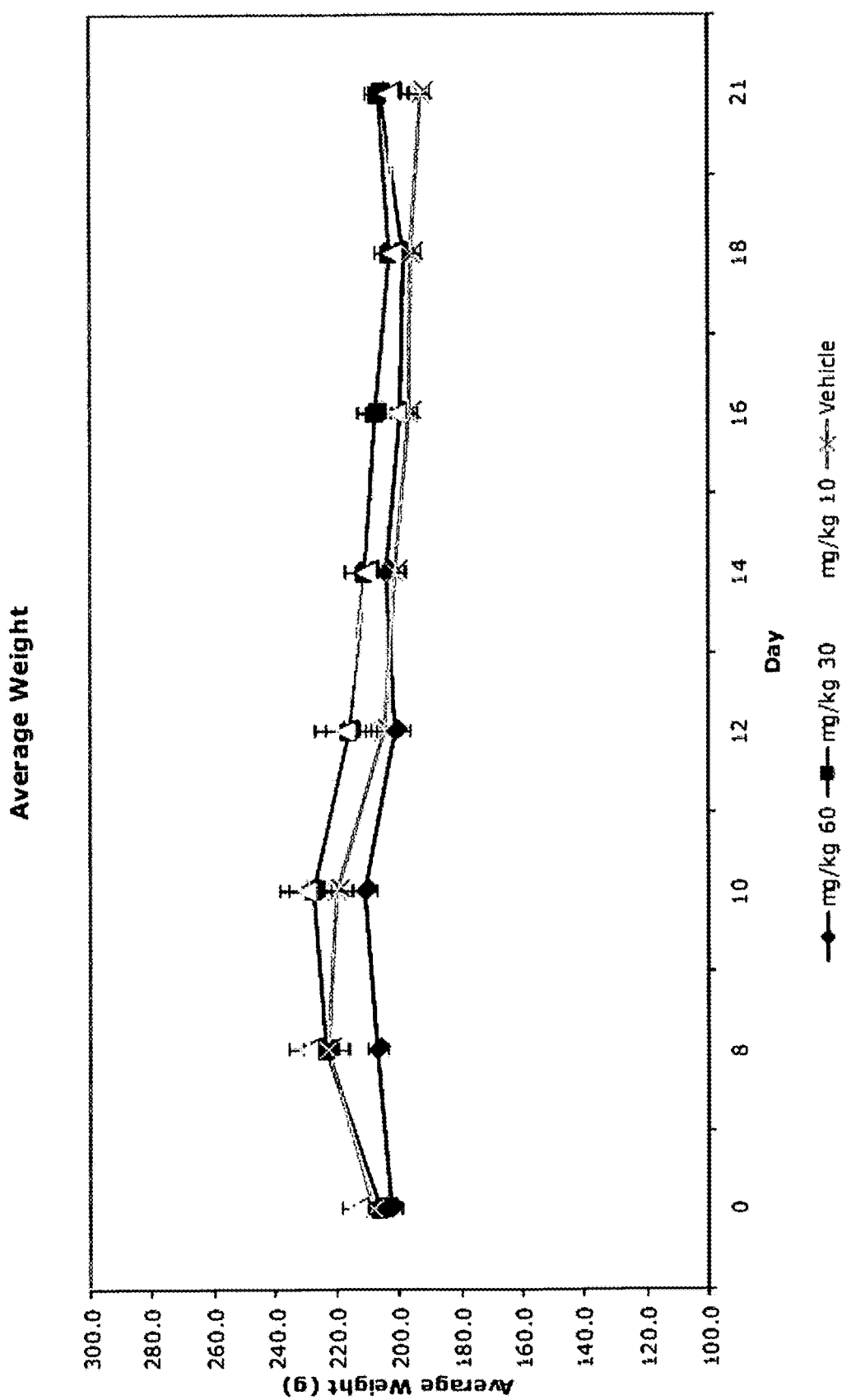

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Glu Ala Ile Tyr Ala Ala Pro Phe Ala Lys Lys Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Tyr Gly Glu Phe Lys Lys Lys
1               5
```

CERTAIN CHEMICAL ENTITIES, COMPOSITIONS AND METHODS

This application is a continuation application of U.S. patent application Ser. No. 15/599,378, filed on May 18, 2017, which is a continuation application of U.S. patent application Ser. No. 14/938,647, filed on Nov. 11, 2015, now U.S. Pat. No. 9,655,892, which is a continuation application of U.S. patent application Ser. No. 14/296,953, filed on Jun. 5, 2014, now U.S. Pat. No. 9,216,982, which is a continuation application of U.S. patent application Ser. No. 13/403,394, filed on Feb. 23, 2012, now U.S. Pat. No. 8,785,456, which is a divisional application of U.S. patent application Ser. No. 12/503,776, filed on Jul. 15, 2009, now U.S. Pat. No. 8,193,182, which is a continuation in part of International Application No. PCT/US09/00038, filed on Jan. 5, 2009 and International Application No. PCT/US09/00042, filed on Jan. 5, 2009, each of which claims the benefit of U.S. Provisional Application Nos. 61/009,971 filed on Jan. 4, 2008, 61/194,294 filed on Sep. 26, 2008, and 61/201,146 filed on Dec. 5, 2008. All of the above-referenced patent applications are hereby incorporated by reference in their entirety for all purposes.

The present application is being filed with a Sequence Listing submitted as filename 12928-143-999_SeqListing.txt, of size 1,026 bytes, which was created on Apr. 20, 2015. The Sequence Listing is incorporated herein by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3-Ks play a key role in intracellular trafficking through the synthesis of PI(3)P and PI(3,4)P2. The PIKKs are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and auto-immune diseases such as lupus.

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

As such, kinases, particularly PI3Ks are prime targets for drug development. There remains a need for PI3K inhibitors suitable for drug development. The present invention addresses this need and provides related advantages as well by providing new classes of kinase inhibitors.

SUMMARY OF THE INVENTION

In one aspect, the present invention provides compounds of Formula I below or pharmaceutically acceptable salts thereof, wherein

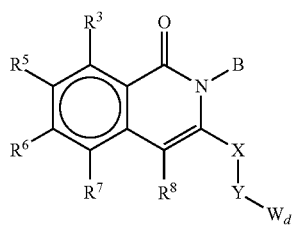

Formula I $W_d$ is heterocycloalkyl, aryl or heteroaryl;
B is alkyl or a moiety of Formula II;

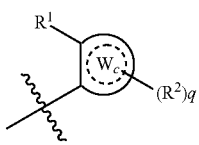

Formula II wherein $W_c$ is aryl, heteroaryl, heterocycloalkyl, or cycloalkyl, and q is an integer of 0, 1, 2, 3, or 4;
X is absent or —(CH($R^9$))$_z$—, and z is an integer of 1;
Y is absent, or —N($R^9$)—;
$R^1$ is hydrogen, alkyl, alkenyl, alkynyl, alkoxy, amido, alkoxycarbonyl, sulfonamido, halo, cyano, or nitro;
$R^2$ is alkyl, alkenyl, alkynyl, cycloalkyl, heterocycloalkyl, aryl, heteroaryl, heteroarylalkyl, alkoxy, amino, halo, cyano, hydroxy or nitro;
$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro;
$R^5$, $R^6$, $R^7$, and $R^8$ are independently hydrogen, alkyl, alkenyl, alkynyl, cycloalkyl, hetercycloalkyl, alkoxy, amido, amino, acyl, acyloxy, sulfonamido, halo, cyano, hydroxy or nitro; and
each instance of $R^9$ is independently hydrogen, alkyl, cycloalkyl, or heterocycloalkyl.

In some embodiments of the compounds of Formula I, when both X and Y are present then Y is —NH—.

In some embodiments of the compounds of Formula I, X is absent or is —(CH($R^9$))$_z$—, and z is independently an integer of 1, 2, 3, or 4; and Y is absent, —O—, —S—, —S(=O)—, —S(=O)$_2$—, —N($R^9$)—, —C(=O)—(CHR$^9$)$_z$—, —C(=O)—, —N($R^9$)(C=O)—, —N($R^9$)(C=O)NH—, or —N($R^9$)C($R^9$)$_2$—.

In some of the embodiments, X is —CH$_2$—, —CH(CH$_2$CH$_3$), or —CH(CH$_3$)—.

In some embodiments, X—Y is —CH$_2$—N(CH$_3$), —CH$_2$—N(CH$_2$CH$_3$), —CH(CH$_2$CH$_3$)—NH— or —CH(CH$_3$)—NH—.

In some embodiments, $W_d$ is a pyrazolopyrimidine of Formula III(a), or purine of Formula III(b), Formula III(c) or Formula III(d) below:

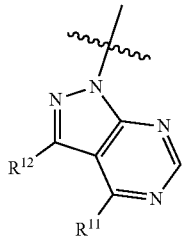

Formula III(a)

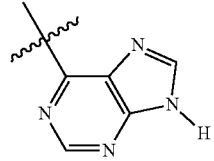

Formula III(b)

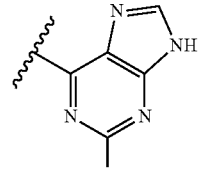

Formula III(c)

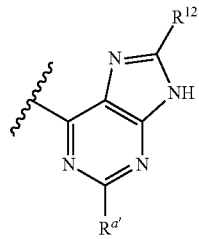

Formula III(d)

wherein $R^{a'}$ if Formula III(d) is hydrogen, halo, phosphate, urea, a carbonate, amino, alkyl, alkenyl, alkynyl, cycloalkyl, heteroalkyl, or heterocycloalkyl; $R^{11}$ of Formula III(a) is H, alkyl, halo, amino, amido, hydroxy, or alkoxy, and $R^{12}$ of Formula III(a), Formula III(c) or Formula III(d) is H, alkyl, alkynyl, alkenyl, halo, aryl, heteroaryl, heterocycloalkyl, or cycloalkyl. In some embodiments, $W_d$ is a pyrazolopyrimidine of Formula III(a), wherein $R^{11}$ is H, alkyl, halo, amino, amido, hydroxy, or alkoxy, and $R^{12}$ is cyano, amino, carboxylic acid, or amido.

In some embodiments, the compound of Formula I has the structure of Formula IV:

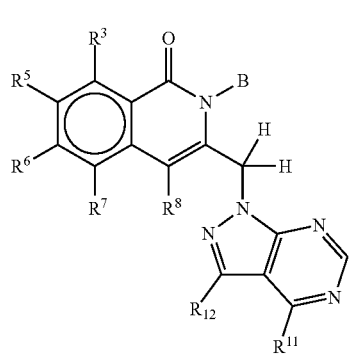

Formula IV wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, the compound of Formula I has the structure of Formula IV wherein $R^{11}$ is H, alkyl, halo, amino, amido, hydroxy, or alkoxy, and $R^{12}$ is cyano, amino, carboxylic acid, or amido.

In some embodiments of the compound of Formula IV, $R^{11}$ is amino. In some embodiments of the compound of Formula IV, $R^{12}$ is alkyl, alkenyl, alkynyl, heteroaryl, aryl, or heterocycloalkyl. In some embodiments of the compound of Formula IV, $R^{12}$ is cyano, amino, carboxylic acid, amido, monocyclic heteroaryl, or bicyclic heteroaryl.

In some embodiments of the compound of Formula I, the compound has the structure of Formula V:

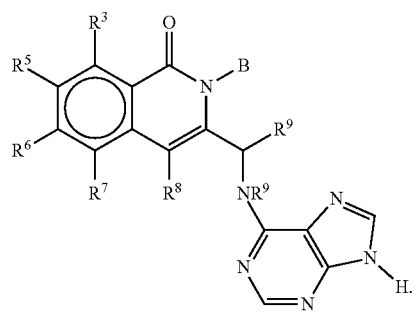

Formula V

In some of the embodiments of Formula V, $NR^9$ is —$N(CH_2CH_3)CH_2$— or $N(CH_3)CH_2$—.

In some of the embodiments of Formula I, the compound has a structure of Formula VI:

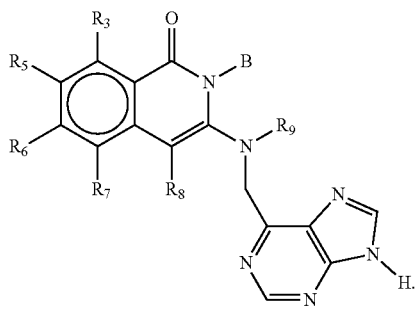

Formula VI

In some of the embodiments of the compound of Formula VI, $R^3$ is —H, —$CH_3$, —Cl, or —F, and $R^5$, $R^6$, $R^7$, and $R^8$ are independently hydrogen.

In some of the embodiments of Formula VI, B is a moiety of Formula II;

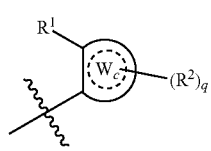

Formula II wherein $W_c$ is aryl, heteroaryl, heterocycloalkyl, or cycloalkyl, and q is an integer of 0, 1, 2, 3, or 4.

In another aspect of the invention a compound and its pharmaceutically acceptable salts having the structure of Formula I-1 is provided, wherein:

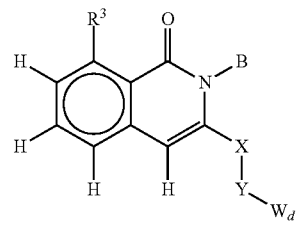

Formula I-1

B is a moiety of Formula II;

wherein $W_c$ in B is aryl, heteroaryl, heterocycloalkyl, or cycloalkyl, and q is an integer of 0, 1, 2, 3, or 4;

X is absent or —$(CH(R^9))_z$—, and z is an integer of 1;

Y is absent, or —$N(R^9)$—;

when Y is absent, Wd is:

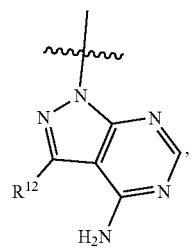

or when Y is present, Wd is:

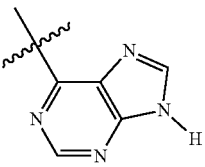 [SMILES: *c1ncnc2[nH]cnc12]

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro;

each instance of $R^9$ is independently hydrogen, $C_1$-$C_{10}$alkyl, cycloalkyl, or hetercyclooalkyl; and $R^{12}$ is H, alkyl, alkynyl, alkenyl, halo, aryl, heteroaryl, heterocycloalkyl, or cycloalkyl.

In some embodiments, a compound of Formula I or Formula I-1 has the structure of Formula IV-A:

Formula IV-A

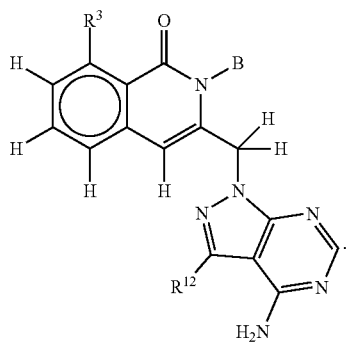

Formula VI-A

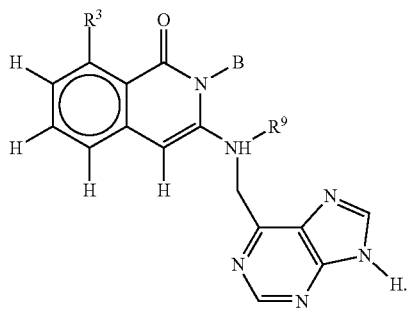

In some embodiments of the compound of Formula IV-A, $R^{12}$ is substituted benzoxazole.

In some embodiments, a compound of Formula I or Formula I-1 has the structure of Formula V-A:

Formula V-A

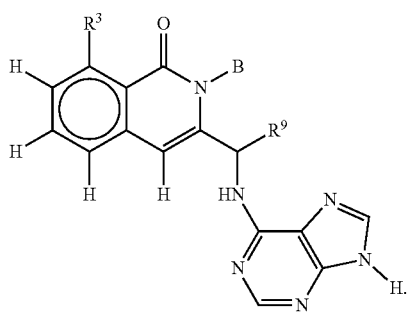

In some embodiments, a compound of Formula I or Formula I-1 has the structure of Formula IV-A or Formula V-A.

In some embodiments, a compound of Formula I or Formula I-1 has the structure of Formula V-B:

Formula V-B

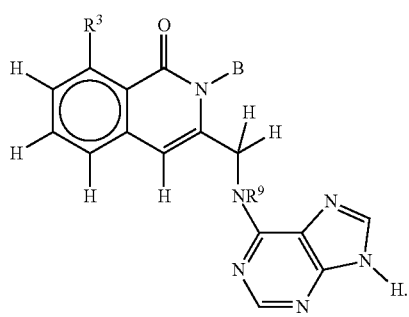

In some embodiments, a compound of Formula I or Formula I-1 has the structure of Formula VI-A:

In some embodiments, a compound of Formula I or Formula I-1 is the compound wherein B is a moiety of Formula II;

Formula II

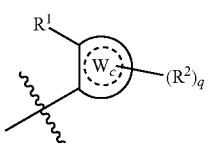

wherein $W_c$ is aryl, heteroaryl, heterocycloalkyl, or cycloalkyl; q is an integer of 0 or 1; $R^1$ is hydrogen, alkyl, or halo; $R^2$ is alkyl or halo; and $R^3$ is hydrogen, alkyl, or halo. In some embodiments, when both X and Y are present then Y is —NH—. In other embodiments, $R^3$ is —H, —CH$_3$, —CH$_2$CH$_3$, —CF$_3$, —Cl or —F. In further embodiments, $R^3$ is methyl or chloro.

In some embodiments of the compound of Formula I or Formula I-1, X is —(CH($R^9$))$_z$—, wherein $R^9$ is methyl and z=1; and Wd is

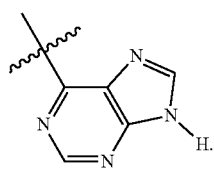

In other embodiments of the compound of Formula I or Formula I-1, the compound is predominately in an (S)-stereochemical configuration.

In further embodiments of the compound of Formula I or Formula I-1, the compound has a structure of Formula V-A2:

Formula V-A2

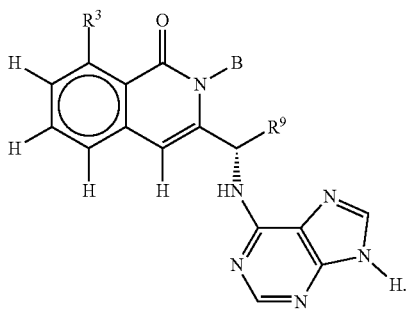

In some other embodiments of the compound of Formula I or Formula I-1, $R^{12}$ is a monocyclic heteroaryl, bicyclic heteroaryl, or heterocycloalkyl.

In some other embodiments of the compound of Formula I or Formula I-1, B is a moiety of Formula II:

Formula II

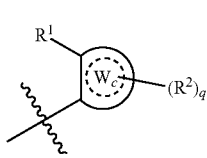

wherein $W_c$ is aryl or cycloalkyl.

In another aspect of the invention, a pharmaceutical composition is provided which comprises a pharmaceutically acceptable excipient and one or more compounds of any formulae provided herein, including but not limited to Formula I, I-1, IV, IV-A, V, V-A, V-A2, V-B, VI, and VI-A. In some embodiments, the composition is a liquid, solid, semi-solid, gel, or an aerosol form.

In another aspect of the invention, a method of inhibiting a phosphatidyl inositol-3 kinase (PI3 kinase), is provided comprising: contacting the PI3 kinase with an effective amount of one or more compounds disclosed herein. For instance, the step of contacting involves the use of one or more compounds of any formulae provided herein including but not limited to Formula I, I-1, IV, IV-A, V, V-A, V-A2, V-B, VI, and VI-A. In some embodiments, the step of contacting comprises contacting a cell that contains said PI3 kinase. In some embodiments of the method, the inhibition takes place in a subject suffering from a disorder associated with malfunctioning of one or more types of PI3 kinase. Some exemplary diseases involving malfunctioning of one or more types of PI3 kinases are selected from the group consisting of autoimmune diseases, rheumatoid arthritis, respiratory disease, allergic reactions, and various types of cancers. Where desired, the compound used in the method has the structure of Formula IV, wherein $R^{11}$ is amino and $R^{11}$ is substituted phenyl.

In some embodiments of the method, the inhibition takes place in a subject suffering from rheumatoid arthritis or a respiratory disease, and wherein the compound has the structure of Formula IV, and wherein $R^{11}$ is amino and $R^{12}$ is bicyclic heteroaryl.

In some embodiments, the method comprises administering a second therapeutic agent to the subject.

In yet another aspect, the present invention provides a method of treating a disease manifesting an undesired immune response. The method comprises the step of administering to a subject in need thereof, one or more compounds disclosed herein including compounds of Formula I, I-1, IV, IV-A, V, V-A, V-B, VI, and/or VI-A, in an amount that is effective in ameliorating said undesired immune response. In some embodiments, the one or more compounds inhibit T-cell independent B-cell activation as evidenced by a reduction in production of anti-TNP IgG3 by at least about five folds when administered in an amount less than about 30 mg/kg BID dose to a test animal.

In some embodiments, the disease treated is associated with swelling or pain of a joint of a subject. The method can be effective in ameliorating one or more rheumatoid arthritis symptoms as evidenced by reduction in mean joint diameter by at least about 10% after 17 days and/or reduction in ankle diameter by at least 5-10% or more after several days to weeks of treatment, including for example reduction in ankle diameter by at least 5% after 7 days of treatment. In another embodiment, the undesired immune response is evidenced by enhanced production of anti-type II collagen antibodies, and the use of one or more subject compounds reduces the serum anti-type II collagen level at an ED50 of less than about 10 mg/kg.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

FIG. 10 depicts the dose-dependent effect of compound 53 of formula IV on the increase in average paw volume in an adjuvant induced arthritis model.

FIG. 11 depicts the effect of compound 53 of formula IV on the average weight over time of rats in an adjuvant induced arthritis model in rats.

DETAILED DESCRIPTION OF THE INVENTION

Figure 1:
FIG. 1 depicts an exemplary protocol for measuring T-cell independent production of TNP specific antibodies in vivo.
Figure 1:
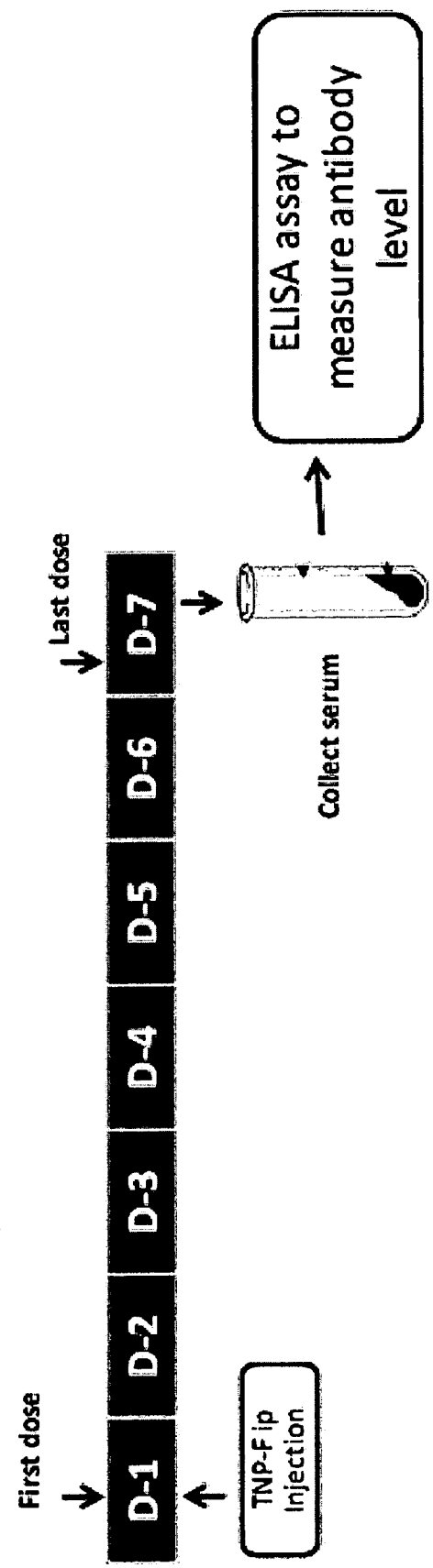

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionucleotides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures wherein hydrogen is replaced by deuterium or tritium, or wherein carbon atom is replaced by $^{13}C$- or $^{14}C$-enriched carbon, are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; $POCl_3$=Phosphorous Oxychloride; KCNS=Potassium Iso-Thiocyanate; TLC=Thin Layer Chromatography; MeOH=Methanol; and $CHCl_3$=Chloroform.

Abbreviations used herein have their conventional meaning within the chemical and biological arts.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)N$(R^a)_2$, —C(O)N$(R^a)_2$, —$N(R^a)$C(O)$OR^a$, —$N(R^a)$C(O)$R^a$, —$N(R^a)$C(O)N$(R^a)_2$, $N(R^a)$C(N$R^a$)N$(R^a)_2$, —$N(R^a)$S(O)$_tR^a$ (where t is 1 or 2), —S(O)$_tOR^a$ (where t is 1 or 2), —S(O)$_tN(R^a)_2$ (where t is 1 or 2), or $PO_3(R^a)_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)N$(R^a)_2$, —C(O)N$(R^a)_2$, —$N(R^a)$C(O)$OR^a$, —$N(R^a)$C(O)$R^a$, —$N(R^a)$C(O)N$(R^a)_2$, N$(R^a)$C(N-$R^a$)N$(R^a)_2$, —$N(R^a)$S(O)$_tR^a$ (where t is 1 or 2), —S(O)$_tOR^a$ (where t is 1 or 2), —S(O)$_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)$N(R^a)_2$, —C(O)$N(R^a)_2$, —$N(R^a)$C(O)$OR^a$, —$N(R^a)$C(O)$R^a$, —$N(R^a)$C(O)$N(R^a)_2$, $N(R^a)$C(N$R^a$)$N(R^a)_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cyclo alkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (ie. $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)$OR^a$, —OC(O)$N(R^a)_2$, —C(O)$N(R^a)_2$, —$N(R^a)$C(O)$OR^a$, —$N(R^a)$C(O)$R^a$, —$N(R^a)$C(O)$N(R^a)_2$, $N(R^a)$C(N$R^a$)$N(R^a)_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl) alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)$OR^a$, —OC(O)$N(R^a)_2$, —C(O)$N(R^a)_2$, —$N(R^a)$C(O)$OR^a$, —$N(R^a)$C(O)$R^a$, —$N(R^a)$C(O)$N(R^a)_2$, $N(R^a)$C(N$R^a$)$N(R^a)_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)$OR^a$, —OC(O)$N(R^a)_2$, —C(O)$N(R^a)_2$, —$N(R^a)$C(O)$OR^a$, —$N(R^a)$C(O)$R^a$, —$N(R^a)$C(O)$N(R^a)_2$, $N(R^a)$C(N$R^a$)$N(R^a)_2$, —$N(R^a)$S(O)$_t R^a$ (where t is 1 or 2), —S(O)$_t OR^a$ (where t is 1 or 2), —S(O)$_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2-S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N($R^a$)$_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N($R^a$)$_2$ group has two $R^a$ other than hydrogen they can be combined with the nitrogen atom to form a 4-, 5-, 6-, or 7-membered ring. For example, —N($R^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl—radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. C$_1$-C$_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule may be through either a heteroatom or a carbon in the heteroalkyl chain A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Heteroalkylheterocycloalkyl" refers to an -(heteroalkyl)heterocycloalkyl radical where heteroalkyl and heteroaryl are as disclosed herein and which are optionally substituted by one or more of the substituents described as suitable substituents for heteroalkyl and heterocycloalkyl respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively.

"Heteroaryl" or, alternatively, "heteroaromatic" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space, i.e. having a different stereochemical configuration. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group may be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts, above.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6-, or 7-membered ring. In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds of the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities include, but are not limited to, compounds of Formula I, I-1, IV, IV-A, V, V-A, V-A2, V-B, VI or VI-A, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

In one aspect, the present invention provides a compound of Formula I:

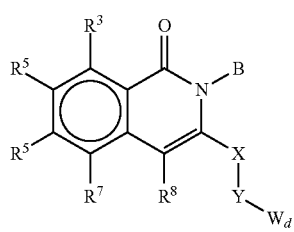

Formula I-1 or its pharmaceutically acceptable salt thereof, wherein
$W_d$ is heterocycloalkyl, aryl or heteroaryl;
B is alkyl, amino, heteroalkyl, or a moiety of Formula II;

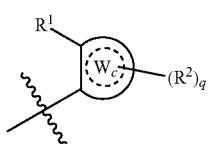

Formula II wherein $W_c$ is aryl, heteroaryl, heterocycloalkyl, or cycloalkyl, and
q is an integer of 0, 1, 2, 3, or 4;
X is absent or is —(CH($R^9$))$_z$— and z is an integer of 1, 2, 3, or 4;
Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, or —N($R^9$)—C(=O)NH—, —N($R^9$)C($R^9$)$_2$—, or —C(=O)—(CHR$^9$)$_z$—;
$R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;
$R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl, or heteroaryl;
$R^5$, $R^6$, $R^7$, and $R^8$ are independently hydrogen, $C_1$-$C_4$alkyl, $C_2$-$C_5$alkenyl, $C_2$-$C_5$alkynyl, $C_3$-$C_5$cycloalkyl, $C_1$-$C_4$heteroalkyl, $C_1$-$C_4$alkoxy, $C_1$-$C_4$amido, amino, acyl, $C_1$-$C_4$acyloxy, $C_1$-$C_4$sulfonamido, halo, cyano, hydroxy or nitro; and
each instance of $R^9$ is independently hydrogen, $C_1$-$C_{10}$alkyl, $C_3$-$C_7$cycloalkyl, heterocycloalkyl, or $C_2$-$C_{10}$heteroalkyl.

In some embodiments, B is unsubstituted or substituted alkyl, including but not limited to —(CH$_2$)$_2$—NR$^a$R$^a$, wherein each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or NR$^a$R$^a$ are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

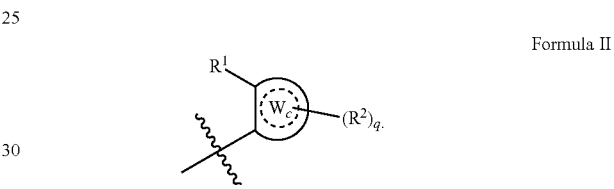

Formula II

In some embodiments, B is a moiety of Formula II and wherein $W_c$ is a member selected from the group consisting of unsubstituted or substituted aryl, substituted phenyl, unsubstituted or substituted heteroaryl including but not limited to pyridin-2-yl, pyridin-3-yl, pyridin-4-yl, pyrimidin-4-yl, pyrimidin-2-yl, pyrimidin-5-yl, or pyrazin-2-yl, unsubstituted or substituted monocyclic heteroaryl, unsubstituted or substituted bicyclic heteroaryl, a heteroaryl comprising two heteroatoms as ring atoms, unsubstituted or substituted heteroaryl comprising a nitrogen ring atom, heteroaryl comprising two nitrogen ring atoms, heteroaryl comprising a nitrogen and a sulfur as ring atoms, unsubstituted or substituted heterocycloalkyl including but not limited to morpholinyl, tetrahydropyranyl, piperazinyl, and piperidinyl, unsubstituted or substituted cycloalkyl including but not limited to cyclopentyl and cyclohexyl.

In some embodiments, B is one of the following moieties:

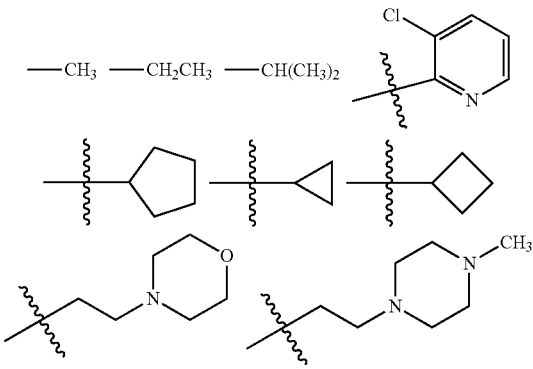

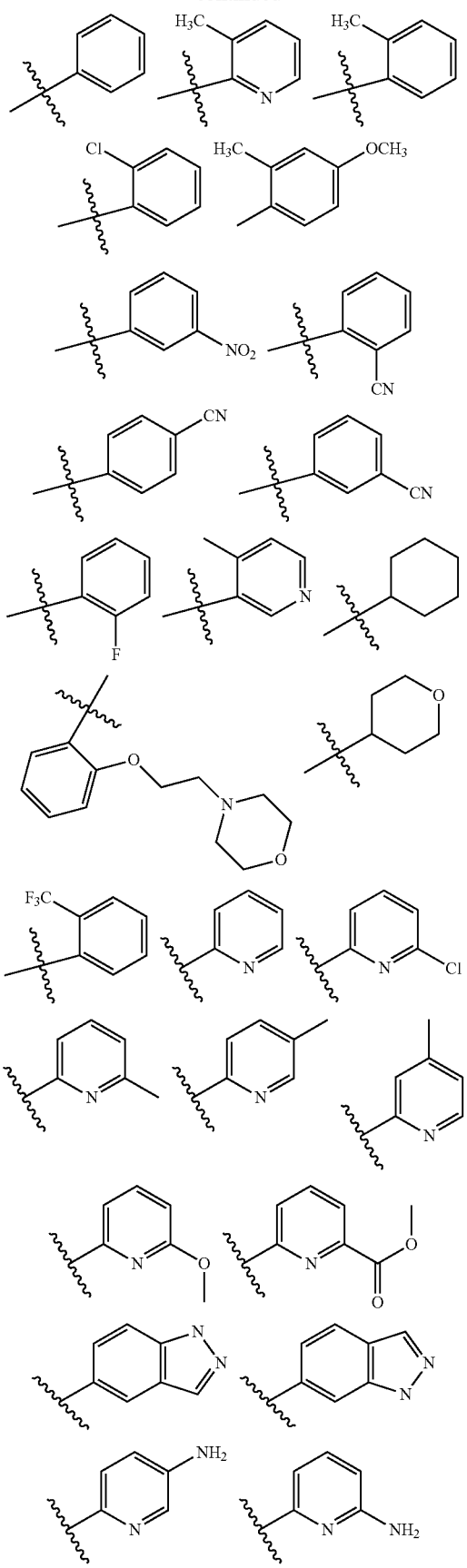
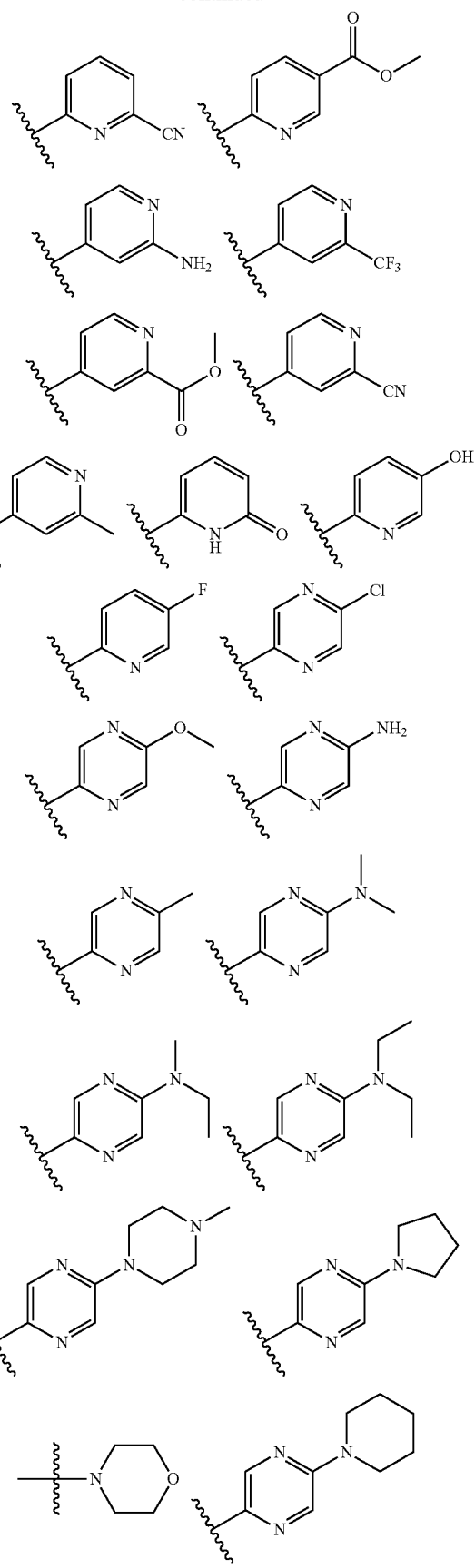

-continued
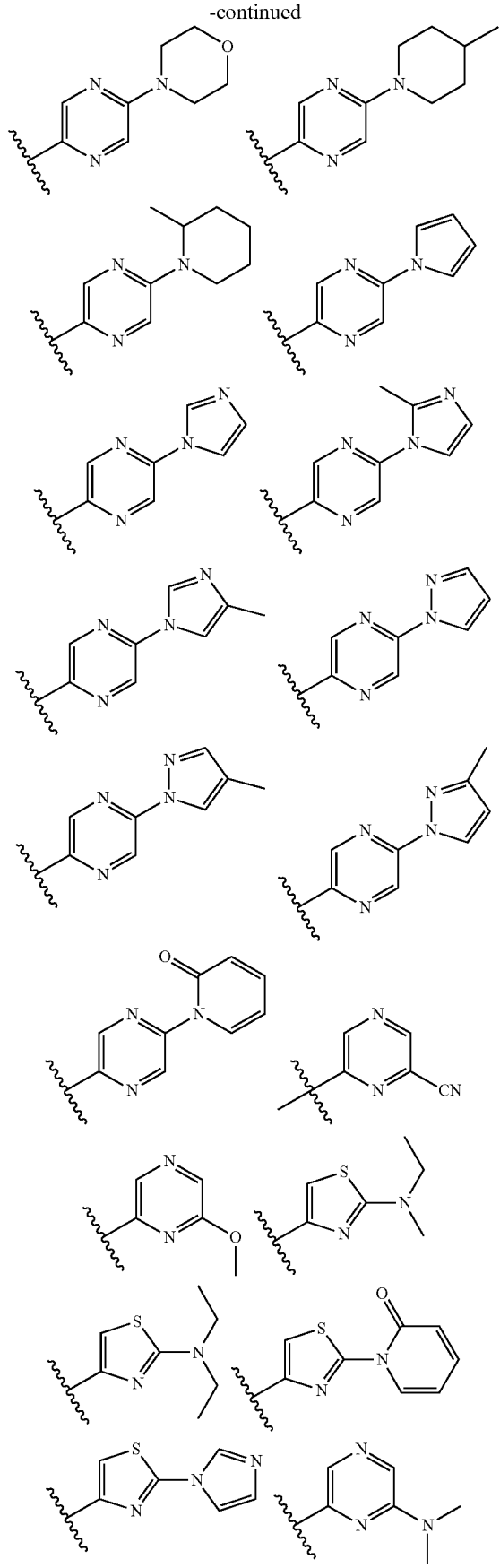
-continued
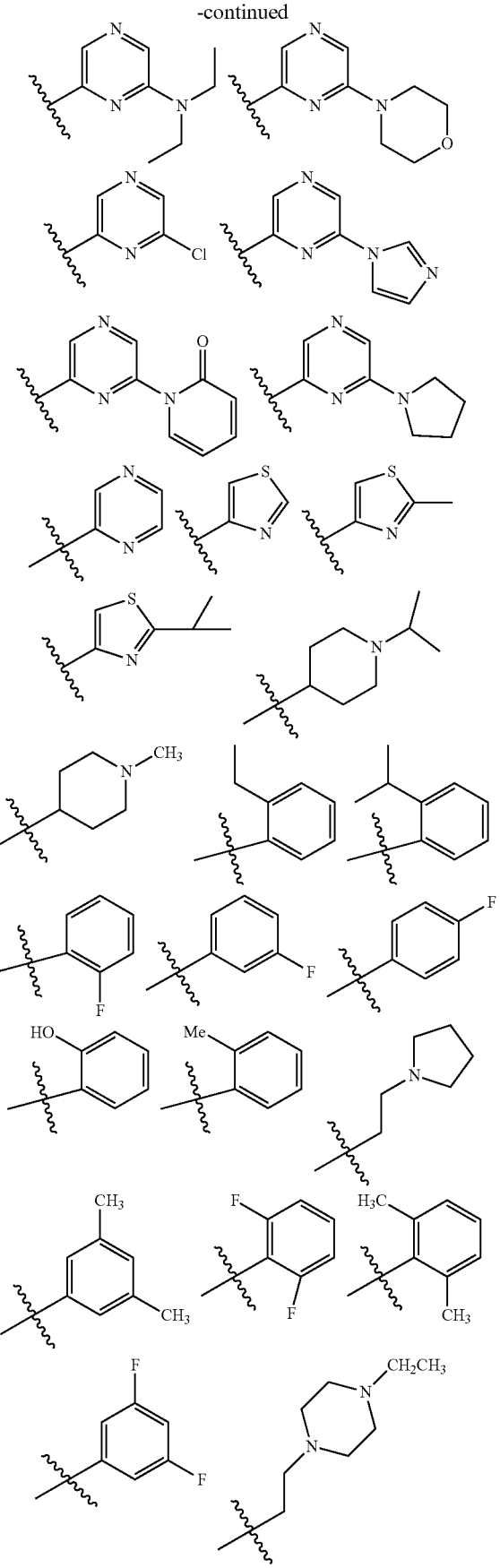

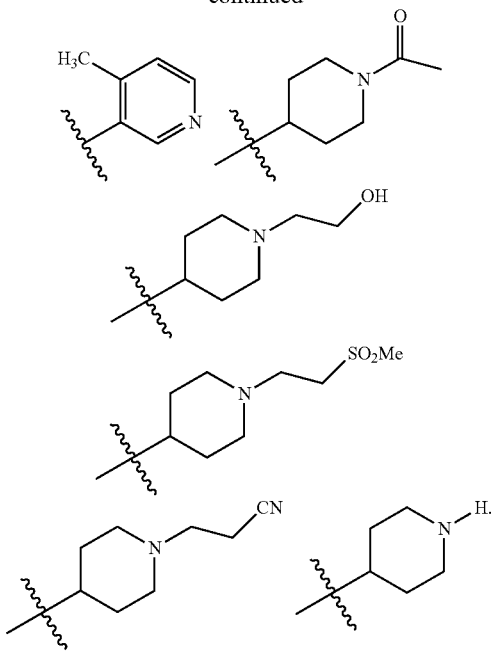

In some embodiments, B is substituted by one or more of alkyl, heteroalkyl, alkenyl, alkynyl, cycloalkyl, heterocycloalkyl, aryl, heteroaryl alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido, may itself be substituted.

In some embodiments, $R^1$ is a member selected from the group consisting of hydrogen, unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocycloalkyl. In some embodiments, $R^1$ is unsubstituted or substituted aryl, unsubstituted or substituted arylalkyl, unsubstituted or substituted heteroaryl, or unsubstituted or substituted heteroarylalkyl. In some embodiments, $R^1$ is unsubstituted or substituted alkoxy, unsubstituted or substituted amido, unsubstituted or substituted amino. In some embodiments, $R^1$ is unsubstituted or substituted acyl, unsubstituted or substituted acyloxy, unsubstituted or substituted alkoxycarbonyl, or unsubstituted or substituted sulfonamido. In some embodiments, $R^1$ is halo which includes —Cl, —F, —I, and —Br. In some embodiments, $R^1$ is selected from the group consisting of cyano, hydroxy, nitro, unsubstituted or substituted phosphate, unsubstituted or substituted urea, and carbonate.

In some embodiments, when $R^1$ is alkyl, $R^1$ is methyl, ethyl, propyl, isopropyl, n-butyl, tert-butyl, sec-butyl, pentyl, hexyl or heptyl.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^1$ is substituted by one or more of alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido may itself be substituted.

In some embodiments, $R^2$ is a member selected from the group consisting of unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, which is —I, —F, —Cl, or —Br. In some embodiments, $R^2$ is selected from the group consisting of cyano, hydroxy, nitro, a carbonic acid, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, it is substituted by phosphate, substituted by urea, or substituted by carbonate.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, q is an integer of 0. In some embodiments, q is an integer of 1. In some embodiments, q is an integer of 2. In some embodiments, q is an integer of 3. In some embodiments, q is an integer of 4.

In some embodiments of the compound of Formula I, $R^3$ is a member selected from the group consisting of hydrogen, unsubstituted or substituted alkyl, unsubstituted or substituted alkenyl, and unsubstituted or substituted alkynyl. In some embodiments, $R^3$ is unsubstituted or substituted aryl, unsubstituted or substituted heteroaryl, unsubstituted or substituted cycloalkyl, or unsubstituted or substituted heterocycloalkyl. In some embodiments, $R^3$ is unsubstituted or substituted alkoxy, unsubstituted or substituted amido, unsubstituted or substituted amino. In some embodiments, $R^3$ is unsubstituted or substituted acyl, unsubstituted or substituted acyloxy, unsubstituted or substituted alkoxycarbonyl, or unsubstituted or substituted sulfonamido. In some embodiments, $R^3$ is halo, which is —I, —F, —Cl, or —Br.

In some embodiments, $R^3$ is selected from the group consisting of cyano, hydroxy, and nitro. In some embodiments, when $R^3$ is alkyl, $R^3$ is methyl, ethyl, propyl, isopropyl, n-butyl, tert-butyl, sec-butyl, pentyl, hexyl or heptyl. In some embodiments, $R^3$ is —$CF_3$.

In some embodiments, when $R^3$ is alkyl, alkenyl, alkynyl, aryl, heteroaryl, cycloalkyl, heterocycloalkyl, alkoxy, amido, amino, acyl, acyloxy, alkoxycarbonyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments of the compound of Formula I, $R^5$ is hydrogen, unsubstituted or substituted alkyl (including but not limited to unsubstituted or substituted $C_1$-$C_4$alkyl). In some embodiments, $R^5$ is unsubstituted or substituted alkenyl including but not limited to unsubstituted or substituted $C_2$-$C_5$alkenyl. In some embodiments, $R^5$ is unsubstituted or substituted alkynyl including but not limited to unsubstituted or substituted $C_2$-$C_5$alkynyl. In some embodiments, $R^5$ is unsubstituted or substituted cycloalkyl including but not limited to unsubstituted or substituted $C_3$-$C_5$cycloalkyl. In some embodiments, $R^5$ is unsubstituted or substituted heterocycloalkyl. In some embodiments, $R^5$ is unsubstituted or substituted heteroalkyl including but not limited to unsubstituted or substituted $C_1$-$C_4$heteroalkyl. In some embodiments, $R^5$ is unsubstituted or substituted alkoxy including but not limited to unsubstituted or substituted $C_1$-$C_4$alkoxy. In some embodiments, $R^5$ is unsubstituted or substituted amido including but not limited to unsubstituted or substituted $C_1$-$C_4$amido. In some embodiments, $R^5$ is unsubstituted or substituted amino. In some embodiments, $R^5$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^5$ is halo, which is —I, —F, —Cl, or —Br. In some embodiments, $R^5$ is selected from the group consisting of cyano, hydroxy, and nitro. In some other embodiments, $R^5$ is —$CH_3$, —$CH_2CH_3$, n-propyl, isopropyl, —$OCH_3$, —$OCH_2CH_3$, or —$CF_3$.

In some embodiments, when $R^5$ is alkyl, alkenyl, alkynyl, cycloalkyl, heteroalkyl, acyl, alkoxy, amido, amino, acyloxy, alkoxycarbonyl, or sulfonamido, $R^5$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments of the compound of Formula I, $R^6$ is hydrogen, unsubstituted or substituted alkyl (including but not limited to unsubstituted or substituted $C_1$-$C_4$alkyl). In some embodiments, $R^6$ is unsubstituted or substituted alkenyl including but not limited to unsubstituted or substituted $C_2$-$C_5$alkenyl. In some embodiments, $R^6$ is unsubstituted or substituted alkynyl including but not limited to unsubstituted or substituted $C_2$-$C_5$alkynyl. In some embodiments, $R^6$ is unsubstituted or substituted cycloalkyl including but not limited to unsubstituted or substituted $C_3$-$C_5$cycloalkyl. In some embodiments, $R^6$ is unsubstituted or substituted heterocycloalkyl. In some embodiments, $R^6$ is unsubstituted or substituted heteroalkyl including but not limited to unsubstituted or substituted $C_1$-$C_4$heteroalkyl. In some embodiments, $R^6$ is unsubstituted or substituted alkoxy including but not limited to unsubstituted or substituted $C_1$-$C_4$alkoxy. In some embodiments, $R^6$ is unsubstituted or substituted amido including but not limited to unsubstituted or substituted $C_1$-$C_4$amido. In some embodiments, $R^6$ is unsubstituted or substituted amino. In some embodiments, $R^6$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^6$ is halo, which is —I, —F, —Cl, or —Br. In some embodiments, $R^6$ is selected from the group consisting of cyano, hydroxy, and nitro. In some other embodiments, $R^6$ is —$CH_3$, —$CH_2CH_3$, n-propyl, isopropyl, —$OCH_3$, —$OCH_2CH_3$, or —$CF_3$.

In some embodiments, when $R^6$ is alkyl, alkenyl, alkynyl, cycloalkyl, heteroalkyl, acyl, alkoxy, amido, amino, acyloxy, alkoxycarbonyl, or sulfonamido, $R^6$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments of the compound of Formula I, $R^7$ is hydrogen, unsubstituted or substituted alkyl (including but not limited to unsubstituted or substituted $C_1$-$C_4$alkyl). In some embodiments, $R^7$ is unsubstituted or substituted alkenyl including but not limited to unsubstituted or substituted $C_2$-$C_5$alkenyl. In some embodiments, $R^7$ is unsubstituted or substituted alkynyl including but not limited to unsubstituted or substituted $C_2$-$C_5$alkynyl. In some embodiments, $R^7$ is unsubstituted or substituted cycloalkyl including but not limited to unsubstituted or substituted $C_3$-$C_5$cycloalkyl. In some embodiments, $R^7$ is unsubstituted or substituted heterocycloalkyl. In some embodiments, $R^7$ is unsubstituted or substituted heteroalkyl including but not limited to unsubstituted or substituted $C_1$-$C_4$heteroalkyl. In some embodiments, $R^7$ is unsubstituted or substituted alkoxy including but not limited to unsubstituted or substituted $C_1$-$C_4$alkoxy. In some embodiments, $R^7$ is unsubstituted or substituted amido including but not limited to unsubstituted or substituted $C_1$-$C_4$amido. In some embodiments, $R^7$ is unsubstituted or substituted amino. In some embodiments, $R^7$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^7$ is halo, which is —I, —F, —Cl, or —Br. In some embodiments, $R^7$ is selected from the group consisting of cyano, hydroxy, and nitro. In some other embodiments, $R^7$ is —$CH_3$, —$CH_2CH_3$, n-propyl, isopropyl, —$OCH_3$, —$OCH_2CH_3$, or —$CF_3$.

In some embodiments, when $R^7$ is alkyl, alkenyl, alkynyl, cycloalkyl, heteroalkyl, acyl, alkoxy, amido, amino, acyloxy, alkoxycarbonyl, or sulfonamido, $R^7$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments of the compound of Formula I, $R^8$ is hydrogen, unsubstituted or substituted alkyl (including but not limited to unsubstituted or substituted $C_1$-$C_4$alkyl). In some embodiments, $R^8$ is unsubstituted or substituted alkenyl including but not limited to unsubstituted or substituted $C_2$-$C_5$alkenyl. In some embodiments, $R^8$ is unsubstituted or substituted alkynyl including but not limited to unsubstituted or substituted $C_2$-$C_5$alkynyl. In some embodiments, $R^8$ is unsubstituted or substituted cycloalkyl including but not limited to unsubstituted or substituted $C_3$-$C_5$cycloalkyl. In some embodiments, $R^8$ is unsubstituted or substituted heterocycloalkyl. In some embodiments, $R^8$ is unsubstituted or substituted heteroalkyl including but not limited to unsubstituted or substituted $C_1$-$C_4$heteroalkyl. In some embodiments, $R^8$ is unsubstituted or substituted alkoxy including but not limited to unsubstituted or substituted $C_1$-$C_4$alkoxy. In some embodiments, $R^8$ is unsubstituted or substituted amido including but not limited to unsubstituted or substituted $C_1$-$C_4$amido. In some embodiments, $R^8$ is unsubstituted or substituted amino. In some embodiments, $R^8$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^8$ is halo, which is —I, —F, —Cl, or —Br. In some embodiments, $R^8$ is selected from the group consisting of cyano, hydroxy, and nitro. In some other embodiments, $R^8$ is —$CH_3$, —$CH_2CH_3$, n-propyl, isopropyl, —$OCH_3$, —$OCH_2CH_3$, or —$CF_3$.

In some embodiments, when $R^8$ is alkyl, alkenyl, alkynyl, cycloalkyl, heteroalkyl, acyl, alkoxy, amido, amino, acyloxy, alkoxycarbonyl, or sulfonamido, $R^8$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments of the compound of Formula I, $R^5$, $R^6$, $R^7$, and $R^8$ are H and the compound has a structure of Formula I-1:

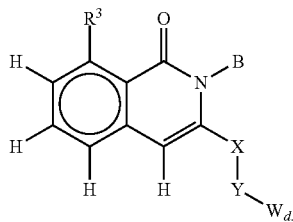

Formula I-1

In some embodiments of the compound of Formula I, X is absent. In some embodiments, X is —$(CH(R^9))z$, and z is an integer of 1, 2, 3 or 4.

In some embodiments, $R^9$ is unsubstituted or substituted alkyl including but not limited to unsubstituted or substituted $C_1$-$C_{10}$alkyl. In some embodiments, $R^9$ is unsubstituted or substituted cycloalkyl including but not limited to unsubstituted or substituted $C_3$-$C_7$cycloalkyl. In some embodiments, $R^9$ is ethyl, methyl or hydrogen. In some embodiments, $R^9$ is unsubstituted or substituted heterocycloalkyl including but not limited to unsubstituted or substituted $C_2$-$C_{10}$heteroalkyl. In some embodiments, $R^9$ is unsubstituted or substituted heteroalkyl including but not limited to unsubstituted or substituted $C_2$-$C_{10}$heteroalkyl.

The invention also provides a compound of Formula I wherein $R^9$ is hydrogen, and X is —$CH_2$—, —$CH_2CH_2$—, —$CH_2CH_2CH_2$—, —$CH(CH_3)$—, or —$CH(CH_2CH_3)$—. In other embodiments, X is —$(CH(R^9))_z$, $R^9$ is not hydrogen, and z is an integer of 1. When X is —$CH(R^9)$— and $R^9$ is not hydrogen, then the compound can adopt either an (S)- or (R)-stereochemical configuration with respect to carbon X. In some embodiments, the compound is a racemic mixture of (S)- and (R) isomers with respect to carbon X. In other embodiments, the present invention provides a mixture of compounds of Formula I wherein individual compounds of the mixture exist predominantly in an (S)- or (R)-isomeric configuration. For example, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In some other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture contains identical chemical entities except for their stereochemical orientations, namely (S)- or (R)-isomers. For instance, in the compounds of Formula I, when X is —$CH(R^9)$—, and $R^9$ is not hydrogen, then the —$CH(R^9)$— is in an (S)- or (R)-sterochemical orientation for each of the identical chemical entities. In some embodiments, the mixture of identical chemical entities of Formula I is a racemic mixture of (S)- and (R)-isomers at the carbon represented by X. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric purity greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound of Formula I, X is —CH($R^9$)—, $R^9$ is methyl or ethyl, and the compound is the (S)-isomer.

In some embodiments of the compound of Formula I, Y is absent. In some embodiments, Y is —O—, —S—, —S(=O)—, —S(=O)$_2$—, —C(=O)—, —N($R^9$)(C=O)—, —N($R^9$)(C=O)NH—, —N($R^9$)C($R^9$)$_2$— (such as —N($R^9$)CH$_2$—, specifically —N(CH$_3$)CH$_2$—, N(CH(CH$_3$)$_2$)CH$_2$— or N(CH$_2$CH$_3$)CH$_2$—), —N($R^9$)—, —N(CH$_3$)—, —N(CH$_2$CH$_3$)—, or —N(CH(CH$_3$)$_2$)—. In some embodiments, Y is —C(=O)—(CHR$^9$)$_z$— and z is an integer of 1, 2, 3, or 4.

In some embodiments, at least one of X and Y is present. In some embodiments of the compound of Formula I, —XY— is —CH$_2$—, —CH$_2$—N(CH$_3$), —CH$_2$—N(CH$_2$CH$_3$), —CH(CH$_3$)—NH—, (S)—CH(CH$_3$)—NH—, or (R)—CH(CH$_3$)—NH—. In other embodiments, X—Y is —N(CH$_3$)—CH$_2$—, N(CH$_2$CH$_3$) CH$_2$—, —N(CH(CH$_3$)$_2$) CH$_2$—, or —NHCH$_2$—. The invention provides other compounds of Formula I wherein when X—Y is X is —(CH($R^9$))$_z$N($R^9$)—, z is an integer of 1, 2, 3 or 4, and —N($R^9$)— is not —NH—, then —XY— is not connected to purinyl.

In some embodiments, $W_d$ in a formula disclosed herein (including but not limited to I, I-1, IV, IV-A, V, V-A, V-A2, V-B, VI and VI-A), is a member selected from the group consisting of unsubstituted or substituted heterocycloalkyl, unsubstituted or substituted aryl, and unsubstituted or substituted heteroaryl.

In various embodiments, $W_d$ is unsubstituted or substituted monocyclic heteroaryl (including but not limited to pyrimidinyl, pyrrolyl, pyrazinyl, triazinyl, or pyridazinyl) or unsubstituted or substituted bicyclic heteroaryl.

In some embodiments, $W_d$ is a monocyclic heteroaryl of the following formula:

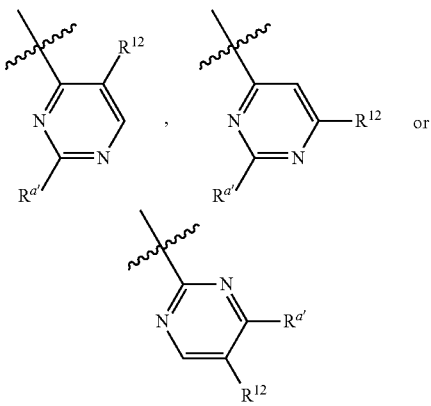

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

The invention provides monocyclic heteroaryl $W_d$ including but not limited to one of the following formulae:

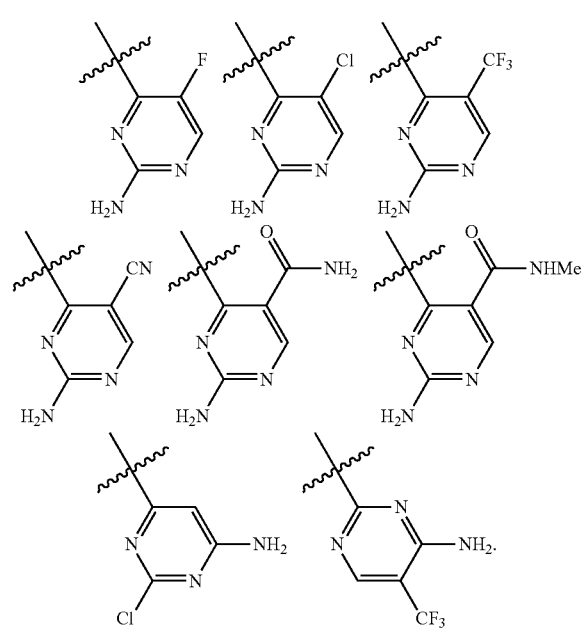

In some embodiments, $W_d$ in a formula disclosed herein (including but not limited to I, I-1, IV, IV-A, V, V-A, V-A2, V-B, VI and VI-A), is a bicyclic heteroaryl having at least one heteroatom, e.g., a bicyclic heteroaryl having at least one nitrogen ring atom. In some embodiments, $W_d$ is a bicyclic heteroaryl having at least two heteroatoms, e.g., a bicyclic heteroaryl having at least two nitrogen ring atoms. In some embodiments, $W_d$ is a bicyclic heteroaryl having two heteroatoms in the ring which is connected to XY. In some embodiments, $W_d$ is a bicyclic heteroaryl having two nitrogen ring atoms in the ring to which XY is connected. In some embodiments, $W_d$ is a bicyclic heteroaryl having four heteroatoms, e.g, a bicyclic heteroaryl having four nitrogen ring atoms. In some embodiments, $W_d$ is unsubstituted or substituted 4-amino-1H-pyrazolo[3,4-d]pyrimidin-1-yl, unsubstituted or substituted 7-amino-2-methyl-2H-pyrazolo[4,3-d]pyrimidin-3-yl. unsubstituted or substituted 6-methylenyl-9H-purin-6-yl, or unsubstituted or substituted 6-amino-9H-purin-9-yl.

In some embodiments $W_d$ is one of the following:

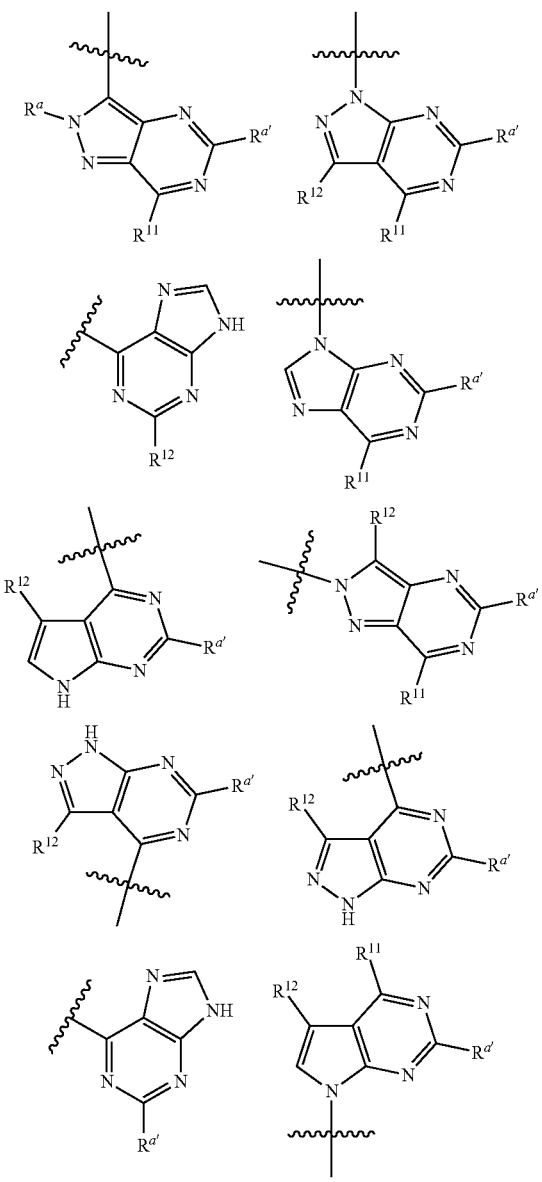
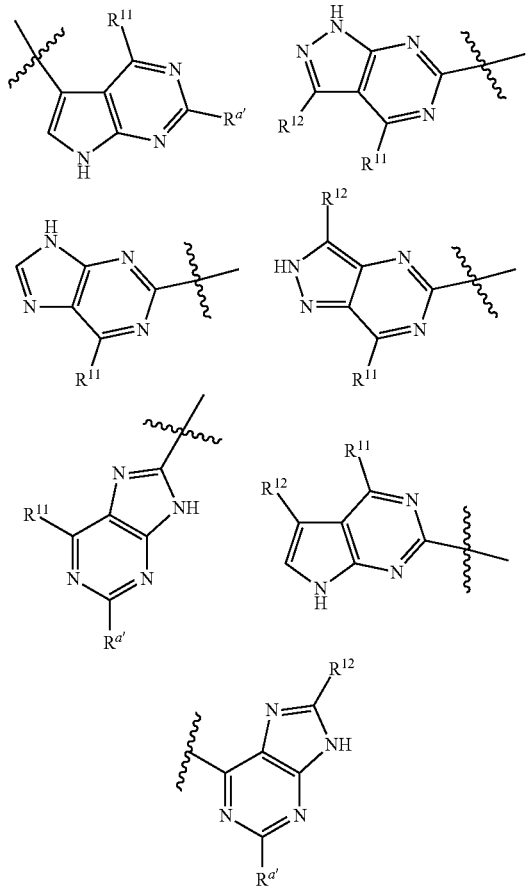

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl;

$R^{11}$ is hydrogen, unsubstituted or substituted alkyl, halo (which includes —I, —F, —Cl, or —Br), unsubstituted or substituted amino, unsubstituted or substituted amido, hydroxy, or unsubstituted or substituted alkoxy, phosphate, unsubstituted or substituted urea, or carbonate; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

In some embodiments of $W_d$ of the compounds of Formula I, when $R^{a'}$ is alkyl, alkynyl, cycloalkyl, heteroalkyl, or heterocycloalkyl, it is substituted by phosphate, urea, or carbonate.

In some embodiments of $W_d$ of the compounds of Formula I, when $R^{11}$ is alkyl, amino, amido, hydroxy, or alkoxy, it is substituted by phosphate, urea, or carbonate.

In some embodiments of the compound of Formula I, —X—Y—W$_d$ is one of the following moieties:
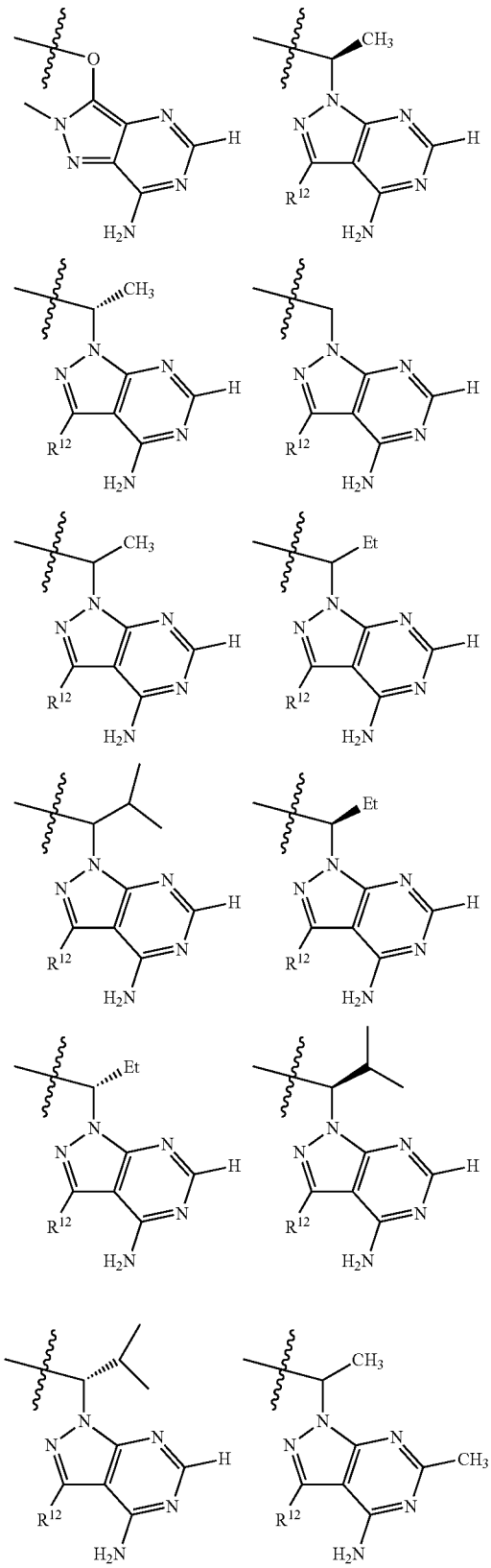
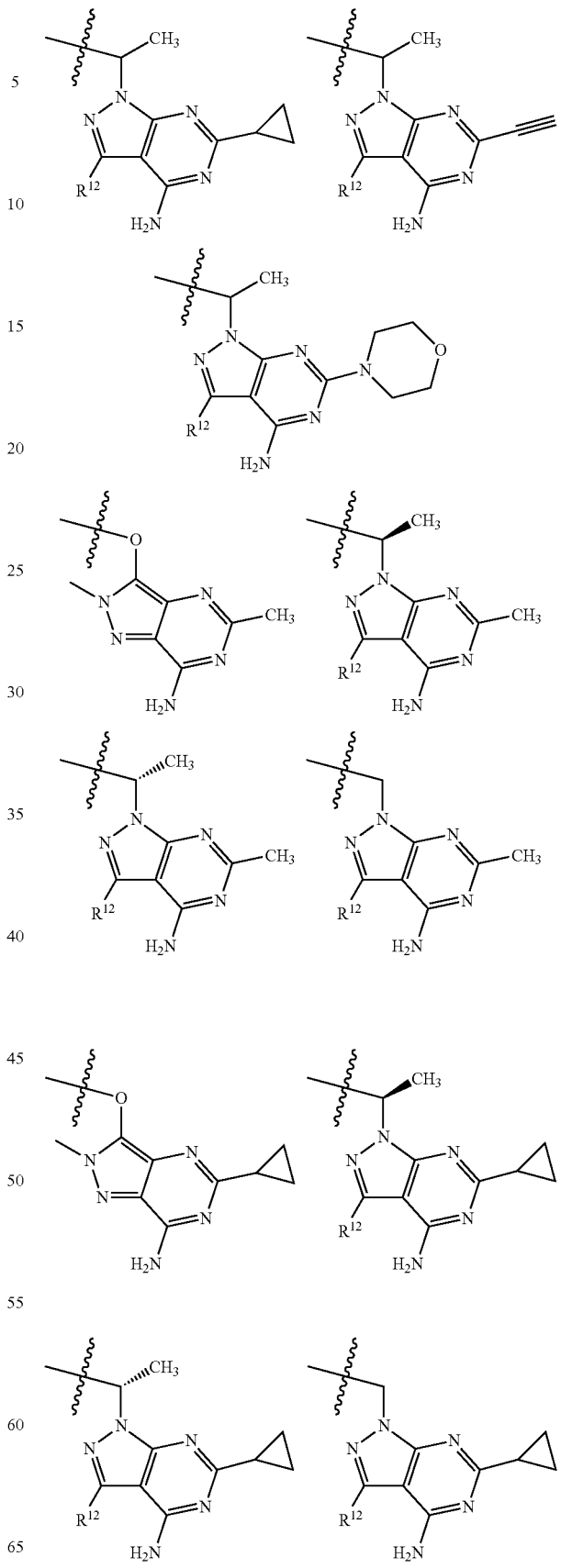

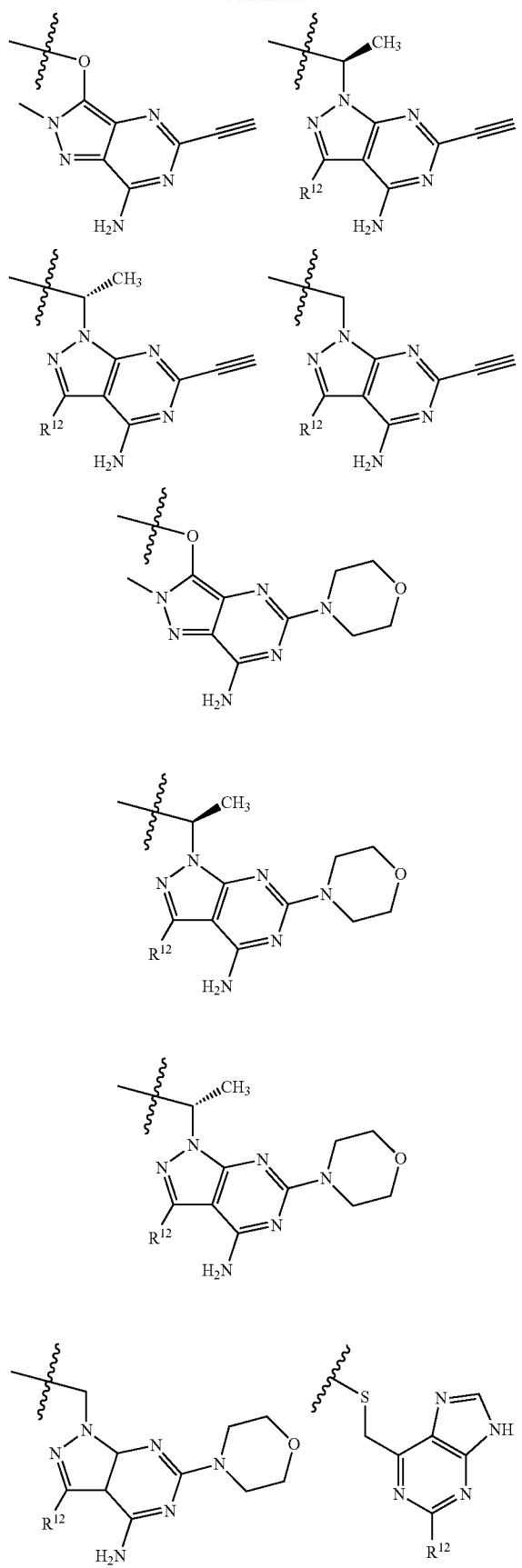
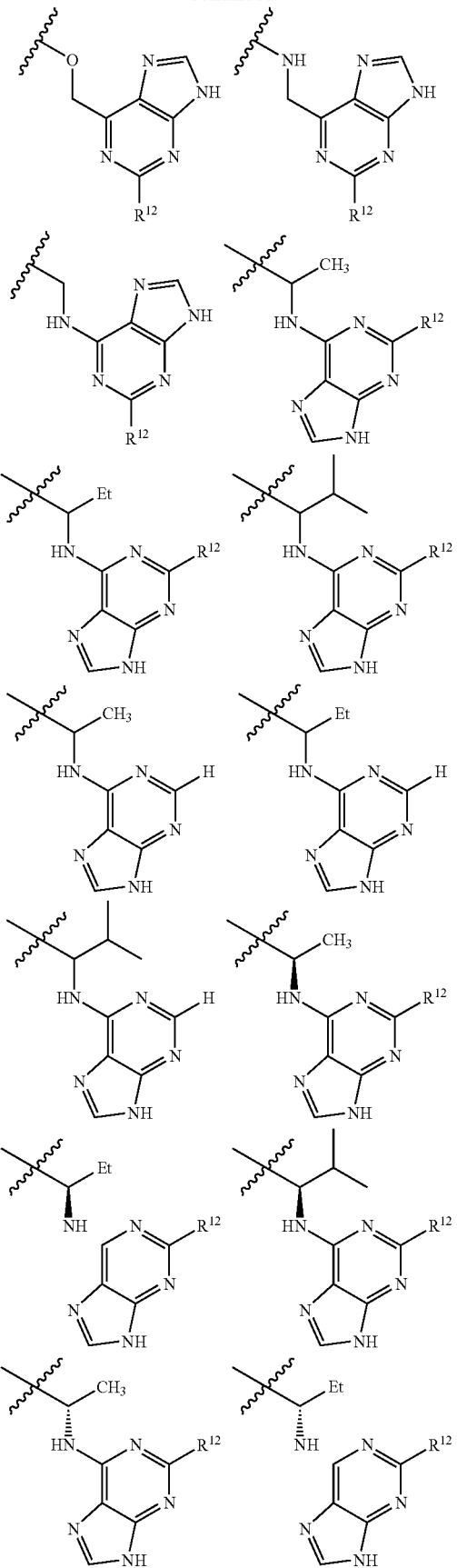

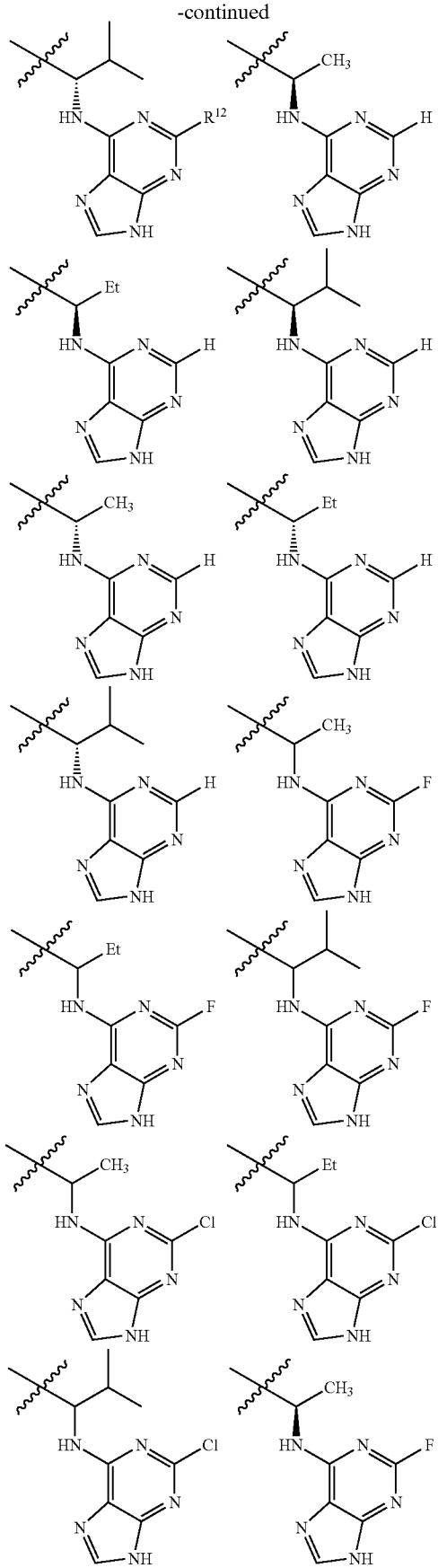
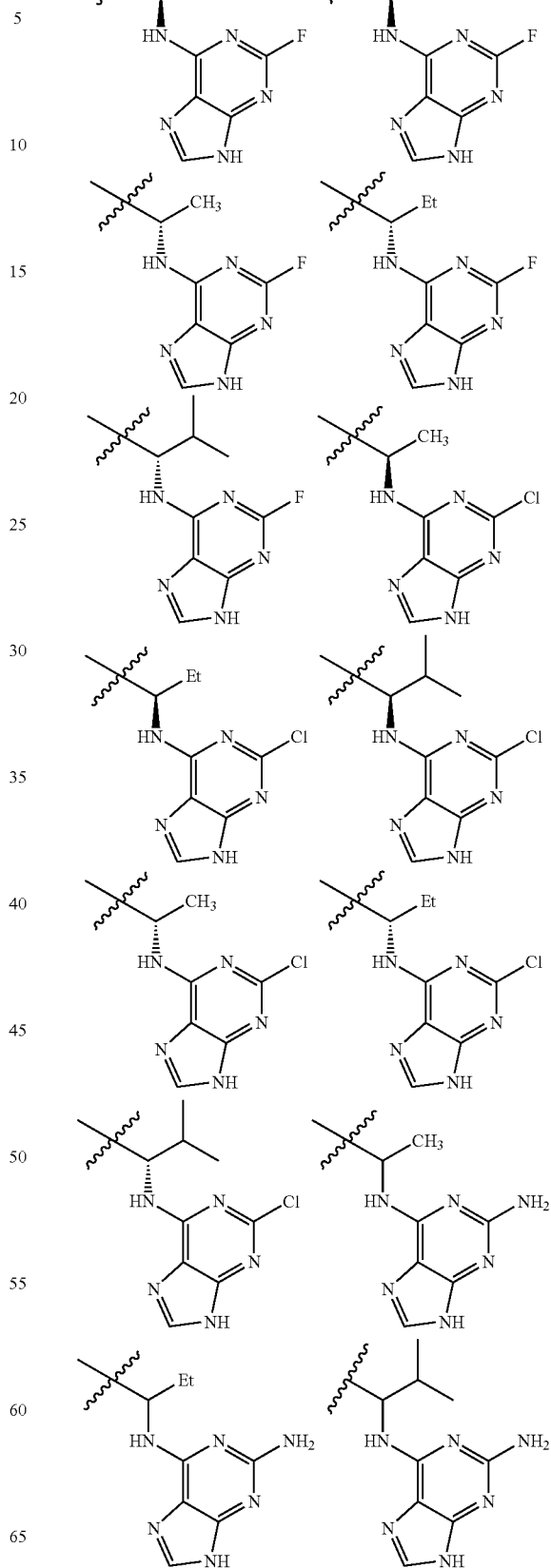

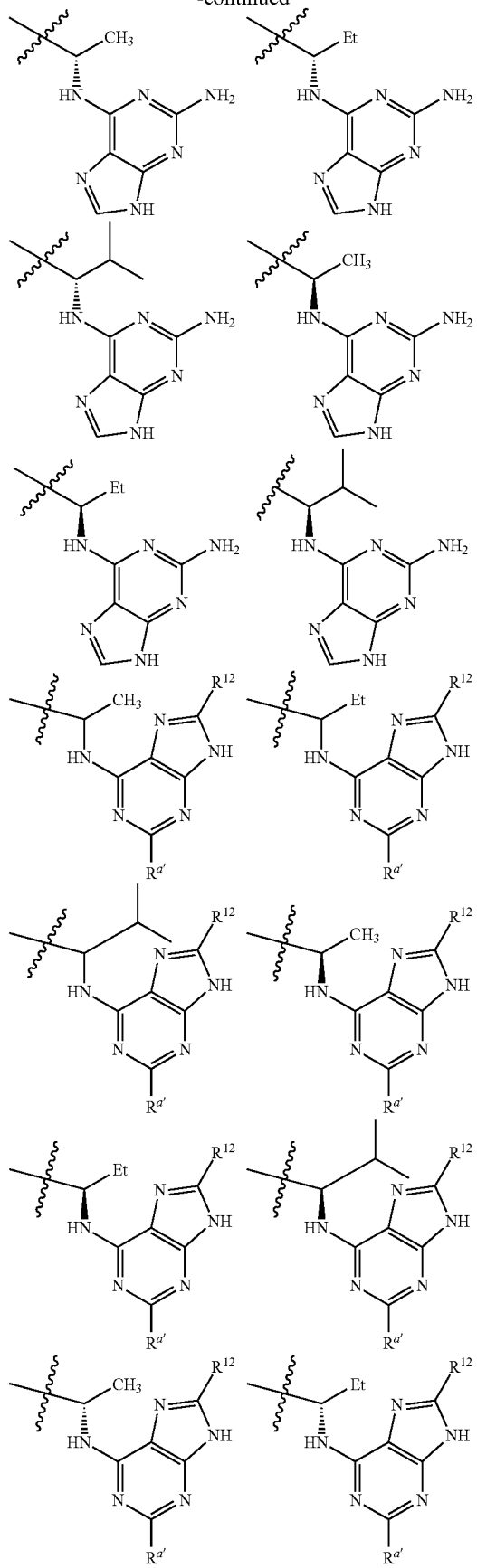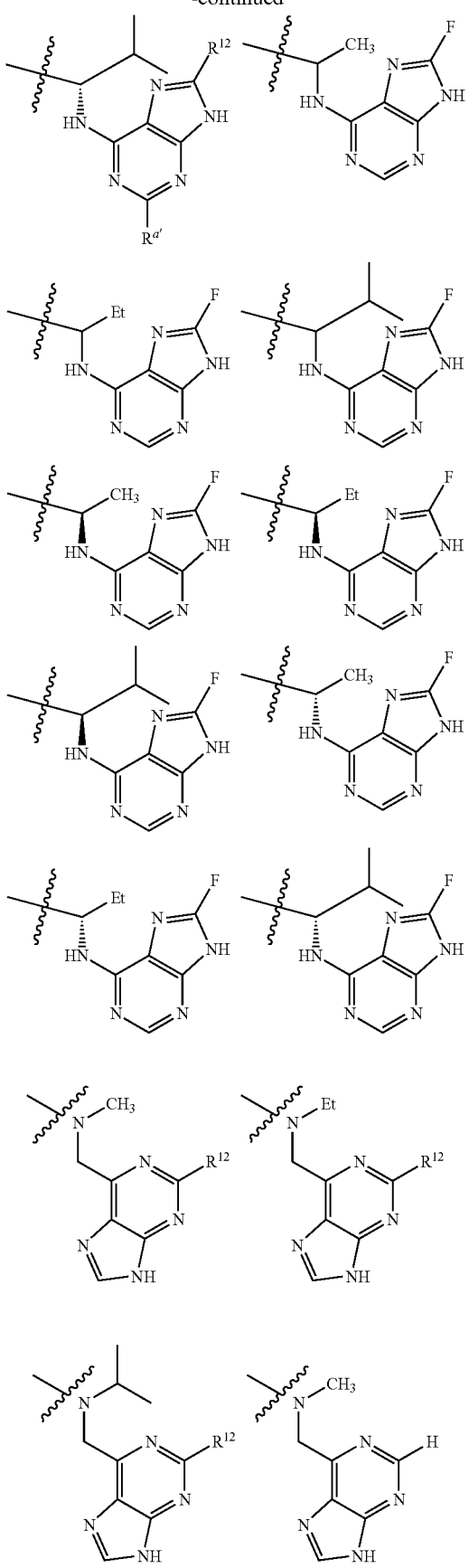

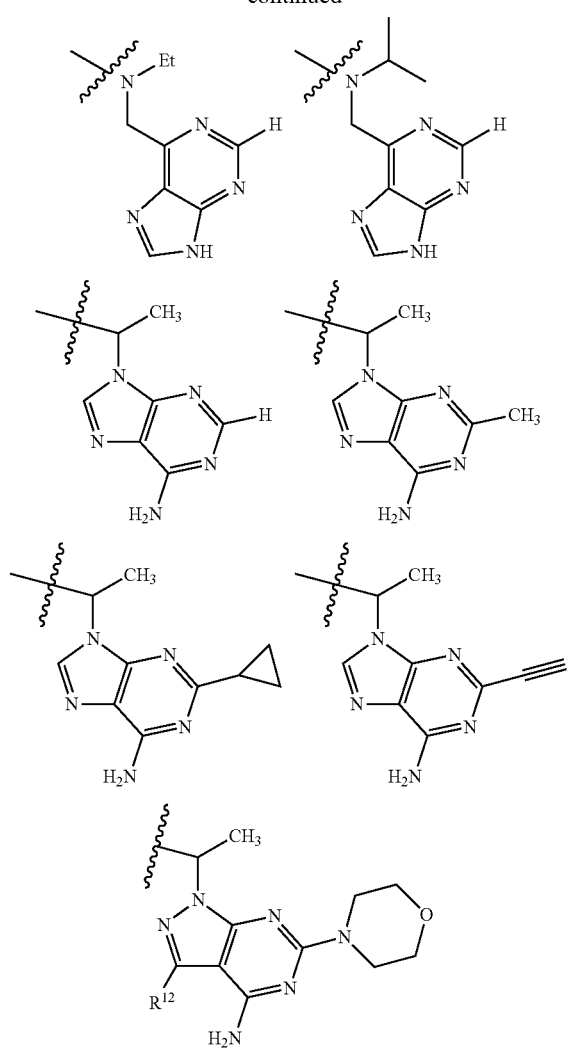
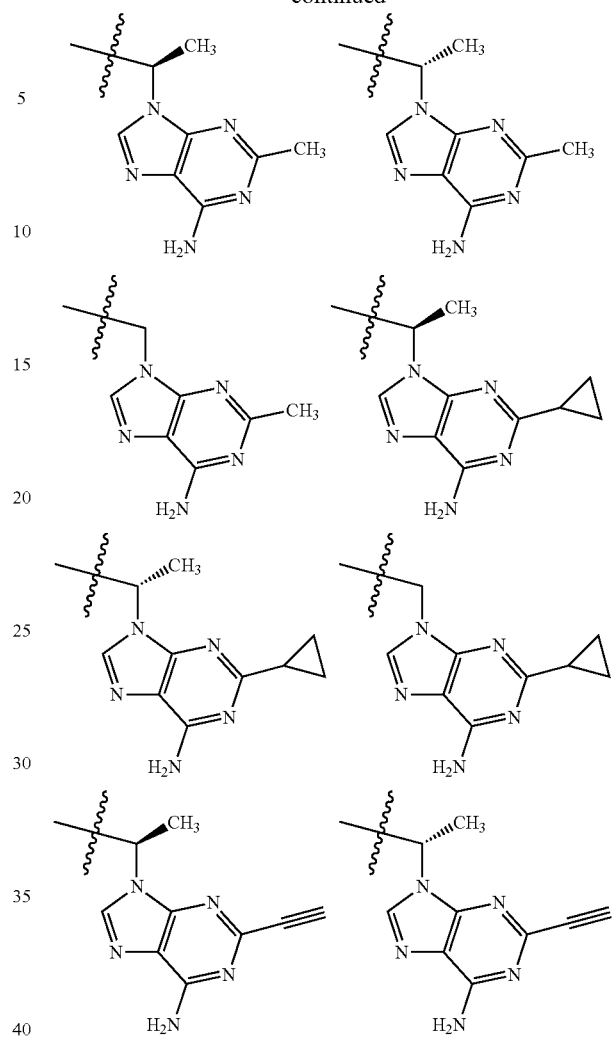
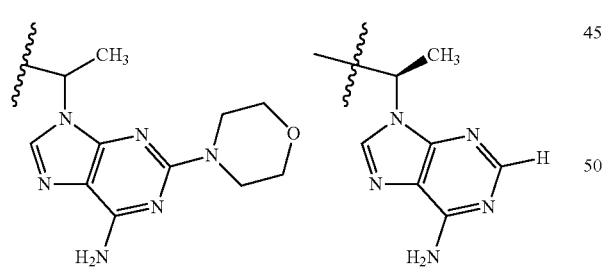
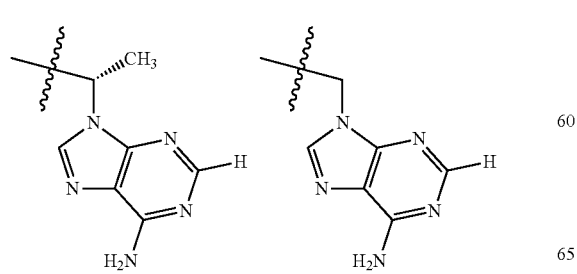
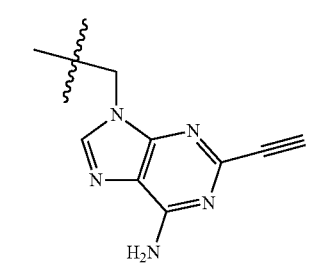
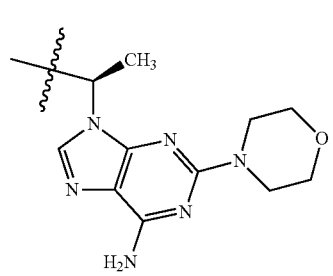

-continued
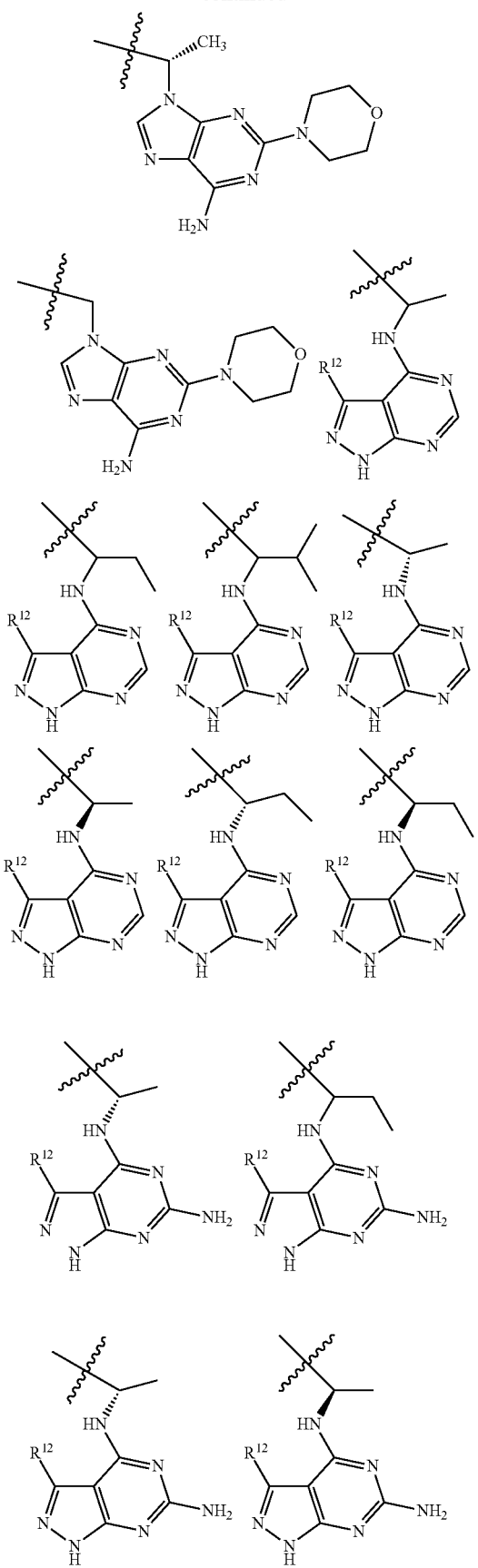
-continued
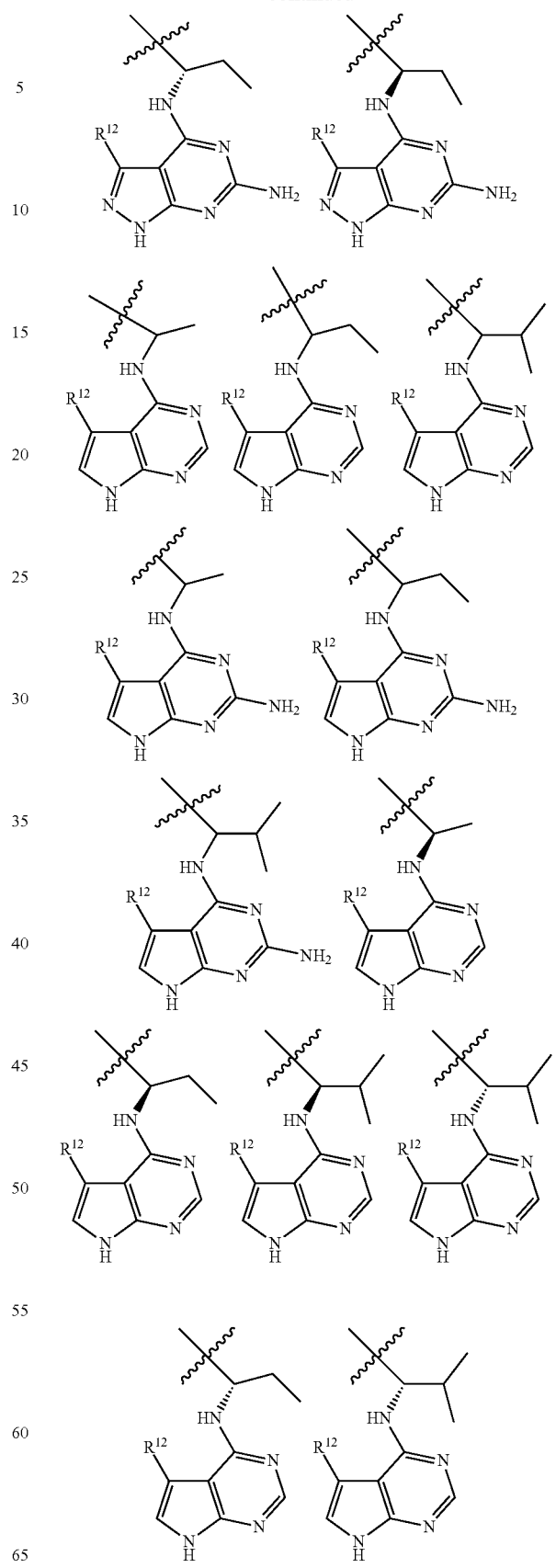

-continued
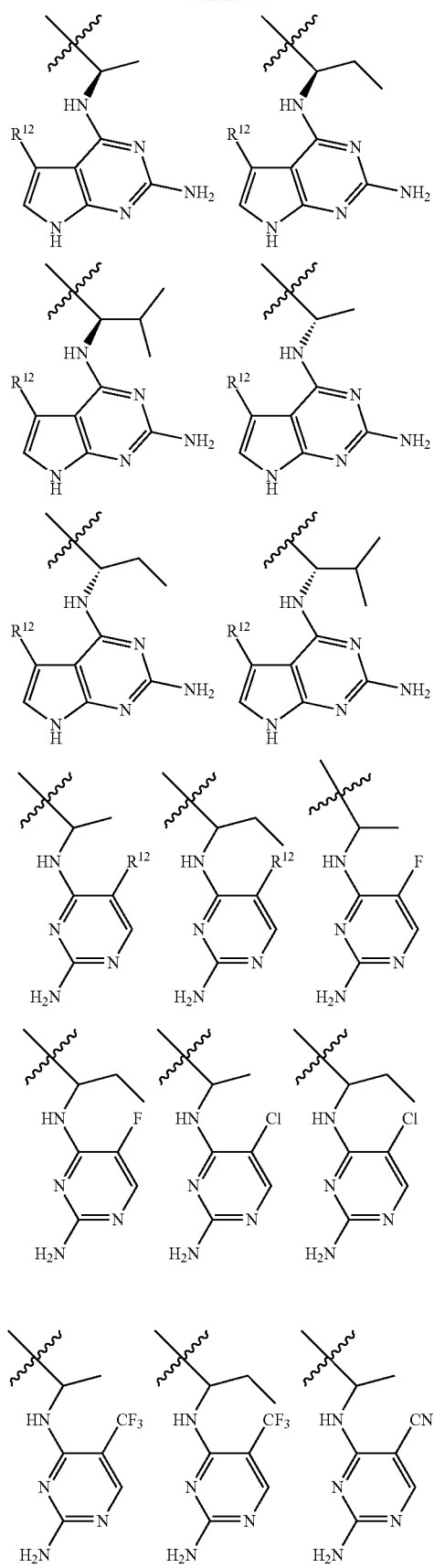
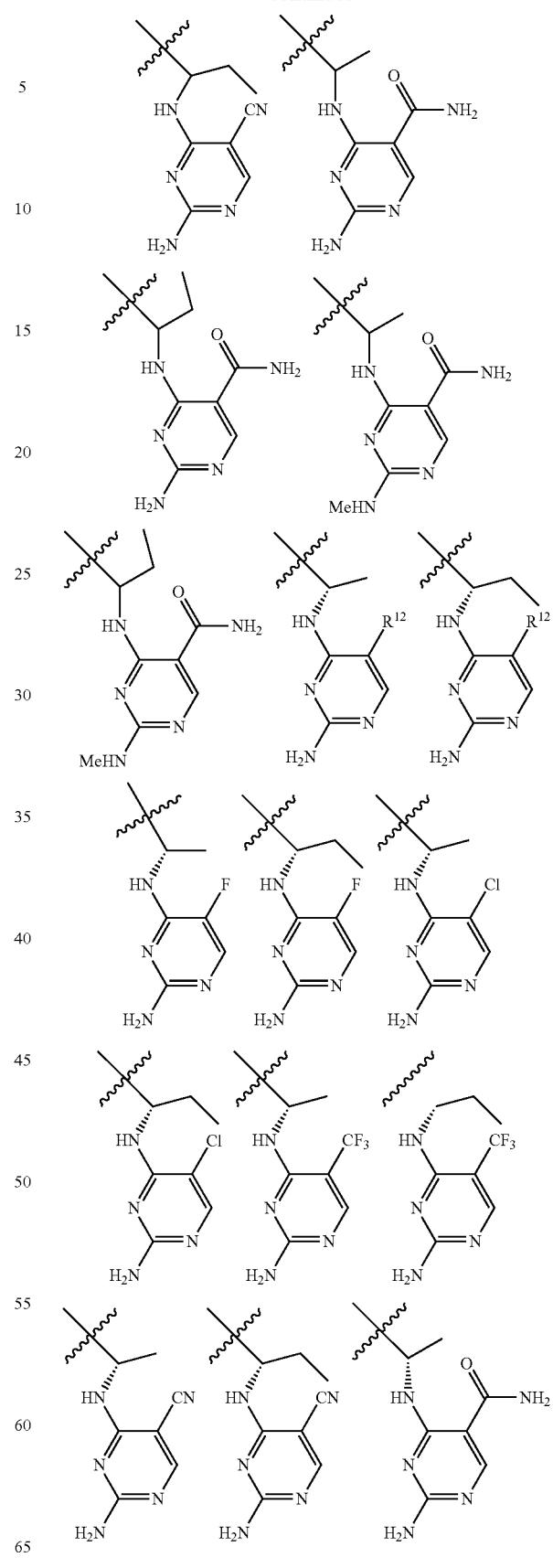

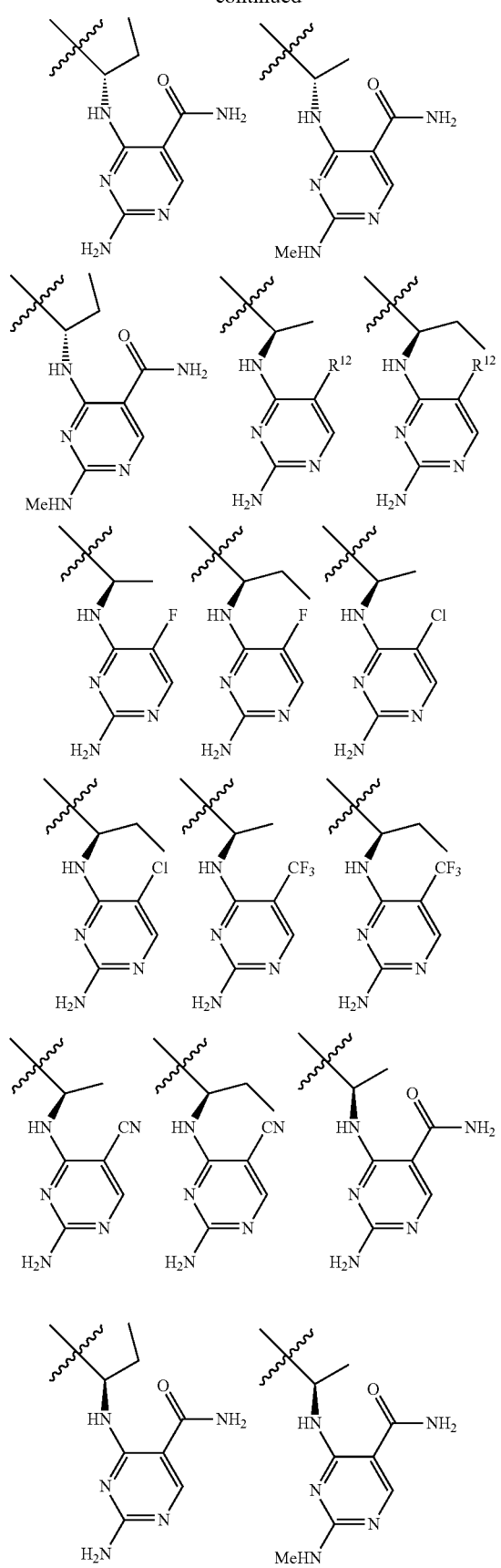
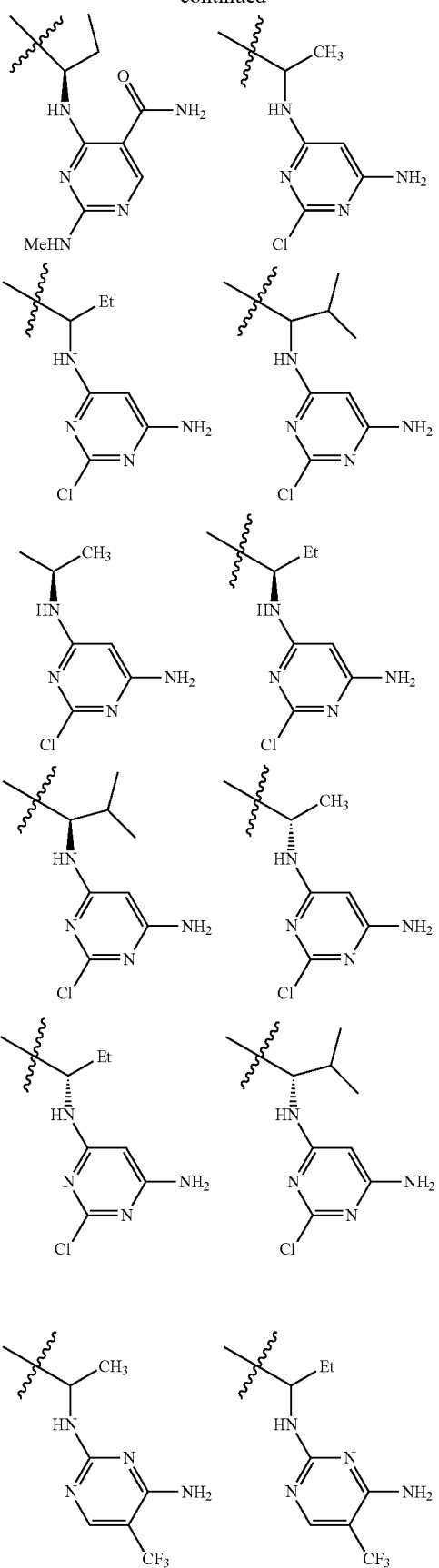

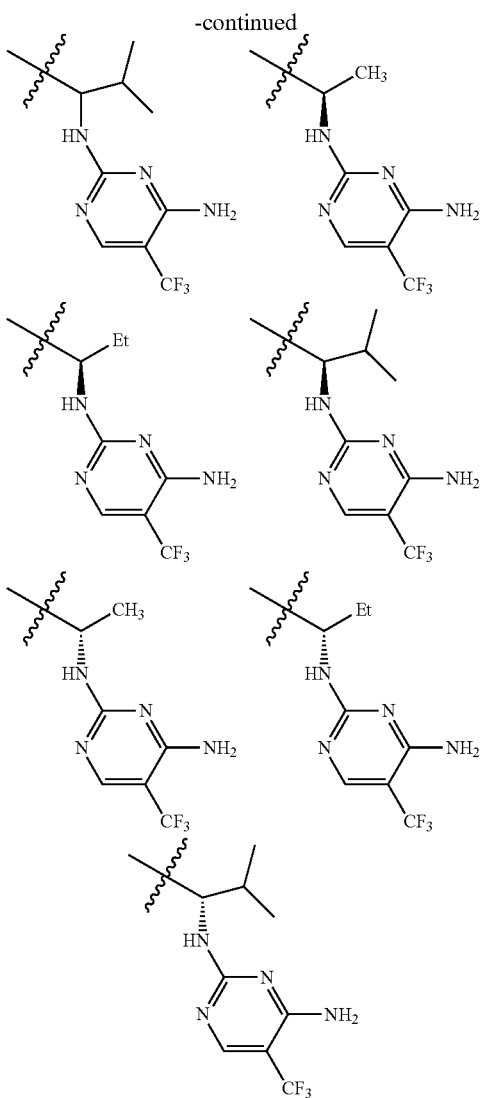

cycloalkyl ring. In some embodiments, $R^{12}$ is unsubstituted or substituted amido, carboxylic acid, unsubstituted or substituted acyloxy, unsubstituted or substituted alkoxycarbonyl, unsubstituted or substituted acyl, or unsubstituted or substituted sulfonamido.

In some embodiments, when $R^{12}$ is alkyl, alkynyl, alkenyl, aryl, heteroaryl, heterocycloalkyl, or cycloalkyl, it is substituted with phosphate. In some embodiments, when $R^{12}$ is alkyl, alkynyl, alkenyl, aryl, heteroaryl, heterocycloalkyl, or cycloalkyl, it is substituted with urea. In some embodiments, when $R^{12}$ is alkyl, alkynyl, alkenyl, aryl, heteroaryl, heterocycloalkyl, or cycloalkyl, it is substituted with carbonate.

In some embodiments, when $R^{12}$ is alkyl, alkynyl, alkenyl, aryl, heteroaryl, heterocycloalkyl, cycloalkyl, alkoxycarbonyl, amido, acyloxy, acyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, aloxycarbonyl, or sulfonamido may itself be substituted.

In some embodiments of the compound of Formula I, $R^{12}$ of $W_d$ is one of the following moieties:

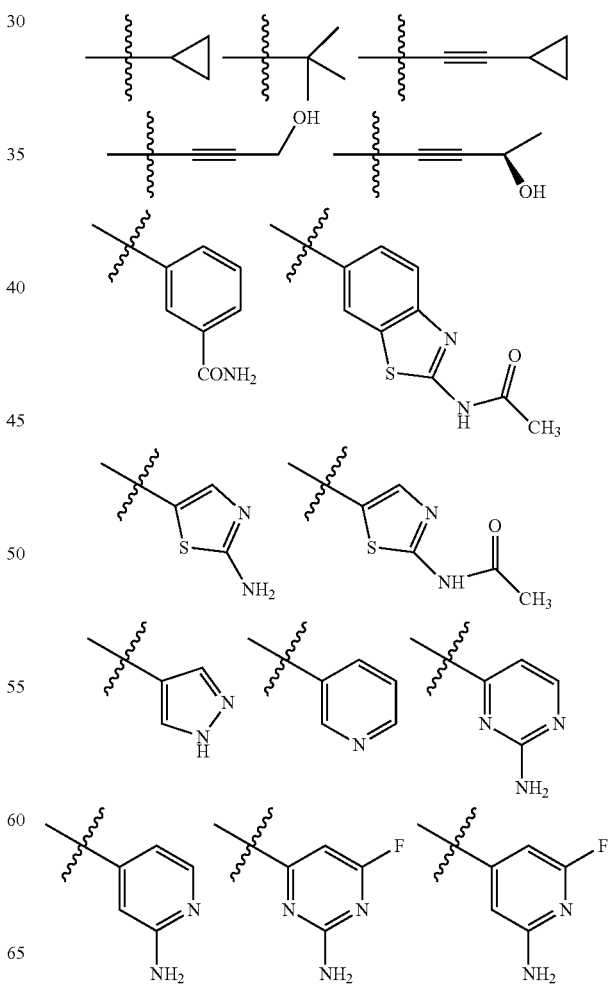

In some embodiments of the compound of Formula I, $R^{12}$ is a member of the group consisting of hydrogen, cyano, halo, unsubstituted or substituted alkyl, unsubstituted or substituted alkynyl, and unsubstituted or substituted alkenyl. In some embodiments, $R^{12}$ is unsubstituted or substituted aryl. In some embodiments, $R^{12}$ is unsubstituted or substituted heteroaryl, which includes but is not limited to heteroaryl having a 5 membered ring, heteroaryl having a six membered ring, heteroaryl with at least one nitrogen ring atom, heteroaryl with two nitrogen ring atoms, monocylic heteroaryl, and bicylic heteroaryl. In some embodiments, $R^{12}$ is unsubstituted or substituted heterocycloalkyl, which includes but is not limited to heterocycloalkyl with one nitrogen ring atom, heterocycloalkyl with one oxygen ring atom, $R^{12}$ is heterocycloalkyl with one sulfur ring atom, 5 membered heterocycloalkyl, 6 membered heterocycloalkyl, saturated heterocycloalkyl, unsaturated heterocycloalkyl, heterocycloalkyl having an unsaturated moiety connected to the heterocycloalkyl ring, heterocycloalkyl substituted by oxo, and heterocycloalkyl substituted by two oxo. In some embodiments, $R^{12}$ is unsubstituted or substituted cycloalkyl, including but not limited to cyclopropyl, cyclobutyl, cyclopentyl, cyclohexyl, cycloalkyl substituted by one oxo, cycloalkyl having an unsaturated moiety connected to the

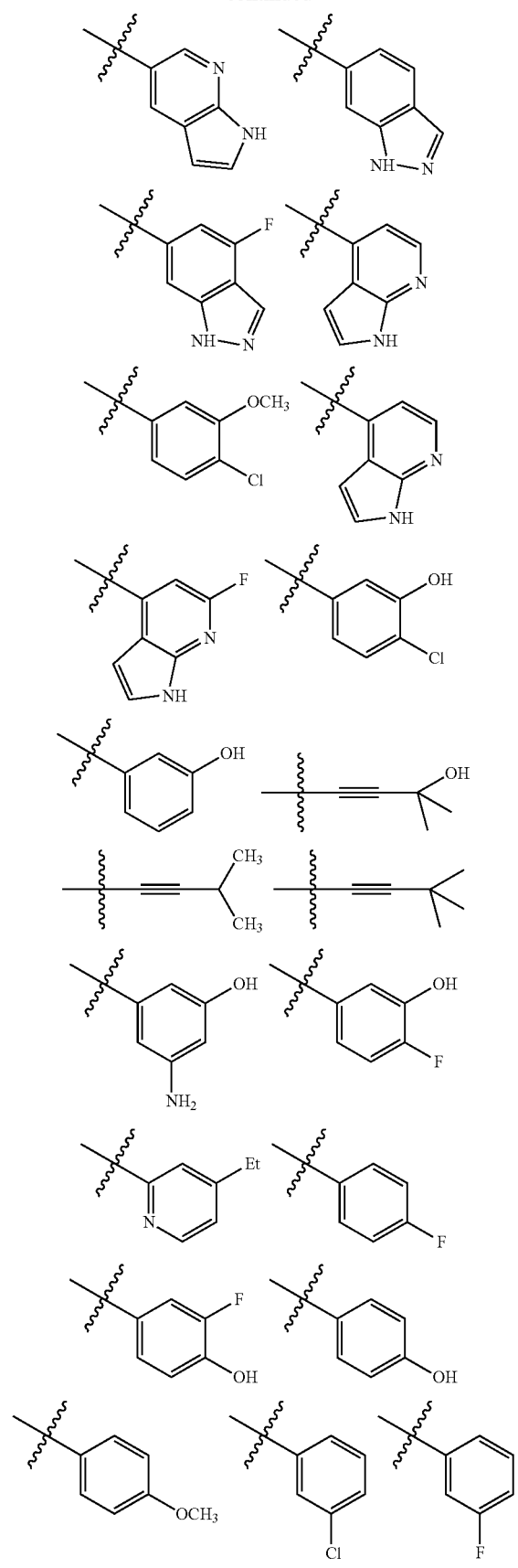
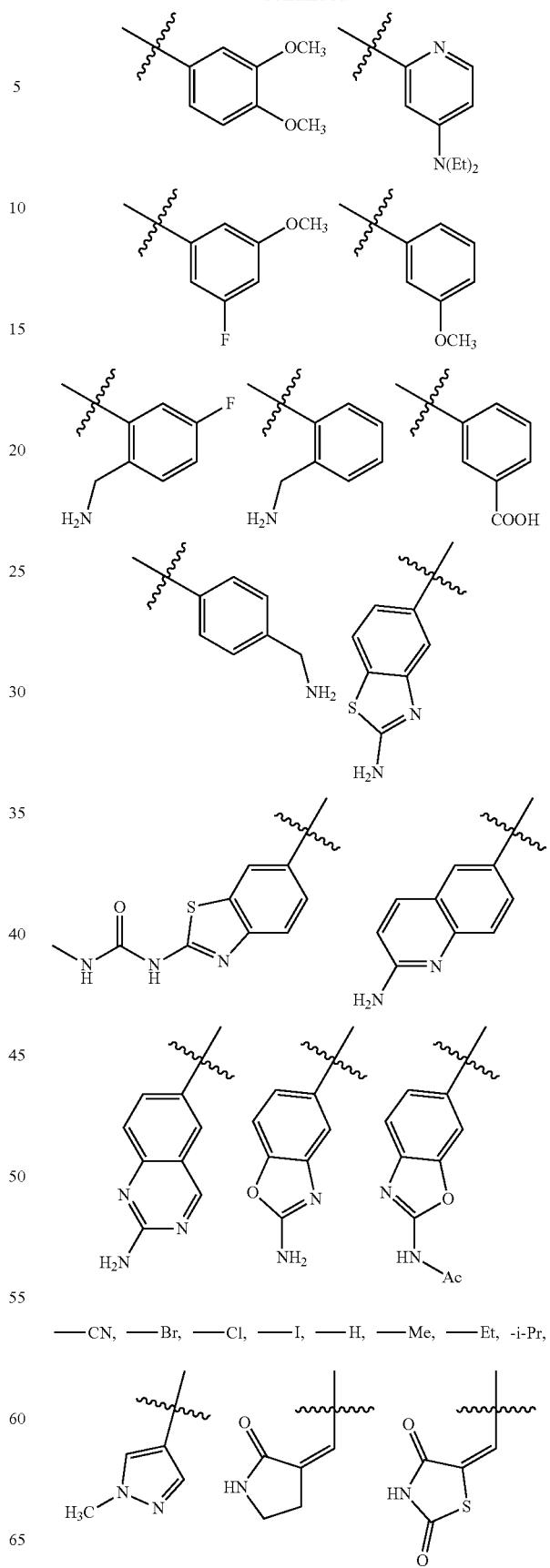

-continued

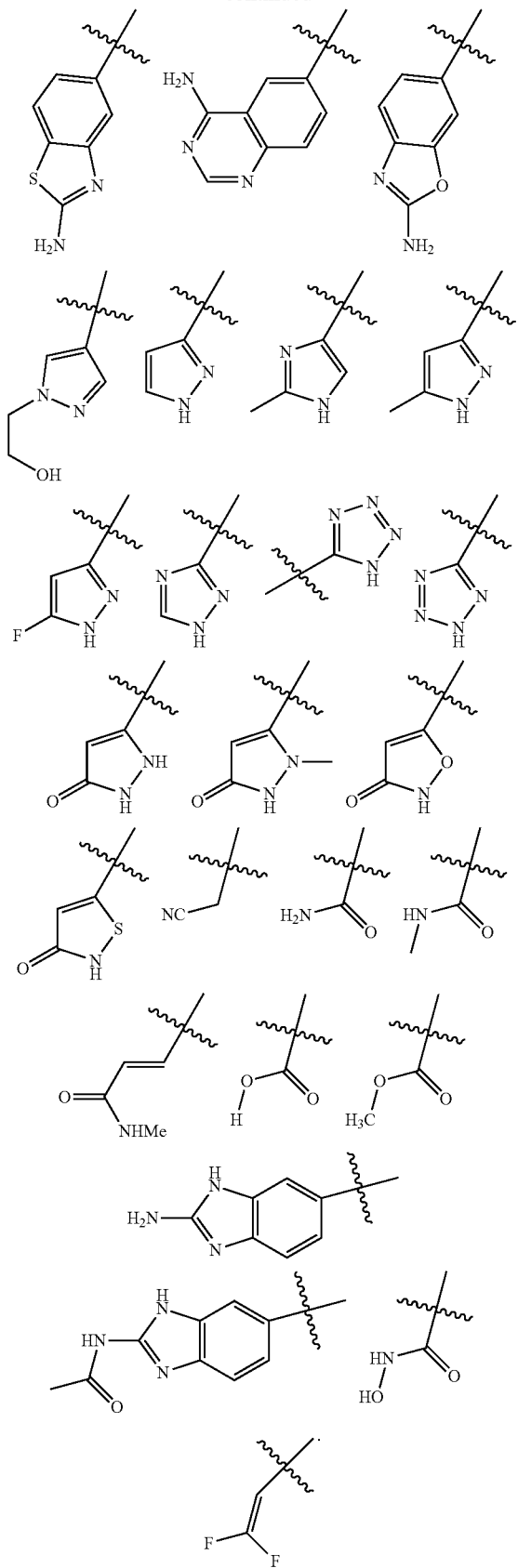

In some embodiments of the compound of Formula I, $W_d$ is a pyrazolopyrimidine of Formula III:

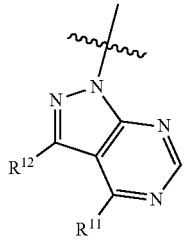

Formula III wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, carboxylic acid, acyloxy, alkoxycarbonyl, or amido.

In some embodiments of the invention, the compound of Formula I is a compound having a structure of Formula IV:

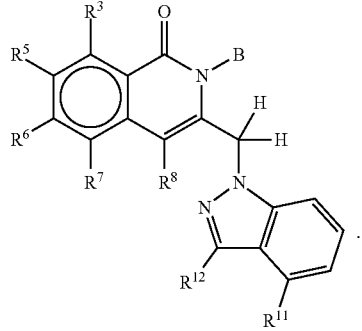

Formula IV

In some embodiments of the compound of Formula IV, $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In another embodiment, $R^{11}$ is amino and $R^{12}$ is alkyl, alkenyl, heteroaryl, aryl, or heterocycloalkyl. In some embodiments, $R^{11}$ is amino and $R^{12}$ is cyano, amino, carboxylic acid, alkoxycarbonyl, or amido.

In some embodiments, the compound of Formula IV is a compound of Formula IV-A:

Formula IV-A
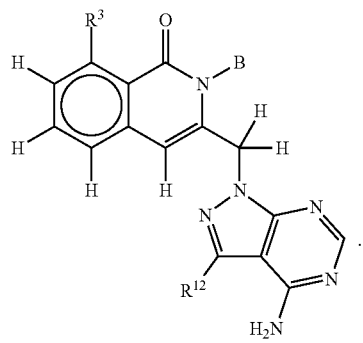
The invention also provides compounds of Formula I having a structure of any of Formulae V, V-A1, V-A2, V-B, VI, VI-A, VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, XIV-A2, XV-A, XV-A1, XV-A2, XVI-A, XVI-A1, XVI-A2, XVII-A, XVII-A1, XVII-A2, XVIII-A, XVIII-A1, or XVIII-A2:
Formula V
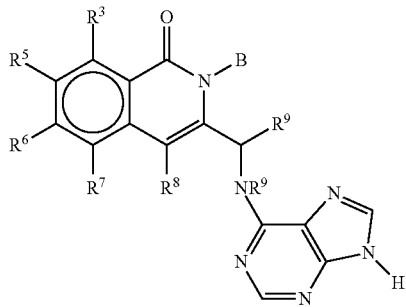
Formula V-A
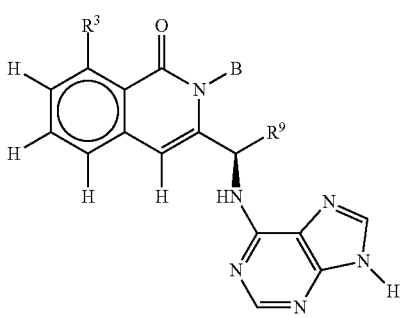
Formula V-A1
Formula V-A2
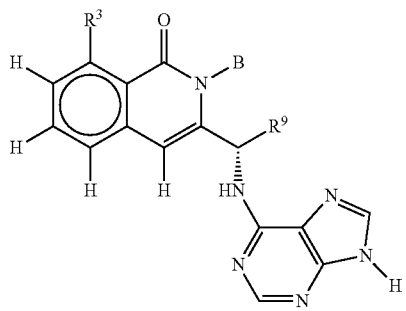
Formula V-B
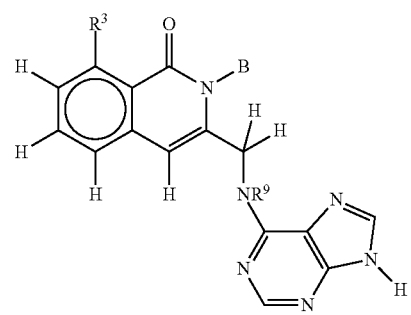
Formula VI
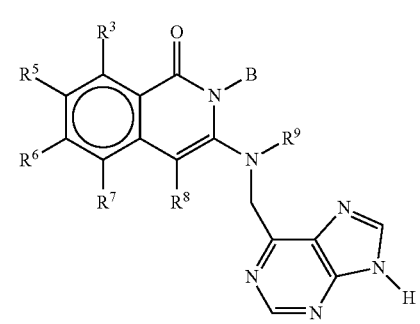
Formula VI-A
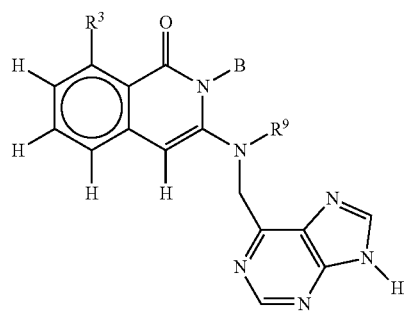
Formula VII-A
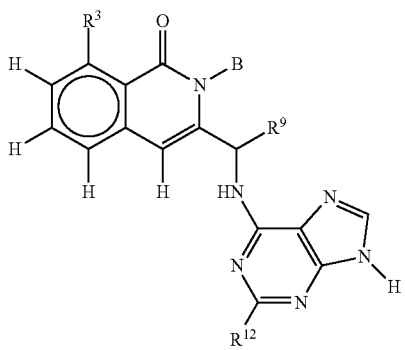

-continued
Formula VII-A1
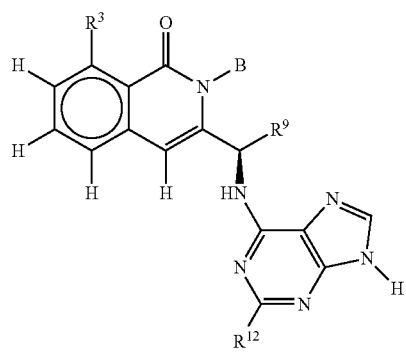
Formula VII-A2
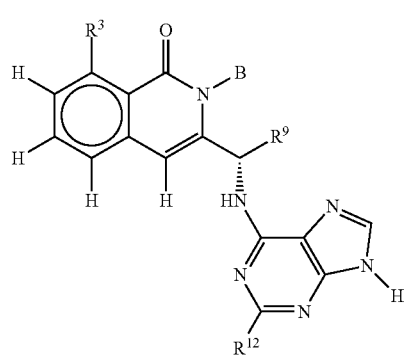
Formula VIII-A
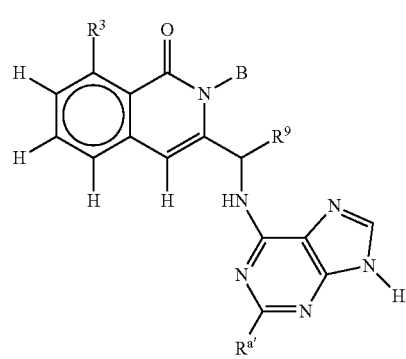
Formula VIII-A1
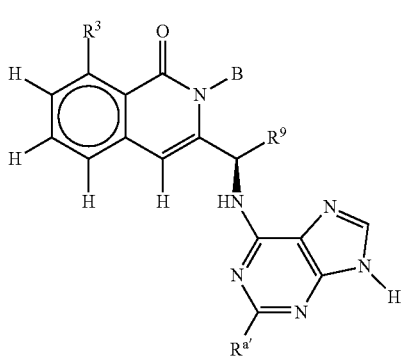
-continued
Formula VIII-A2
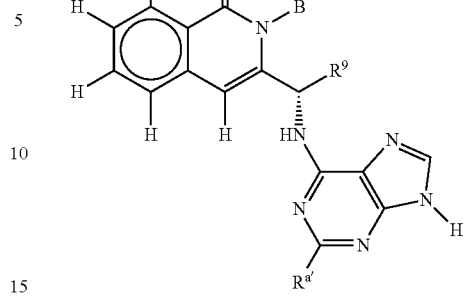
Formula IX-A
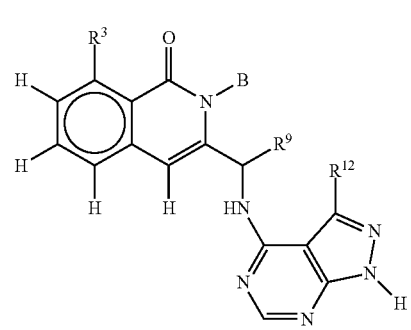
Formula IX-A1
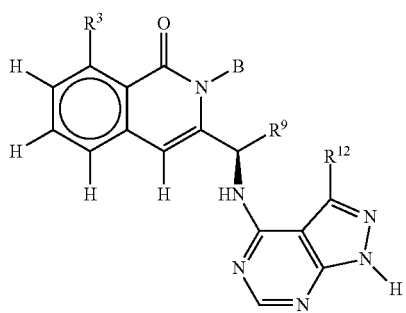
Formula IX-A2
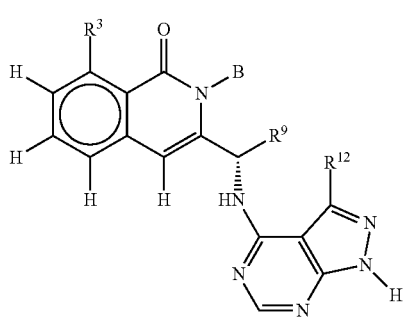
Formula X-A
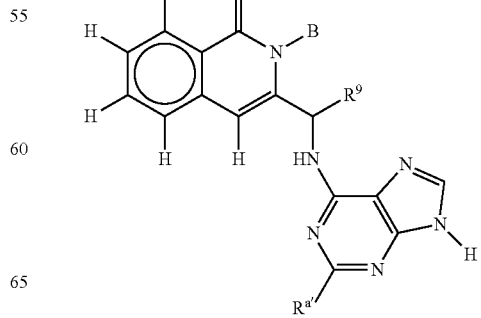

Formula X-A1
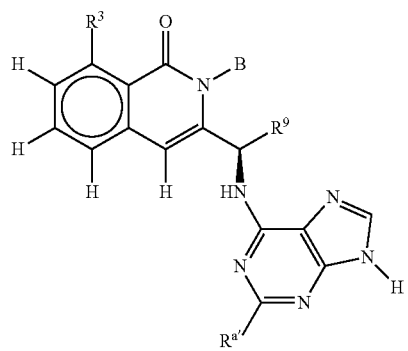
Formula X-A2
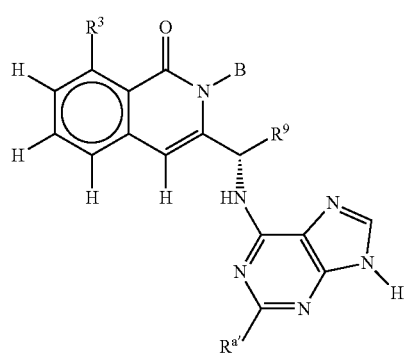
Formula XI-A
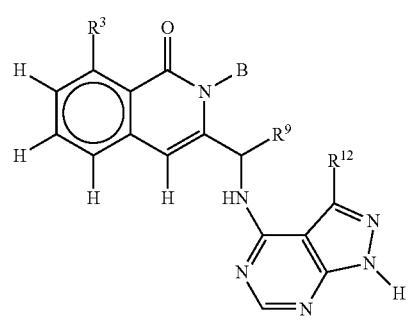
Formula XI-A1
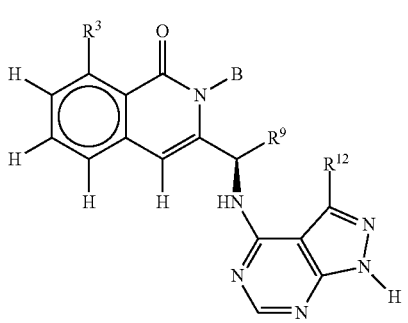
Formula XI-A2
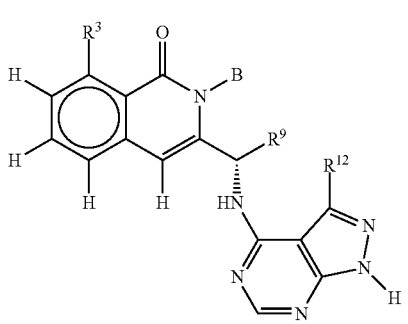
Formula XII-A
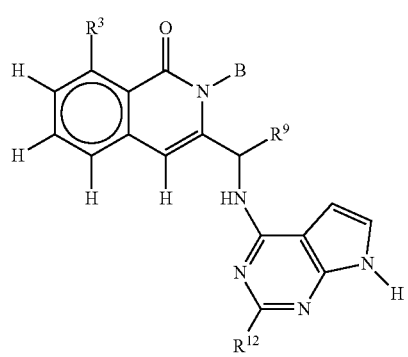
Formula XII-A1
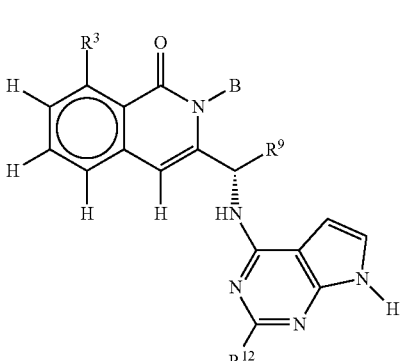
Formula XII-A2
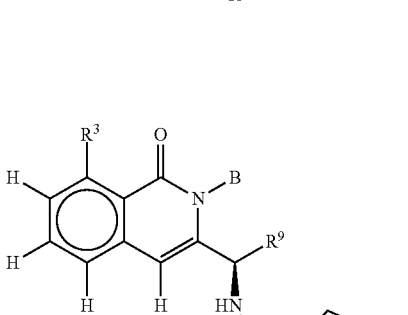
Formula XIII-A
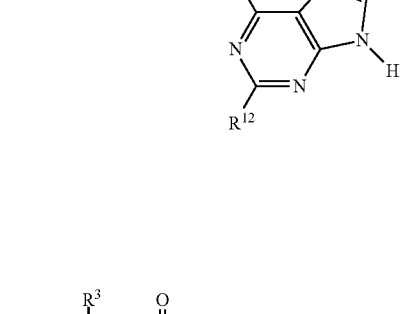

Formula XIII-A1
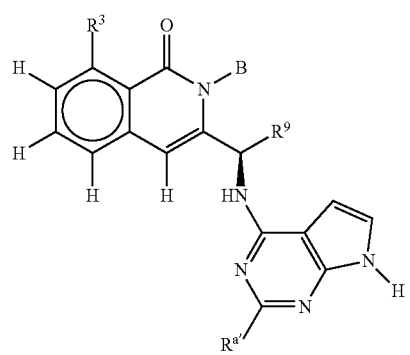
Formula XIII-A2
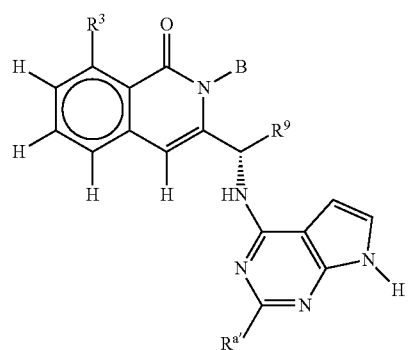
Formula XIV-A
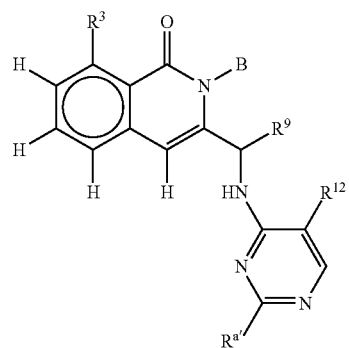
Formula XIV-A1
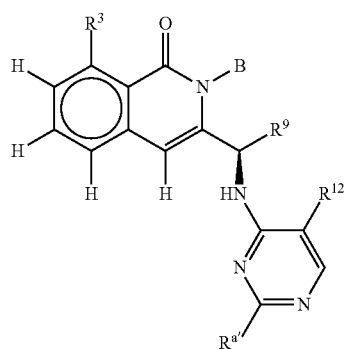
Formula XIV-A2
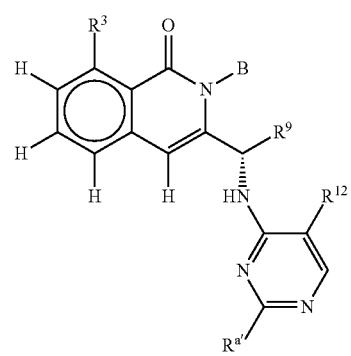
Formula XV-A
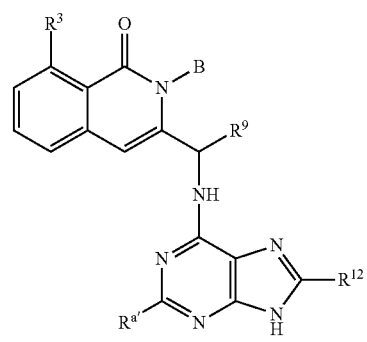
Formula XV-A1
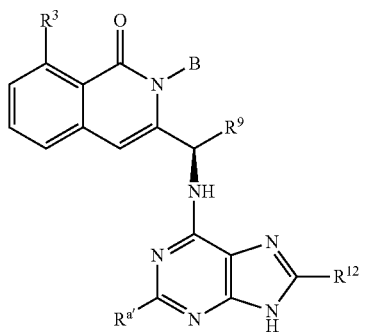
Formula XV-A2
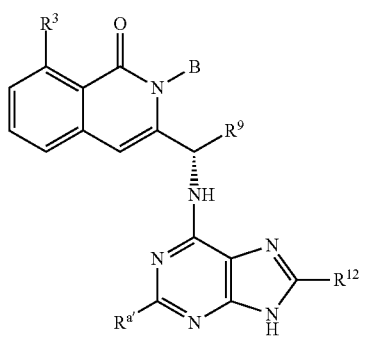

-continued
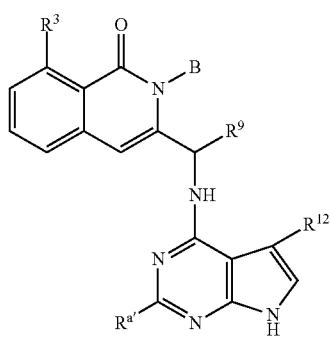
Formula XVI-A
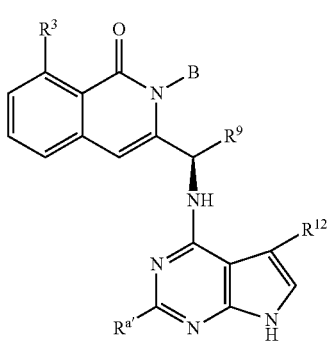
Formula XVI-A1
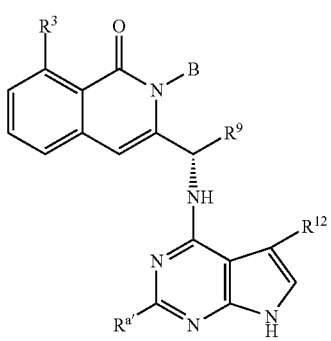
Formula XVI-A2
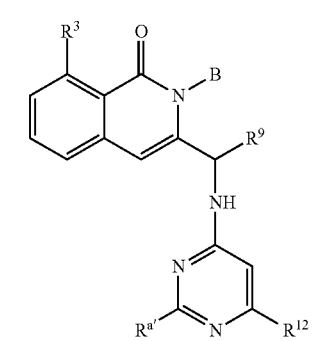
Formula XVII-A
-continued
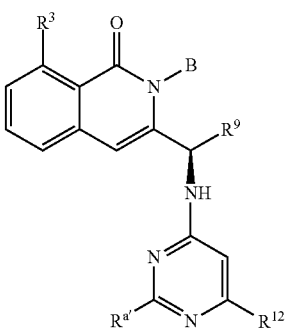
Formula XVII-A1
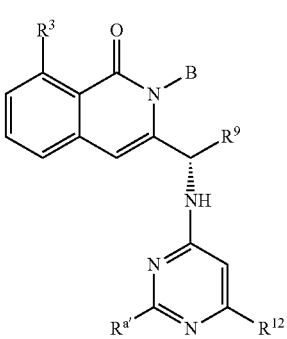
Formula XVII-A2
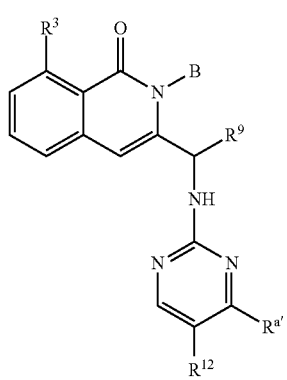
Formula XVIII-A
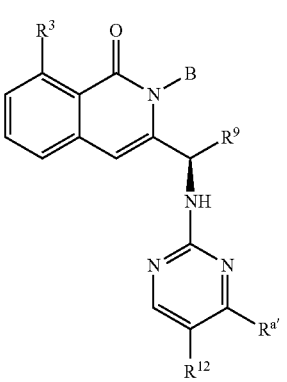
Formula XVIII-A1

-continued

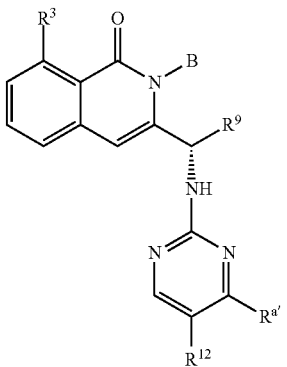

Formula XVIII-A2

Any of the disclosed elements and their substituents for the compounds of Formula I can be used in any combination.

In one aspect, for the compounds of Formula I, $R_3$ is H, $CH_3$, $CF_3$, Cl, or F; and B is a moiety of Formula II:

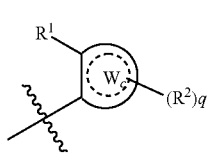

Formula II wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, or nitro; q is an integer of 0, 1, 2, 3, or 4; $R^5$, $R^6$, $R^7$, and $R^8$ are H; X is absent or $(CH_2)_z$; z is 1; Y is absent or —N($R^9$)—; $R^9$ is hydrogen, $C_1$-$C_{10}$alkyl, $C_3$-$C_7$cycloalkyl, or $C_2$-$C_{10}$heteroalkyl; at least one of X and Y is present; and $W_d$ is pyrazolopyrimidine or purine. In some embodiments, when X and Y are present and $W_d$ is purine, then —N($R^9$)— is —NH—.

In another aspect, for the compounds of Formula I, $R_3$ is H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; $R^5$, $R^6$, $R^7$, and $R^8$ are H; X is absent or $(CH_2)z$; z is 1; Y is absent or —N($R^9$)—; $R^9$ is hydrogen, methyl, or ethyl; at least one of X and Y is present; $W_d$ is:

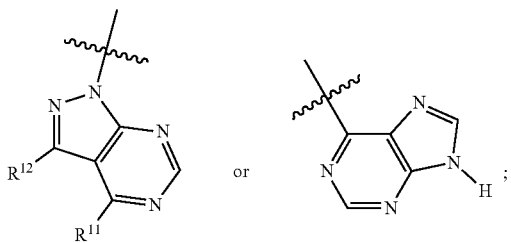

$R^{11}$ is amino; and $R^{12}$ is H, alkyl, alkynyl, alkenyl, halo, aryl, heteroaryl, heterocycloalkyl, or cycloalkyl. In some embodiments, when X and Y are present and $W_d$ is purine, then —N($R^9$)— is —NH—.

In another aspect, for the compounds of Formula I, $R_3$ is H, $CH_3$, $CF_3$, Cl, or F; B is a moiety of Formula II, which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; X is $(CH_2)_z$; z is 1; $R^5$, $R^6$, $R^7$, and $R^8$ are H; Y is absent and $W_d$ is:

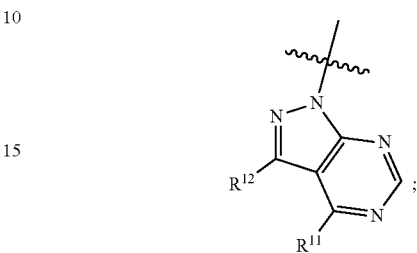

$R^{11}$ is amino; and $R^{12}$ is H, alkyl, alkynyl, alkenyl, halo, aryl, heteroaryl, heterocycloalkyl, or cycloalkyl.

In another aspect, $R_3$ is H, $CH_3$, $CF_3$, Cl, or F; B is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; $R^5$, $R^6$, $R^7$, and $R^8$ are H; X is $(CH_2)_z$; z is 1; X is $(CH_2)_z$; z is 1; Y is —N($R^9$)—; $R^9$ is hydrogen, methyl, or ethyl; and $W_d$ is In some embodiments, Y is —NH—.

In another aspect, for the compounds of Formula I $R_3$ is aryl, heteroaryl, H, $CH_3$, $CF_3$, Cl, or F; B is alkyl or a moiety of Formula II;

wherein $W_c$ is aryl, heteroaryl, heterocycloalkyl, or cycloalkyl, and q is an integer of 0, 1, 2, 3, or 4; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —N($R^9$)—, or —N($R^9$)CH($R^9$)—; $R^9$ is hydrogen, alkyl, cycloalkyl, or heteroalkyl; at least one of X and Y is present; and $W_d$ is pyrazolopyrimidine or purine. In some embodiments, when X is present, Y is —N($R^9$)—, and $W_d$ is purine, then Y is —NH—.

In another aspect, for the compounds of Formula I, $R_3$ is aryl, heteroaryl, H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —N($R^9$)—, or —N($R^9$)CH($R^9$)—; $R^9$ is hydrogen, methyl, or ethyl; at least one of X and Y is present; $W_d$ is:

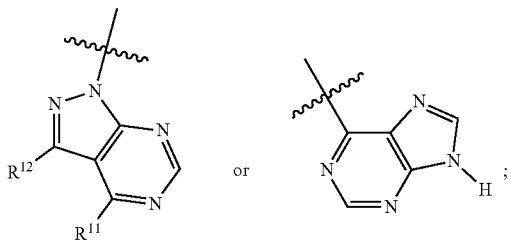

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido. In some embodiments, when X is present, Y is —N($R^9$)—, and $W_d$ is purine, then Y is —NH—.

In another aspect, for the compounds of Formula I, $R_3$ is H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is $(CH(R^9))_z$; z is an integer of 1; Y is absent-; $R^9$ is hydrogen, methyl, or ethyl; $W_d$ is:

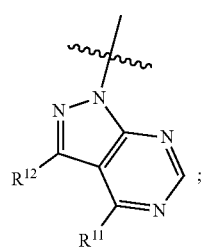

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for the compounds of Formula I, $R_3$ is aryl, heteroaryl, H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1; Y is absent, —N($R^9$)—, or —N($R^9$)CH($R^9$)—; $R^9$ is hydrogen, methyl, or ethyl; at least one of X and Y is present, and $W_d$ is:

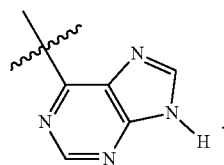 [SMILES: *c1ncnc2[nH]cnc12]

In some embodiments, when X is present, Y is —N($R^9$)—, and $W_d$ is purine, then Y is —NH—.

In another aspect, for the compounds of Formula I, $R_3$ is aryl, heteroaryl, H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent; Y is —N($R^9$) CH($R^9$)—; $R^9$ is hydrogen, methyl, or ethyl; and $W_d$ is:

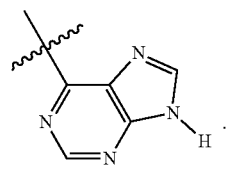 [SMILES: *c1ncnc2[nH]cnc12]

In another aspect, for the compounds of Formula I, $R_3$ is aryl, heteroaryl, H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —N($R^9$)—, or —N($R^9$) CH($R^9$)—; $R^9$ is hydrogen, methyl, or ethyl; at least one of X and Y is present; $W_d$ is:

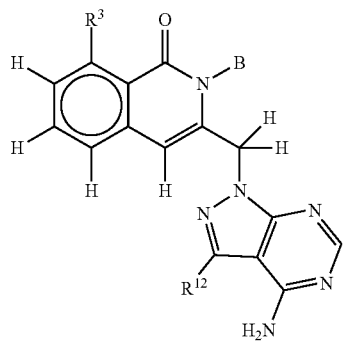

$R^{a'}$ is hydrogen, halo, or amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido. In some embodiments, when X is present, Y is —N($R^9$)—, and $W_d$ is purine, then Y is —NH—.

Additional exemplary compounds of the present invention are disclosed having a sub-structure of Formula IV-A.

Formula VI-A

Some illustrative compounds of the present invention having a structure of Formula IV-A include those in which R³ is —H, —Cl, —F, or —CH₃ in combination with any B moiety described in Table 1, and any R¹² as described in Table 2. A compound of Formula IV-A includes any combination of R³, B, and R¹². Additional exemplary compounds of Formula IV-A are illustrated in Table 4.

TABLE 1

Illustrative B moieties of the compounds of Formula I.

| Sub-class # | B |
|---|---|
| B-1 | cyclopentyl |
| B-2 | 4-(N-isopropyl)piperidinyl |
| B-3 | —CH(CH₃)2 |
| B-4 | 2-(trifluoromethyl)phenyl |
| B-5 | cyclopropyl |
| B-6 | 2-chlorophenyl |
| B-7 | 2-methylphenyl |
| B-8 | 3-methylpyridin-2-yl |
| B-9 | 2-ethylphenyl |
| B-10 | 3-fluoropyridin-2-yl |

TABLE 1-continued

Illustrative B moieties of the compounds of Formula I.

| Sub-class # | B |
|---|---|
| B-11 | 1-methylpiperidin-4-yl |
| B-12 | 2-isopropylphenyl |
| B-13 | 2-methoxyphenyl |
| B-14 | 3-fluorophenyl |
| B-15 | 2-hydroxyphenyl |
| B-16 | 2-cyanophenyl |
| B-17 | 3-cyanophenyl |
| B-18 | 4-cyanophenyl |
| B-19 | 3-morpholinopropyl |
| B-20 | phenyl |

TABLE 1-continued

Illustrative B moieties of the compounds of Formula I.

| Sub-class # | B |
|---|---|
| B-21 | 2-methyl-4-methoxyphenyl |
| B-22 | 4-methylpyridin-3-yl |
| B-23 | 3-nitrophenyl |
| B-24 | 2-(2-morpholinoethoxy)phenyl |
| B-25 | tetrahydro-2H-pyran-4-yl |
| B-26 | 3-(4-methylpiperazin-1-yl)propyl |
| B-27 | pyridin-2-yl |
| B-28 | 6-chloropyridin-2-yl |
| B-29 | 6-methylpyridin-2-yl |
| B-30 | 5-methylpyridin-2-yl |
| B-31 | 4-methylpyridin-2-yl |
| B-32 | 6-methoxypyridin-2-yl |
| B-33 | 2-(trifluoromethyl)pyridin-4-yl |
| B-34 | 1H-indazol-5-yl |
| B-35 | 1H-indazol-6-yl |
| B-36 | 5-aminopyridin-2-yl |
| B-37 | 6-aminopyridin-2-yl |
| B-38 | 6-cyanopyridin-2-yl |
| B-39 | methyl 6-pyridinecarboxylate-2-yl |

TABLE 1-continued

Illustrative B moieties of the compounds of Formula I.

| Sub-class # | B |
|---|---|
| B-40 | pyrazine with Cl |
| B-41 | pyridine-2-carboxylate methyl ester (6-substituted) |
| B-42 | pyridine-2-carboxylate methyl ester (4-substituted) |
| B-43 | 2-cyanopyridine (4-substituted) |
| B-44 | 2-methylpyridine (4-substituted) |
| B-45 | 2-pyridone (6-substituted) |
| B-46 | 5-hydroxypyridine (2-substituted) |
| B-47 | 5-fluoropyridine (2-substituted) |
| B-48 | 2-aminopyridine (4-substituted) |
| B-49 | 5-methoxypyrazine |
| B-50 | 5-aminopyrazine |
| B-51 | 5-methylpyrazine |
| B-52 | 5-(dimethylamino)pyrazine |
| B-53 | 5-(N-methyl-N-ethylamino)pyrazine |
| B-54 | 5-(diethylamino)pyrazine |
| B-55 | 5-(4-methylpiperazin-1-yl)pyrazine |
| B-56 | 5-(pyrrolidin-1-yl)pyrazine |
| B-57 | 5-(piperidin-1-yl)pyrazine |

TABLE 1-continued
Illustrative B moieties of the compounds of Formula I.
| Sub-class # | B |
|---|---|
| B-58 | 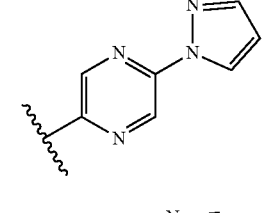 |
| B-59 | 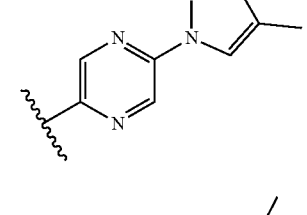 |
| B-60 | 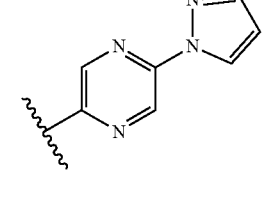 |
| B-61 | 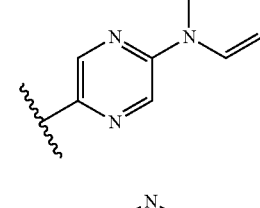 |
| B-62 | 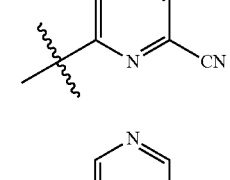 |
| B-63 | 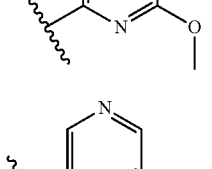 |
| B-64 | 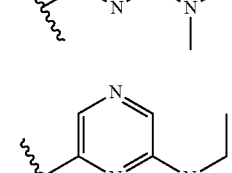 |
| B-65 | |
| B-66 | |
| B-67 | |
| B-68 | |
| B-69 | |
| B-70 | |
| B-71 | |
| B-72 |  |

TABLE 1-continued
Illustrative B moieties of the compounds of Formula I.
| Sub-class # | B |
|---|---|
| B-73 | 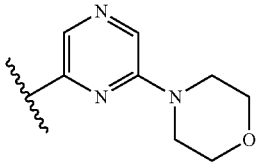 [SMILES: *c1cncc(N2CCOCC2)n1] |
| B-74 | 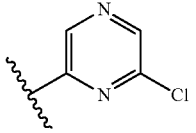 [SMILES: *c1cncc(Cl)n1] |
| B-75 | 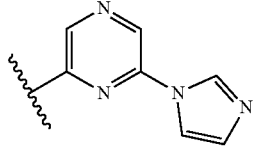 [SMILES: *c1cncc(-n2ccnc2)n1] |
| B-76 | 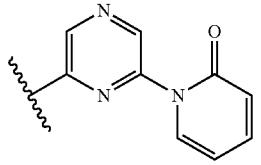 [SMILES: *c1cncc(-n2ccccc2=O)n1] |
| B-77 | 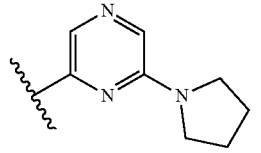 [SMILES: *c1cncc(N2CCCC2)n1] |
| B-78 | 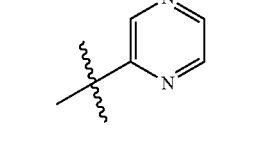 |
| B-79 | 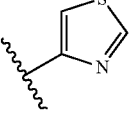 |
| B-80 | 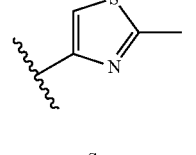 |
| B-81 | 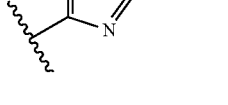 |
| B-82 | 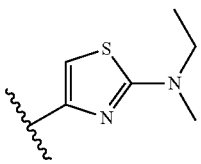 [SMILES: *c1csc(N(C)CC)n1] |
| B-83 | 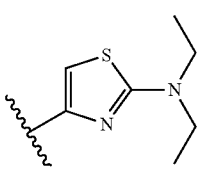 [SMILES: *c1csc(N(CC)CC)n1] |
| B-84 |  |
| B-85 | 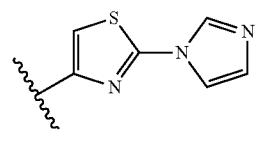 |
| B-86 | 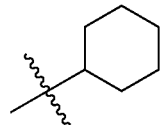 [SMILES: *C1CCCCC1] |
| B-87 | —CH$_3$ |
| B-88 | —CH$_2$CH$_3$ |
| B-89 |  |
| B-90 |  |
| B-91 | 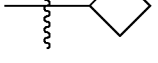 |

TABLE 1-continued

Illustrative B moieties of the compounds of Formula I.

| Sub-class # | B |
|---|---|
| B-92 | 3,5-dimethylphenyl |
| B-93 | 2,6-difluorophenyl |
| B-94 | 2,6-dimethylphenyl |
| B-95 | 3,5-difluorophenyl |
| B-96 | 4-(2-(4-ethylpiperazin-1-yl)ethyl) |
| B-97 | piperidin-4-yl (N-H) |
| B-98 | 1-acetylpiperidin-4-yl |
| B-99 | 1-(2-hydroxyethyl)piperidin-4-yl |
| B-100 | 1-(2-(methylsulfonyl)ethyl)piperidin-4-yl |
| B-101 | 1-(2-cyanoethyl)piperidin-4-yl |
| B-102 | 4-fluorophenyl |

TABLE 2

Illustrative $R^{12}$ of compounds of Formula I.

| Sub-class # | $R^{12}$ |
|---|---|
| 12-1 | —CN |
| 12-2 | —Br |
| 12-3 | —Cl |
| 12-4 | —CH$_2$CH$_3$ |
| 12-5 | —CH$_3$ |
| 12-6 | —CH(CH$_3$)$_2$ |
| 12-7 | cyclopropyl |
| 12-8 | tert-butyl |
| 12-9 | pyridin-3-yl |
| 12-10 | —C≡C—CH$_2$OH |
| 12-11 | —C≡C—CH(OH)CH$_3$ |
| 12-12 | —C≡C-cyclopropyl |

TABLE 2-continued

Illustrative R$^{12}$ of compounds of Formula I.

| Sub-class # | R$^{12}$ |
|---|---|
| 12-13 | 4-pyrazolyl (1H-pyrazol-4-yl) |
| 12-14 | 3-(aminocarbonyl)phenyl (3-CONH$_2$-C$_6$H$_4$-) |
| 12-15 | 2-(acetylamino)thiazol-5-yl |
| 12-16 | 2-(acetylamino)benzothiazol-6-yl |
| 12-17 | 2-aminothiazol-5-yl |
| 12-18 | 2-aminopyridin-4-yl |
| 12-19 | 2-amino-6-fluoropyridin-4-yl |
| 12-20 | 2-aminopyrimidin-4-yl |
| 12-21 | 2-amino-6-fluoropyrimidin-4-yl |
| 12-22 | 1H-pyrrolo[2,3-b]pyridin-5-yl (5-position of 7-azaindole) |
| 12-23 | 1H-indazol-6-yl |
| 12-24 | 4-fluoro-1H-indazol-6-yl |
| 12-25 | 1H-pyrrolo[2,3-b]pyridin-4-yl |
| 12-26 | 3-methoxyphenyl |
| 12-27 | 6-fluoro-1H-pyrrolo[2,3-b]pyridin-4-yl |
| 12-28 | 3-hydroxy-3-methylbut-1-yn-1-yl (-C≡C-C(CH$_3$)$_2$OH) |
| 12-29 | 3,3-dimethylbut-1-yn-1-yl (-C≡C-C(CH$_3$)$_3$) |

TABLE 2-continued
Illustrative R[12] of compounds of Formula I.
| Sub-class # | R[12] |
|---|---|
| 12-30 | 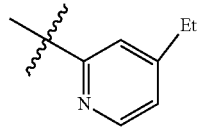 [SMILES: *c1cc(CC)ccn1] |
| 12-31 | 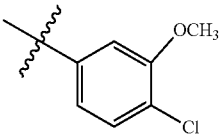 [SMILES: *c1ccc(Cl)c(OC)c1] |
| 12-32 | 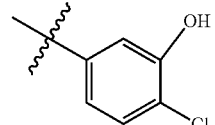 |
| 12-33 | 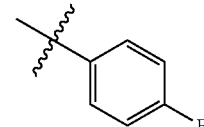 |
| 12-34 | 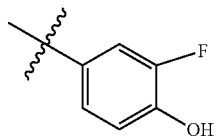 [SMILES: *c1ccc(O)c(F)c1] |
| 12-35 | —H |
| 12-36 | 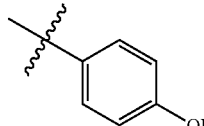 |
| 12-37 | 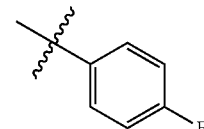 |
| 12-38 | 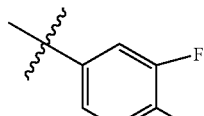 |
| 12-39 | 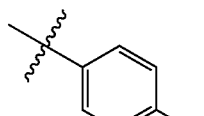 |
| 12-40 | 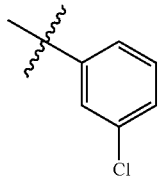 [SMILES: *c1cccc(Cl)c1] |
| 12-41 | 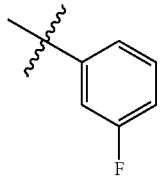 [SMILES: *c1cccc(F)c1] |
| 12-42 | 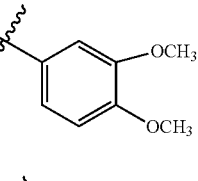 |
| 12-43 | 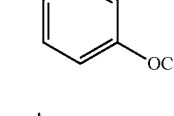 |
| 12-44 | 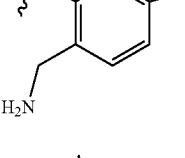 |
| 12-45 | 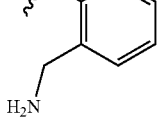 |
| 12-46 | 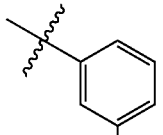 |
| 12-47 | 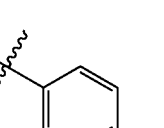 |

TABLE 2-continued
Illustrative R$^{12}$ of compounds of Formula I.
| Sub-class # | R$^{12}$ |
|---|---|
| 12-48 | 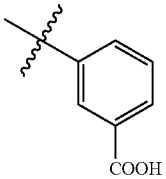 [SMILES: *c1cccc(C(=O)O)c1] |
| 12-49 | 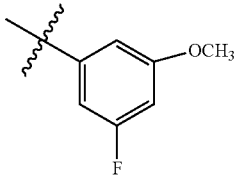 [SMILES: *c1cc(F)cc(OC)c1] |
| 12-50 | 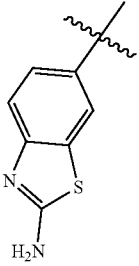 [SMILES: *c1ccc2nc(N)sc2c1] |
| 12-51 | 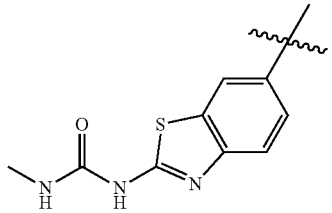 [SMILES: *c1ccc2nc(NC(=O)NC)sc2c1] |
| 12-52 | 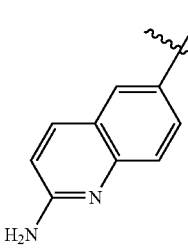 |
| 12-53 | 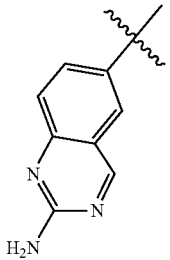 [SMILES: *c1ccc2nc(N)ncc2c1] |
| 12-54 | 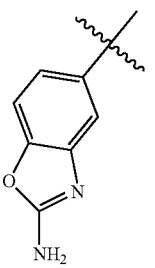 [SMILES: *c1ccc2oc(N)nc2c1] |
| 12-55 | 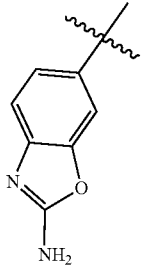 [SMILES: *c1ccc2nc(N)oc2c1] |
| 12-56 | 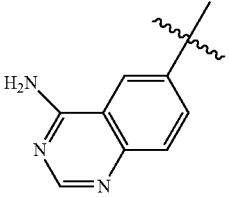 [SMILES: *c1ccc2ncnc(N)c2c1] |
| 12-57 | 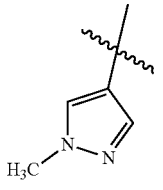 |
| 12-58 | 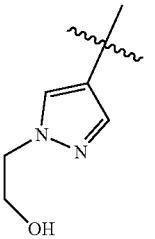 [SMILES: *c1cnn(CCO)c1] |
| 12-59 | 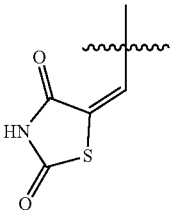 [SMILES: */C=C1/SC(=O)NC1=O] |

TABLE 2-continued

Illustrative R$^{12}$ of compounds of Formula I.

| Sub-class # | R$^{12}$ |
|---|---|
| 12-60 | 3-oxo-pyrrolidin-4-ylidene methyl |
| 12-61 | —I |
| 12-62 | 3-hydroxyphenyl |
| 12-63 | 3-hydroxy-5-fluorophenyl |
| 12-64 | 3-hydroxy-4-fluorophenyl |
| 12-65 | 3-methylbut-1-yn-1-yl |
| 12-66 | 4-(diethylamino)pyridin-2-yl |
| 12-67 | 2-aminobenzo[d]thiazol-5-yl |
| 12-68 | 1H-pyrazol-3-yl |
| 12-69 | 2-methyl-1H-imidazol-4-yl |
| 12-70 | 3-methyl-1H-pyrazol-5-yl |
| 12-71 | 3-fluoro-1H-pyrazol-5-yl |
| 12-72 | 1H-1,2,4-triazol-3-yl |
| 12-73 | 3-oxo-2,3-dihydro-1H-pyrazol-5-yl |
| 12-74 | 1-methyl-3-oxo-2,3-dihydro-1H-pyrazol-5-yl |
| 12-75 | 3-oxo-2,3-dihydroisoxazol-5-yl |
| 12-76 | 3-oxo-2,3-dihydroisothiazol-5-yl |

TABLE 2-continued

Illustrative R¹² of compounds of Formula I.

| Sub-class # | R¹² |
|---|---|
| 12-77 | (structure: NC-CH-) |
| 12-78 | (structure: H₂N-C(=O)-C-) |
| 12-79 | (structure: MeHN-C(=O)-C-) |
| 12-80 | (structure: MeHN-C(=O)-CH=CH-C-) |
| 12-81 | (structure: morpholine-N-CH₂-C-) |
| 12-82 | (structure: H₃C-O-C(=O)-C-) |
| 12-83 | (structure: H-C(=O)-O-C-) |
| 12-84 | (structure: HO-NH-C(=O)-C-) |
| 12-85 | (structure: 2-amino-benzimidazol-5-yl) |
| 12-86 | (structure: 2-acetamido-benzimidazol-5-yl) |
| 12-87 | (structure: F₂C=CH-) |
| 12-88 | (structure: 1H-pyrazol-3-yl) |
| 12-89 | (structure: 1-methyl-pyrazol-5-yl) |
| 12-90 | (structure: H₂N-C(=O)-CH₂-C-) |
| 12-91 | (structure: 2-(acetylamino)-benzoxazol-6-yl) |
| 12-92 | (structure: morpholine-N-C(=O)-CH=CH-C-) |
| 12-93 | (structure: morpholine-N-C(=O)-CH₂-C-) |

TABLE 2-continued

Illustrative $R^{12}$ of compounds of Formula I.

| Sub-class # | $R^{12}$ |
|---|---|
| 12-94 | acrylamide group (CH=CH-C(O)-NH₂) |
| 12-95 | 1H-tetrazol-5-yl (attached via C) |
| 12-96 | 1H-tetrazol-5-yl (attached via N) |
| 12-97 | —F |
| 12-98 | —S(O)₂NH₂ |
| 12-99 | —S(O)₂NHCH₃ |
| 12-100 | —S(O)₂N(CH₃)₂ |
| 12-101 | 2-acetamido-benzoxazol-5-yl |
| 12-102 | 2-acetamido-benzothiazol-5-yl |

Other illustrative compounds of the present invention have a structure of Formula V-A, V-A1, or V-A2, wherein B is a moiety described in Table 1, in combination with $R^3$, which is —H, —Cl, —F, or CH₃, and $R^9$, which is —H, —CH₃, or —CH₂CH₃. A compound of Formula V-A, V-A1, or V-A2 includes any combination of $R^3$, B, and $R^9$.

Formula V-A

Formula V-A1

Formula V-A2

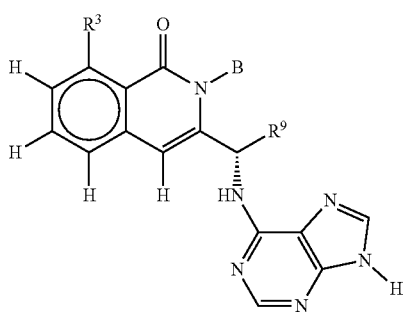

Yet other illustrative compounds of the present invention have a structure of Formula V-B, wherein B is a moiety described in Table 1, in combination with $R^3$, which is —H, —Cl, —F, or $CH_3$, and $R^9$, which is —H, —$CH_3$, or —$CH_2CH_3$. A compound of Formula V-B includes any combination of $R^3$, B, and $R^9$.

Formula V-B

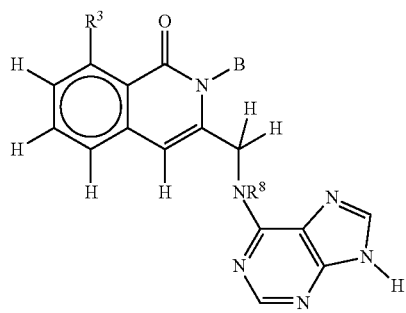

Some other illustrative compounds of the present invention have a structure of Formula VI-A, wherein B is a moiety described in Table 1, in combination with $R^3$, which is —H, —Cl, —F, or $CH_3$, and $R^9$, which is —H, —$CH_3$, or —$CH_2CH_3$. A compound of Formula VI-A includes any combination of $R^3$, B, and $R^9$.

Formula VI-A

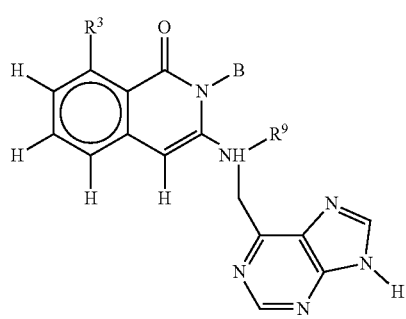

Further illustrative compounds of the invention have a structure of one of Formulae VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, or XIV-A2: wherein B is a moiety described in Table 1, any $R^{12}$ as described in Table 2, in combination with $R^3$, which is —H, —Cl, —F, or $CH_3$, $R^9$ which is —H, —$CH_3$, or —$CH_2CH_3$, and $R^{a'}$ which is —H, —Cl, —F, or —$NH_2$. A compound of Formulae VII-A1, VII-A2, VIII-A1, VIII-A2, IX-A1, IX-A2, X-A1, X-A2, XI-A1, XI-A2, XII-A, XII-A1, XII-A2, XIII-A, XIII-A1, XIII-A2, XIV-A, XIV-A1, or XIV-A2: includes any combination of $R^a$, $R^3$, B, $R^9$ and $R^{12}$.

Additional exemplary compounds of the present invention include but are not limited to the following:

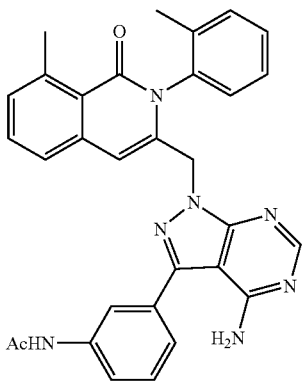

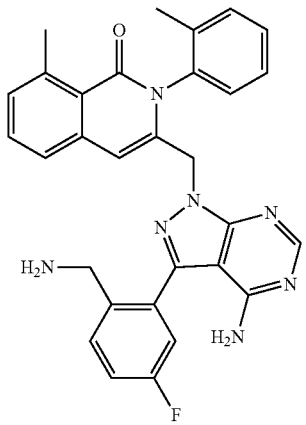

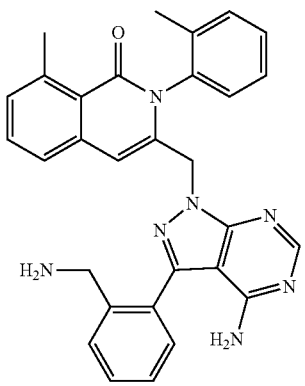

105
-continued
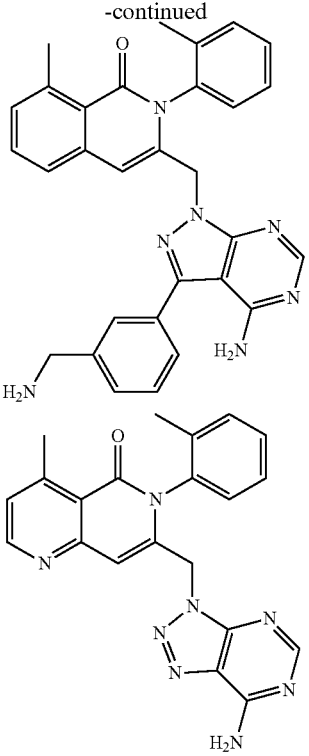
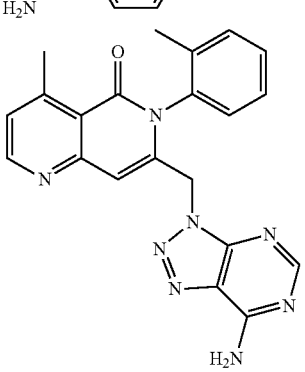
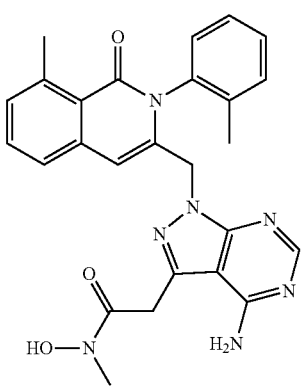
106
-continued
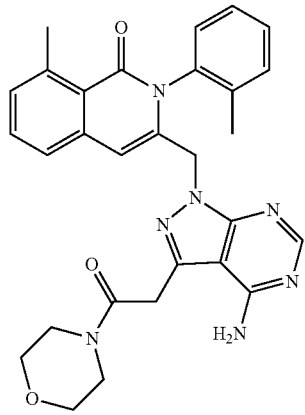
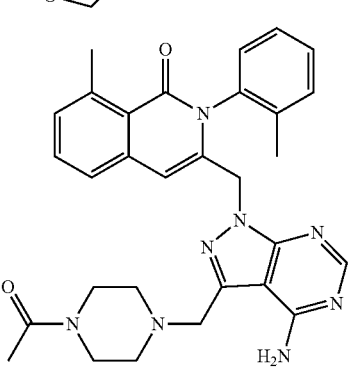
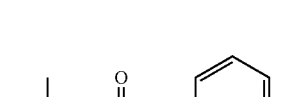
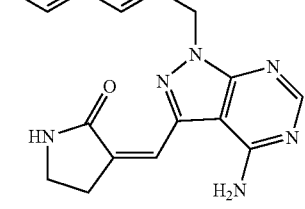

107
-continued
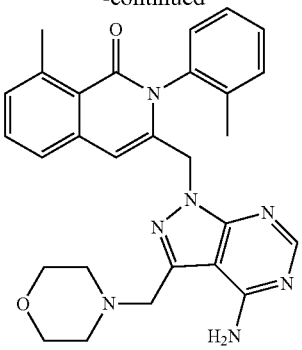
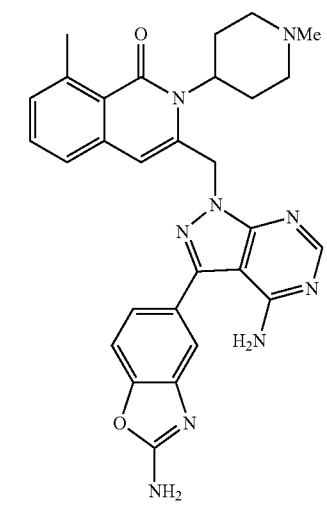
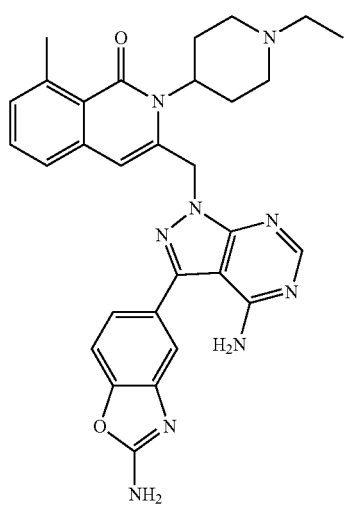
108
-continued
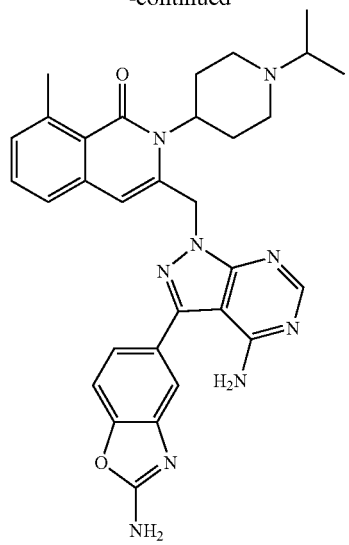
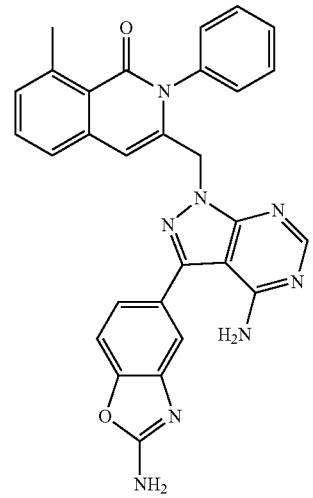
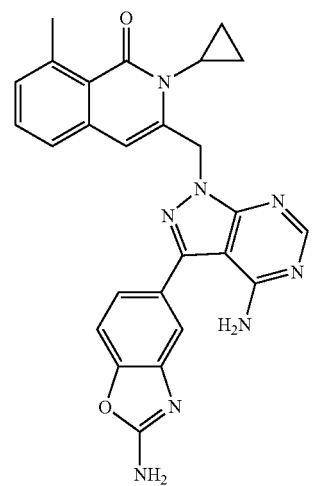

109
-continued
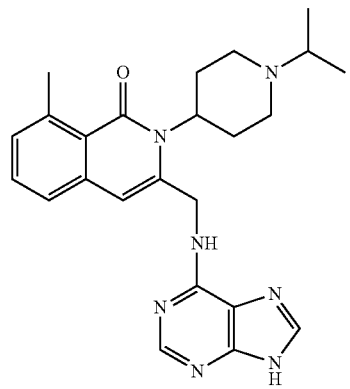
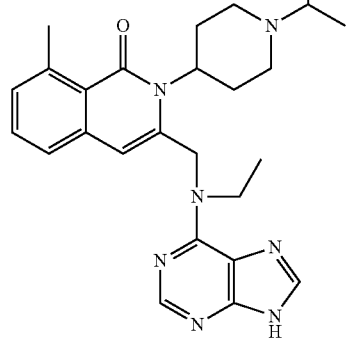
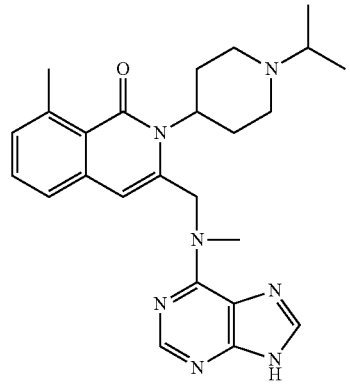
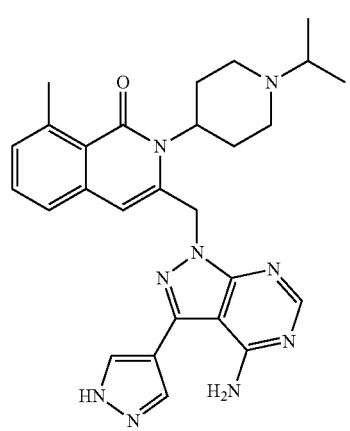
110
-continued
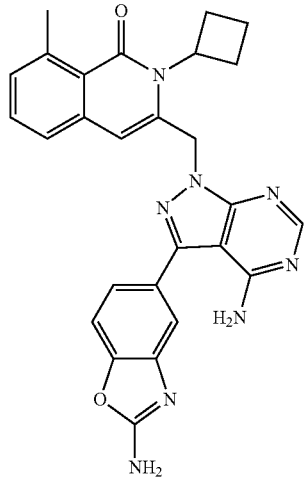
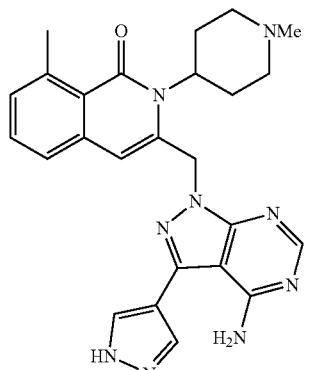
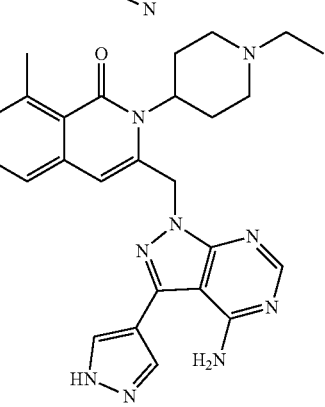
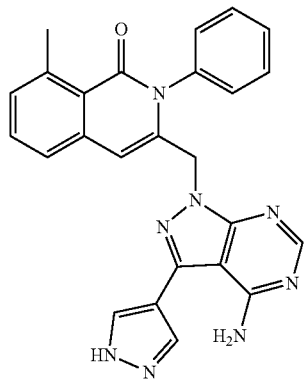

-continued
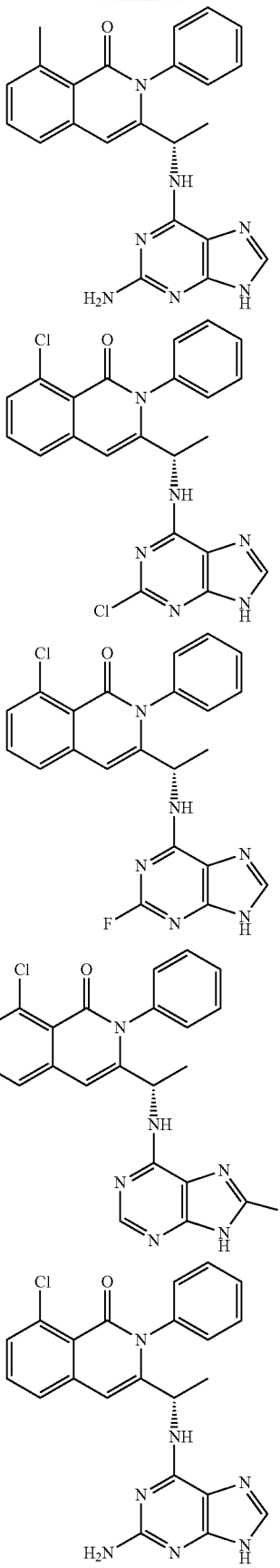
-continued
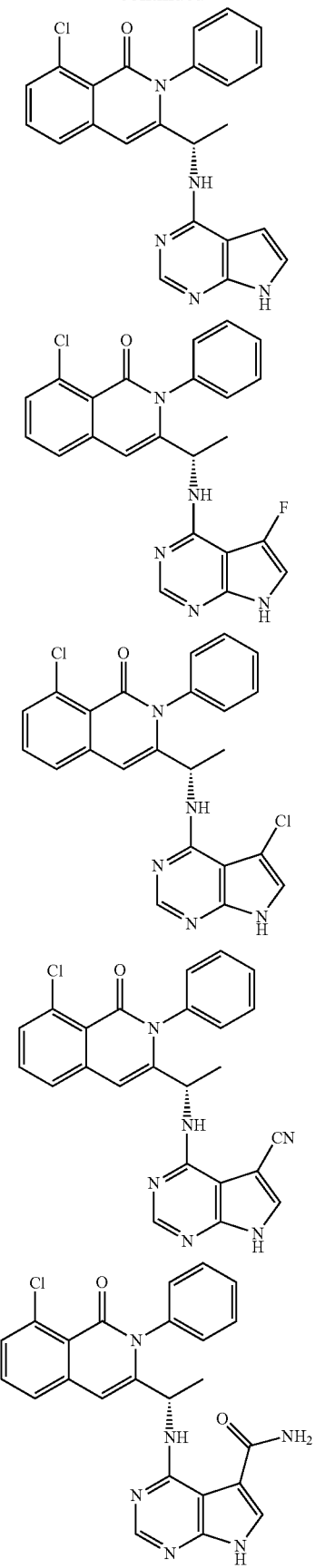

113
-continued
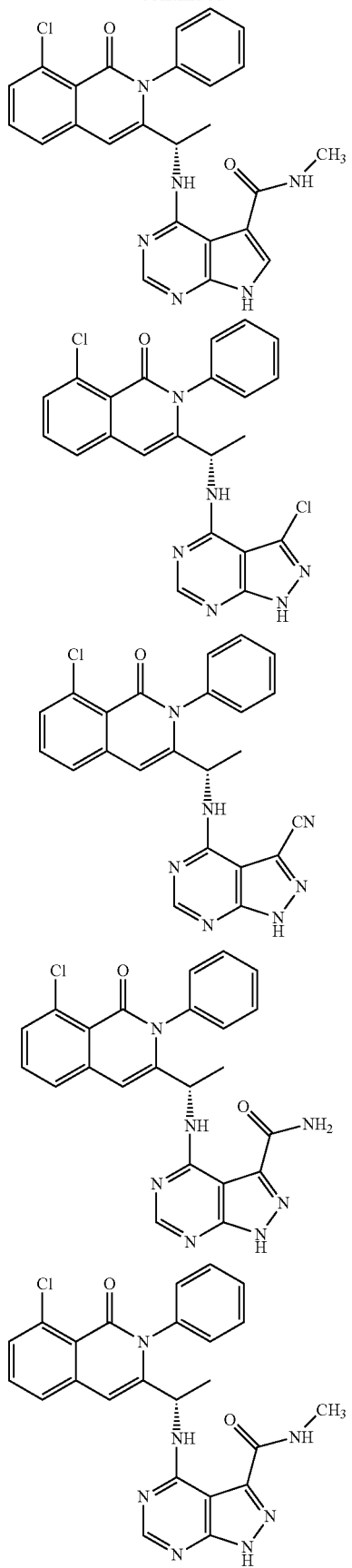
114
-continued
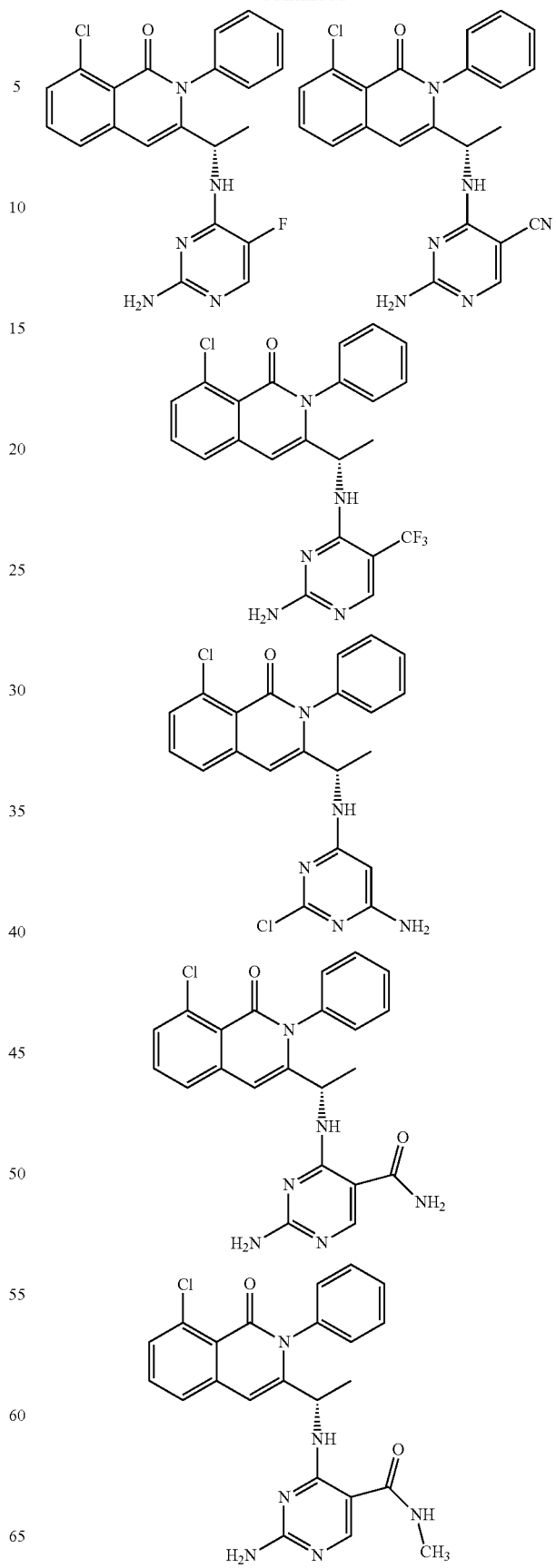

115
-continued
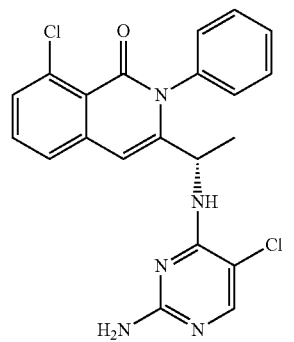
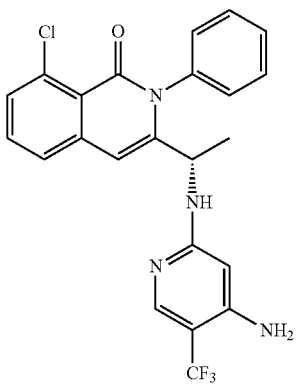
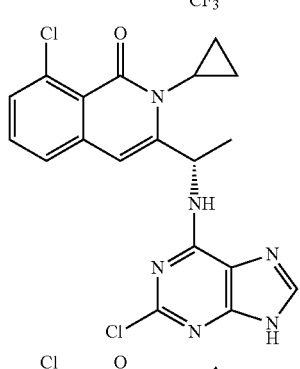
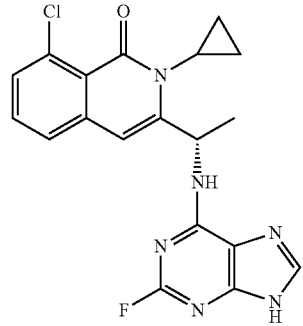
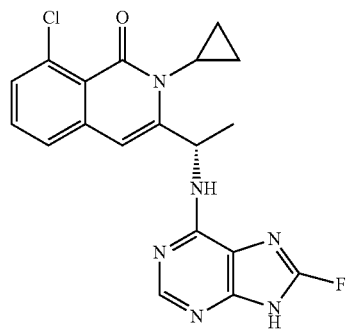
116
-continued
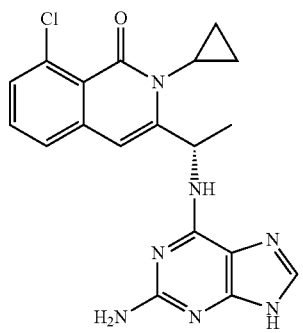
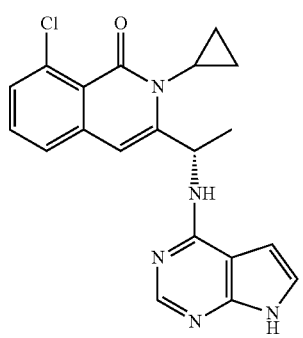
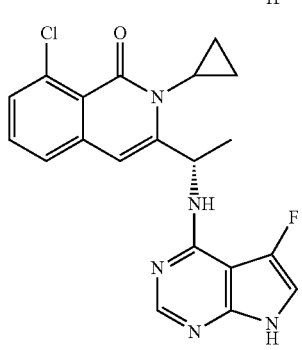
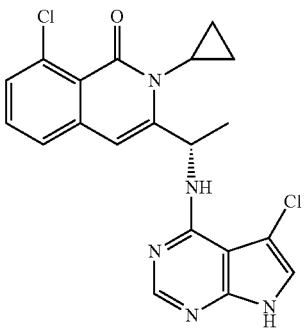
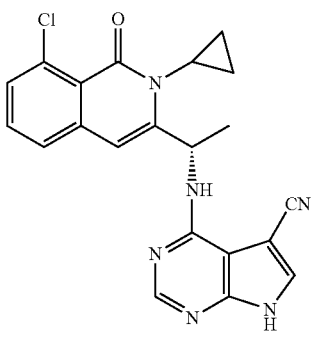

117
-continued
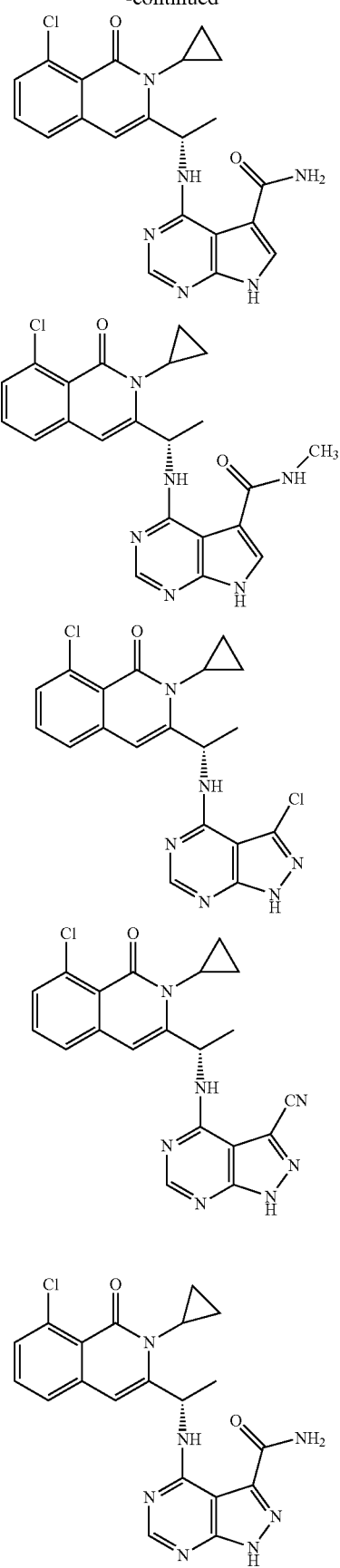
118
-continued
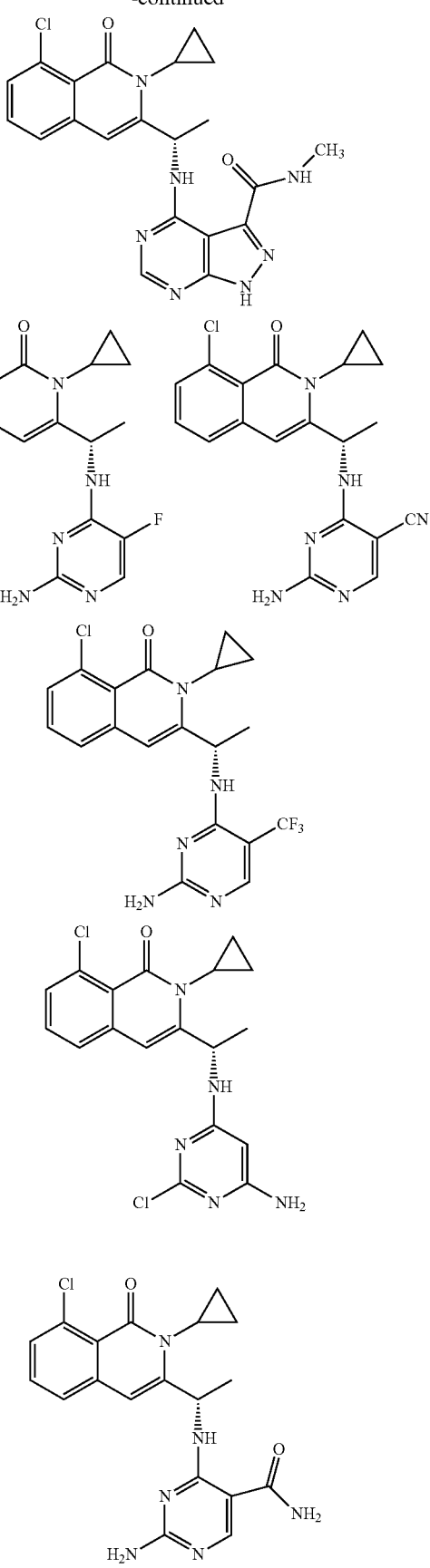

-continued

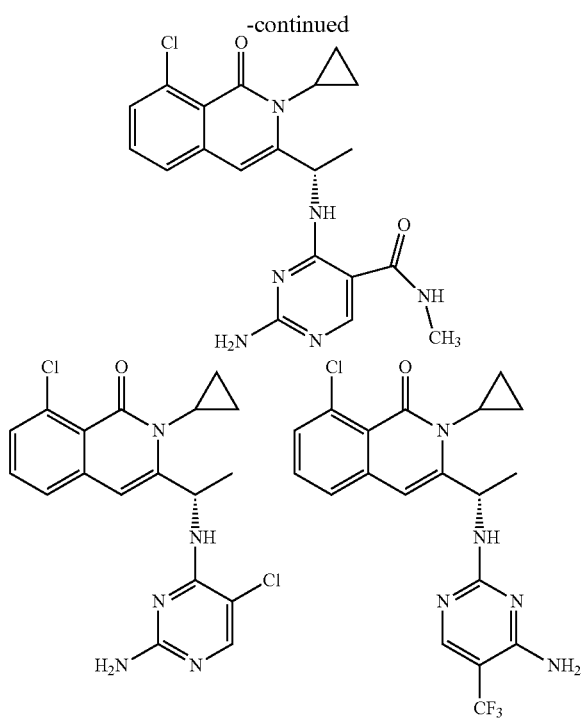

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can generally be synthesized by an appropriate combination of generally well known synthetic methods. Techniques useful in synthesizing these chemical entities are both readily apparent and accessible to those of skill in the relevant art, based on the instant disclosure.

The compounds of the invention can be synthesized by an appropriate combination of known synthetic methods in the art. The discussion below is offered to illustrate certain of the diverse methods available for use in making the compounds of the invention and is not intended to limit the scope of reactions or reaction sequences that can be used in preparing the compounds of the present invention.

Reaction Scheme 1

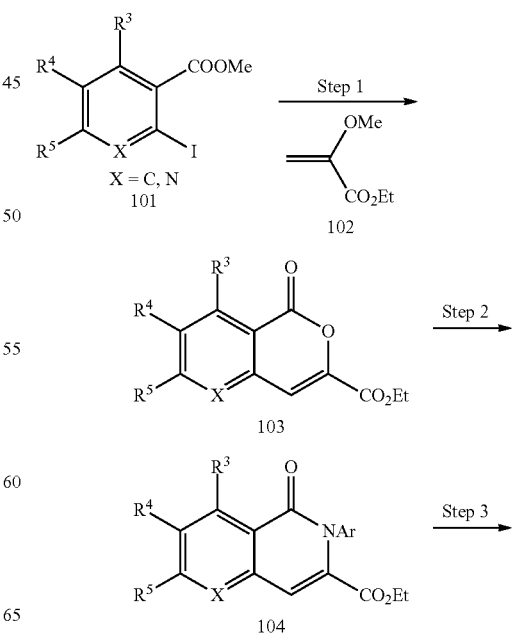

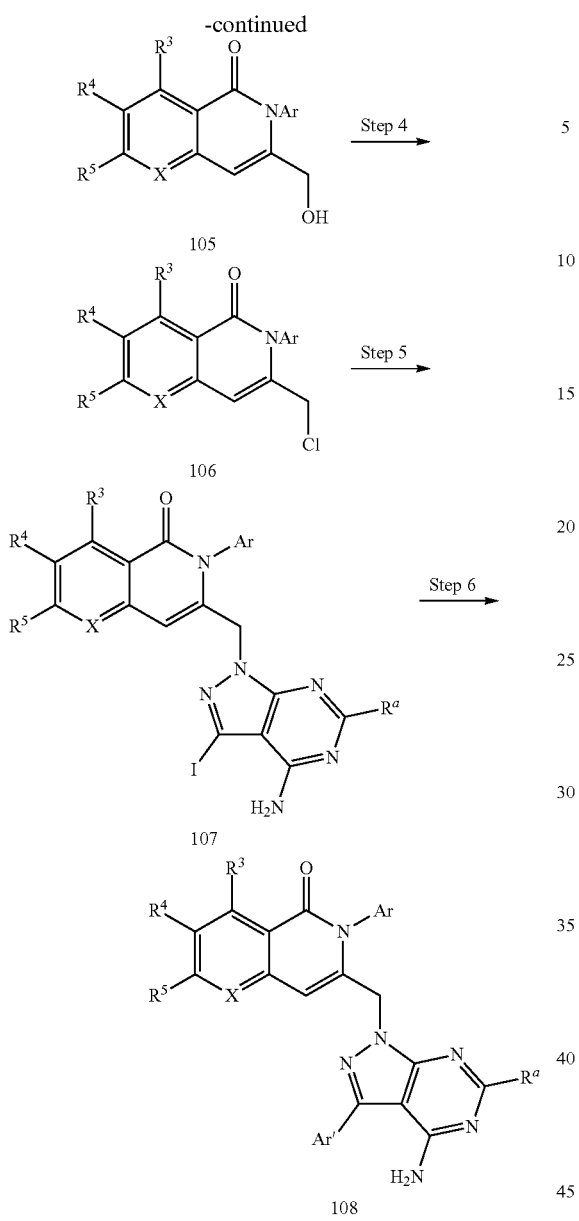

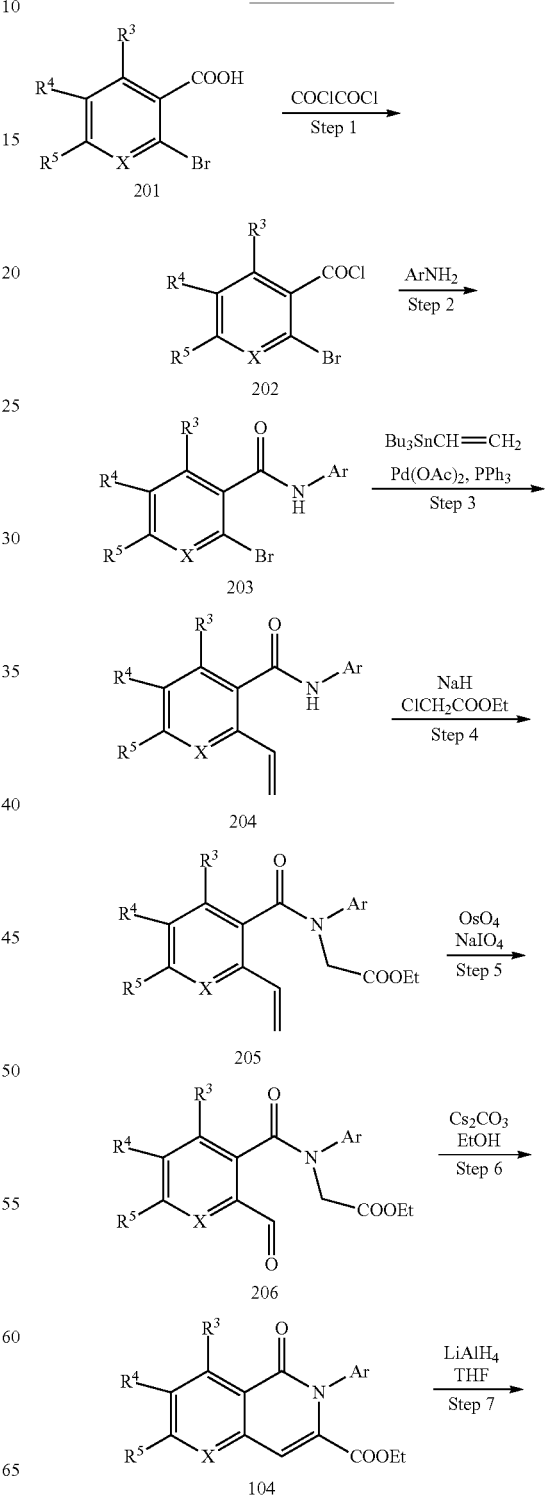

with a pyrrazolopyrimidine using a base such as potassium carbonate. The product, a compound of Formula 107, is isolated. Referring to Scheme 1, Step 6, a compound of Formula 107 is converted to a compound of Formula 108, for example, via a Suzuki reaction. The product, a compound of Formula 108, is isolated and optionally purified.

Referring to Scheme 1, Step 1, a compound of Formula 101, wherein X is N or $CR^7$, is converted to a compound of Formula 103, for example, via a two step process of Heck coupling with a compound of Formula 102, followed by acid catalyzed cyclization in methanol. The product, a compound of Formula 103, is isolated. Referring to Scheme 1, Step 2, a compound of Formula 103 is converted to a compound of Formula 404, for example, via reaction with an appropriately substituted aniline. The product, a compound of Formula 104, is isolated. Referring to Scheme 1, Step 3, a compound of Formula 104 is converted to a compound of Formula 105, for example, though reduction with lithium aluminum hydride. The product, a compound of Formula 105, is isolated. Referring to Scheme 1, Step 4, a compound of Formula 105 is converted to a compound of Formula 106, for example, via reaction with thionyl chloride. The product, a compound of Formula 106, is isolated. Referring to Scheme 1, Step 5, a compound of Formula 106 is converted to a compound of Formula 107, for example, via alkylation

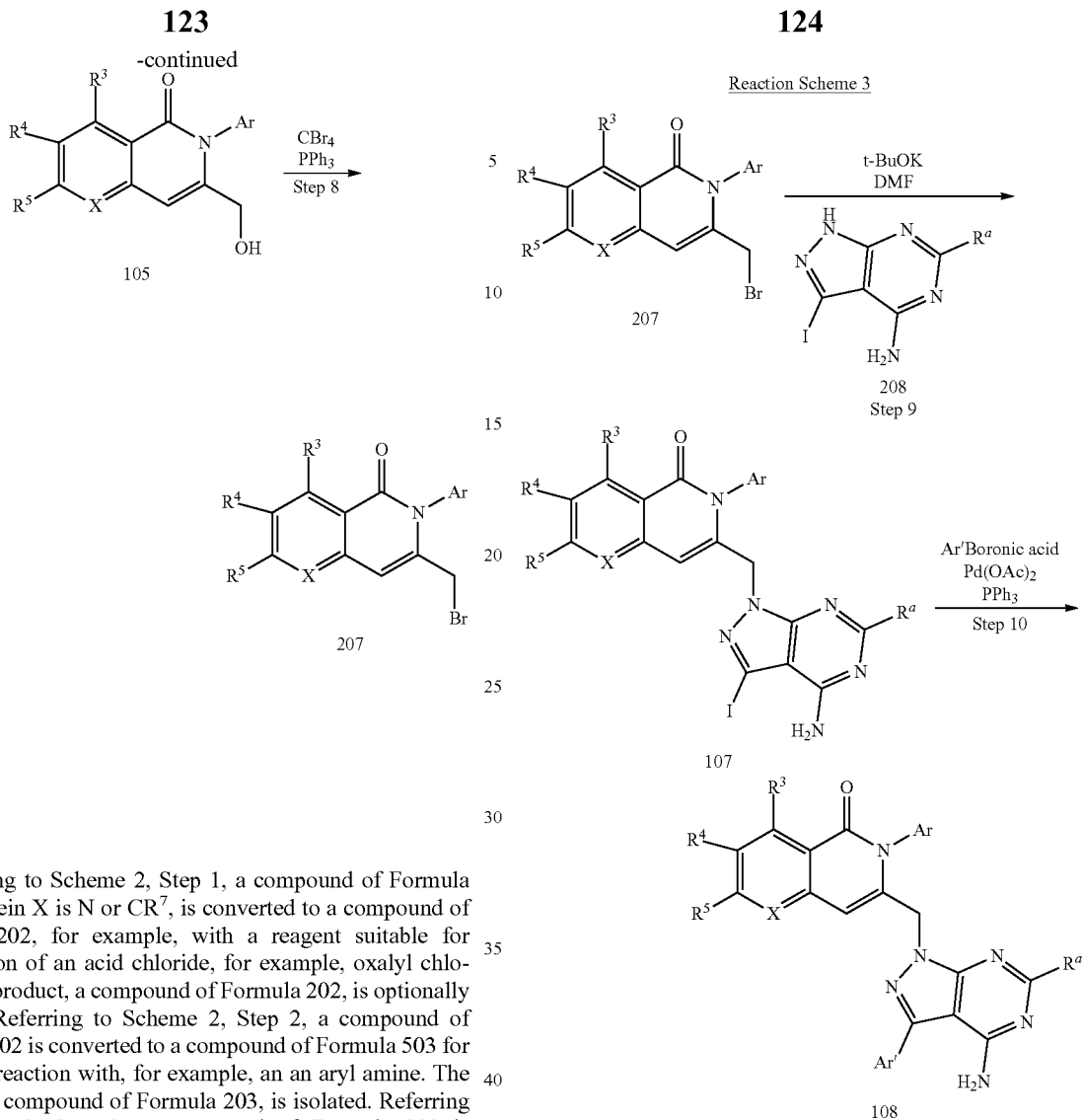

Reaction Scheme 3

Referring to Scheme 2, Step 1, a compound of Formula 201, wherein X is N or $CR^7$, is converted to a compound of Formula 202, for example, with a reagent suitable for introduction of an acid chloride, for example, oxalyl chloride. The product, a compound of Formula 202, is optionally isolated. Referring to Scheme 2, Step 2, a compound of Formula 202 is converted to a compound of Formula 503 for example, reaction with, for example, an an aryl amine. The product, a compound of Formula 203, is isolated. Referring to Scheme 2, Step 3, a compound of Formula 203 is converted to a compound of Formula 204, for example, via a Stille coupling using an appropriate vinyl-stannane. The product, a compound of Formula 204, is isolated. Referring to Scheme 2, Step 4, a compound of Formula 204 is converted to a tertiary amide, a compound of Formula 205, via reaction with chloroethyl acetate and sodium hydride base. The compound of Formula 205 is isolated. Referring to Scheme 2, Step 5, a compound of Formula 205 is oxidized to an aldehyde, using, for example, osmonium tetraoxide and sodium periodinate. The product, a compound of Formula 206, is isolated. Referring to Scheme 2, Step 6, a compound of Formula 206 is converted to a compound of Formula 104, for example, though aldol reaction in ethanol with a base, such as cesium carbonate. The product, a compound of Formula 104, is isolated. Referring to Scheme 2, Step 7, a compound of Formula 104 is reduced to a primary alcohol via reduction with, for example, lithium aluminum hydride, to produce a compound of Formula 105, which isolated. Referring to Scheme 2, Step 8, a compound of Formula 105 is converted to a compound of Formula 207 via reaction with carbon tetrabromide and triphenylphosphine. The compound of Formula 207 is isolated. This compound can be a central intermediate in the synthesis of the compounds of the invention.

Referring to Scheme 3, Step 9, a compound of Formula 207, wherein X is N or $CR^7$, is synthesized as described in Reaction Scheme 2 and is converted to a compound of Formula 107 via coupling with the compound of Formula 208 in the presence of base, for example, potassium t-butoxide. The compound of Formula 107 is isolated. Referring to Scheme 3, Step 10, a compound of Formula 107 is converted to a compound of Formula 108 via coupling with, for example, an aryl boronic acid, in the presence of coupling catalysts and base, for example, palladium acetate, triphenylphosphine and sodium carbonate, for example. The compound of Formula 108 is isolated.

Reaction Scheme 4A

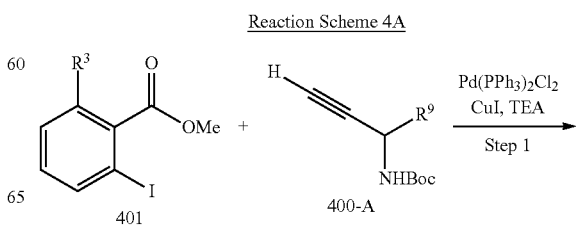

125
-continued
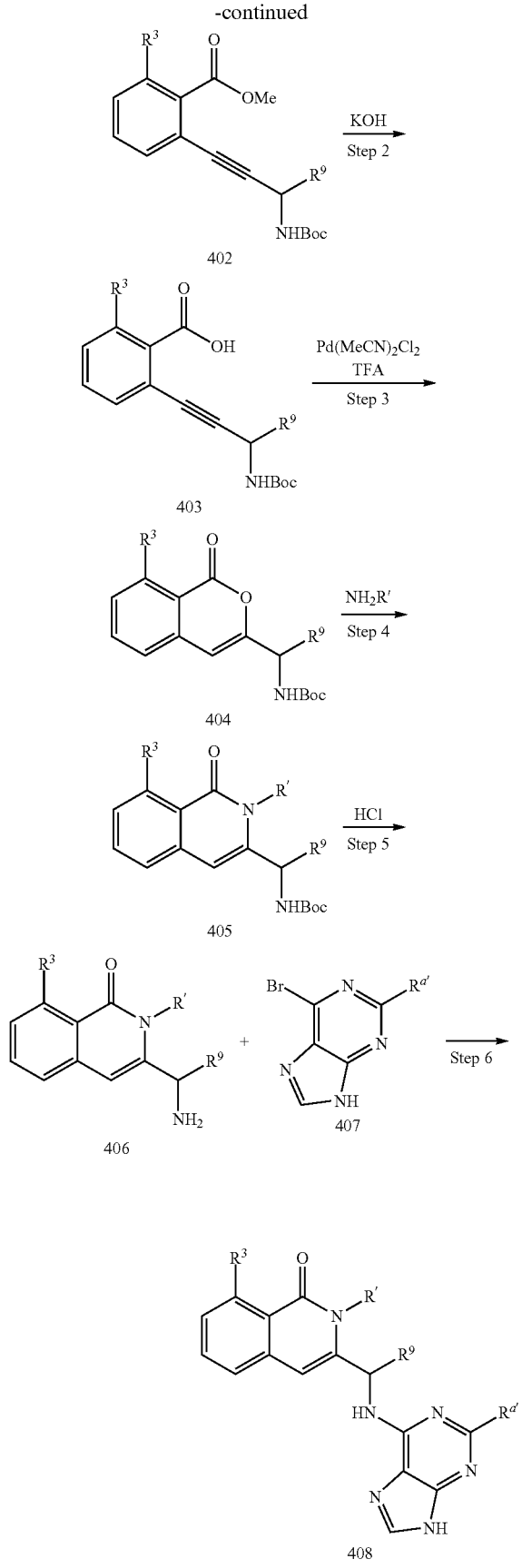
126
Reaction Scheme 4B
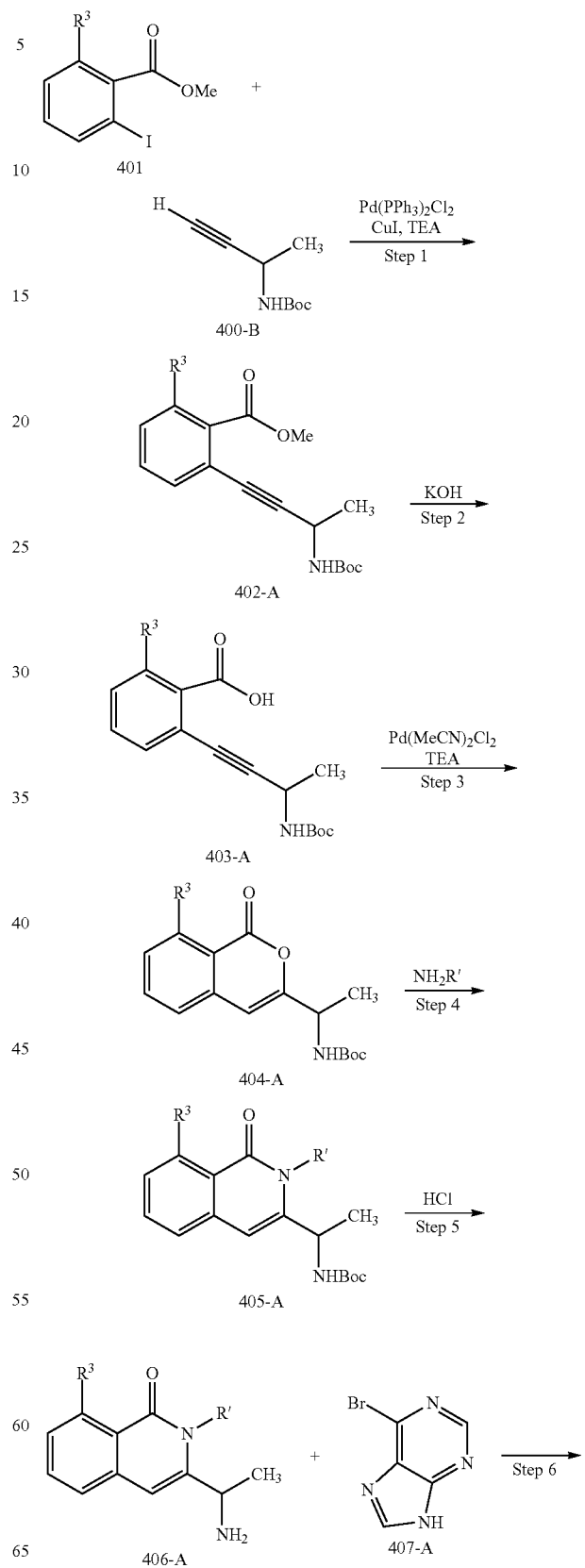

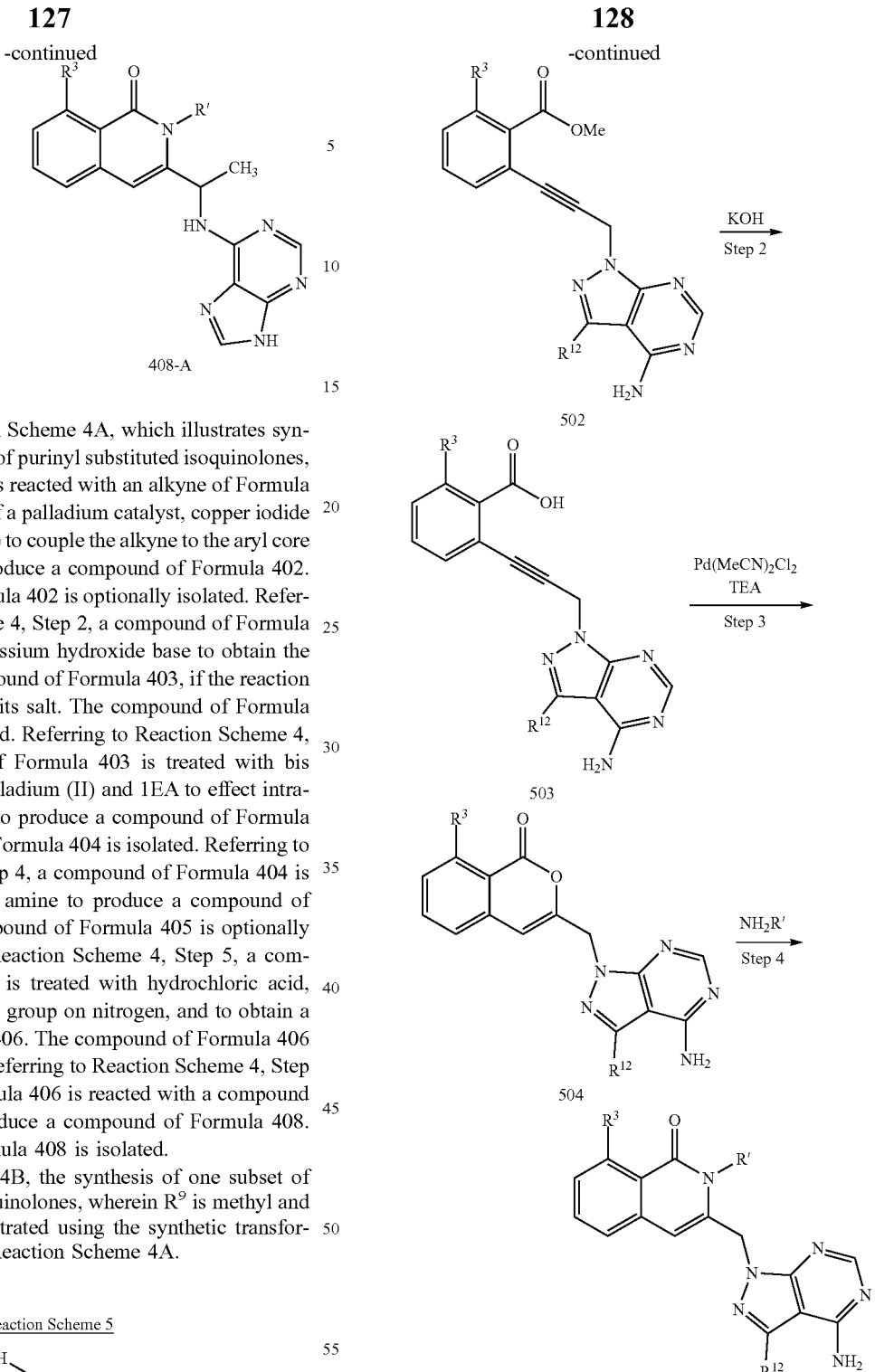

Referring to Reaction Scheme 4A, which illustrates synthesis of a general class of purinyl substituted isoquinolones, Step 1, iodo ester 401, is reacted with an alkyne of Formula 400-A in the presence of a palladium catalyst, copper iodide and triethylamine (TEA) to couple the alkyne to the aryl core of compound 401 to produce a compound of Formula 402. The compound of Formula 402 is optionally isolated. Referring to Reaction Scheme 4, Step 2, a compound of Formula 402 is treated with potassium hydroxide base to obtain the carboxylic acid, a compound of Formula 403, if the reaction product is acidified, or its salt. The compound of Formula 403 is optionally isolated. Referring to Reaction Scheme 4, Step 3, a compound of Formula 403 is treated with bis(acetonitrile)dichloropalladium (II) and 1EA to effect intramolecular ring closure to produce a compound of Formula 404. The compound of Formula 404 is isolated. Referring to Reaction Scheme 4, Step 4, a compound of Formula 404 is reacted with a primary amine to produce a compound of Formula 405. The compound of Formula 405 is optionally isolated. Referring to Reaction Scheme 4, Step 5, a compound of Formula 405 is treated with hydrochloric acid, removing the protecting group on nitrogen, and to obtain a compound of Formula 406. The compound of Formula 406 is optionally isolated. Referring to Reaction Scheme 4, Step 6, a compound of Formula 406 is reacted with a compound of Formula 407, to produce a compound of Formula 408. The compound of Formula 408 is isolated.

In Reaction Scheme 4B, the synthesis of one subset of purinyl substituted isoquinolones, wherein $R^9$ is methyl and $R^a$ is hydrogen, is illustrated using the synthetic transformations described for Reaction Scheme 4A.

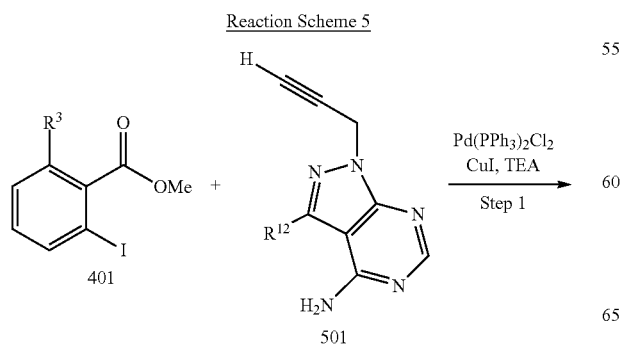

Reaction Scheme 5

Referring to Reaction Scheme 5, Step 1, iodo ester 401 is reacted with alkyne 501 in the presence of palladium coupling catalyst, copper iodide, and TEA, to obtain a compound of Formula 502. The compound of Formula 502 is optionally isolated. Referring to Reaction Scheme 5, Step 2, the compound of Formula 502 is treated with potassium hydroxide base to obtain the carboxylate or free acid of a compound of Formula 503. Referring to Reaction Scheme 5, Step 3, the compound of Formula 503 is treated with bis(acetonitrile)dichloropalladium (II) and 1EA to effect intramolecular ring closure to produce a compound of Formula 504. The compound of Formula 504 is optionally isolated. Referring to Reaction Scheme 5, Step 4, the compound of Formula 504 is treated with a primary amine to produce a compound of Formula 505. The compound of Formula 505 is isolated.

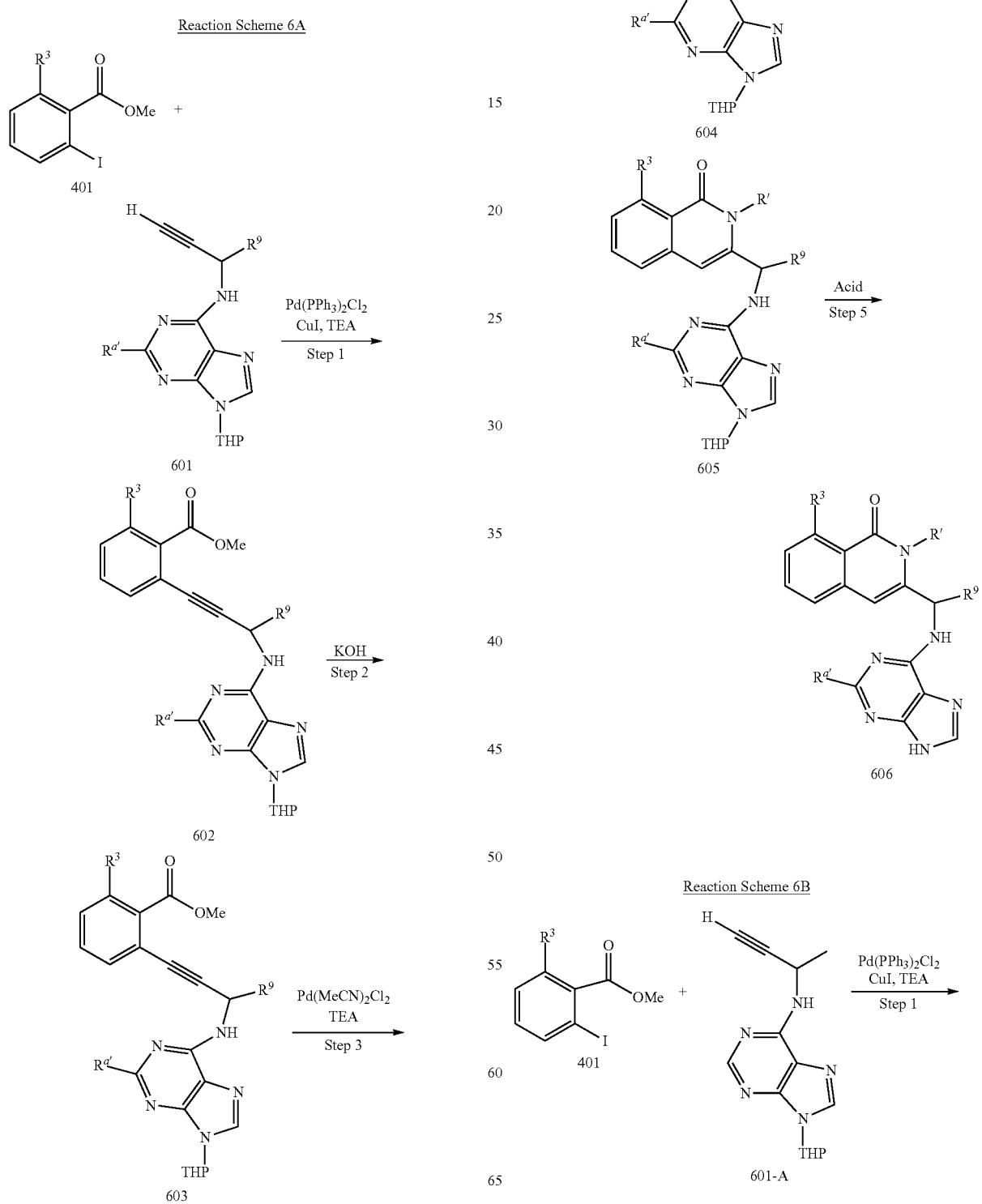

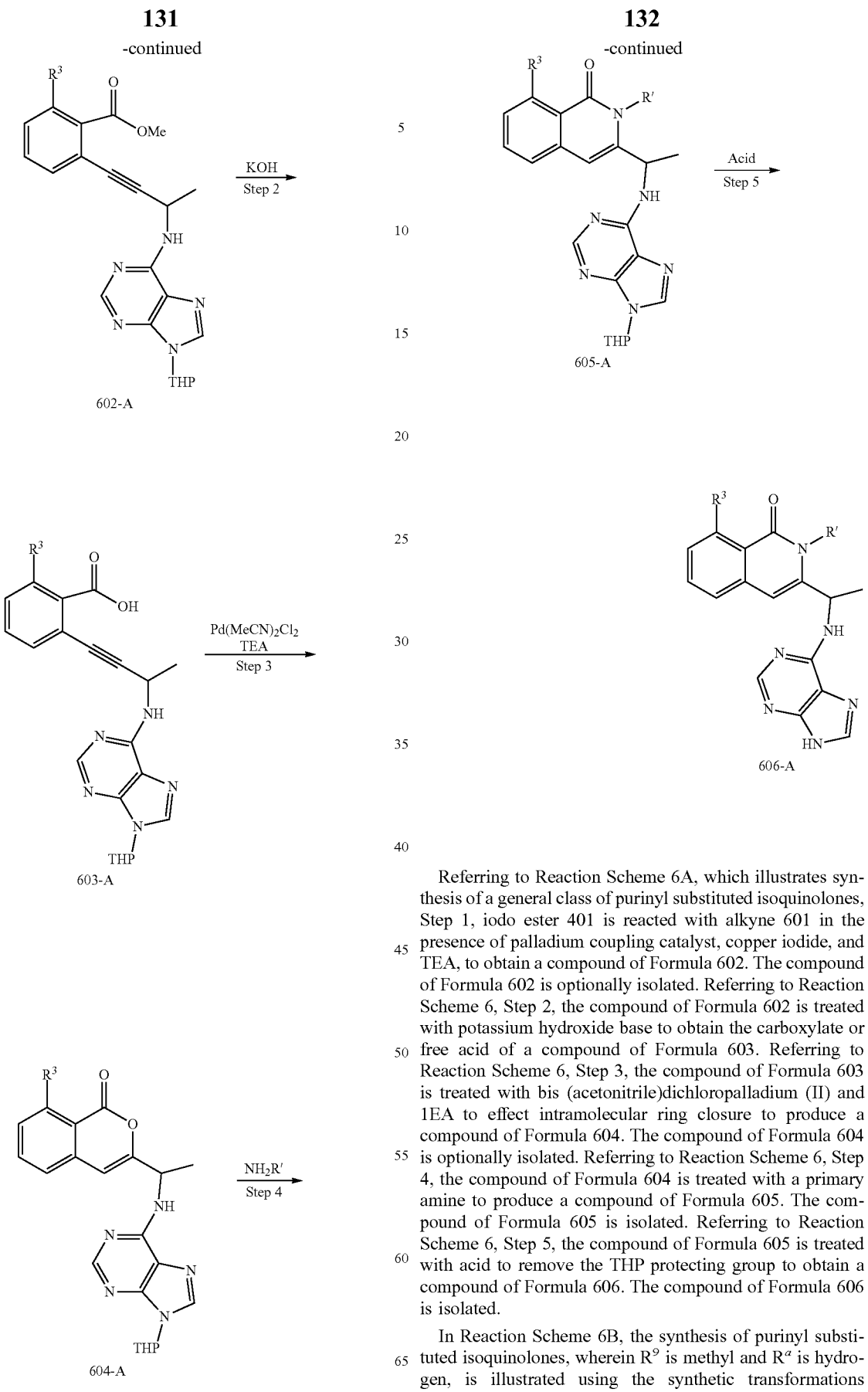

Referring to Reaction Scheme 6A, which illustrates synthesis of a general class of purinyl substituted isoquinolones, Step 1, iodo ester 401 is reacted with alkyne 601 in the presence of palladium coupling catalyst, copper iodide, and TEA, to obtain a compound of Formula 602. The compound of Formula 602 is optionally isolated. Referring to Reaction Scheme 6, Step 2, the compound of Formula 602 is treated with potassium hydroxide base to obtain the carboxylate or free acid of a compound of Formula 603. Referring to Reaction Scheme 6, Step 3, the compound of Formula 603 is treated with bis (acetonitrile)dichloropalladium (II) and 1EA to effect intramolecular ring closure to produce a compound of Formula 604. The compound of Formula 604 is optionally isolated. Referring to Reaction Scheme 6, Step 4, the compound of Formula 604 is treated with a primary amine to produce a compound of Formula 605. The compound of Formula 605 is isolated. Referring to Reaction Scheme 6, Step 5, the compound of Formula 605 is treated with acid to remove the THP protecting group to obtain a compound of Formula 606. The compound of Formula 606 is isolated.

In Reaction Scheme 6B, the synthesis of purinyl substituted isoquinolones, wherein $R^9$ is methyl and $R^a$ is hydrogen, is illustrated using the synthetic transformations described for Reaction Scheme 6A.

Reaction Scheme 7A
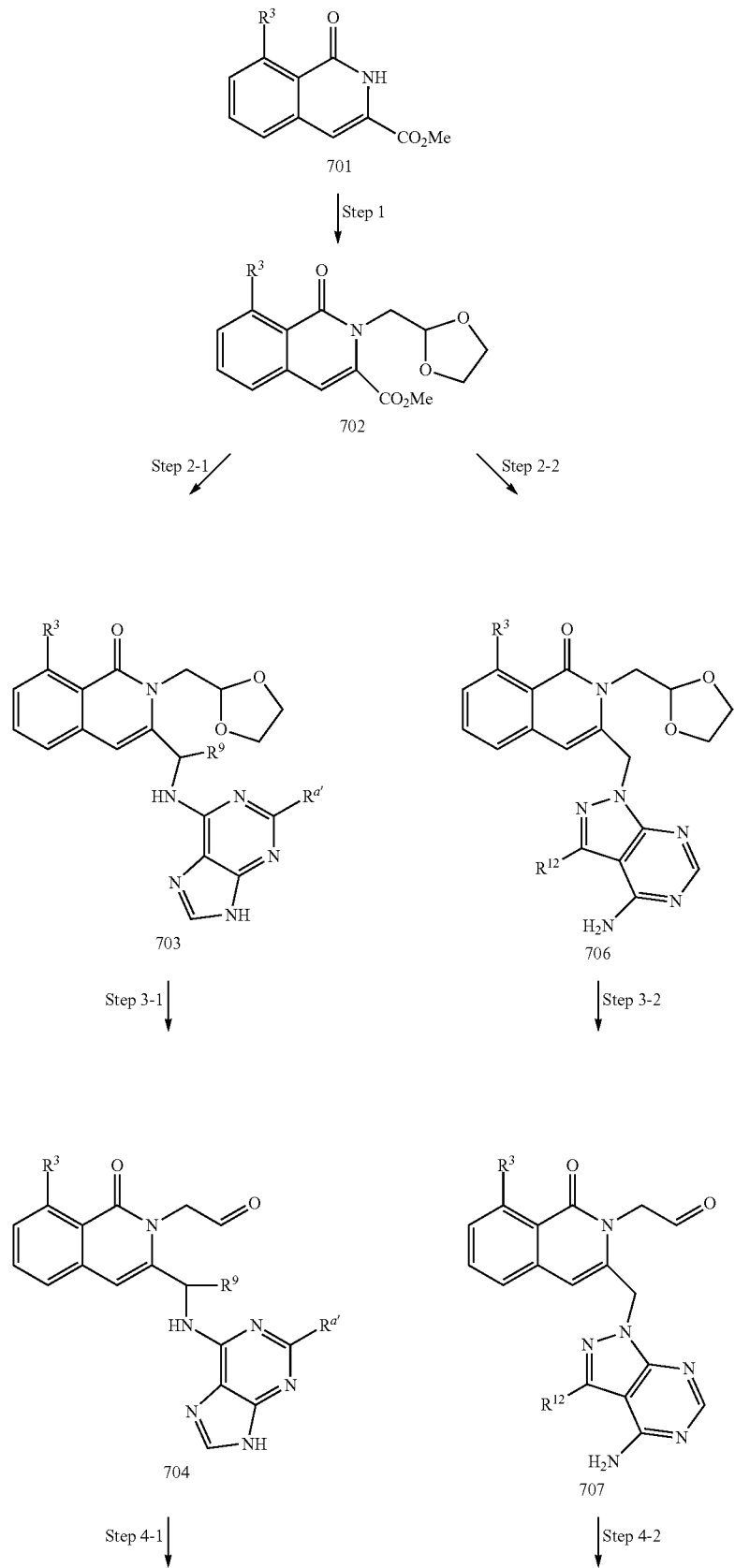

-continued

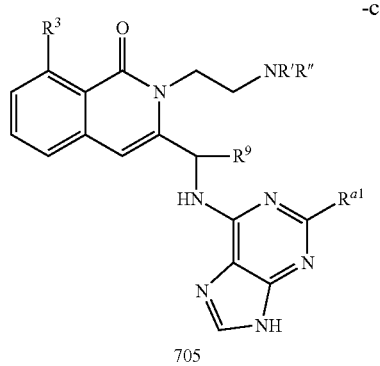
705

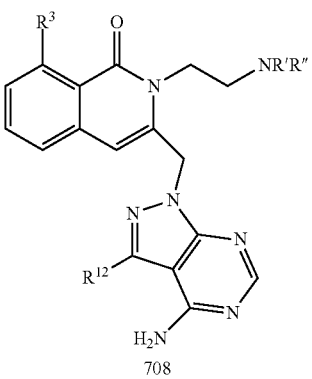
708

Reaction Scheme 7B

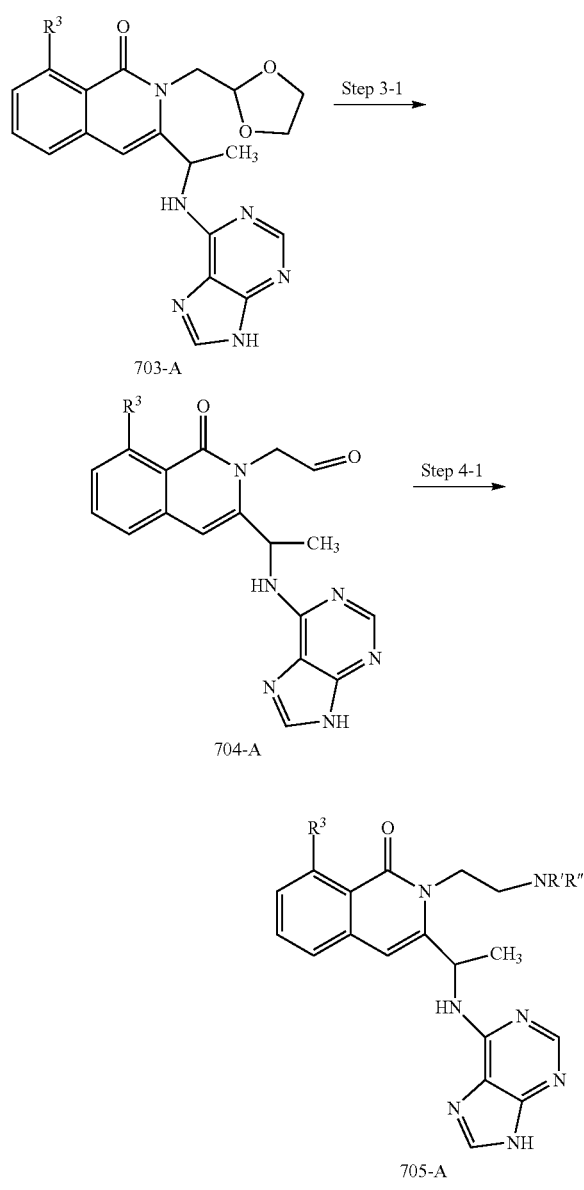

Referring to Reaction Scheme 7A, which illustrates the synthesis of purinyl or pyrazolopyrimidinyl substituted isoquinoliones comprising an alkyl amine substituent at the position represented by B in Formula I, Step 1 the compound of Formula 701 is synthesized by a variety of synthetic routes, including variations of Schemes 1 or 2 where, for example, a benzyl amine is used in the step of converting a compound of Formula 103 to a compound of Formula 104. The benzyl protecting group of the amine may be removed by standard deprotection chemistry to produce a compound of 701. Another example of a conversion of a compound of Formula 103 to a compound of Formula 701, treatment of the compound of Formula 103 with ammonia produces the compound of Formula 701. The compound of Formula 701 is converted to a compound of Formula 702 by alkylation of the amide nitrogen with a number of 2-carbon containing synthons which can be deprotected, oxidized and reprotected as the respective ketal, the compound of Formula 702. Referring to Reaction Scheme 7, Step 2-1, the compound of Formula 702 is transformed by, for example, reductive amination of the ester moiety to introduce the purinyl moiety of a compound of Formula 703, or alternatively, is alkylated to so introduce a purinyl moiety and obtain a compound of Formula 703. Referring to Reaction Scheme 7, Step 3-1, the compound of Formula 703 is treated with acid to remove the ketal protecting group to produce a compound of Formula 704. The compound of Formula 704 is isolated. Referring to Reaction Scheme 7, Step 4-1, the compound of Formula 704 is reductively aminated with an amine to produce a compound of Formula 705. The compound of Formula 705 is isolated. Referring to Reaction Scheme 7, Step 2-2, the compound of Formula 702 is transformed by, steps 7 and 8 of Scheme 2 and step 9 of Scheme 3 to introduce the pyrazolopyrimidine moiety of a compound of Formula 706. The compound of Formula 706 is isolated. Referring to Reaction Scheme 7, Step 3-2, the compound of Formula 706 is treated with acid to remove the ketal protecting group to produce a compound of Formula 707. The compound of Formula 707 is isolated.

Referring to Reaction Scheme 7, Step 4-2, the compound of Formula 707 is reductively aminated with an amine to produce a compound of Formula 708. The compound of Formula 708 is isolated.

In Reaction Scheme 7B, the synthesis of compounds wherein $R^9$ is methyl and $R^a$ is hydrogen is illustrated, using the steps described in Scheme 7A.

Reaction Scheme 8

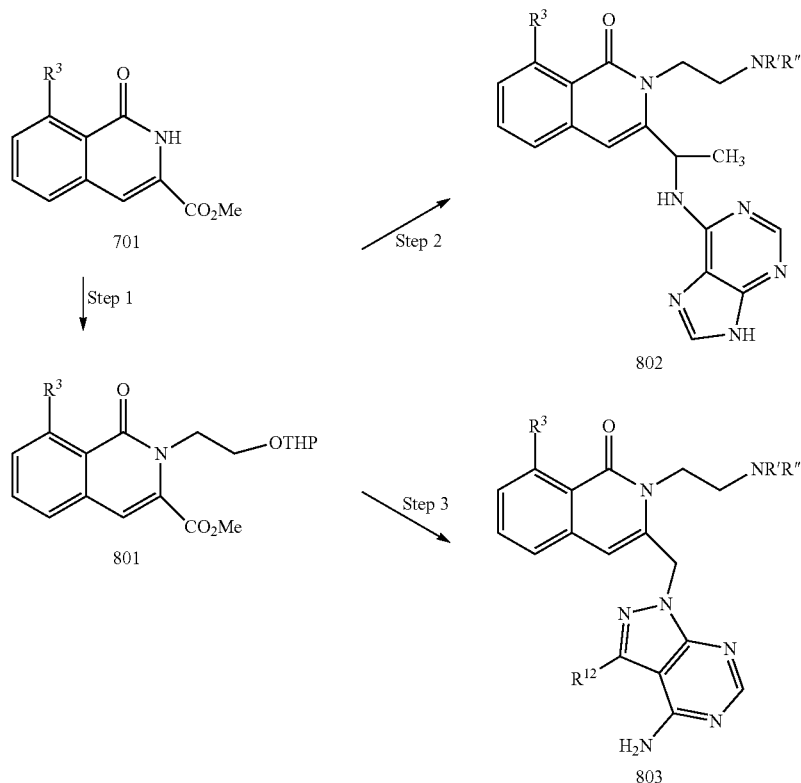

Referring to Reaction Scheme 8, Step 1, the compound of Formula 701 is synthesized as described in Scheme 7 or any other generally known chemistry. The compound of Formula 701 is transformed by alkylation of the amide nitrogen with a number of 2-carbon containing synthons which can be deprotected, and converted to the alkoxy protected species as shown in the compound of Formula 801, which can be isolated. Referring to Reaction Scheme 8, Step 2, the compound of Formula 801 is converted via chemistry described in Step 2-1 of Scheme 7 to introduce a purinyl moiety, and that resultant compound is transformed by deprotection, activation and amination with an amine to produce a compound of Formula 802, which isolated.

Referring to Reaction Scheme 8, Step 3, the compound of Formula 801 is converted via chemistry described in Step 2-2 of Scheme 7 to introduce a pyrazolopyrimidine moiety, and that resultant compound is transformed by deprotection, activation and amination with an amine to produce a compound of Formula 803, which isolated.

Reaction Scheme 9

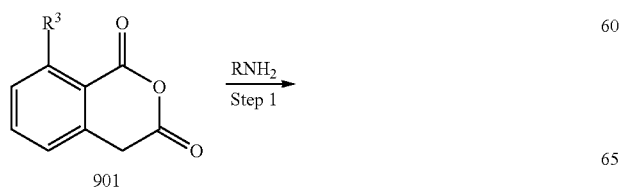

-continued

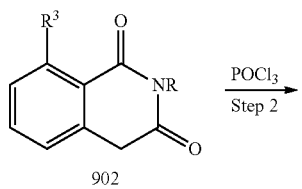

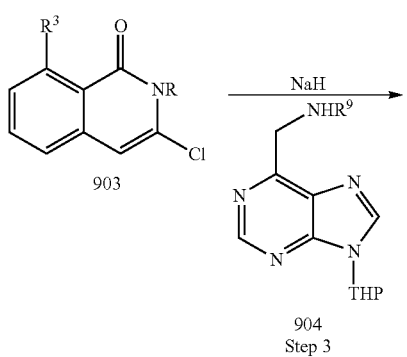

-continued

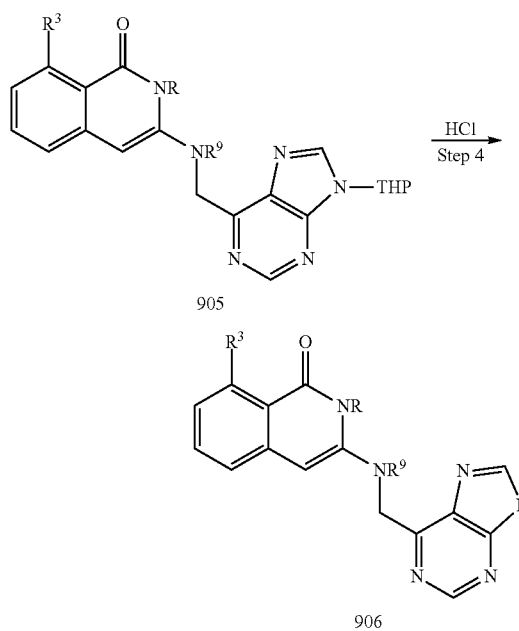

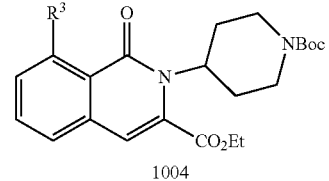

Referring to Reaction Scheme 10, Step 1, the compound of Formula 1001 is treated with vinylogous ester 1002 using, for example a Heck reaction with subsequent cyclization, to produce a compound of Formula 1003. The compound of Formula 1003 is isolated. Referring to Reaction Scheme 10, Step 2, the compound of Formula 1003 is reacted with 4-amino N-Boc piperidine to produce a compound of Formula 1004. The compound of Formula 1004 is isolated. The compound of Formula 1004 can be used as an intermediate in the synthesis of the compounds of the invention.

Referring to Reaction Scheme 9, Step 1, the compound of Formula 901 is treated with an amine to produce a compound of Formula 902. The compound of Formula 902 is isolated. Referring to Reaction Scheme 9, Step 2, the compound of Formula 902 is treated with phosphorus oxychloride to generate a compound of Formula 903. The compound of Formula 903 is isolated. Referring to Reaction Scheme 9, Step 3, the compound of Formula 903 is reacted with an amino purine of Formula 904 to obtain a compound of Formula 905. The compound of Formula 905 is isolated. Referring to Reaction Scheme 9, Step 4, the compound of Formula 905 is treated with hydrochloric acid to remove the protecting group at nitrogen on the purine moiety to produce a compound of Formula 906. The compound of 906 is isolated.

Reaction Scheme 11

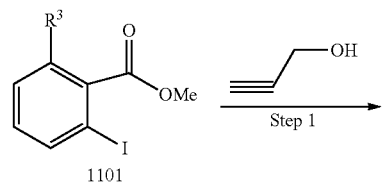

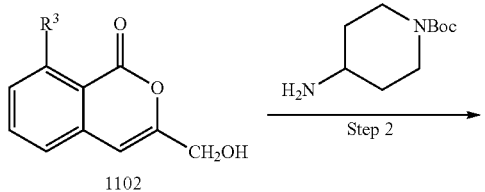

Reaction Scheme 10

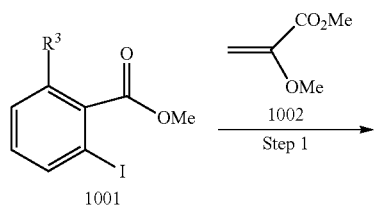

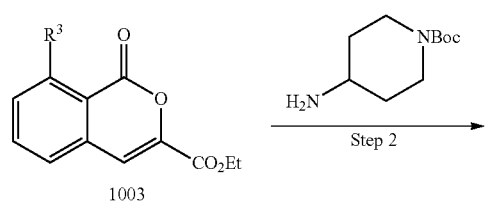

Referring to Reaction Scheme 11, Step 1, the compound of Formula 1101 is treated with an alkynyl alcohol, for example, of Formula 1102, in the presence of copper iodide and palladium on carbon catalyst, to produce a compound of Formula 1103. The compound of Formula 1103 is isolated. Referring to Reaction Scheme 11, Step 1, the compound of Formula 1102 is reacted with 4-amino N-Boc piperidine to produce a compound of Formula 1103. The compound of Formula 1103 is isolated. The compound of Formula 1103 can be used as an intermediate in the synthesis of the compounds of the invention.

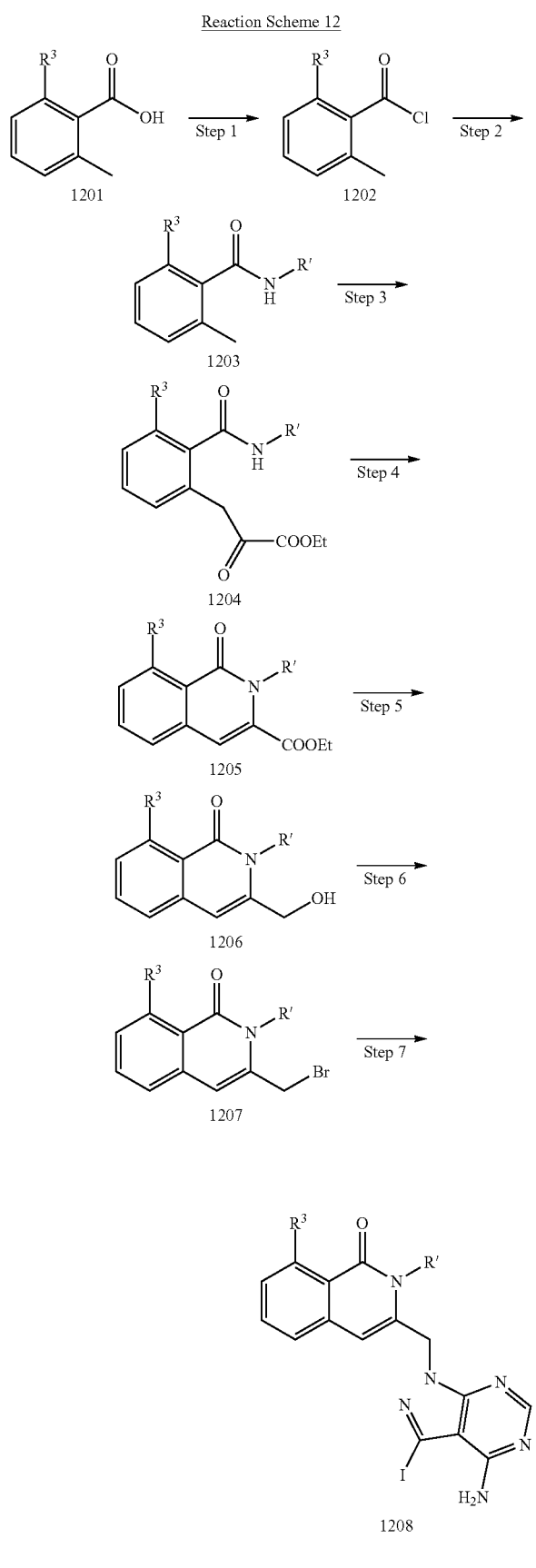

Another approach to synthesis of compounds of Formula I is illustrated in Scheme 12. Referring to Step 1, the compound of Formula 1201 is treated with a chlorinating agent such as oxalyl chloride to produce an acid chloride of Formula 1202. In Step 2, the compound of Formula 1202 is reacted with a compound of Formula R'NH$_2$ in the presence of a base such as triethylamine, to produce a compound of Formula 1203. In Step 3, the compound of Formula 1203 is treated with n-butyllithium and then reacted with an dialkyl oxalate such as diethyl oxalate to produce a compound of Formula 1204. In Step 4, the compound of Formula 1204 is refluxed in an acidic solution, for example, hydrochloric acid in methanol to produce a compound of Formula 1205. In Step 5, the compound of Formula 1205 is treated with a reducing agent such as lithium aluminum hydride to produce a compound of Formula 1206. In Step 6, the compound of Formula 1206 is reacted with a brominating agent such as phosphorus tribromide, in the presence of dimethylformamide in acetonitrile to produce a bromo compound of Formula 1207. In Step 7, the compound of Formula 1207 is reacted with a heteroaryl compound, for example 3-iodo 1H-pyrazolo[3,4-d]pyrimidin-4-amine, in the presence of a base such as potassium tert-butoxide in dimethylformamide to produce a compound of Formula 1208.

Reaction Scheme 13

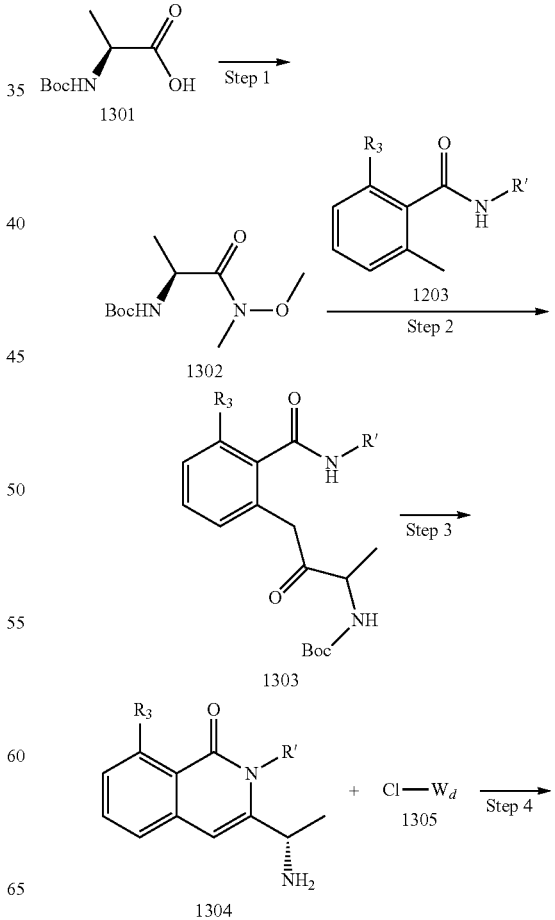

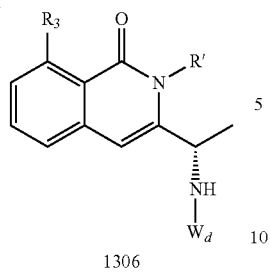

1306

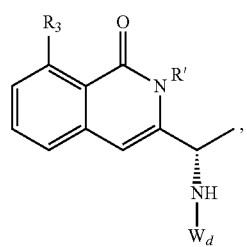

wherein $R^3$ is chloro.

Compounds disclosed herein can be synthesized using the reaction schemes as disclosed herein, variants thereof, or other synthetic methods known in the art.

In some embodiments, the compounds of the present invention exhibits one or more functional characteristics disclosed herein. For example, one or more subject compounds bind specifically to a PI3 kinase. In some embodiments, the IC50 of a subject compound for p110α, p110β, p110γ, or p110δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compounds may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

Additionally, a compound of Formula having an (S)-isomeric configuration with respect to carbon X may exhibit greater potency against one or more target PI3-kinases than the corresponding compound having an (R)-isomeric configuration with respect to carbon X. For example, the compound of Formula I having an (S)-isomeric configuration with respect to carbon X may have a PI3-kinase IC50 value which is 1, 2, 3, or 4 orders of magnitude lower than the PI3-kinase IC50 value of the corresponding compound having an (R)-configuration.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase In Scheme 13, an approach is described for synthesizing compounds of Formula I having a XY linker wherein X is predominantly or solely (S)—C(CH₃)H— and Y is —NH—. Wd is a monocyclic or bicyclic heteroaryl, including but not limited to purinyl, pyrimidinyl, pyrrolopyrimidinyl, or pyrazolopyrimidinyl. Referring to Step 1 of Scheme 13, the compound of Formula 1301, (the S-isomer) is coupled to N, O— dimethylhydroxylamine using hydroxybenzotriazole (HOBt) and 1-ethyl-3-(3'-dimethylaminopropyl)carbodiimide (EDCI) in the presence of triethylamine to produce a compound of Formula 1302. In Step 2, a compound of Formula 1203, which may be synthesized as described in Scheme 12, is deprotonated with n-butyllithium in THF and hexamethylphosphoramide at −78° C. under an argon atmosphere. The compound of Formula 1302 is added and the reaction mixture is allowed to warm to −50° C., quenched with the addition of water and a compound of Formula 1303 is isolated. In Step 3 the compound of Formula 1303 is treated with hydrochloric acid in methanol at reflux, and then the reaction mixture is basified with the addition of sodium carbonate solution to a pH of about 7-about 8, to produce a compound of Formula 1304. The compound of formula 1304 may be partly epimerized as a result of the preceding reaction steps. Highly enantiopure 1304 may be isolated by preparing the tartaric acid salt by dissolving the compound of Formula 1304 in methanol and adding D-tartaric acid. The resulting reaction mixture is refluxed for one hour, then stirred at room temperature for 16 hours, and permits isolation of the salt of the compound of Formula 1304 wherein the enantiomeric purity is greater than 90% of the (S)-isomer. The free amine of the compound of Formula 1304 is regenerated before its use in the next synthesis step. The compound of Formula 1304, which is substantially the (S)-enantiomer is coupled to a chloro substituted heteroaryl $W_d$, a compound of Formula 1305, including but not limited to 6-chloro-9(tetrahydro-2H-pyran-2-yl)-9H-purine, 2,4,5,-trichloropyrimidine, 4-chloro-7H-pyrrolo[2,3-d] pyrimidine, and 4-chloro-1H-pyrazolo[3,4-d]pyrimidine in the presence of base such as diisopropylethylamine or ammonia, to produce a compound of Formula 1306, and where the compound of Formula 1306 is the (S)-isomer.

Synthesis of $R^3$-halo analogs, e.g. chloro substituted isoquinolone analogs. The same reaction scheme 13 applies to the generation of a compound having the formula:

mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, at least 10,100-fold, or lower, than the inhibitor's IC50 with respect to the rest of the other type I PI3-kinases.

Pharmaceutical Compositions

The invention provides pharmaceutical compositions comprising one or more compounds of the present invention.

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rheumatoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e. g., psoriasis), restenosis, or prostate (e. g., benign prostatic hypertrophy (BPH)).

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same.

Pharmaceutical compositions for oral administration. In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, E-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds, Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined by the following procedure, as well as the procedure described in the examples below. The activity of the kinase is assessed by measuring the incorporation of $\gamma$-$^{33}$P-phosphate from $\gamma$-$^{33}$P-ATP onto N-terminal His tagged substrate, which is expressed in $E.\ coli$ and is purified by conventional methods, in the presence of the kinase. The assay is carried out in 96-well polypropylene plate. The incubation mixture (100 μL) comprises of 25 mM Hepes, pH 7.4, 10 mM $MgCl_2$, 5 mM β-glycerolphosphate, 100 μM Na-orthovanadate, 5 mM DTT, 5 nM kinase, and 1 μM substrate. Inhibitors are suspended in DMSO, and all reactions, including controls are performed at a final concentration of 1% DMSO. Reactions are initiated by the addition of 10 μM ATP (with 0.5 μCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filter plates, and excess labeled ATP washed off using a Tomtec MACH III harvestor. Plates are allowed to air-thy prior to adding 30 μL/well of Packard Microscint 20, and plates are counted using a Packard TopCount.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Methods

The invention also provides methods of using the compounds or pharmaceutical compositions of the present invention to treat disease conditions, including but not limited to diseases associated with malfunctioning of one or more types of PI3 kinase A detailed description of conditions and disorders mediated by p110δ kinase activity is set forth in Sadu et al., WO 01/81346, which is incorporated herein by reference in its entirety for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e g a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3K-δ may further provide for a reduction in the inflammatory or undesirable immune response without a concomittant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polouxyl-40 hydrogenated castor oil, polyoxyl-60 hydrogenated castor oil or polyoxyl-100 hydrogenated castor oil.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80 90, 95, or 99% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase α, PI3 kinase PI3 kinase γ, PI3 kinase δ; DNA-PK; mTor; Abl, VEGFR, Ephrin receptor B4 (EphB4); ILK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

Combination Treatment

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R®; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, 1-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, intercede and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, Mycobacterium avium complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Synthesis of 3-((4-amino-3-(3-hydroxyphenyl)-1H-pyrazolo[3,4-d]pyrimidin-1-yl)methyl)-8-methyl-2-o-tolylisoquinolin-1(2H)-one (Compound 1613) (Method A)

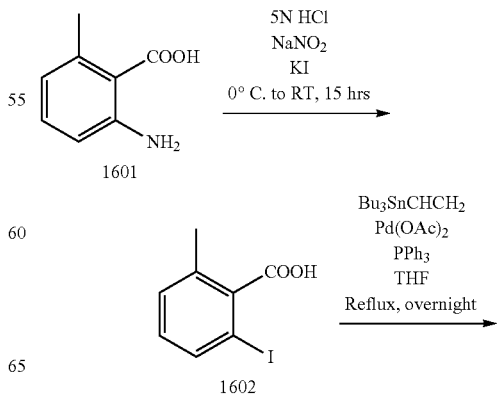

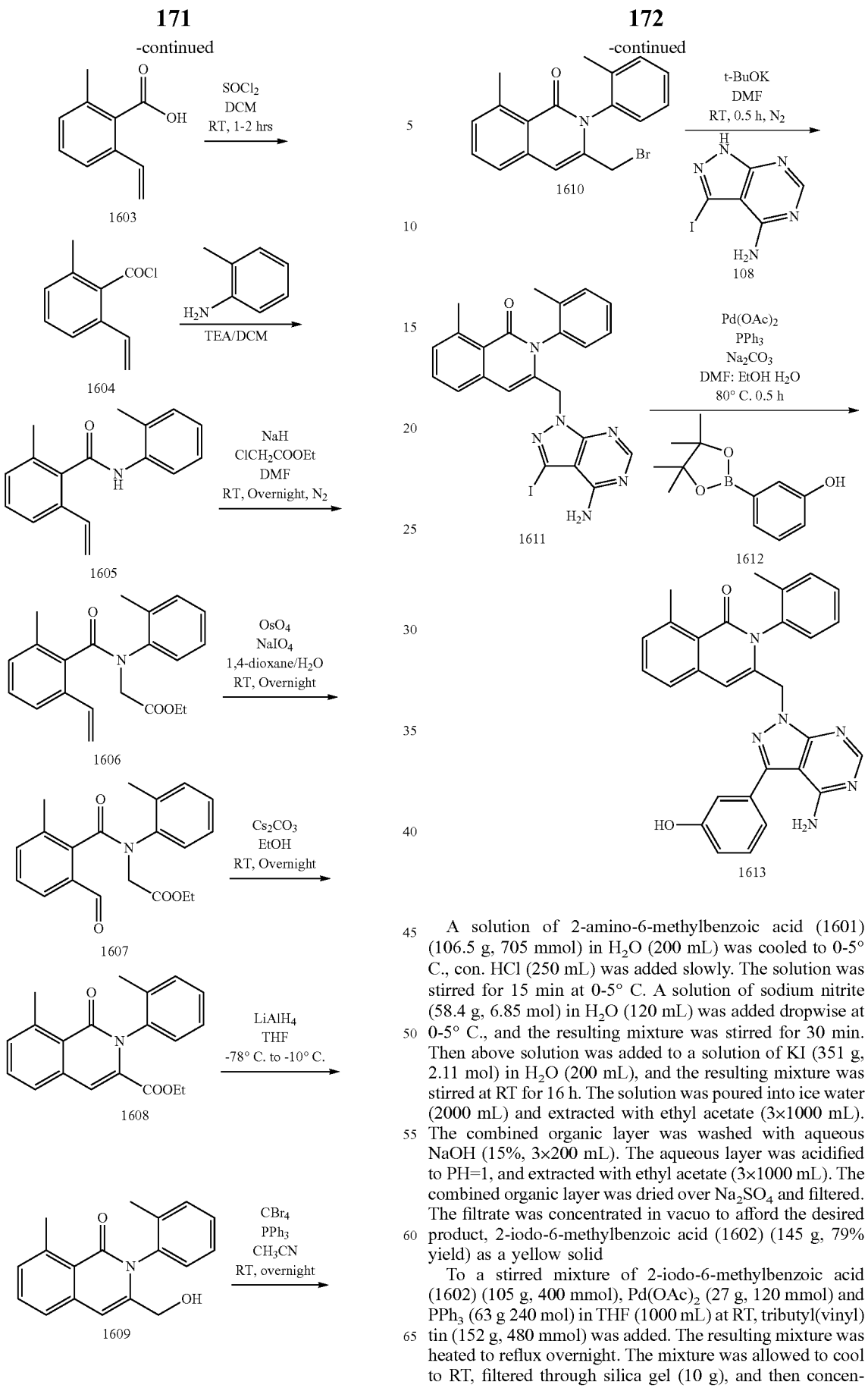

A solution of 2-amino-6-methylbenzoic acid (1601) (106.5 g, 705 mmol) in H₂O (200 mL) was cooled to 0-5° C., con. HCl (250 mL) was added slowly. The solution was stirred for 15 min at 0-5° C. A solution of sodium nitrite (58.4 g, 6.85 mol) in H₂O (120 mL) was added dropwise at 0-5° C., and the resulting mixture was stirred for 30 min. Then above solution was added to a solution of KI (351 g, 2.11 mol) in H₂O (200 mL), and the resulting mixture was stirred at RT for 16 h. The solution was poured into ice water (2000 mL) and extracted with ethyl acetate (3×1000 mL). The combined organic layer was washed with aqueous NaOH (15%, 3×200 mL). The aqueous layer was acidified to PH=1, and extracted with ethyl acetate (3×1000 mL). The combined organic layer was dried over Na₂SO₄ and filtered. The filtrate was concentrated in vacuo to afford the desired product, 2-iodo-6-methylbenzoic acid (1602) (145 g, 79% yield) as a yellow solid To a stirred mixture of 2-iodo-6-methylbenzoic acid (1602) (105 g, 400 mmol), Pd(OAc)₂ (27 g, 120 mmol) and PPh₃ (63 g 240 mol) in THF (1000 mL) at RT, tributyl(vinyl) tin (152 g, 480 mmol) was added. The resulting mixture was heated to reflux overnight. The mixture was allowed to cool to RT, filtered through silica gel (10 g), and then concentrated in vacuo. The residue was poured into ice water (1000 mL) and extracted with ethyl acetate (3×1000 mL). The combined organic layer was washed with aqueous NaOH (15%, 5×200 mL). The combined aqueous layer was acidified to PH=1, extracted with ethyl acetate (3×1000 mL). The combined organic layer was dried over $Na_2SO_4$ and filtered. The filtrate was concentrated in vacuo to afford the desired product, 2-methyl-6-vinylbenzoic acid (1603) (61 g, 95% yield) as a yellow solid.

A mixture of 2-methyl-6-vinylbenzoic acid (1603) (56 g, 350 mmol) and thionyl chloride (208 g, 1750 mmol) in toluene (400 mL) was stirred at reflux for 2 h. The mixture was concentrated in vacuo to afford the desired product, 2-methyl-6-vinylbenzoyl chloride (1604) (63 g, 95% yield) as a yellow oil. The product obtained was used directly in the next step without purification.

A mixture of o-toluidine (45 g, 420 mmol) and Triethylamine (71 g, 70 mmol) in $CH_2Cl_2$ (300 mL) was stirred for 10 min at RT. To this mixture, 2-methyl-6-vinylbenzoyl chloride (1604) (63 g, 35 mmol) was added, and the resulting mixture was stirred at RT for 30 min. The solution was poured into water (300 mL) and extracted with $CH_2Cl_2$ (3×200 mL), dried over $Na_2SO_4$ and filtered. The filtrate was concentrated in vacuo to afford the crude product. The crude product was suspended in IPE (isopropyl ether) (300 mL), stirred at reflux for 30 min, and then cooled to 0-5° C. The precipitate was collected by filtration and further dried in vacuo to afford the desired product, 2-methyl-N-o-tolyl-6-vinylbenzamide (1605) (81 g, 80% yield) as a yellow solid.

To a solution of 2-methyl-N-o-tolyl-6-vinylbenzamide (1605) (80 g, 320 mmol) in DMF (250 mL) at RT, NaH (60% in mineral oil, 25.6 g, 640 mmol) was slowly added and the resulting mixture was stirred at RT for 30 min. To this mixture, ethyl chloroacetate (78 g, 640 mmol) was added and the resulting mixture was stirred at RT for 2 h. The solution was poured into water (500 mL) and extracted with ethyl acetate (3×200 mL), dried over $Na_2SO_4$ and filtered. The filtrate was concentrated in vacuo. The crude product was suspended in MeOH (160 mL), stirred at reflux for 10 min, and then cooled to 0-5° C. The precipitate was collected by filtration and further dried in vacuo to afford the desired product, ethyl 2-(2-methyl-N-o-tolyl-6-vinylbenzamido) acetate (1606) (67 g, 62% yield) as a white solid.

To a stirred mixture of ethyl 2-(2-methyl-N-o-tolyl-6-vinylbenzamido) acetate (1606) (67 g, 200 mmol) in 1,4-dioxane (300 mL) and $H_2O$ (100 mL) at RT, Osmium tetroxide (20 mg) was added was and stirred at RT for 30 min. To this mixture, sodium periodate (86 g, 400 mmol) was added and the resulting mixture was stirred at RT for 16 h. The reaction mixture was filtered through silica gel (10 g), the filtrate was extracted with ethyl acetate (3×200 mL). The combined organic layers were washed with brine (100 mL), dried over $Na_2SO_4$ and filtered. The filtrate was concentrated in vacuo and the residue was further dried in vacuo to afford the desired product, ethyl 2-(2-formyl-6-methyl-N-o-tolyl-benzamido) acetate (1607) (38 g, 57% yield) as a yellow solid.

To a stirred solution of ethyl 2-(2-formyl-6-methyl-N-o-tolylbenzamido) acetate (1607) (38 g, 112 mmol) in EtOH (200 mL) and ethyl acetate (100 mL) at RT, cesium carbonate (22 g, 112 mmol) was added. The resulting mixture was degassed and back-filled with argon three times and then stirred at 50° C. for 5 h. The mixture was allowed to cool to RT, filtered through silica gel (10 g), and the filtrate was concentrated in vacuo. The residue was poured into $H_2O$ (200 mL), extracted with ethyl acetate (3×200 mL). The combined organic layer was washed with brine (50 mL), dried over $Na_2SO_4$ and filtered. The filtrate was concentrated in vacuo. The crude product was suspended in IPE (120 mL), heated to reflux for 10 min, and then cooled to 0-5° C. The precipitate was collected by filtration and further dried in vacuo to afford the desired product, ethyl 8-methyl-1-oxo-2-o-tolyl-1,2-dihydroisoquinoline-3-carboxylate (1608) (28 g, 77% yield) as a white solid.

To a stirred solution of lithium aluminum hydride (8.28 g, 218 mol) in anhydrous THF (500 mL) at −78° C. under a nitrogen atmosphere, ethyl 8-methyl-1-oxo-2-o-tolyl-1,2-dihydroisoquinoline-3-carboxylate (1608) (28 g, 87 mmol) was slowly added over a 10 min period of time. The resulting mixture was allowed to warm to −30° C., stirred for 30 min and TLC showed the completion of the reaction. Then the mixture was cooled to −78° C., and water (50 mL) was slowly added. The mixture was allowed to warm to RT, filtered through silica gel (10 g), and the filtrate was concentrated in vacuo. The crude product was poured into $H_2O$ (200 mL) and extracted with ethyl acetate (3×200 mL). The combined organic layer was washed with brine (50 mL), dried over $Na_2SO_4$ and filtered. The filtrate was concentrated in vacuo. The crude product was suspended in ethyl acetate (30 mL) and stirred for 10 min. The solid was collected by filtration and further dried in vacuo to afford the desired product, 3-(hydroxymethyl)-8-methyl-2-o-tolylisoquinolin-1(2H)-one (1609) (22 g, 92% yield) as a white solid.

$PBr_3$ (25.6 g, 95 mmol) was slowly added to a stirred solution of DMF (11.5 g, 158 mol) in acetonitrile (200 mL) at 0° C., and the resulting mixture was stirred at 0 C for 30 min. 3-(Hydroxymethyl)-8-methyl-2-o-tolylisoquinolin-1-(2H)-one (1609) (22 g, 78.8 mmol) was slowly added. Then the reaction mixture was allowed to warm to RT and stirred for 30 min. Saturated aqueous $NaHCO_3$ solution (50 mL) was slowly added and extracted with ethyl acetate (3×200 mL). The combined organic layer was washed with brine, dried over $Na_2SO_4$ and filtered. The filtrate was concentrated in vacuo. The crude product was suspended in IPE (50 mL) and then stirred for 10 min. The precipitate was collected by filtration and further dried in vacuo to afford the desired product, 3-(bromomethyl)-8-methyl-2-o-tolylisoquinolin-1 (2H)-one (1610) (21 g, 80% yield) as a white solid.

3-Iodo-1H-pyrazolo[3,4-d]pyrimidin-4-amine (108) (10.8 g, 41.4 mmol) and potassium tert-butoxide (4.4 g, 40 mmol) were dissolved in anhydrous DMF (150 mL) and stirred at RT for 30 min. 3-(Bromomethyl)-8-methyl-2-o-tolylisoquinolin-1(2H)-one (1610) (13.7 g, 40 mmol) was added. The resulting mixture was stirred at RT for 30 min, poured into ice water (300 mL) and then extracted with ethyl acetate (3×200 mL). The combined organic layer was washed with brine (50 mL), dried over $Na_2SO_4$ and filtered. The filtrate was concentrated to about 100 ml in vacuo, the precipitate was collected by filtration to afford the first batch of desired product, 3-((4-amino-3-iodo-1H-pyrazolo[3,4-d]pyrimidin-1-yl)methyl)-8-methyl-2-o-tolylisoquinolin-1(2H)-one (1611) (12 g, 60% yield) as a white solid. The filtrate was concentrated in vacuo and the residue was purified by flash column chromatography on silica gel (2-20% MeOH/DCM) to afford the second batch of desired product, 3-((4-amino-3-iodo-1H-pyrazolo[3,4-d]pyrimidin-1-yl)methyl)-8-methyl-2-o-tolylisoquinolin-1(2H)-one (1611) (6 g, 30% yield) as a white solid.

3-((4-amino-3-iodo-1H-pyrazolo[3,4-d]pyrimidin-1-yl) methyl)-8-methyl-2-o-tolylisoquinolin-1(2H)-one (1611) (13 g, 24.9 mmol) and 3-(4,4,5,5-tetramethyl-1,3,2-dioxaborolan-2-yl)phenol (1612) (6.6 g, 30 mmol) were dissolved in DMF-EtOH-$H_2O$ (120 mL, 40 mL, 40 mL). $Pd(OAc)_2$ (1.684 g, 7.5 mmol), $PPh_3$ (3.935 g 15 mmol) and $Na_2CO_3$ (13.25 g 125 mmol) were added sequentially. The resulting mixture was degassed and back-filled with argon three times and then stirred at 100° C. for 1 h. The mixture was allowed to cool to RT, filtered through silica gel (10 g) and concentrated in vacuo. The residue was purified by flash column chromatography on silica gel (2-20% MeOH/DCM) to afford the product (1613) (9 g, 76% yield) as a slight yellow solid. Then above product was suspended in EtOH (100 mL) and heated to reflux for 30 min. The mixture was allowed to cool to RT, and the solid was collected by filtration. The solid was then suspended in EA (100 mL) and stirred overnight. The precipitate was collected by filtration and further dried in vacuo to afford the desired product, 3-(((4-amino-3-(3-hydroxyphenyl)-1H-pyrazolo[3,4-d]pyrimidin-1-yl)methyl)-8-methyl-2-o-tolylisoquinolin-1(2H)-one (1613) (8.4 g, 69% yield) as a white solid.

Example 2

Synthesis of 3-((4-amino-3-(3-hydroxyphenyl)-1H-pyrazolo[3,4-d]pyrimidin-1-yl)methyl)-8-methyl-2-o-tolylisoquinolin-1(2H)-one (Compound 1613) (Method B)

Scheme 15. Synthesis of 3-((4-amino-3-(3-hydroxyphenyl)-1H-pyrazol[3,4-d]pyrimidin-1-yl)methyl)-8-methyl-2-o-tolylisoquinolin-1(2H)-one (Compound 1613) via method B is described.

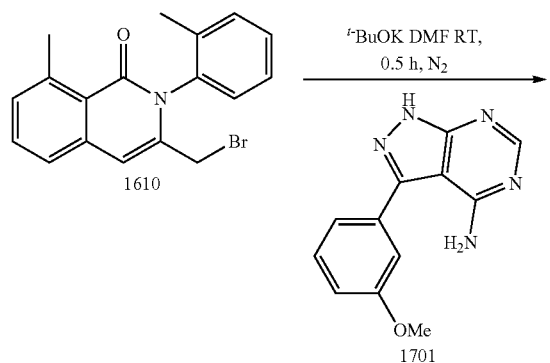

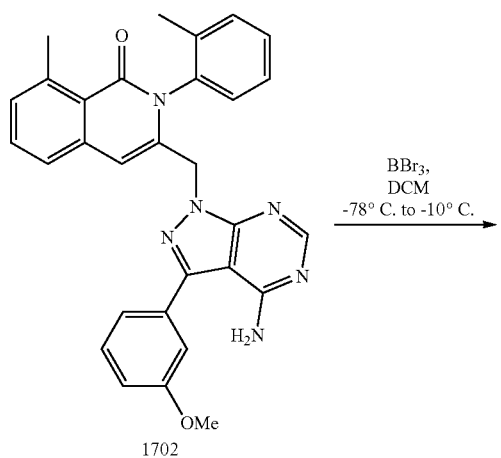

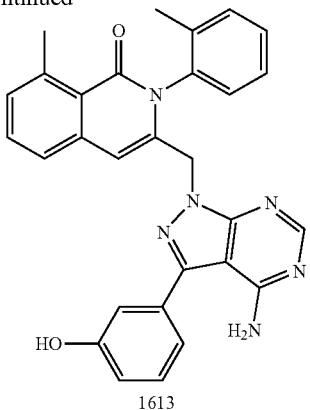

3-(3-Methoxyphenyl)-1H-pyrazolo[3,4-d]pyrimidin-4-amine (1701) (964 mg, 4 mmol) and potassium tert-butoxide (0.44 g, 4 mmol) were dissolved in anhydrous DMF (150 mL) and stirred at RT for 30 min. 3-(Bromomethyl)-8-methyl-2-o-tolylisoquinolin-1(2H)-one (1610) (1.37 g, 4.0 mmol) was added. The resulting mixture was stirred at RT for 30 min, poured into ice water (30 mL) and then extracted with ethyl acetate (3×50 mL). The combined organic layer was washed with brine (25 mL), dried over Na$_2$SO$_4$ and filtered. The filtrate was concentrated in vacuo and the residue was purified by flash column chromatography on silica gel (2-20% MeOH/DCM) to afford the desired product, 3-((4-amino-3-(3-methoxyphenyl)-1H-pyrazolo[3,4-d]pyrimidin-1-yl)methyl)-8-methyl-2-o-tolylisoquinolin-1(2H)-one (1702) (1.4 g, 70% yield) as a white solid.

To a solution of 3-((4-amino-3-(3-methoxyphenyl)-1H-pyrazolo[3,4-d]pyrimidin-1-yl)methyl)-8-methyl-2-o-tolylisoquinolin-1(2H)-one (1702) (100 mg, 0.2 mmol) in CH$_2$Cl$_2$ (20 mL) at −78° C. under a nitrogen atmosphere, BBr$_3$ (1 mL) was added and the resulting mixture was stirred at −78° C. from 3 h. The mixture was allowed to warm to RT, poured into ice-water (200 mL) and extracted with ethyl acetate (3×50 mL). The combined organic layer was washed with brine (20 mL), dried over Na$_2$SO$_4$ and filtered. The filtrate was concentrated in vacuo and the residue was purified by flash column chromatography on silica gel (10-50% MeOH/CH$_2$Cl2) to afford the desired product, 3-((4-amino-3-(3-hydroxyphenyl)-1H-pyrazolo[3,4-d]pyrimidin-1-yl)methyl)-8-methyl-2-o-tolylisoquinolin-1(2H)-one (1613) (87 mg, 91% yield) as a white solid.

Example 3

Synthesis of (R)-3-((4-amino-3-(3-hydroxybut-1-ynyl)-1H-pyrazolo[3,4-d]pyrimidin-1-yl)methyl)-8-methyl-2-o-tolylisoquinolin-1(2H)-one (Compound 1802)

Scheme 16. Synthesis of (R)-3-((4-amino-3-(3-hydroxybut-1-ynyl)-1H-pyrazolo[3,4-d]pyrimidin-1-yl)methyl)-8-methyl-2-o-tolylisoquinolin-1(2H)-one (Compound 1802) is described.

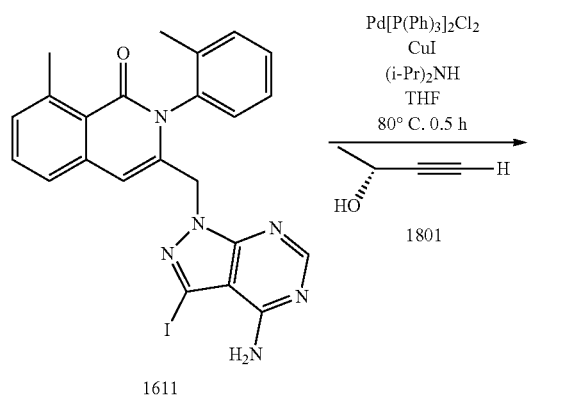

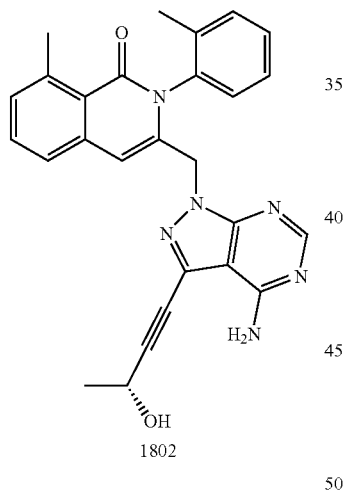

3-((4-amino-3-iodo-1H-pyrazolo[3,4-d]pyrimidin-1-yl)methyl)-8-methyl-2-o-tolylisoquinolin-1(2H)-one (1611) (522 mg, 1 mmol) and (R)-but-3-yn-2-ol (84 mg, 1.2 mmol) were dissolved in anhydrous THF (40 mL). The mixture was degassed and back-filled with nitrogen three times. Pd(PPh$_3$)$_2$Cl$_2$ (12 mg, 0.1 mmol), CuI (47 mg 0.25 mmol) and (i-Pr)$_2$NH (505 mg, 5 mmol) were added sequentially. The resulting mixture was degassed and back-filled with argon three times and then stirred at reflux for 4 h. The mixture was allowed to cool to RT, filtered through silica gel (10 g) and concentrated in vacuo. The residue was purified by flash column chromatography on silica gel (2-20% MeOH/DCM) to afford the product, 3 (R)-3-((4-amino-3-(3-hydroxybut-1-ynyl)-1H-pyrazolo[3,4-d]pyrimidin-1-yl) methyl)-8-methyl-2-o-tolylisoquinolin-1(2H)-one (1802) (324 mg, 70% yield) as a slightly yellow solid.

Example 4

Synthesis of 3-((6-amino-9H-purin-9-yl)methyl)-8-methyl-2-o-tolylisoquinolin-1(2H)-one (Compound 1902)

Scheme 17. Synthesis of 3-((6-amino-9H-purin-9-yl)methyl)-8-methyl-2-o-tolylisoquinolin-1(2H)-one (Compound 1902) is described.

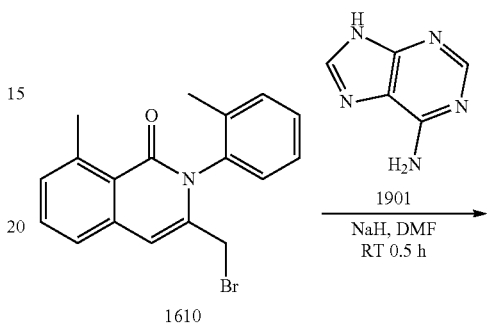

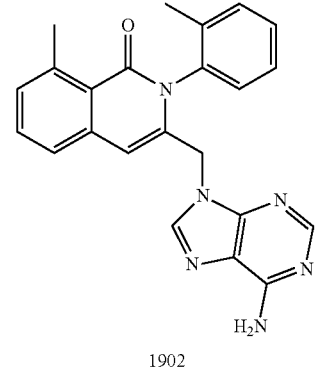

9H-Purin-6-amine (1901) (540 mg, 4.0 mmol) was dissolved in anhydrous DMF (20 mL). NaH (60% in mineral oil, 160 mg, 4.0 mmol) was added and the resulting mixture was stirred at RT for 30 min. 3-(Bromomethyl)-8-methyl-2-o-tolylisoquinolin-1(2H)-one (1610) (1.37 g, 4.0 mmol) was added. The reaction mixture was stirred at RT for 30 min, poured into ice-water (30 mL) and then extracted with ethyl acetate (3×50 mL). The combined organic layer was washed with brine (25 mL), dried over Na$_2$SO$_4$ and filtered. The filtrate was concentrated in vacuo and the residue was purified by flash column chromatography on silica gel (2-20% MeOH/DCM) to afford the desired product, 3-((6-amino-9H-purin-9-yl)methyl)-8-methyl-2-o-tolylisoquinolin-1(2H)-one (1902) (1.1 g, 70% yield) as a white solid.

Example 5

Synthesis of 3-((4-amino-3-(3-hydroxyphenyl)-1H-pyrazolo[3,4-d]pyrimidin-1-yl)methyl)-2-isopropyl-8-methylisoquinolin-1(2H)-one (Compound 2013)

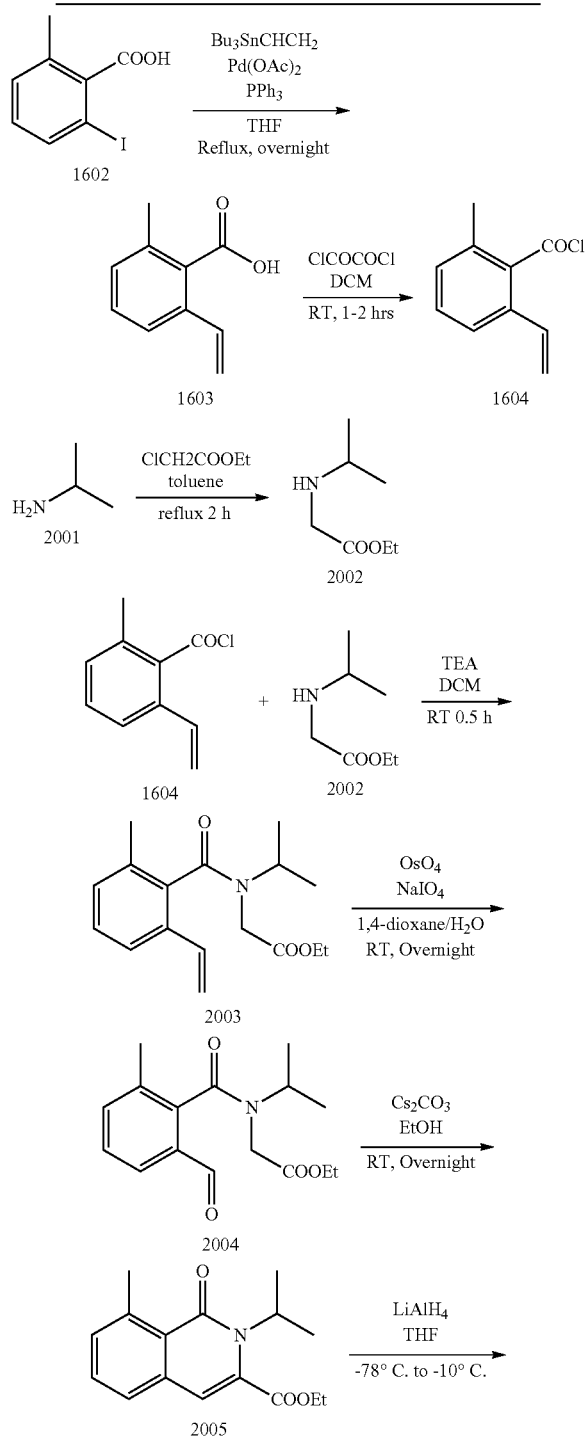

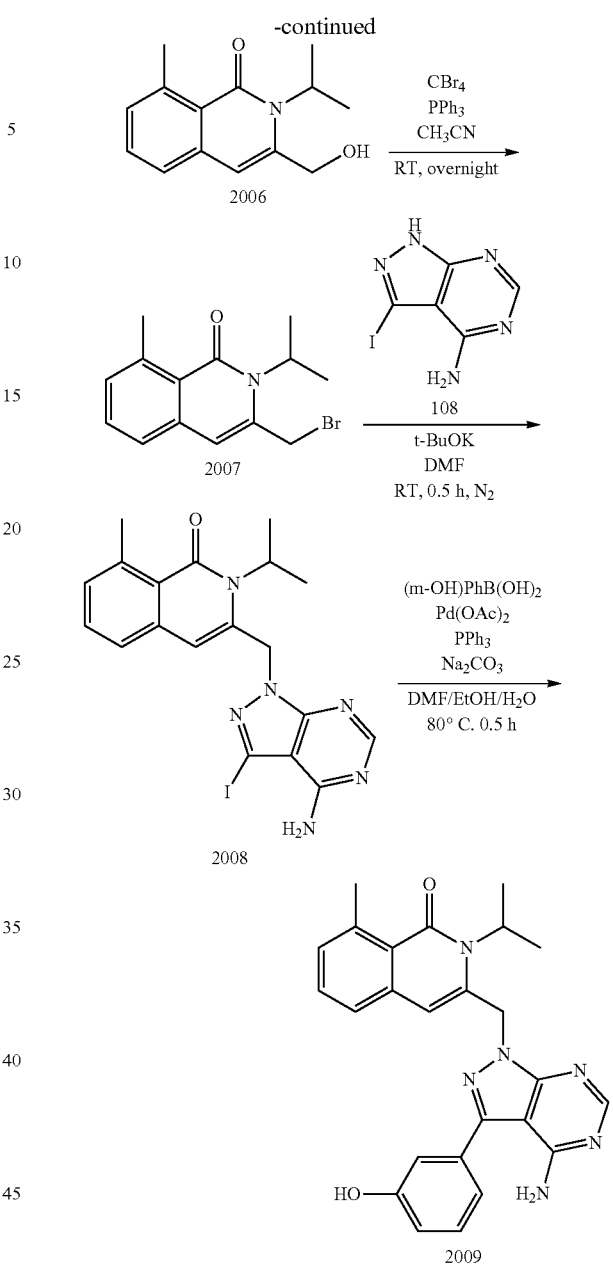

To a stirred mixture of 2-iodo-6-methylbenzoic acid (1602) (105 g, 400 mmol), Pd(OAc)$_2$ (27 g, 120 mmol) and PPh$_3$ (63 g 240 mol) in THF (1000 mL) at RT, tributyl(vinyl)tin (152 g, 480 mmol) was added. The resulting mixture was heated to reflux overnight. The mixture was allowed to cool to RT, filtered through silica gel (10 g), and then concentrated in vacuo. The residue was poured into ice water (1000 mL) and extracted with ethyl acetate (3×1000 mL). The combined organic layer was washed with aqueous NaOH (15%, 5×200 mL). The combined aqueous layer was acidified to PH=1, extracted with ethyl acetate (3×1000 mL). The combined organic layer was dried over Na$_2$SO$_4$ and filtered. The filtrate was concentrated in vacuo to afford the desired product, 2-methyl-6-vinylbenzoic acid (1603) (61 g, 95% yield) as a yellow solid.

A mixture of 2-methyl-6-vinylbenzoic acid (1603) (56 g, 350 mmol) and thionyl chloride (208 g, 1750 mmol) in toluene (400 mL) was stirred at reflux for 2 h. The mixture was concentrated in vacuo to afford the desired product, 2-methyl-6-vinylbenzoyl chloride (1604) (63 g, 95% yield) as a yellow oil. The product obtained was used directly in the next step without purification.

Propan-2-amine (2001) (59 g, 1.0 mol) and ethyl chloroacetate (122 g, 1.0 mol) were dissolved in toluene (200 mL) and the mixture was stirred at reflux for 2 h. The reaction mixture was allowed to cool to RT, poured into ice-water (500 mL) and extracted with ethyl acetate (3×250 mL). The combined organic layer was washed with brine (50 mL), dried over $Na_2SO_4$ and filtered. The filtrate was concentrated in vacuo and the residue was purified by flash column chromatography on silica gel (10-50% EA/PE) to afford the product, ethyl 2-(isopropylamino)acetate (2002) (70 g, 51% yield) as an oil.

Ethyl 2-(isopropylamino)acetate (2002) (14.5 g, 100 mmol) and triethylamine (200 g, 200 mmol) were dissolved in $CH_2Cl_2$ (300 mL) and the mixture was stirred for 10 min at RT. 2-Methyl-6-vinylbenzoyl chloride (1604) (18 g, 100 mmol) was added, and the resulting mixture was stirred at RT for 30 min. The reaction mixture was poured into water (300 mL) and extracted with $CH_2Cl_2$ (3×200 mL). The combined organic layer was washed with brine (50 mL), dried over $Na_2SO_4$ and filtered. The filtrate was concentrated in vacuo to afford the crude product. The crude product was suspended in IPE (isopropyl ether) (300 mL), stirred at reflux for 30 min, and then cooled to 0-5° C. The precipitate was collected by filtration and further dried in vacuo to afford the desired product, ethyl 2-(N-isopropyl-2-methyl-6-vinylbenzamido)acetate (2003) (14.5 g, 50% yield) as a yellow solid.

To a stirred solution of ethyl 2-(N-isopropyl-2-methyl-6-vinylbenzamido)acetate (2003) (14.0 g, 48.0 mmol) in 1,4-dioxane (100 mL) and $H_2O$ (30 mL), Osmium tetroxide (20 mg) was added and the resulting mixture was stirred at RT for 30 min. To this mixture, sodium periodate (22 g, 100 mmol) was added and then stirred at RT for 16 h. The reaction mixture was filtered through silica gel (10 g), the filtrate was extracted with ethyl acetate (3×200 mL). The combined organic layer was washed with brine (50 mL), dried over $Na_2SO_4$ and filtered. The filtrate was concentrated in vacuo and the residue was further dried in vacuo to afford the desired product, ethyl 2-(2-formyl-N-isopropyl-6-methylbenzamido)acetate (2004) (8.33 g, 57% yield) as a yellow solid.

To a stirred solution of ethyl 2-(2-formyl-N-isopropyl-6-methylbenzamido)acetate (2004) (8.3 g, 28.0 mmol) in EtOH (100 mL) and ethyl acetate (50 mL) at RT, cesium carbonate (5.9 g, 30 mmol) was added. The resulting mixture was degassed and back-filled with argon three times and then stirred at 50° C. for 5 h. The mixture was allowed to cool to RT, filtered through silica gel (10 g), and the filtrate was concentrated in vacuo. The residue was poured into $H_2O$ (200 mL), extracted with ethyl acetate (3×200 mL). The combined organic layer was washed with brine (50 mL), dried over $Na_2SO_4$ and filtered. The filtrate was concentrated in vacuo. The crude product was suspended in IPE (120 mL), stirred at reflux for 10 min, and then cooled to 0-5° C. The precipitate was collected by filtration and further dried in vacuo to afford the desired product, ethyl 2-isopropyl-8-methyl-1-oxo-1,2-dihydroisoquinoline-3-carboxylate (2005) (5.35 g, 70% yield) as a white solid.

To a stirred solution of lithium aluminum hydride (2.88 g, 76 mol) in anhydrous THF (200 mL) at −78° C. under a nitrogen atmosphere, ethyl 2-isopropyl-8-methyl-1-oxo-1,2-dihydroisoquinoline-3-carboxylate (2005) (5.2 g, 19 mmol) was slowly added over a 10 min period of time. The resulting mixture was allowed to warm to −30° C., stirred for 30 min and TLC showed the completion of the reaction. Then the mixture was cooled to −78° C., and water (50 mL) was slowly added. The mixture was allowed to warm to RT, filtered through silica gel (10 g), and the filtrate was concentrated in vacuo. The crude product was poured into $H_2O$ (200 mL) and extracted with ethyl acetate (3×200 mL). The combined organic layer was washed with brine (50 mL), dried over $Na_2SO_4$ and filtered. The filtrate was concentrated in vacuo. The crude product was suspended in ethyl acetate (30 mL) and stirred for 10 min. The solid was collected by filtration and further dried in vacuo to afford the desired product, 3-(hydroxymethyl)-2-isopropyl-8-methylisoquinolin-1(2H)-one (2006) (3.51 g, 80% yield) as a white solid.

To a solution of 3-(hydroxymethyl)-2-isopropyl-8-methylisoquinolin-1(2H)-one (2006) (1.61 g, 7.0 mmol) in $CH_2Cl_2$, $PPh_3$ (3.67 g, 14.0 mmol) was added and the mixture was stirred at RT for 30 min. The mixture was cooled to 0° C., and $CBr_4$ (4.64 g, 14.0 mmol) was added in portions. The resulting mixture was stirred from 0° C. to RT for 30 min, and then concentrated in vacuo. The crude product was purified by flash column chromatography on silica gel (30-50% EA/PE) to afford the desired product, 3-(bromomethyl)-2-isopropyl-8-methylisoquinolin-1(2H)-one (2007) (1.65 g, 80% yield) as a white solid.

A mixture of 3-iodo-1H-pyrazolo[3,4-d]pyrimidin-4-amine (108) (1.3 g, 5 mmol) and potassium tert-butoxide (0.55 g, 5 mmol) in anhydrous DMF (20 mL) was stirred at RT for 30 min and then 3-(bromomethyl)-2-isopropyl-8-methylisoquinolin-1(2H)-one (2007) (1.47 g, 5 mmol) was added. The resulting mixture was stirred at RT for 30 min, poured into ice-water (30 mL) and then extracted with ethyl acetate (3×50 mL). The combined organic layer was washed with brine (25 mL), dried over $Na_2SO_4$ and filtered. The filtrate was concentrated in vacuo, and the residue was purified by flash column chromatography on silica gel (2-20% MeOH/DCM) to afford the desired product, 3-((4-amino-3-iodo-1H-pyrazolo[3,4-d]pyrimidin-1-yl)methyl)-2-isopropyl-8-methylisoquinolin-1(2H)-one (2008) (1.66 g, 70% yield) as a white solid.

To a stirred mixture of 3-((4-Amino-3-iodo-1H-pyrazolo[3,4-d]pyrimidin-1-yl)methyl)-2-isopropyl-8-methylisoquinolin-1(2H)-one (2008) (95 mg, 0.2 mmol) and 3-(4,4,5,5-tetramethyl-1,3,2-dioxaborolan-2-yl)phenol (66 mg, 0.3 mmol) in DMF-EtOH-$H_2O$ (3:1:1, 20 mL), $Pd(OAc)_2$ (16 mg, 0.075 mmol), $PPh_3$ (39.3 mg 0.15 mmol) and $Na_2CO_3$ (132 mg, 1.25 mmol) were added sequentially. The resulting mixture was degassed and back-filled with argon three times and then stirred at 100° C. for 1 h. The mixture was allowed to cool to RT, filtered through silica gel (10 g) and concentrated in vacuo. The residue was purified by flash column chromatography on silica gel (2-20% MeOH/DCM) to afford the product, 3-((4-amino-3-(3-hydroxyphenyl)-1H-pyrazolo[3,4]pyrimidin-1-yl)methyl)-2-isopropyl-8-methylisoquinolin-1(2H)-one (2009) (53 mg, 61% yield) as a slightly yellow solid.

Example 6

Synthesis of 8-methyl-3-((methyl(9H-purin-6-yl)amino)methyl)-2-o-tolylisoquinolin-1(2H)-one Scheme 19. The synthesis of 8-methyl-3-((methyl(9H-purin-6-yl)amino)methyl)-2-o-tolylisoquinolin-1(2H)-one (Compound 4004) is described.

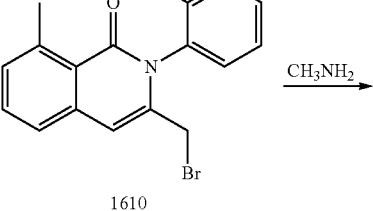

1610

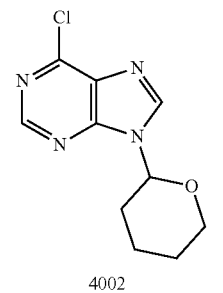

4002

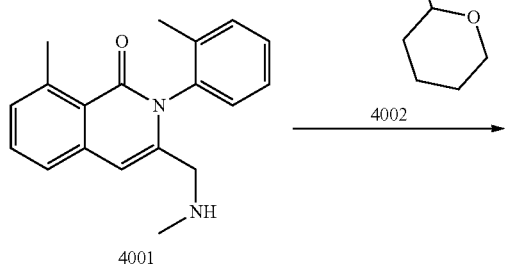

4001

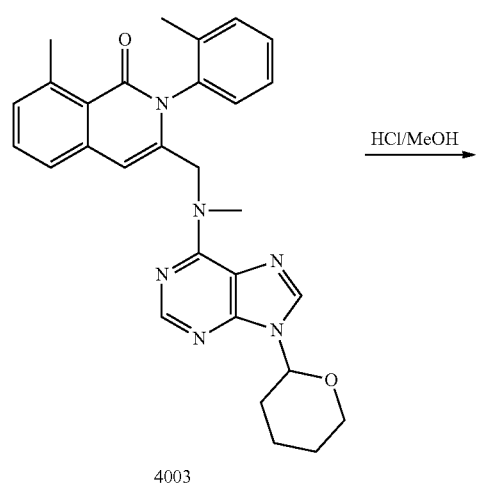

4003

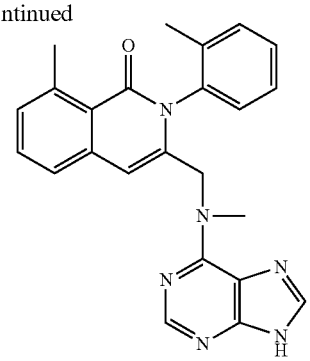

4004

3-(Bromomethyl)-8-methyl-2-o-tolylisoquinolin-1(2H)-one (342 mg, 1.0 mmol) 1610 was dissolved in methylamine solution (100 mL) and stirred for 2 h. The mixture was poured into ice-water (200 mL) and extracted with ethyl acetate (3×50 mL). The combined organic layer was washed with brine (20 mL), dried over $Na_2SO_4$ and filtered. The filtrate was concentrated in vacuo to afford the desired product, 8-methyl-3-((methylamino)methyl)-2-o-tolylisoquinolin-1(2H)-one (4001) (250 mg, 86% yield) as a yellow solid. The product obtained was used directly in the next step without purification.

8-Methyl-3-((methylamino)methyl)-2-o-tolylisoquinolin-1(2H)-one (233 mg, 0.8 mmol) (4001) and 6-chloro-9-(tetrahydro-2H-pyran-2-yl)-9H-purine (4002) (238 mg, 1.0 mmol) were dissolved in EtOH (50 mL) and the resulting mixture was stirred at reflux for 2 h. The mixture was allowed to cool to RT, and concentrated in vacuo. The residue was purified by flash column chromatography on silica gel (2-20% MeOH/DCM) to afford the product, 8-Methyl-3-((methyl(9-(tetrahydro-2H-pyran-2-yl)-9H-purin-6-yl)amino)methyl)-2-o-tolylisoquinolin-1(2H)-one (4003) (200 mg, 51% yield) as a slight yellow solid.

8-Methyl-3-((methyl(9-(tetrahydro-2H-pyran-2-yl)-9H-purin-6-yl)amino)methyl)-2-o-tolylisoquinolin-1(2H)-one (4003) (180 mg 0.36 mmol) was dissolved in MeOH (HCl) (50 mL) and the mixture was stirred at RT for 2 h. Aqueous $NaHCO_3$ solution was added to the reaction mixture and the pH value was adjusted to 9. The mixture was filtered and the filtrate was concentrated in vacuo to afford the desired product, 8-methyl-3-((methyl(9H-purin-6-yl)amino)methyl)-2-o-tolylisoquinolin-1(2H)-one (4004) (80 mg, 54% yield) as a yellow solid.

Example 7

Synthesis of 3-(1-(9H-purin-6-ylamino)ethyl)-8-methyl-2-o-tolylisoquinolin-1(2H)-one Scheme 20. The synthesis of 3-(1-(9H-purin-6-ylamino)ethyl)-8-methyl-2-o-tolylisoquinolin-1(2H)-one (Compound 4106) is described.

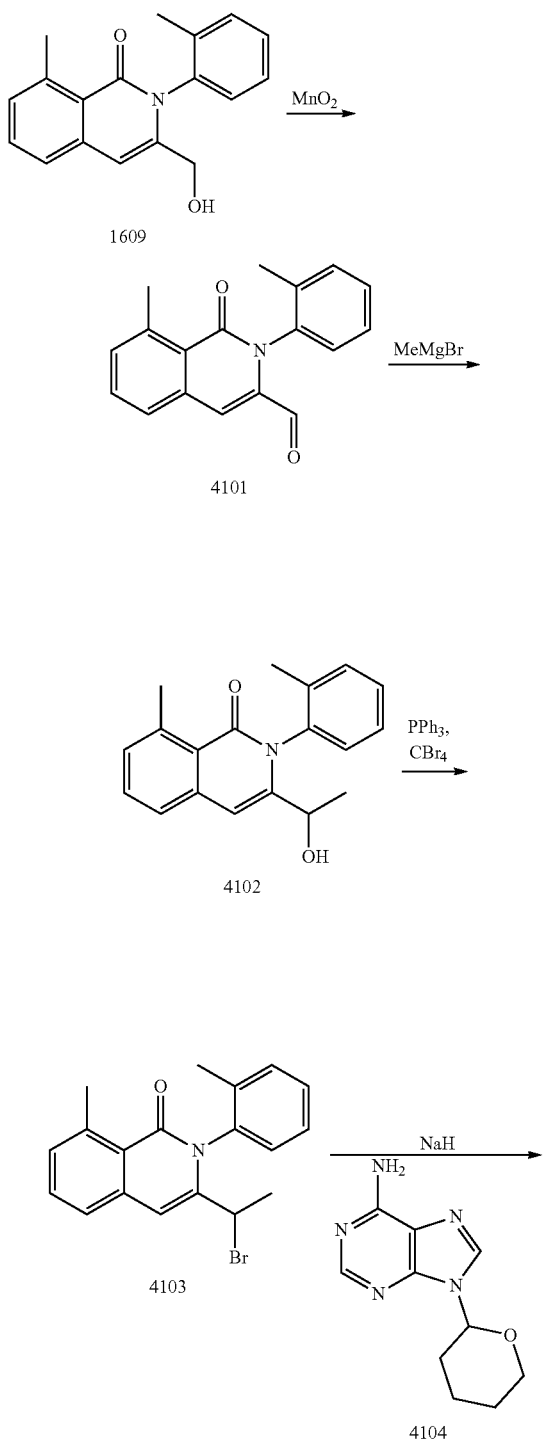

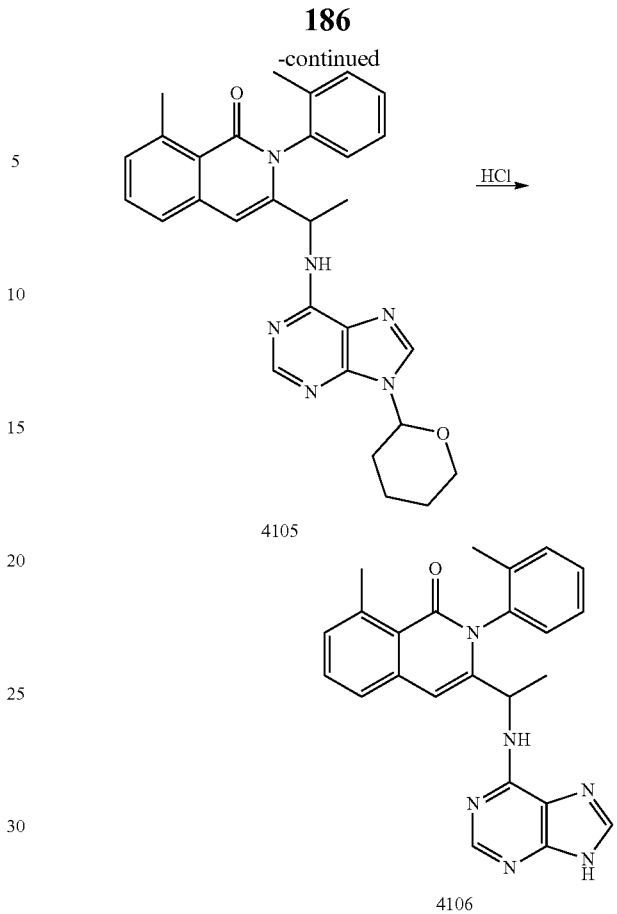

To a stirred solution of 3-(hydroxymethyl)-8-methyl-2-o-tolylisoquinolin-1(2H)-one 1609 (2.79 g, 10 mmol) in $CH_2Cl_2$ (200 mL), $MnO_2$ (5 g) was added and the resulting mixture was stirred at reflux for 3 h. The mixture was allowed to cool to RT, and concentrated in vacuo. The residue was purified by flash column chromatography on silica gel (10-50% EA/PE) to afford the product, 8-methyl-1-oxo-2-o-tolyl-1,2-dihydroisoquinoline-3-carbaldehyde 4101 (2.5 g, 90% yield) as a white solid.

8-Methyl-1-oxo-2-o-tolyl-1,2-dihydroisoquinoline-3-carbaldehyde 4101 (2.4 g, 8.6 mmol) was dissolved in anhydrous THF (280 mL) and cooled to −78° C. under a nitrogen atmosphere. Methyl MgBr (2 M, 5 mL, 10 mmol) was added slowly, and the resulting mixture was stirred at −78° C. for 2 h. $H_2O$ (5 mL) was added and then the solution was poured into ice-water (200 mL) and extracted with ethyl acetate (3×50 mL). The combined organic layer was washed with brine, dried over $Na_2SO_4$ and filtered. The filtrate was concentrated in vacuo, and the residue product was purified by flash column chromatography on silica gel (10-50% EA/PE) to afford the product, 3-(1-hydroxyethyl)-8-methyl-2-o-tolylisoquinolin-1(2H)-one 4102 (1.8 g, 71% yield) as a white solid.

To a solution of 3-(1-hydroxyethyl)-8-methyl-2-o-tolylisoquinolin-1(2H)-one 4102 (1.6 g, 5.5 mmol) in $CH_2Cl_2$, $PPh_3$ (2.88 g, 11.0 mmol) was added and the resulting mixture was stirred at RT for 30 min. Then $CBr_4$ (3.64 g, 11.0 mmol) was added in portions to the mixture at 0° C. The resulting mixture was allowed to warm to RT, stirred for 30 min, and concentrated in vacuo. The crude product was purified by flash column chromatography on silica gel (30-50% EA/PE) to afford the desired product, 3-(1-bromoethyl)-8-methyl-2-o-tolylisoquinolin-1(2H)-one 4103 (1.8 g, 91% yield) as a white solid.

To a stirred solution of 9-(tetrahydro-2H-pyran-2-yl)-9H-purin-6-amine 4103 (436 mg 2 mmol) in anhydrous DMF (10 mL), NaH (60% in mineral oil, 77 mg, 2 mmol) was added and the mixture was stirred for 30 min. 3-(1-Bromoethyl)-8-methyl-2-o-tolylisoquinolin-1(2H)-one 4104 (700 mg, 2 mmol) was added. The mixture was stirred for 2 h, poured into ice-water (200 mL) and extracted with ethyl acetate (3×50 mL). The combined organic layer was washed with brine (20 mL), dried over $Na_2SO_4$ and filtered. The filtrate was concentrated in vacuo and the residue was purified by flash column chromatography on silica gel (10-50% MeOH/DCM) to afford the product, 8-methyl-3-(1-(9-(tetrahydro-2H-pyran-2-yl)-9H-purin-6-ylamino)ethyl)-2-o-tolylisoquinolin-1(2H)-one 4105 (500 mg, 51% yield) as a white solid.

8-Methyl-3-(1-(9-(tetrahydro-2H-pyran-2-yl)-9H-purin-6-ylamino)ethyl)-2-o-tolylisoquinolin-1(2H)-one 4105 (180 mg, 0.36 mmol) was dissolved in MeOH (HCl) (50 mL) and stirred for 2 h. Aqueous $NaHCO_3$ solution was added to the reaction mixture and the pH value was adjusted to 9. The mixture was then filtered and the filtrate was concentrated in vacuo to afford the desired product, 3-(1-(9H-purin-6-ylamino)ethyl)-8-methyl-2-o-tolylisoquinolin-1(2H)-one 4106 (80 mg, 54% yield) as a yellow solid.

Example 8

Synthesis of 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate Scheme 21. The synthesis of 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate (Compound 4303) is described.

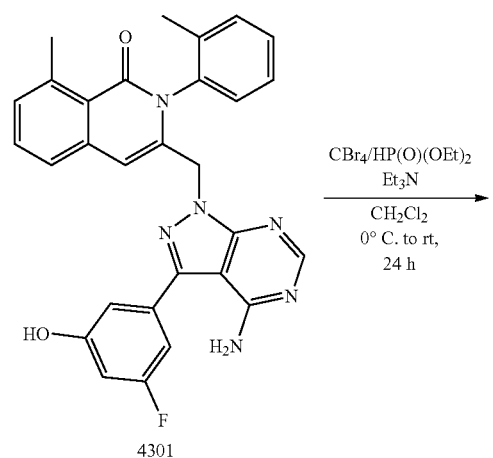

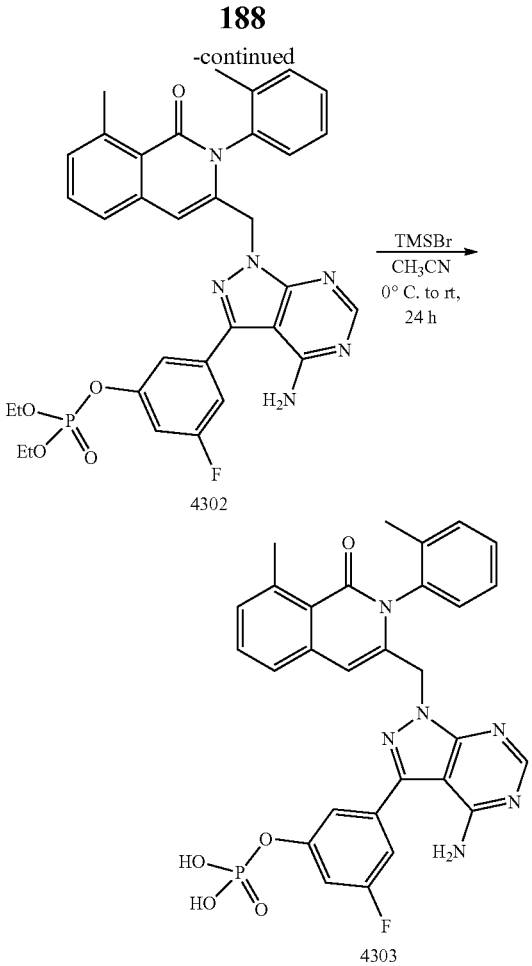

3-((4-Amino-3-(3-fluoro-5-hydroxyphenyl)-1H-pyrazolo[3,4-d]pyrimidin-1-yl)methyl)-8-methyl-2-o-tolylisoquinolin-1(2H)-one 4301 (250 mg, 0.5 mmol) was dissolved in anhydrous THF (15 mL) in a round bottom flask in dark (covered by aluminum foil) and cooled to 0° C. under an argon atmosphere. $CBr_4$ (498 mg, 1.5 mmol) was added followed by diethylphosphite (129 μL, 1.0 mmol) and triethylamine (417 μL, 1.5 mmol). The resulting mixture was stirred in dark from 0° C. to RT for 16 h. The mixture was then partitioned between ethyl acetate and brine. The organic layer was dried over $Na_2SO_4$, filtered and concentrated in vacuo. The residue was purified by column chromatography on silica gel eluting with methanol and dichloromethane to afford the desired product, 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl diethyl phosphate 4302 (200 mg, 62% yield) as an off-white solid.

3-(4-Amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl diethyl phosphate 4302 (170 mg, 0.26 mmol) was dissolved in anhydrous $CH_3CN$ (5 mL) and cooled to 0° C. under an argon atmosphere. TMSBr (0.34 mL, 2.64 mmol) was slowly added via a syringe and the resulting mixture was stirred from 0° C. to RT for 16 h. LC-MS showed small amount of starting material left, additional amount of TMSBr (0.1 mL) was added and stirred at RT for 5 h. LC-MS showed the complete conversion. The mixture was concentrated in vacuo, and the residue was dissolved in $Et_2O$ (10 mL) and $H_2O$ (0.5 mL) and stirred for 30 min. The mixture was concentrated in vacuo to affords the desired product, 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate 4303 (140 mg, 91% yield).

Example 9

Synthesis of 3-((4-amino-3-iodo-1H-pyrazolo[3,4-d]pyrimidin-1-yl)methyl)-8-methyl-2-o-tolylisoquinolin-1(2H)-one (Compound 1611)

Scheme 22. The synthesis of 3-((4-amino-3-iodo-1H-pyrazolo[3,4-d]pyrimidin-1-yl)methyl)-8-methyl-2-o-tolylisoquinolin-1(2H)-one (compound 1611) is described.

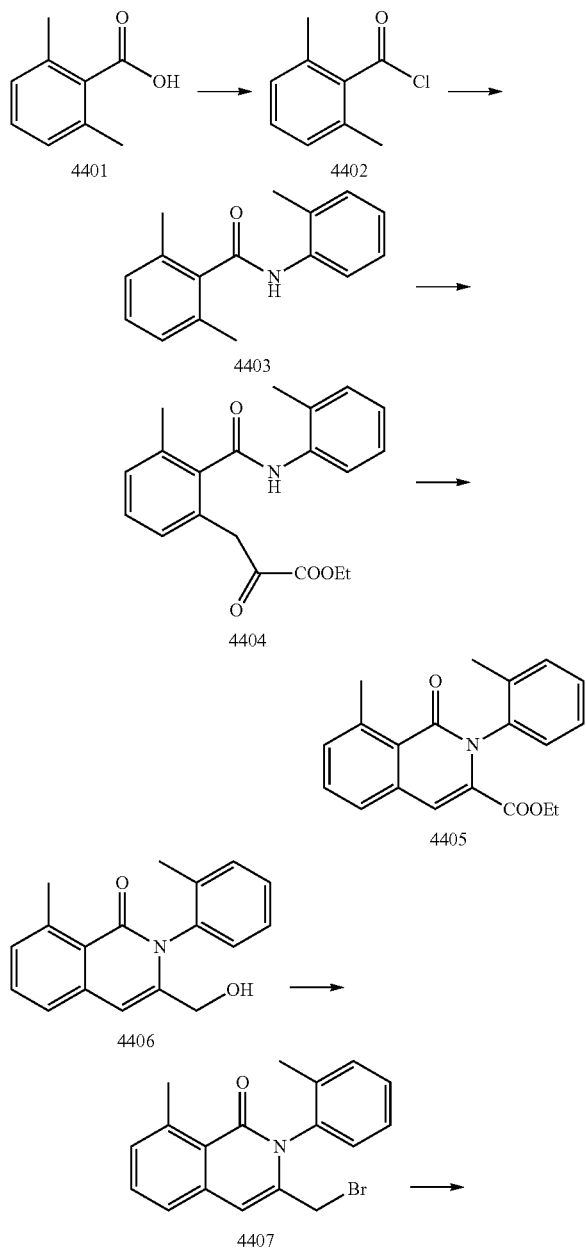

-continued

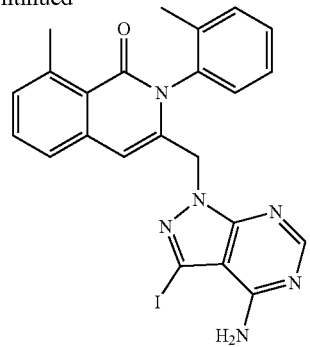

1611

A mixture of 2,6-dimethylbenzoic acid (compound 4401) (60 g, 400 mmol) and oxalyl chloride (101 g, 800 mmol) in CH$_2$Cl$_2$ (400 mL) was stirred at room temperature for 2 h. The mixture was concentrated in vacuo to afford the desired product, 2,6-dimethylbenzoyl chloride (compound 4402) (64 g, 95% yield) as a yellow oil. The material obtained was used directly in the next step without purification.

A mixture of o-toluidine (45 g, 420 mmol) and triethylamine (71 g, 700 mmol) in CH$_2$Cl$_2$ (300 mL) was stirred at room temperature for 10 min. To this mixture, 2,6-dimethylbenzoyl chloride (compound 4402) (64 g, 400 mmol) was added dropwise and the resulting mixture was stirred at room temperature for 30 min. The reaction mixture was poured into water (300 mL), extracted with CH$_2$Cl$_2$ (3×200 mL), dried over anhydrous Na$_2$SO$_4$ and filtered. The filtrate was concentrated in vacuo to afford the crude product. The crude product was suspended in isopropyl ether (300 mL), stirred at reflux for 30 min and then was cooled to 0-5° C. The solid was collected by filtration and further dried in vacuo to afford the desired product, 2,6-dimethyl-N-o-tolylbenzamide (compound 4403) (81 g, 80% yield) as a yellow solid.

To a stirred solution of 2,6-dimethyl-N-o-tolylbenzamide (compound 4403) (23.9 g, 0.1 mol, 1 eq) and HMPA (17.9 g, 0.1 mol, 1 eq) in anhydrous THF (250 mL) at −78° C. under an argon atmosphere, n-butyllithium (100 mL, 2.5 M, 0.25 mol, 2.5 eq) was carefully added over 1 h and the reaction temperature was kept below −60° C. during the addition. The resulting mixture was stirred at −78° C. for 1 h, and then diethyl oxalate (17.6 g, 0.12 mol, 1.2 eq) was quickly added (the reaction temperature rose to −20° C. upon addition). The mixture was stirred at −50° C. for 10 min, and then quenched with water (100 mL). The inorganic salt was removed by filtration, and the filtrate was extracted with ethyl acetate (2×100 mL). The combined organic layer was washed with brine (100 mL), dried over MgSO$_4$ and filtered. The filtrate was concentrated in vacuo to afford the crude product as a semi-solid oil. The crude product was slurried in isopropyl ether (100 mL) at room temperature for 10 min. The solid was collected by filtration and further dried in vacuo to afford the desired product, ethyl 3-(3-methyl-2-(o-tolylcarbamoyl)phenyl)-2-oxopropanoate (compound 4404) (16.1 g, 47.4% yield) as a white solid.

3-(3-Methyl-2-(o-tolylcarbamoyl)phenyl)-2-oxopropanoate (compound 4404) (11.0 g, 32.4 mmol, 1 eq) was dissolved in HCl/MeOH (10 M, 100 mL, 10 mL/1 g of 4404) and stirred at reflux for 1 h. The reaction mixture was concentrated in vacuo, and the residue was slurried in ethyl acetate (10 mL) at room temperature for 30 min. The solid was collected by filtration and further dried in vacuo to afford the desired product, ethyl 8-methyl-1-oxo-2-o-tolyl-1,2-dihydroisoquinoline-3-carboxylate (compound 4405) (7.52 g, 72.5% yield) as a white solid.

To a stirred solution of lithium aluminum hydride (8.28 g, 218 mol) in anhydrous THF (500 mL) at −78° C. under a nitrogen atmosphere, ethyl 8-methyl-1-oxo-2-o-tolyl-1,2-dihydroisoquinoline-3-carboxylate (compound 4405) (28 g, 87 mmol) was slowly added over a 10 min period of time. The resulting mixture was allowed to warm to −30° C., stirred for 30 min and analysis by thin layer chromatography showed completion of the reaction. Then the mixture was cooled to −78° C., and water (50 mL) was slowly added. The mixture was allowed to warm to room temperature, filtered through silica gel (10 g), and the filtrate was concentrated in vacuo. The crude product was poured into $H_2O$ (200 mL) and extracted with ethyl acetate (3×200 mL). The combined organic layer was washed with brine (50 mL), dried over $Na_2SO_4$ and filtered. The filtrate was concentrated in vacuo. The crude product was suspended in ethyl acetate (30 mL) and stirred for 10 min. The solid was collected by filtration and further dried in vacuo to afford the desired product, 3-(hydroxymethyl)-8-methyl-2-o-tolylisoquinolin-1(2H)-one (compound 4406) (22 g, 92% yield) as a white solid.

Phosphorus tribromide (25.6 g, 95 mmol) was slowly added to a stirred solution of DMF (11.5 g, 158 mol) in acetonitrile (200 mL) at 0° C., and the resulting mixture was stirred at 0° C. for 30 min. 3-(Hydroxymethyl)-8-methyl-2-o-tolylisoquinolin-1-(2H)-one (compound 4406) (22 g, 78.8 mmol) was slowly added. Then the reaction mixture was allowed to warm to room temperature and stirred for 30 min. saturated aqueous $NaHCO_3$ solution (50 mL) was slowly added and extracted with ethyl acetate (3×200 mL). The combined organic layer was washed with brine, dried over $Na_2SO_4$ and filtered. The filtrate was concentrated in vacuo. The crude product was suspended in isopropyl ether (50 mL) and then stirred for 10 min. The precipitate was collected by filtration and further dried in vacuo to afford the desired product, 3-(bromomethyl)-8-methyl-2-o-tolylisoquinolin-1 (2H)-one (compound 4407) (21 g, 80% yield) as a white solid.

3-Iodo-1H-pyrazolo[3,4-d]pyrimidin-4-amine (10.8 g, 41.4 mmol) and potassium tert-butoxide (4.4 g, 40 mmol) were dissolved in anhydrous DMF (150 mL) and stirred at room temperature for 30 min. 3-(Bromomethyl)-8-methyl-2-o-tolylisoquinolin-1(2H)-one (compound 4407) (13.7 g, 40 mmol) was added. The resulting mixture was stirred at room temperature for 30 min, poured into ice water (300 mL) and then extracted with ethyl acetate (3×200 mL). The combined organic layer was washed with brine (50 mL), dried over $Na_2SO_4$ and filtered. The filtrate was concentrated to about 100 ml in vacuo, the precipitate was collected by filtration to afford the first batch of desired product, 3-((4-amino-3-iodo-1H-pyrazolo[3,4-d]pyrimidin-1-yl)methyl)-8-methyl-2-o-tolylisoquinolin-1(2H)-one (compound 1611) (12 g, 60% yield) as a white solid. The filtrate was concentrated in vacuo and the residue was purified by flash column chromatography on silica gel (2-20% MeOH/DCM) to afford the second batch of desired product, 3-((4-amino-3-iodo-1H-pyrazolo[3,4-d]pyrimidin-1-yl)methyl)-8-methyl-2-o-tolylisoquinolin-1(2H)-one (compound 1611) (6 g, 30% yield) as a white solid.

Example 10

Synthesis of 3-((4-amino-3-(fluoromethyl)-1H-pyrazolo[3,4-d]pyrimidin-1-yl)methyl)-8-methyl-2-o-tolylisoquinolin-1(2H)-one (Compound 4504)

Scheme 23. The synthesis of 3-((4-amino-3-(fluoromethyl)-1H-pyrazolo[3,4-d]pyrimidin-1-yl)methyl)-8-methyl-2-o-tolylisoquinolin-1(2H)-one (compound 4504) is described.

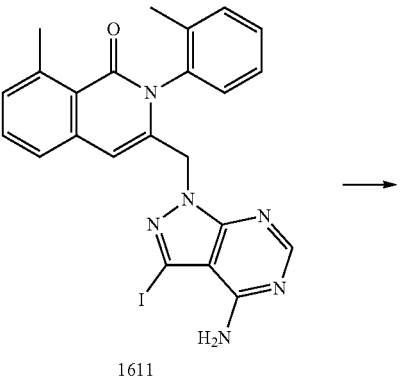

1611

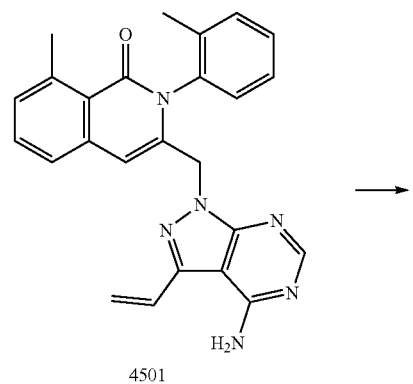

4501

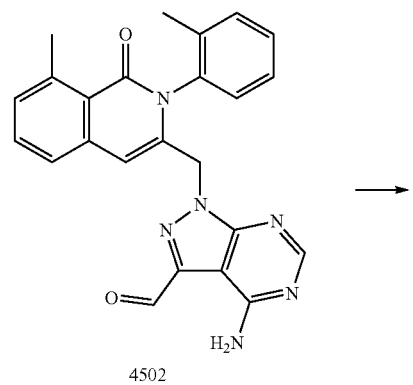

4502

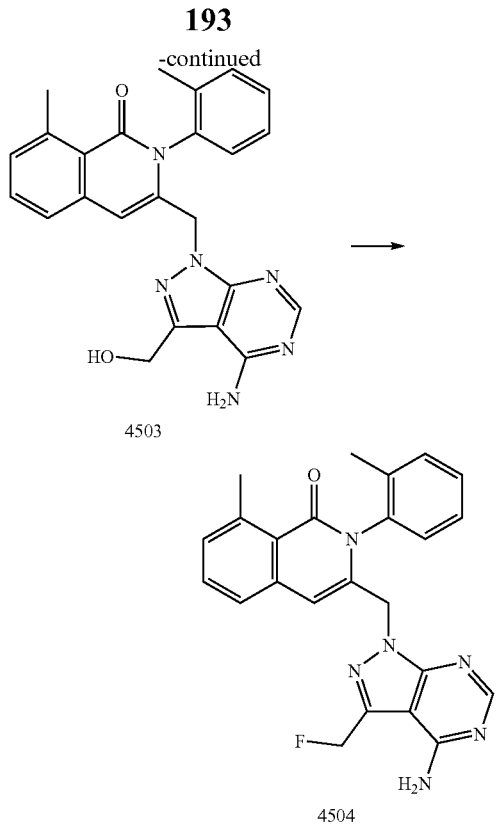

To a stirred mixture of 3-((4-amino-3-iodo-1H-pyrazolo[3,4-d]pyrimidin-1-yl)methyl)-8-methyl-2-o-tolylisoquinolin-1(2H)-one (compound 1611) (1.50 g, 2.87 mmol) and tetrakis(triphenylphosphine)palladium (166 mg, 0.14 mmol) in anhydrous DMF (15 mL) under an argon atmosphere, tributyl vinyl tin (1.26 mL, 4.31 mmol) was added and the resulting mixture was stirred at 80° C. for 3 h. The reaction mixture was allowed to cool to room temperature, and then partitioned between water and ethyl acetate. The organic layer was washed with brine, dried over Na₂SO₄ and filtered. The filtrate was concentrated in vacuo and the residue was triturated with a minimal amount of anhydrous ethyl ether and filtered to afford the desired product, 3-((4-amino-3-vinyl-1H-pyrazolo[3,4-d]pyrimidin-1-yl)methyl)-8-methyl-2-o-tolylisoquinolin-1(2H)-one (compound 4501) (853 mg, 70% yield) as an off-white solid.

To a stirred solution of 3-((4-amino-3-vinyl-1H-pyrazolo[3,4-d]pyrimidin-1-yl)methyl)-8-methyl-2-o-tolylisoquinolin-1(2H)-one (compound 4501) (853 mg, 2.0 mmol) in 1,4-dioxane-H₂O (3:1, 30 mL) under an argon atmosphere, osmium tetroxide (2.5 wt % in t-BuOH, 252 µL, 0.020 mmol) was added and the resulting mixture was stirred at RT for 30 min. To this mixture, sodium periodate (863 mg, 4.0 mmol) was added and the resulting mixture was stirred for 3 h. The reaction mixture partitioned between water and ethyl acetate. The organic layer was washed with brine, dried over Na₂SO₄ and filtered. The filtrate was concentrated in vacuo to afford the desired product, 4-amino-1-((8-methyl-1-oxo-2-o-tolyl-1,2-dihydroisoquinolin-3-yl)methyl)-1H-pyrazolo[3,4-d]pyrimidine-3-carbaldehyde as a tan/brown solid (compound 4502) (716 mg, 84% yield).

To a stirred mixture of 4-amino-1-((8-methyl-1-oxo-2-o-tolyl-1,2-dihydroisoquinolin-3-yl)methyl)-1H-pyrazolo[3,4-d]pyrimidine-3-carbaldehyde as a tan/brown solid (compound 4502) (841 mg, 1.98 mmol) in anhydrous MeOH (35 mL) at 0° C. under an argon atmosphere, NaBH₄ (89 mg, 2.38 mmol) was added in portions. The mixture was stirred from 0° C. to RT for 2 h, and then was partitioned between water and ethyl acetate. The organic layer was washed with brine, dried over Na₂SO₄ and filtered. The filtrate was concentrated in vacuo to afford the desired product, 3-((4-amino-3-(hydroxymethyl)-1H-pyrazolo[3,4-d]pyrimidin-1-yl)methyl)-8-methyl-2-o-tolylisoquinolin-1(2H)-one (compound 4503) (626 mg, 74% yield) as dark brown solid.

To a stirred suspension of 3-((4-amino-3-(hydroxymethyl)-1H-pyrazolo[3,4-d]pyrimidin-1-yl)methyl)-8-methyl-2-o-tolylisoquinolin-1(2H)-one (compound 4503) (50 mg, 0.12 mmol) in anhydrous DCM (2 mL) at 0° C. under an argon atmosphere, diethylaminosulfur trifluoride (DAST, 77 µL, 0.59 mmol) was slowly added and the resulting mixture was stirred from 0° C. to room temperature for 5 h. The reaction was quenched with water and extracted with ethyl acetate. The combined organic layer was washed with brine, dried over Na₂SO₄ and filtered. The filtrate was concentrated in vacuo and the residue was purified by prep-TLC plate (7% MeOH/DCM) to afford the desired product, 3-((4-amino-3-(fluoromethyl)-1H-pyrazolo[3,4-d]pyrimidin-1-yl)methyl)-8-methyl-2-o-tolylisoquinolin-1(2H)-one (compound 4504) (10.3 mg, 20% yield) as a white solid.

Example 11

Synthesis of 4-amino-1-((8-methyl-1-oxo-2-o-tolyl-1,2-dihydroisoquinolin-3-yl)methyl)-1H-pyrazolo[3,4-d]pyrimidine-3-carboxamide (Compound 4602)

Scheme 24. The synthesis of 4-amino-1-((8-methyl-1-oxo-2-tolyl-1,2-dihydroisoquinolin-3-yl)methyl)-1H-pyrazolo[3,4-d]pyrimidine-3-carboxamide (compound 4602) is described.

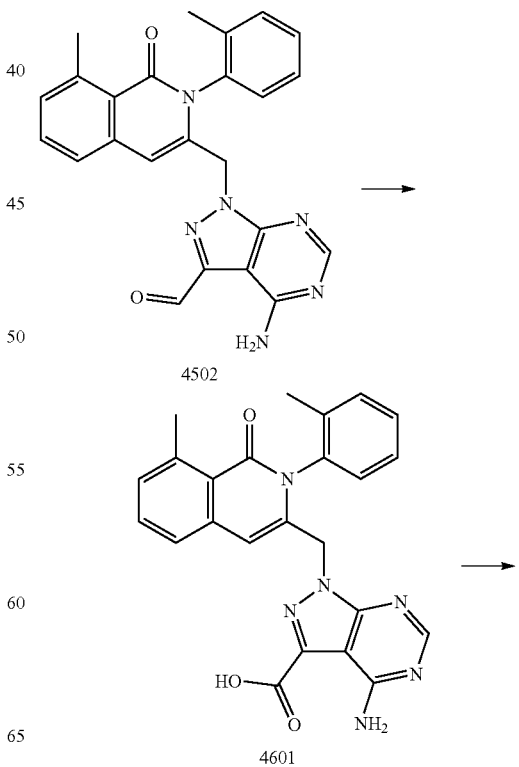

195
-continued

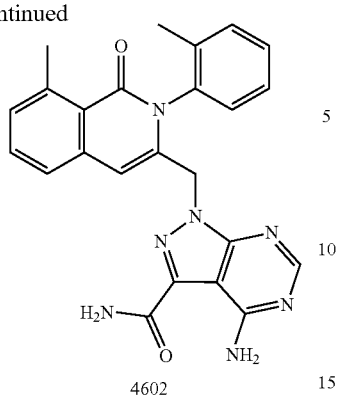

4602

To a stirred solution of 4-amino-1-((8-methyl-1-oxo-2-o-tolyl-1,2-dihydroisoquinolin-3-yl)methyl)-1H-pyrazolo[3,4-d]pyrimidine-3-carbaldehyde (compound 4502) (400 mg, 0.94 mmol) in t-BuOH (1.8 mL), a solution of $NaH_2PO_4$ (3.90 g, 28.27 mmol) in water (4.8 mL), methyl-2-butene (1.0 mL) and (dropwise) a solution of $NaClO_2$ (767 mg, 6.78 mmol) in water (4.8 mL) were added sequentially. The mixture was stirred at RT for 3 h under an argon atmosphere. The pale yellow solution was acidified with aqueous HCl solution (2 M, 4 mL) to PH=2 and extracted with ethyl acetate. The combined organic layer was washed with brine, dried over anhydrous $Na_2SO_4$ and filtered. The filtrate was concentrated in vacuo, and the residue was triturated with anhydrous ethyl ether and ethyl acetate. The solid was collected by filtration to afford the desired product, 4-amino-1-((8-methyl-1-oxo-2-o-tolyl-1,2-dihydroisoquinolin-3-yl)methyl)-1H-pyrazolo[3,4-d]pyrimidine-3-carboxylic acid (compound 4601) (200 mg, 47% yield) as a yellow solid.

To a stirred solution of 4-amino-1-((8-methyl-1-oxo-2-o-tolyl-1,2-dihydroisoquinolin-3-yl)methyl)-1H-pyrazolo[3,4-d]pyrimidine-3-carboxylic acid (compound 4601) (150 mg, 0.34 mmol) in anhydrous DCM (10 mL), oxalyl chloride (2.0 M in DCM, 0.22 mL) was slowly added followed by a catalytic amount of anhydrous DMF (1 drop). The resulting mixture was stirred at room temperature for 30 min and then concentrated in vacuo. The residue was re-dissolved in DCM (6 mL) and an excess amount of ammonium hydroxide was added (0.35 mL). The mixture was stirred at room temperature for 2 h, and then partitioned between ethyl acetate and water. The organic layer was washed with brine, dried over anhydrous $Na_2SO_4$ and filtered. The filtrate was concentrated in vacuo, and the residue was purified by flash column chromatography on silica gel (eluting with 5% MeOH/DCM) to afford the desired product, 4-amino-1-((8-methyl-1-oxo-2-o-tolyl-1,2-dihydroisoquinolin-3-yl)methyl)-1H-pyrazolo[3,4-d]pyrimidine-3-carboxamide (compound 4602) (22 mg, 15% yield) as a white solid.

196
Example 12

Synthesis of (S)-3-(1-(9H-purin-6-ylamino)ethyl)-8-methyl-2-phenylisoquinolin-1(2H)-one (Compound 4704) (Method A)

Scheme 25. The synthesis of (S)-3-(1-(9H-purin-6-ylamino)ethyl)-8-methyl-2-phenylisoquinolin-1(2H)-one (compound 4704) via Method A is described.

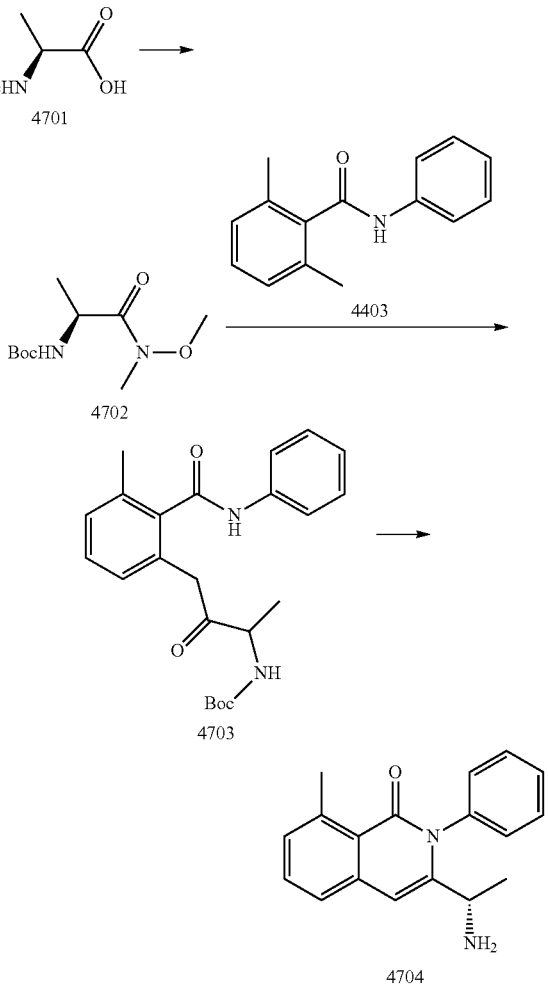

To a stirred mixture of (S)-2-(tert-butoxycarbonylamino) propanoic acid (compound 4701) (189.1 g, 1 mol, 1 eq), triethylamine (404.8 g, 4 mol, 4 eq) and HOBt (135 g, 1.0 mol, 1 eq) in anhydrous dichloromethane (1.8 L) at 0° C., EDCI (384.3 g, 2 mol, 2 eq) was added in portions over 30 min. The resulting mixture was stirred at RT for 30 min, and then N,O-dimethylhydroxylamine hydrochloride (107.3 g, 1.1 mol, 1.1 eq) was added. The reaction mixture was stirred at RT for 20 h, and then quenched with water (1 L). The organic layer was washed with water (2×1 L) and brine (500 mL), dried over anhydrous $MgSO_4$ and filtered. The filtrate was concentrated in vacuo. The crude product was slurried in petroleum ether (1 L) and stirred at RT for 10 min. The solid was collected by filtration and further dried in vacuo to afford the desired product, (S)-tert-butyl 1-(methoxy (methyl)amino)-1-oxopropan-2-ylcarbamate (compound 4702) (218 g, 93.9% yield) as a white solid.

To a stirred mixture of 2,6-dimethyl-N-phenylbenzamide (compound 4403, which may be synthesized as described in Example 9) (30 g, 0.13 mol, 1 eq) and HMPA (26 g, 0.16 mol, 1.2 eq) in anhydrous THF (300 mL) at −78° C. under an argon atmosphere, n-butyllithium (2.5 M, 100 mL, 0.25 mol, 2.5 eq) was carefully added (dropwise) over a 1 h and the reaction temperature was kept below −60° C. during the addition. The resulting mixture was stirred at −78° C. for 1 h. To this mixture, tert-butyl 1-(methoxy(methyl)amino)-1-oxopropan-2-yl carbamate (compound 4702) (40 g, 0.173 mol, 1.3 eq) was quickly added (the reaction temperature rose to −50° C. upon addition). The mixture was stirred at −50° C. for 10 min, quenched with water (300 mL) and extracted with ethyl acetate (2×100 mL). The combined organic layer was washed with water (500 mL×2) and brine (50 mL), dried over anhydrous MgSO$_4$ and filtered. The filtrate was concentrated in vacuo to give the crude product as a semi-solid oil. The crude product was slurried in EA and stirred for 10 min. The white solid was removed by filtration. The filtrate was concentrated in vacuo, and the residue was stirred in a mixture of ethyl acetate (30 mL) and isopropyl alcohol (200 mL) at RT for 10 min. The solid was collected by filtration and further dried in vacuo to afford the desired product, tert-butyl4-(3-methyl-2-(phenylcarbamoyl)pheny)-3-oxobutan-2-yl carbamate (compound 4703) (9.23 g, 17.5% yield) as a white solid.

Tert-Butyl-4-(3-methyl-2-(phenylcarbamoyl) pheny)-3-oxobutan-2-yl carbamate (compound 4703) (9.23 g, 23 mmol) was dissolved in HCl/MeOH (100 mL) and stirred at reflux for 30 min. The mixture was allowed to cool to RT, concentrated in vacuo, and then saturated Na$_2$CO$_3$ solution was added to adjust the PH to 7-8. The solid was collected by filtration and further dried in vacuo to afford the desired product, 3-(1-aminoethyl)-8-methyl-2-phenylisoquinolin-1(2H)-one (compound 4704) (5.8 g, 90% yield, S:R isomers=7:1) as a white solid.

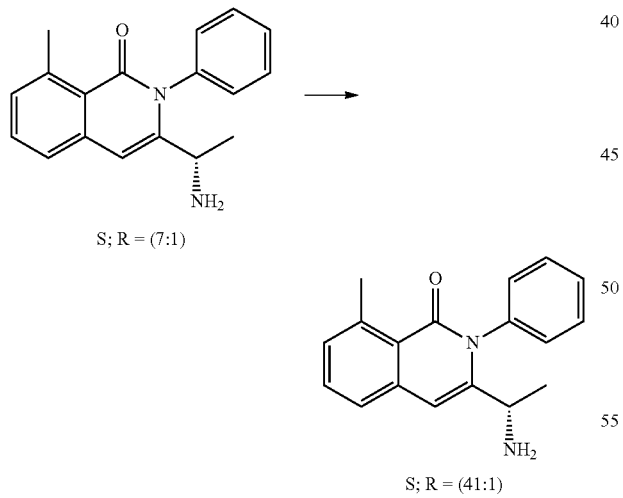

Resolution of isomers to increase the enantiomeric purity: 3-(1-Aminoethyl)-8-methyl-2-phenylisoquinolin-1(2H)-one (compound 4704) (where the ratio of isomers is S:R=7:1) (5 g, 18 mmol) was dissolved in MeOH (100 mL), (D)-tartaric-acid (2.7 g, 18 mmol) was added. The mixture was stirred at RT for 30 min and the solid was precipitated. The resulting mixture was stirred at reflux for 1 h, and then stirred at RT for 16 h. The solid was collected by filtration and rinsed with methanol (10 mL). The solid was then dissolved in H$_2$O (15 mL) and saturated NaHCO$_3$ (5 mL) was added to adjust the PH to 8. The solid was collected by filtration, rinsed with water (5 mL), and then dried in vacuo to afford the enantiomerically enriched product (compound 4704) (2.7 g, 58% yield) where the ratio of isomers, S:R>41:1. This is an enantiomeric purity of greater than about 97.6% of the (S)-enantiomer. The ratio of two enantiomers was confirmed by coupling with (R)-(−)-alpha-methoxyphenylacetic acid and detection of the resultant diastereomers by Nuclear Magnetic Resonance Spectroscopy.

Example 13

Synthesis of (S)-3-(1-aminoethyl)-8-methyl-2-phenylisoquinolin-1(2H)-one (Method B) (Compound 4704

Scheme 26. The synthesis of (S)-3-(1-aminoethyl)-8-methyl-2-phenylisoquinolin-1(2H)-one (compound 4704) via Method B is described.

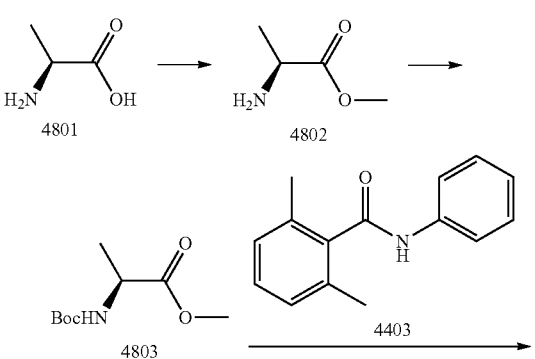

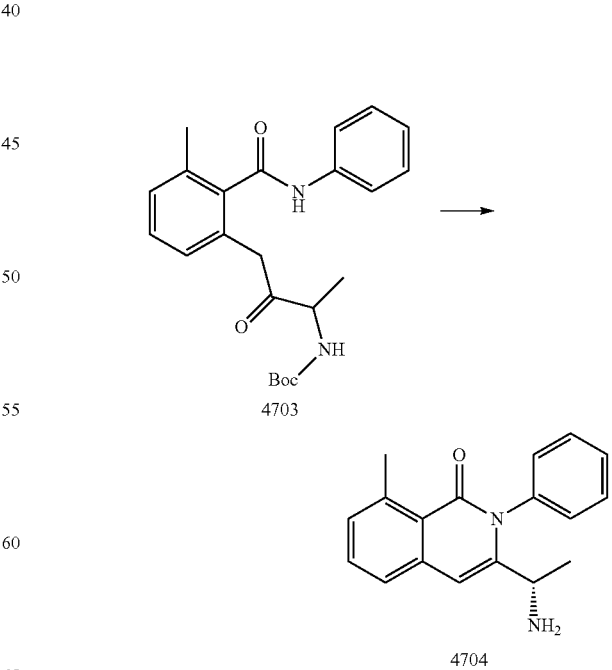

Thionyl chloride (320.8 g, 2.7 mol, 1.2 eq) was added dropwise to stirred anhydrous MeOH (2 L) at 0° C. over 50 min and the reaction temperature was kept below 25° C. during the addition. The mixture was allowed to warm to room temperature and then (S)-2-aminopropanoic acid (compound 4801) (200 g, 2.24 mol, 1 eq) was added. The resulting mixture was stirred at room temperature for 20 h, and concentrated in vacuo to afford the desired product, (S)-methyl 2-aminopropanoate hydrochloride (compound 4802) as a white solid.

To a stirred solution of above obtained (S)-methyl 2-aminopropanoate hydrochloride (compound 4802) in water (1.6 L) at room temperature, NaHCO$_3$ (566.2 g, 6.741 mol, 3 eq) and a solution of di-tert-butyl dicarbonate (490.4 g, 2.247 g, 1 eq) in THF (1.6 L) were added sequentially. The resulting mixture was stirred at room temperature for 20 h. The inorganic salt was removed by filtration, and the filtrate was extracted with ethyl acetate (2×500 mL). The combined organic layer was washed with brine (500 mL), dried over anhydrous MgSO$_4$ and filtered. The filtrate was concentrated in vacuo to afford the desired product, (S)-methyl 2-(tert-butoxycarbonylamino)propanoate (compound 4803) (448 g, 98.2% yield) as a colorless crystal.

To a stirred solution of 2,6-dimethyl-N-phenylbenzamide (compound 4403), which may be synthesized as described in Example 9) (30 g, 0.13 mol, 1 eq) and HMPA (26 g, 0.16 mol, 1.2 eq) in anhydrous THF (300 mL) at −78° C. under an argon atmosphere, n-butyllithium (100 mL, 2.5 M, 0.25 mol, 2.5 eq) was added carefully over 1 h and the reaction temperature was kept below −60° C. during addition. The resulting mixture was stirred at −78° C. for 1 h, and then (S)-methyl 2-(tert-butoxycarbonylamino)-propanoate (compound 4803) (35 g, 0.173 mol, 1.3 eq) was quickly added (the reaction temperature rose to −50° C. during addition). The mixture was stirred at −50° C. for 10 min, quenched with water (300 mL) and extracted with ethyl acetate (2×100 mL). The organic layer was washed with water (500 mL×2), dried over anhydrous MgSO$_4$ and filtered. The filtrate was concentrated in vacuo to afford the crude product as a semi-solid oil. The crude product was slurried in ethyl acetate (500 mL) and stirred for 10 min. The solid was removed by filtration, and the filtrate was concentrated in vacuo. The oil residue was stirred in a mixture of ethyl acetate (30 mL) and isopropyl alcohol (200 mL) at room temperature for 10 min. The solid was collected by filtration and further dried in vacuo to afford the desired product, tert-butyl4-(3-methyl-2-(phenylcarbamoyl)pheny)-3-oxobutan-2-ylcarbamate (compound 4703) (4.61 g, 9% yield) as a white solid.

Tert-Butyl 4-(3-methyl-2-(phenylcarbamoyl)phenyl)-3-oxobutan-2-ylcarbamate (compound 4703) (4.61 g, 0.012 mol) was dissolved in HCl/MeOH (50 mL) and stirred at reflux for 30 min. The mixture was concentrated in vacuo and then saturated Na$_2$CO$_3$ solution was added to adjust PH to about 7-8. The resulting solid was collected by filtration and further dried in vacuo to afford the desired product, 3-(1-aminoethyl)-8-methyl-2-phenylisoquinolin-1(2H)-one (compound 4704) (2.9 g, 90% yield, where the ratio of isomers is S:R=5:1) as a white solid.

Example 14a

Synthesis of (S)-3-(1-(9H-purin-6-ylamino)ethyl)-8-methyl-2-phenylisoquinolin-1(2H)-one (9) (Compound 4902)

Scheme 27a. The synthesis of (S)-3-(1-(9H-purin-6-ylamino)ethyl)-8-methyl-2-phenylisoquinolin-1(2H)-one (9) (compound 4902) is described.

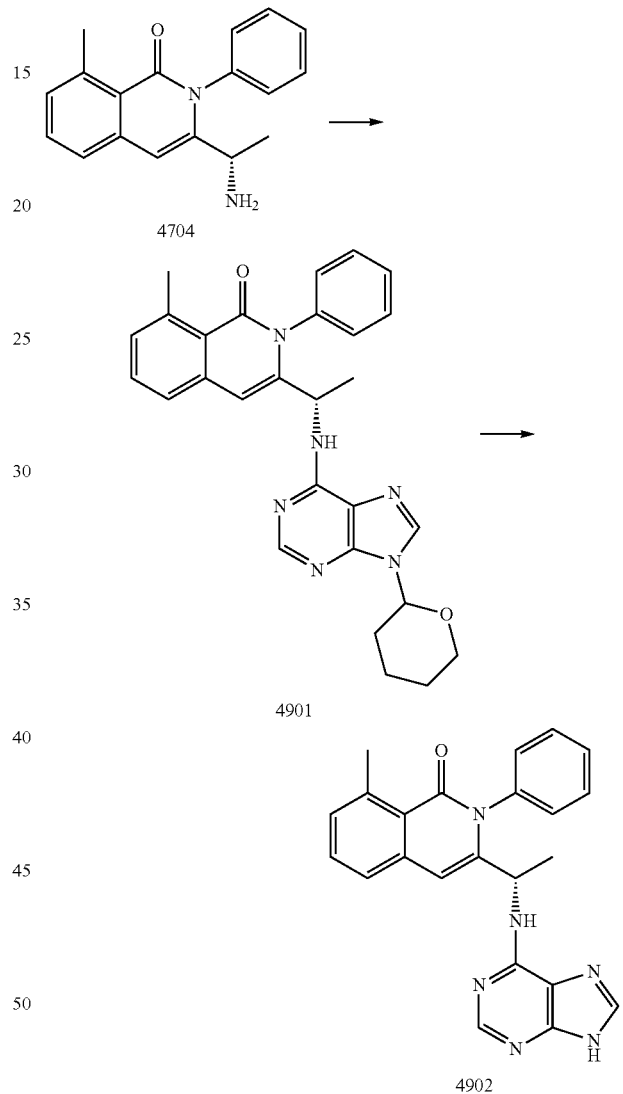

3-(1-Aminoethyl)-8-methyl-2-phenylisoquinolin-1(2H)-one (compound 4704) (200 mg, 0.72 mmol), 6-chloro-9-(tetrahydro-2H-pyran-2-yl)-9H-purine (344 mg, 1.44 mmol) and DIPEA (279 mg, 2.16 mmol) were dissolved in n-BuOH (20 ml), and the resulting mixture was stirred at reflux for 16 h. The reaction mixture was concentrated in vacuo and purified by flash column chromatography on silica gel (eluting with 30% to 50% Hex/EA) to afford the desired product, 8-methyl-2-phenyl-3-((1S)-1-(9-(tetrahydro-2H-pyran-2-yl)-9H-purin-6-ylamino)ethyl)isoquinolin-1(2H)-one (compound 4901) (207 mg, 60% yield) as a white solid.

8-Methyl-2-phenyl-3-((1S)-1-(9-(tetrahydro-2H-pyran-2-yl)-9H-purin-6-ylamino)ethyl)-isoquinolin-1(2H)-one (compound 4901) (200 mg, 0.42 mmol) was dissolved in HCl/EtOH (3 M, 5 mL) and the resulting mixture was stirred at room temperature for 1 h. The reaction mixture was quenched with saturated NaHCO$_3$ aqueous solution and the PH was adjusted to about 7-8. The mixture was extracted with CH$_2$Cl$_2$ (50 mL×3), dried over anhydrous Na$_2$SO$_4$ and filtered. The filtrate was concentrated in vacuo, and the residue was recrystallized from ethyl acetate and hexanes (1:1). The solid was collected by filtration and dried in vacuo to afford the desired product, (S)-3-(1-(9H-purin-6-ylamino)ethyl)-8-methyl-2-phenylisoquinolin-1(2H)-one (compound 4902) (150 mg, 90% yield) as a white solid.

Example 14b

Synthesis of (S)-3-(1-(9H-purin-6-ylamino)ethyl)-8-chloro-2-phenylisoquinolin-1(2H)-one (9) (Compound 4904)

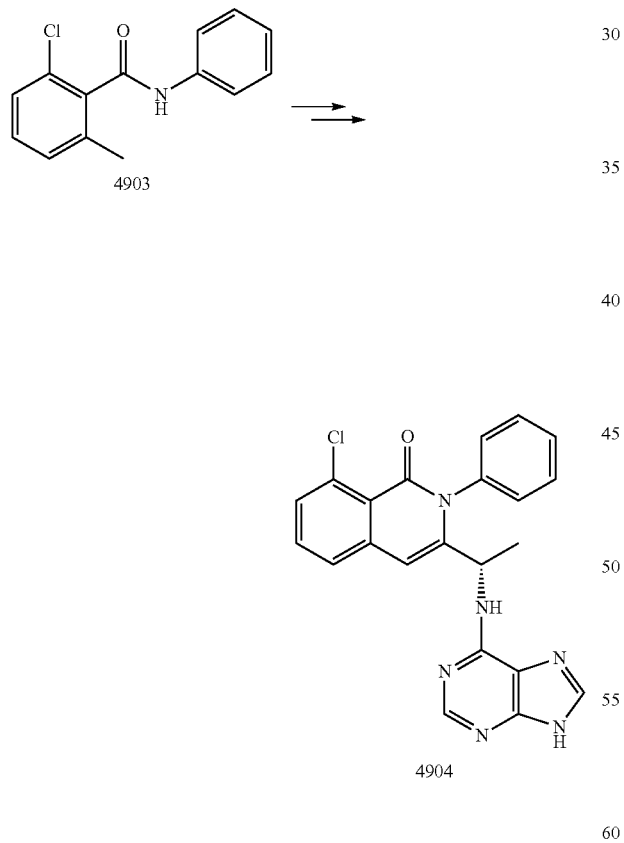

Scheme 27b. The synthesis of (S)-3-(1-(9H-purin-6-ylamino)ethyl)-8-chloro-2-phenylisoquinolin-1(2H)-one (9) (compound 4904) is described.

The compound of Formula 4904 was synthesized using the synthetic transformations as described in Examples 13 and 14a, but 2-chloro-6-methyl benzoic acid (compound 4903) was used instead of 2,6,dimethyl benzoic acid (compound 4403).

Example 15a

Synthesis of (S)-3-(1-(9H-purin-6-ylamino)ethyl)-2-cyclopropyl-8-methylisoquinolin-1(2H)-one (Compound 5005)

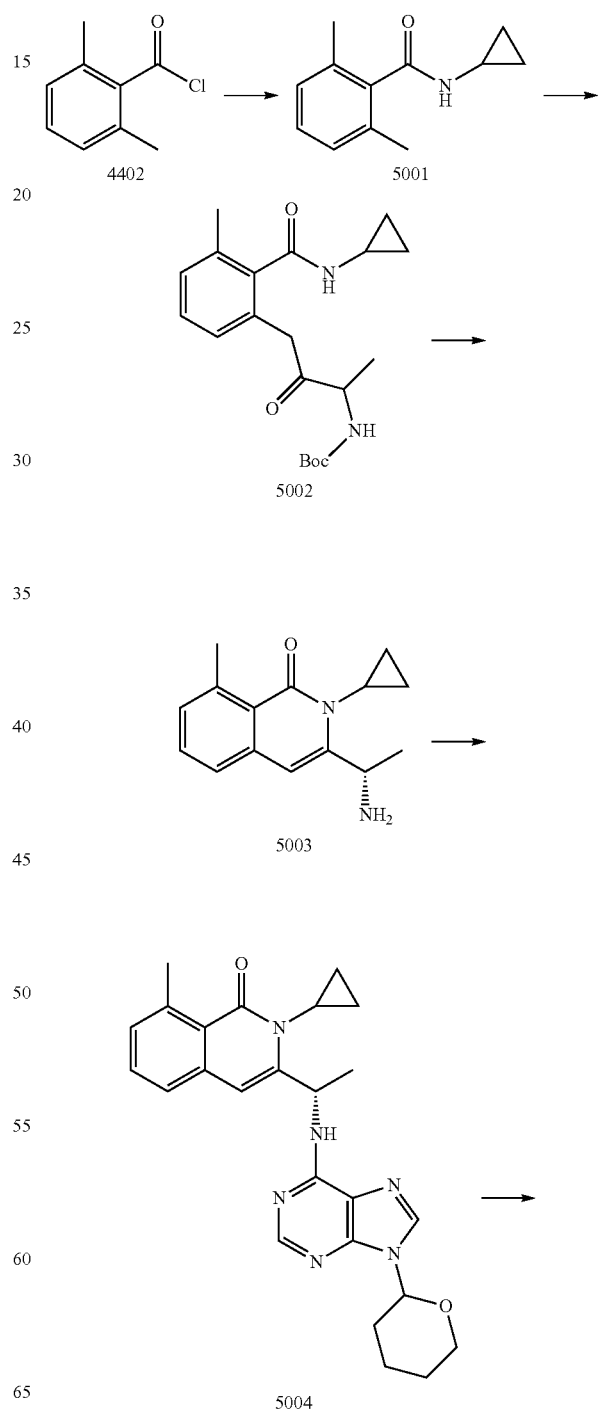

Scheme 28a. The synthesis of (S)-3-(1-(9H-purin-6-ylamino)ethyl)-2-cyclopropyl-8-methylisoquinolin-1(2H)-one is described.

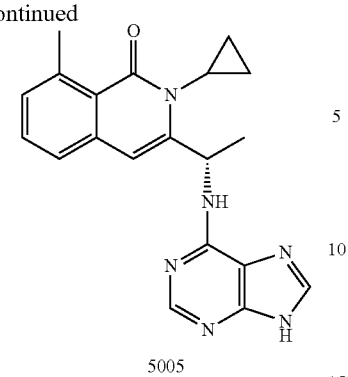

5005

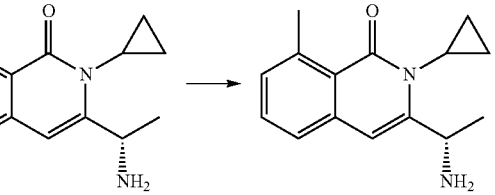

S; R = (7:1)    S

A mixture of cyclopropanamine (24 g, 420 mmol) and triethylamine (71 g, 700 mmol) in CH₂Cl₂ (300 mL) was stirred at RT for 10 min. To this mixture, 2,6-dimethylbenzoyl chloride (compound 4402) (64 g, 400 mmol) was added dropwise, and the resulting mixture was stirred at room temperature for 30 min. The reaction mixture was poured into water (300 mL) and extracted with CH₂Cl₂ (3×200 mL). The combined organic layer was dried over anhydrous Na₂SO₄ and filtered. The filtrate was concentrated in vacuo to afford the crude product. The crude product was suspended in isopropyl ether (IPE) (300 mL), stirred at reflux for 30 min and then was allowed to cool to 0-5° C. The precipitate was collected by filtration and further dried in vacuo to afford the desired product, N-cyclopropyl-2,6-dimethylbenzamide (compound 5001) (61 g, 80% yield) as a yellow solid.

To a stirred solution of N-cyclopropyl-2,6-dimethylbenzamide (compound 5001) (25 g, 0.13 mol, 1 eq) and HMPA (26 g, 0.16 mol, 1.2 eq) in anhydrous THF (300 mL) at −78° C. under an argon atmosphere, n-butyllithium (2.5M, 100 mL, 0.25 mol, 2.5 eq) was added carefully over 1 h and the temperature was kept below −60° C. during addition. The resulting mixture was stirred at −78° C. for 1 h, and then tert-butyl 1-(methoxy(methyl)amino)-1-oxopropan-2-ylcarbamate (40 g, 0.173 mol, 1.3 eq) was quickly added (the reaction temperature rose to −50° C. during addition). The mixture was stirred at −50° C. for 10 min, quenched with water (300 mL) and extracted with ethyl acetate (2×100 mL). The combined organic layer was washed with water (500 mL×2) and brine (100 mL), dried over anhydrous MgSO₄ and filtered. The filtrate was concentrated in vacuo to afford the desired product, tert-butyl 4-(2-(cyclopropylcarbamoyl)-3-methylphenyl)-3-oxobutan-2-ylcarbamate (compound 5002) (32 g, 70% yield) as a yellow oil.

Tert-Butyl 4-(2-(cyclopropylcarbamoyl)-3-methylphenyl)-3-oxobutan-2-ylcarbamate (compound 5002) (32 g, 88 mmol) was dissolved in HCl/MeOH (300 mL) and stirred at room temperature for 16 h. The mixture was concentrated in vacuo, and then saturated Na₂CO₃ aqueous solution was added to adjust the pH to about 7-8. The resulting solid was collected by filtration and further dried in vacuo to afford the desired product, 3-(1-aminoethyl)-8-methyl-2-phenylisoquinolin-1(2H)-one (compound 5003) (17 g, 80% yield, S:R=7:1) as a white solid.

To a stirred solution of 3-(1-aminoethyl)-2-cyclopropyl-8-methylisoquinolin-1(2H)-one (S:R=7:1) (4.84 g, 20 mmol) (compound 5003) in MeOH (96.8 mL), (L) tartaric-acid (3.0 g, 20 mmol) was added and the resulting mixture was stirred at room temperature for 16 h. The precipitate was collected by filtration and rinsed with MeOH (10 mL). The solid was dissolved in H₂O (15 mL) and saturated NaHCO₃ (5 mL) was added to adjust the pH to about 8. The resulting solid was collected by filtration, rinsed with water (5 mL), and dried in vacuo to afford the desired product (compound 5003) (1.94 g. 40% yield) as a single enantiomer (S configuration). The enantiomeric purity was confirmed by coupling with (R)-(−)-alpha-methoxyphenylacetic acid and performing Nuclear Magnetic Resonance Spectroscopy on the resulting diastereomeric mixture.

(S)-3-(1-Aminoethyl)-2-cyclopropyl-8-methylisoquinolin-1(2H)-one (242 mg, 1 mmol) (compound 5003), 6-chloro-9-(tetrahydro-2H-pyran-2-yl)-9H-purine (344 mg, 1.44 mmol) and DIPEA (279 mg, 2.16 mmol) were dissolved in n-BuOH (20 mL), and the resulting mixture was stirred at reflux for 16 h. The reaction mixture was concentrated in vacuo and the residue was purified by flash column chromatography on silica gel (eluting with 30% to 50% Hex/EA) to afford the desired product, 2-cyclopropyl-8-methyl-3-((1S)-1-(9-(tetrahydro-2H-Pyran-2-yl)-9H-purin-6-ylamino)ethyl)isoquinolin-1(2H)-one (compound 5004) (288 mg, 65% yield) as a white solid.

2-Cyclopropyl-8-methyl-3-((1S)-1-(9-(tetrahydro-2H-pyran-2-yl)-9H-purin-6-ylamino)ethyl)isoquinolin-1(2H)-one (compound 5004) (222 mg, 0.5 mmol) was dissolved in HCl/EtOH (3 M, 5 mL) and the resulting mixture was stirred at room temperature for 1 h. The reaction mixture was neutralized with saturated NaHCO₃ solution to pH=7-8, and then extracted with CH₂Cl₂ (50 mL×3). The combined organic layer was washed with brine, dried over anhydrous Na₂SO₄ and filtered. The filtrate was concentrated in vacuo and the residue was recrystallized from ethyl acetate and hexanes (1:1). The solid was collected by filtration and dried in vacuo to afford the desired product, (S)-3-(1-(9H-purin-6-ylamino)ethyl)-2-cyclopropyl-8-methylisoquinolin-1(2H)-one (compound 5005) (150 mg, 83% yield) as a white solid.

Example 15b

Synthesis of (S)-3-(1-(9H-purin-6-ylamino)ethyl)-2-cyclopropyl-8-chloro-isoquinolin-1(2H)-one (Compound 5011)

Scheme 28b. The synthesis of (S)-3-(1-(9H-purin-6-ylamino)ethyl)-2-cyclopropyl-8-chloro-isoquinolin-1(2H)-one is described

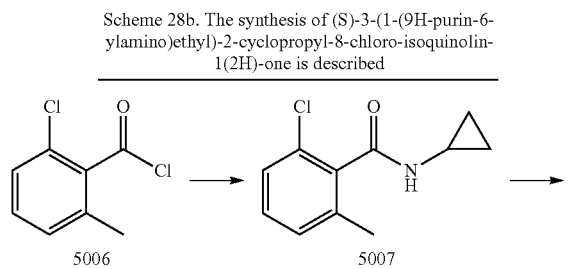

5006 → 5007

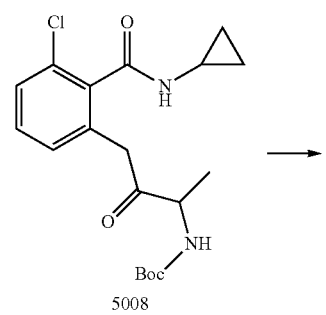

5008

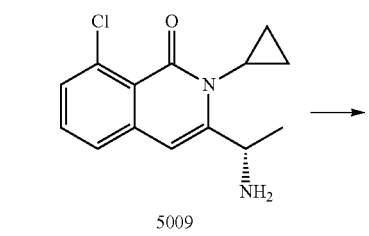

5009

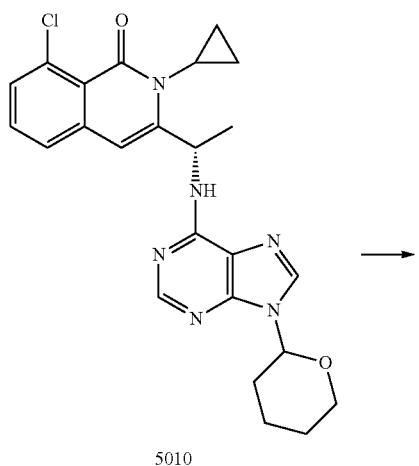

5010

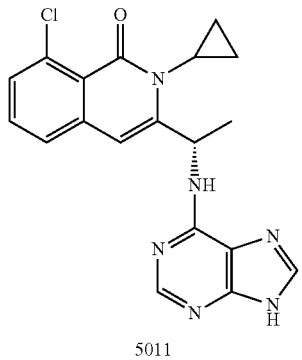

5011

The compound of Formula 5011 was synthesized using the synthetic transformations as described in Example 15a, but 2-chloro-6-methyl benzoyl chloride (compound 5006) was used instead of 2,6,dimethyl benzoyl chloride (compound 4402).

Example 16

Synthesis of (S)-3-(1-(2-amino-5-chloropyrimidin-4-ylamino)ethyl)-8-methyl-2-phenylisoquinolin-1(2H)-one (Compound 5102)

Scheme 29. The synthesis of (S)-3-(1-(2-amino-5-chloropyrimidin-4-ylamino)ethyl)-8-methyl-2-phenylisoquinolin-1(2H)-one (compound 5102) is described.

4704

5101

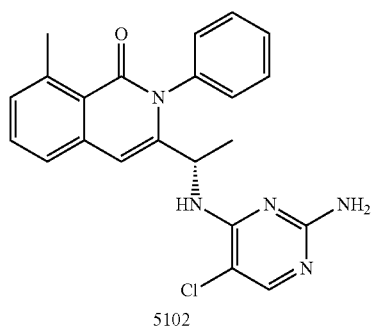

5102

A mixture of 3-(1-aminoethyl)-8-methyl-2-phenylisoquinolin-1(2H)-one (compound 4704) (150 mg, 0.54 mmol), 2,4,5-trichloropyrimidine (119 mg, 0.65 mmol) and triethylamine (137 mg, 1.35 mmol) in n-BuOH (10 mL) was stirred at reflux for 2 h. The mixture was allowed to cool to room temperature and then concentrated in vacuo. The residue was purified by flash column chromatography on silica gel (MeOH:CH$_2$Cl$_2$=1:100) to afford the desired product, (S)-3-(1-(2,5-dichloropyrimidin-4-ylamino)ethyl)-8-methyl-2-phenylisoquinolin-1(2H)-one (2H)-one (compound 5101) (170 mg, 74% yield) as a white solid.

A mixture of (S)-3-(1-(2,5-dichloropyrimidin-4-ylamino)ethyl)-8-methyl-2-phenylisoquinolin-1(2H)-one (compound 5101) (85 mg, 0.20 mmol) in ammonia water (15 mL) in a sealed tube was stirred at 150° C. for 16 h. The solution was allowed to cool to room temperature and then partitioned between water (30 mL) and ethyl acetate (3×30 mL). The combined organic layer was washed with brine (2×20 mL), dried over anhydrous Na$_2$SO$_4$ and filtered. The filtrate was concentrated in vacuo to afford the desired product, (S)-3-(1-(2-amino-5-chloropyrimidin-4-ylamino)ethyl)-8-methyl-2-phenylisoquinolin-1(2H)-one (compound 5102) (40 mg, 49.6% yield) as a white solid.

Example 17

Synthesis of (S)-3-(1-(2-fluoro-9H-purin-6-ylamino)ethyl)-8-methyl-2-phenylisoquinolin-1(2H)-one (Compound 5204)

Scheme 30. The synthesis of (S)-3-(1-(2-fluoro-9H-purin-6-ylamino)ethyl)-8-methyl-2-phenylisoquinolin-1(2H)-one (compound 5204) is described.

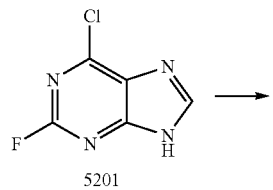

5201

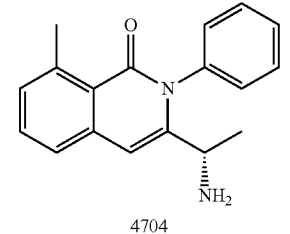

5202

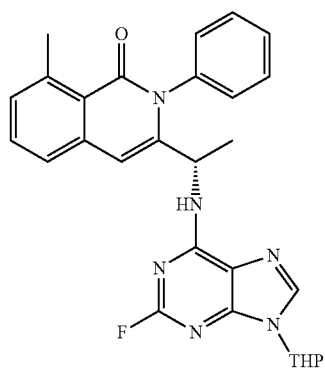

5203

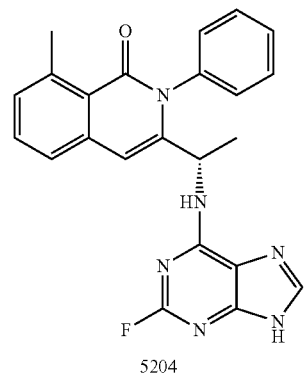

5204

To a stirred mixture of 6-chloro-2-fluoro-9H-purine (compound 5201) (2.07 g, 12.0 mmol) and p-toluenesulfonic acid monohydrate (34 mg, 0.18 mmol) in ethyl acetate (50 mL) under an argon atmosphere, 3,4-dihydropyran (3.03 g, 36.0 mmol) was added and the resulting mixture was stirred at reflux for 16 h. The reaction mixture was concentrated in vacuo and the residue was purified by flash column chromatography on silica gel (eluting with 10% Hex/EA) to afford the desired product, 6-chloro-2-fluoro-9-(tetrahydro-2H-pyran-2-yl)-9H-purine (compound 5202) (1.82 g, 59% yield) as a white solid.

3-(1-Aminoethyl)-8-methyl-2-phenylisoquinolin-1(2H)-one (200 mg, 0.72 mol), 6-chloro-2-fluoro-9-(tetrahydro-2H-pyran-2-yl)-9H-purine (compound 5202) (369 mg, 1.44 mmol) and DIPEA (279 mg, 2.16 mmol) were dissolved in n-BuOH (20 mL) in a sealed tube, and the resulting mixture was stirred at 120° C. for 16 h. The reaction mixture was concentrated in vacuo and the residue was purified by flash column chromatography on silica gel (eluting with 30% to 50% Hex/EA) to afford the desired product, 3-(1-(2-fluoro-9-(tetrahydro-2H-pyran-2-yl)-9H-purin-ylamino)ethyl)-8-methyl-2-phenylisoquinolin-1(2H)-one (compound 5203) (167 mg, 47% yield) as a white solid.

3-(1-(2-Fluoro-9-(tetrahydro-2H-pyran-2-yl)-9H-purin-6-ylamino)ethyl)-8-methyl-2-phenylisoquinolin-1(2H)-one (compound 5203) (160 mg, 0.32 mmol) was dissolved in HCl/EtOH (3 M, 5 mL) and the resulting mixture was stirred at room temperature for 1 h. The mixture was neutralized with saturated NaHCO$_3$ aqueous solution to pH=7-8, and extracted with CH$_2$Cl$_2$ (50 mL×3). The combined organic layer was washed with brine, dried over anhydrous Na$_2$SO$_4$ and filtered. The filtrate was concentrated in vacuo and the residue was recrystallized from ethyl acetate and hexanes. The solid was collected by filtration and dried in vacuo to afford the desired product, 3-(1-(2-fluoro-9H-purin-6-ylamino)ethyl)-8-methyl-2-phenylisoquinolin-1(2H)-one (compound 5204) (125 mg, 94% yield) as a white solid.

Example 18

Synthesis of (S)-3-(1-(2-chloro-9H-purin-6-ylamino)ethyl)-8-methyl-2-phenylisoquinolin-1(2H)-one (Compound 5304)

Scheme 31. The synthesis of (S)-3-(1-(2-chloro-9H-purin-6-ylamino)ethyl)-8-methyl-2-phenylisoquinolin-1(2H)-one (compound 5304) is described.

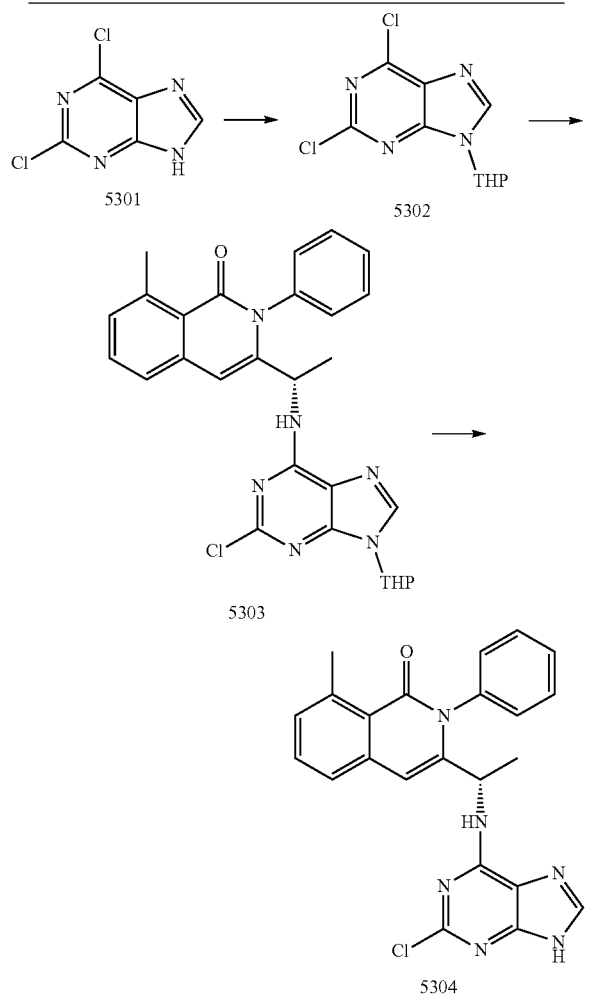

To a stirred mixture of 2,6-dichloro-9H-purine (compound 5301) (2.27 g, 12.0 mmol) and p-toluenesulfonic acid monohydrate (34 mg, 0.18 mmol) in ethyl acetate (50 mL) under an argon atmosphere, 3,4-dihydropyran (3.03 g, 36.0 mmol) was added and the resulting mixture was stirred at reflux for 16 h. The reaction mixture was concentrated in vacuo and the residue was purified by flash column chromatography on silica gel (eluting with 10% Hex/EA) to afford the desired product, 2,6-dichloro-9-(tetrahydro-2H-pyran-2-yl)-9H-purine (compound 5302) (2.04 g, 62% yield) as a white solid.

3-(1-Aminoethyl)-8-methyl-2-phenylisoquinolin-1(2H)-one (compound 4704) (200 mg, 0.72 mol), 2,6-dichloro-9-(tetrahydro-2H-pyran-2-yl)-9H-purine (compound 5302) (393 mg, 1.44 mmol) and DIPEA (279 mg, 2.16 mmol) were dissolved in n-BuOH (20 mL) in a sealed tube, and the resulting mixture was stirred at 120° C. for 16 h. The reaction mixture was concentrated in vacuo and the residue was purified by flash column chromatography on silica gel (eluting with 30% to 50% Hex/EA) to afford the desired product, 3-(1-(2-chloro-9-(tetrahydro-2H-pyran-2-yl)-9H-purin-6-ylamino)ethyl)-8-methyl-2-phenylisoquinolin-1(2H)-one (compound 5303) (172 mg, 46% yield) as a white solid.

3-(1-(2-Chloro-9-(tetrahydro-2H-pyran-2-yl)-9H-purin-6-ylamino)ethyl)-8-methyl-2-phenylisoquinolin-1(2H)-one (compound 5303) (172 mg, 0.33 mmol) was dissolved in HCl/EtOH (3 M, 5 mL) and the resulting mixture was stirred at room temperature for 1 h. The mixture was neutralized with saturated NaHCO$_3$ aqueous solution to pH=7-8, and then extracted with CH$_2$Cl$_2$ (50 mL×3). The combined organic layer was washed with brine, dried over Na$_2$SO$_4$ and filtered. The filtrate was concentrated in vacuo and recrystallized from ethyl acetate and hexanes. The solid was collected by filtration and dried in vacuo to afford the desired product, 3-(1-(2-chloro-9H-purin-6-ylamino)ethyl)-8-methyl-2-phenylisoquinolin-1(2H)-one (compound 5304) (128 mg, 90% yield) as a white solid.

Example 19

Synthesis of (S)-3-(1-(2-amino-9H-purin-6-ylamino)ethyl)-8-methyl-2-phenylisoquinolin-1(2H)-one (Compound 5402)

Scheme 32. The synthesis of (S)-3-(1-(2-amino-9H-purin-6-ylamino)ethyl)-8-methyl-2-phenylisoquinolin-1(2H)-one (compound 5402) is described.

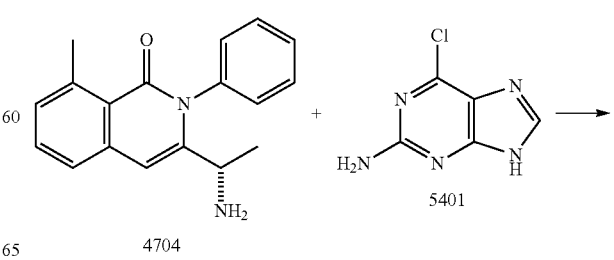

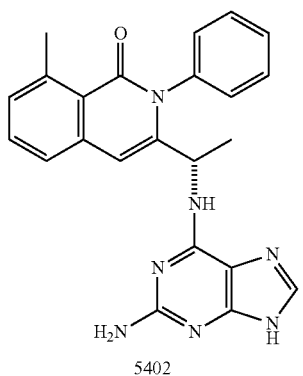

5402

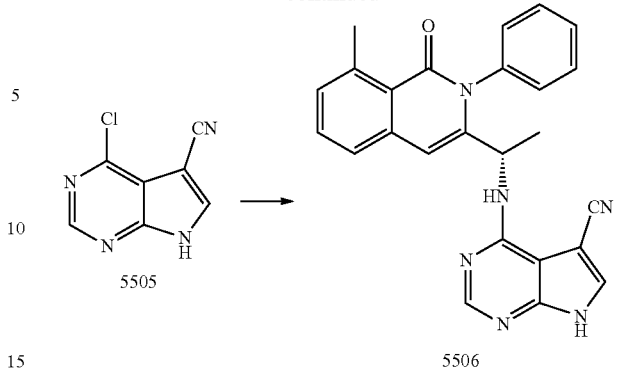

5505

5506

(S)-3-(1-Aminoethyl)-8-methyl-2-phenylisoquinolin-1 (2H)-one (compound 4704) (100 mg, 0.36 mmol), 2-Amino-6-chloropurine (compound 5401) (60.9 mg, 0.36 mmol) and N,N-diisopropylethyl amine (69 µL, 0.40 mmol) were suspended in n-BuOH (4 mL) in a sealed tube, and the resulting mixture was stirred at 100° C. for 48 h and then at 120° C. for 24 h. The mixture was allowed to cool to room temperature and concentrate in vacuo to remove n-BuOH. The residue was partitioned between ethyl acetate and water. The organic layer was washed with brine, dried over $Na_2SO_4$ and filtered. The filtrate was concentrated in vacuo. The residue was triturated with anhydrous ethyl ether and further purified by flash column chromatography on silica gel (eluting with 0-8% MeOH/DCM) to afford the desired product, (S)-3-(1-(2-amino-9H-purin-6-ylamino)ethyl)-8-methyl-2-phenylisoquinolin-1(2H)-one as a off white/yellow solid (compound 5402), (28 mg, 20%).

Example 20

Synthesis of (S)-4-(1-(8-methyl-1-oxo-2-phenyl-1,2-dihydroisoquinolin-3-yl)ethylamino)-7H-pyrrolo[2,3-d]pyrimidine-5-carbonitrile (Compound 5506)

Scheme 33. The synthesis of (S)-4-(1-(8-methyl-1-oxo-2-phenyl-1,2-dihydroisoquinolin-3-yl)ethylamino)-7H-pyrrolo[2,3-d]pyrimidine-5-carbonitrile (compound 5506) is described.

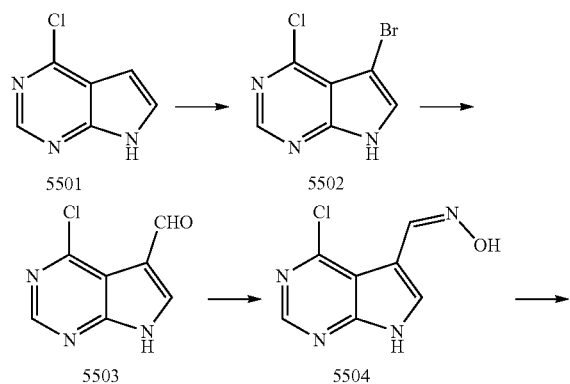

To a stirred mixture of 4-chloro-7H-pyrrolo[2,3-d]pyrimidine (compound 5501) (3.99 g, 26.0 mmol) in dry $CH_2Cl_2$ (150 mL) under an argon atmosphere, N-bromosuccinimide (6.02 g, 33.8 mmol) was added. The reaction mixture was stirred at room temperature for 3 h, diluted with MeOH (30 mL), and then concentrated in vacuo to yield a slight brown solid. The residue was triturated with $H_2O$ (150 mL) and then recrystallized from MeOH (120 mL). The solid was collected by filtration and dried in vacuo to afford the desired product, 5-bromo-4-chloro-7H-pyrrolo[2,3-d]pyrimidine (compound 5502) (4.0 g, 66% yield) as a white solid.

To a stirred solution of 5-bromo-4-chloro-7H-pyrrolo[2,3-d]pyrimidine (compound 5502) (2.33 g, 10.0 mmol) in anhydrous THF (100 mL) at −78° C. under an argon atmosphere, a solution of n-BuLi (8.8 mL, 22.0 mmol) in THF (50 mL) was added dropwise over 10 min. The reaction mixture was stirred at −78° C. for 1 h and then DMF (2.00 g, 11.0 mmol) was added dropwise over 10 min. The reaction mixture was stirred at −78° C. for 30 min, and then was allowed to slowly warm to room temperature and stirred at room temperature for 16 h. The mixture was diluted with $H_2O$ (50 mL), and then concentrated in vacuo to remove THF. The resulting slurry was treated with saturated $NH_4Cl$ aqueous solution (50 mL), filtered, washed with ethyl acetate (100 mL), and dried in vacuo to afford the desired product, 4-chloro-7H-pyrrolo[2,3-d]pyrimidine-5-carbaldehyde (compound 5503) (1.17 g, 65% yield) as a white solid.

To a stirred mixture of 4-chloro-7H-pyrrolo[2,3-d]pyrimidine-5-carbaldehyde (compound 5503) (1.17 g, 6.47 mmol) in EtOH (25 mL), hydroxylamine hydrochloride solid (0.54 g, 7.77 mmol) and a solution of NaOH (0.311 g, 7.77 mmol) in $H_2O$ (4 mL) were added sequentially. The reaction mixture was stirred at room temperature for 30 min and diluted with a sufficient amount of EtOH (30 mL) and stirring was continued for 30 min. The solid was collected by filtration, rinsed with $H_2O$ (100 mL) and dried in vacuo to afford the desired product, 4-chloro-7H-pyrrolo[2,3-d]pyrimidine-5-carbaldehyde oxime (compound 5504) (0.89 g, 70% yield) as a mixture of isomers.

To a stirred mixture of 4-chloro-7H-pyrrolo[2,3-d]pyrimidine-5-carbaldehyde oxime (compound 5504) (865 mg, 4.40 mmol) in $CH_2Cl_2$ (20 mL), $SOCl_2$ (3.1 mL, 43.7 mmol) was added and the resulting mixture was stirred at room temperature for 16 h. The reaction mixture was concentrated in vacuo. The residue was treated with ethyl acetate (20 mL), $H_2O$ (20 mL) and then saturated $NaHCO_3$ aqueous solution (50 mL) to adjust pH to about 3-4. The mixture was stirred at room temperature for 15 min and the solid was collected by filtration. The filtrate was extracted with ethyl acetate (80 mL×3), dried over $Na_2SO_4$ and filtered. The filtrate was concentrated in vacuo to afford the second batch of product. The combined solid was recrystallized from ethyl acetate and hexanes (1:1, 20 mL). The solid was collected by filtration and dried in vacuo to afford the desired product, 4-chloro-7H-pyrrolo[2,3-d]pyrimidine-5-carbonitrile (compound 5505) (763 mg, 97% yield).

(S)-3-(1-Aminoethyl)-8-methyl-2-phenylisoquinolin-1(2H)-one (compound 4704) (208 mg, 0.75 mol), 4-chloro-7H-pyrrolo[2,3-d]pyrimidine-5-carbonitrile (compound 5505) (160 mg, 0.90 mmol) and $Et_3N$ (228 mg, 2.25 mmol) were dissolved in n-BuOH (20 mL) in a sealed tube, and the resulting mixture stirred at 150° C. for 16 h. The reaction mixture was concentrated in vacuo, and the residue was purified by flash column chromatography on silica gel (eluting with 50% Hex/EA) to afford the desired product, (S)-4-(1-(8-methyl-1-oxo-2-phenyl-1,2-dihydroisoquinolin-3-yl)ethylamino)-7H-pyrrolo[2,3-d]pyrimidine-5-carbonitrile (compound 5506) (90 mg, 28% yield) as a white solid.

Example 21

IC50 Values for Selected Compounds

TABLE 3

In Vitro $IC_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| PI3K δ | Compound No. 197, 199, 241, 259, 261, 263, 280, 282, 283, 314, 315, 318, 321, 322 | Compound No. 1, 5, 22, 27, 38, 39, 40, 41, 46, 92, 117, 118, 120, 129, 132, 164, 165, 172, 188, 186, 193, 194, 195, 217, 242, 246, 281, 284, 305, 317, 325 | Compound No. 4, 14, 15, 17, 18, 21, 26, 29, 31, 32, 34, 35, 36, 42, 43, 44, 45, 47, 49, 57, 69, 71, 85, 87, 94, 106, 107, 143, 175, 179, 181, 182, 183, 187, 189, 192, 225, 226, 228, 235, 236, 239, 248, 250, 258, 269, 274, 275, 285, 286, 297, 298, 299, 300, 307, 309, 313, 319, | Compound No. 2, 3, 6, 7, 8, 9, 10, 11, 12, 13, 16, 19, 20, 23, 24, 25, 28, 30, 33, 37, 48, 50, 51, 52, 53, 54, 55, 56, 58, 59, 60, 61, 62, 63, 64, 65, 66, 67, 68, 70, 72, 73, 74, 75, 76, 77, 78, 79, 80, 81, 82, 83, 84, 86, 88, 89, 90, 91, 93, 95, 96, 97, 98, 99, 100, 101, 102, 103, 104, 105, 108, 109, 110, 111, 112, 113, 114, 115, 119, 123, 124, 125, 126, 128, 134, 135, 136, 137, 138, 139, 141, 142, 144, 145, 146, 147, 148, 149, 150, 151, 152, 153, 154, 155, 156, 157, 158, 159, 160, 161, 162, 166, 167, 168, 169, 170, 171, 173, 174, 176, 177, 178, 180, 185, 188, 190, 191, 196, 198, 200, 201, 202, 203, 204, 205, 206, 207, 208, 209, 210, 211, 212, 213, 214, 215, 216, 218, 219, 220, 221, 222, 223, 224, 227, 229, 230, 231, 232, 233, 234, 237, 238, 240, 243, 244, 245, 247, 249, 251, 252, 253, 254, 255, 256, 257, 260, 262, 264, 265, 266, 267, 268, 270, 271, 272, 273, 276, 277, 278, 279, 287, 288, 289, 290, 291, 292, 293, 294, 295, 296, 301, 302, 303, 306, 308, 310, 311, 312, 316, 320, 323, 324 |
| PI3K γ | Compound No. 1, 4, 5, 18, 38, 43, 60, 69, 169, 172, 192, 193, 194, 199, 227, 228, 233, 259, 263, 280, 281, 282, 283, 314, 315, 317, 318, 321, 322, 325 | Compound No. 17, 34, 35, 37, 38, 40, 42, 57, 61, 65, 91, 92, 94, 105, 107, 164, 170, 175, 179, 181, 183, 184, 186, 187, 189, 195, 197, 219, 221, 224, 232, 239, 241, 242, 246, 248, 258, 261, 274, 284, | Compound No. 2, 8, 9, 10, 11, 14, 15, 20, 22, 27, 28, 39, 41, 46, 47, 49, 51, 55, 58, 66, 70, 71, 73, 76, 78, 80, 93, 98, 99, 100, 103, 104, 106, 108, 109, 161, 162, 163, 165, 166, 180, 188, 202, 206, 209, 212, | Compound No. 3, 6, 7, 12, 13, 16, 19, 21, 23, 24, 25, 26, 29, 30, 31, 33, 36, 44, 45, 48, 50, 52, 53, 54, 56, 59, 62, 63, 64, 67, 68, 72, 74, 75, 77, 79, 81, 82, 83, 84, 86, 87, 88, 89, 90, 95, 96, 97, 101, 102, 142, 145, |

TABLE 3-continued

In Vitro IC$_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| | | 285, 294, 299, 303, 305, 307, 309, 312, 313, 319 | 214, 216, 218, 220, 222, 229, 234, 236, 238, 250, 267, 268, 269, 271, 275, 279, 286, 293, 298, 300, 301, 308, 316 | 146, 147, 148, 149, 150, 151, 152, 160, 167, 168, 171, 173, 174, 176, 177, 178, 182, 185, 190, 191, 196, 198, 200, 201, 203, 204, 205, 207, 208, 210, 211, 213, 215, 223, 230, 231, 235, 237, 240, 243, 244, 245, 247, 249, 251, 252, 253, 254, 255, 256, 257, 260, 262, 264, 265, 266, 270, 272, 273, 276, 277, 278, 287, 288, 289, 290, 291, 292, 295, 296, 302, 304, 306, 310, 311, 320, 323, 324 |
| PI3K α | Compound No. 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 54, 55, 56, 57, 58, 59, 60, 61, 62, 64, 65, 67, 68, 69, 70, 71, 72, 73, 74, 79, 80, 81, 82, 83, 85, 87, 88, 91, 93, 96, 98, 99, 100, 103, 104, 105, 106, 107, 109, 110, 111, 112, 114, 146, 160, 161, 162, 163, 164, 165, 166, 167, 169, 170, 172, 174, 175, 179, 180, 181, 182, 183, 184, 186, 187, 188, 189, 191, 192, 193, 194, 197, 202, 211, 212, 214, 215, 216, 218, 219, 220, 221, 222, 224, 227, 228, 238, 239, 241, 242, 246, 247, 248, 249, 250, 258, 259, 261, 263, 265, 266, 267, 268, 271, 274, 275, 280, 281, 282, 283, 284, 285, 286, 290, 293, 294, 298, 299, 300, 304, 308, 309, 313, 314, 315, 316, 317, 318, 319, 321, 322, 324, 325 | Compound No. 3, 7, 63, 66, 84, 86, 89, 90, 97, 108, 113, 115, 152, 168, 171, 173, 185, 190, 198, 203, 204, 205, 206, 207, 209, 210, 213, 223, 235, 237, 240, 243, 244, 245, 251, 253, 254, 255, 256, 269, 273, 279, 291, 292, 295, 296 | Compound No. 53, 95, 101, 102, 145, 147, 149, 151, 177, 208, 257, 260, 262, 264, 270, 272, 276, 277, 278, 287, 288, 289, 320, 323 | Compound No. 142, 148, 150, 153, 154, 155, 156, 157, 158, 159, 176, 201, 252 |
| PI3K β | Compound No. 8, 9, 10, 11, 14, 21, 22, 24, 26, 27, 28, 29, 34, 35, 36, 37, 38, 39, 40, 41, 42, 43, 44, 46, 52, 54, 56, 57, 59, 60, 64, 68, 69, 70, 73, 76, 78, 79, 80, 87, 88, 91, 93, 98, 103, 104, 105, 107, 109, 112, 146, 152, 162, 163, 164, 165, 166, 169, 170, 172, 175, 179, 180, 181, 182, 183, 184, 186, 187, 188, 189, 192, 193, 194, 197, | Compound No. 3, 12, 13, 23, 25, 53, 55, 58, 61, 63, 65, 67, 71, 72, 74, 75, 77, 81, 82, 83, 84, 85, 86, 96, 99, 106, 108, 110, 111, 113, 114, 115, 145, 147, 149, 151, 154, 158, 160, 161, 167, 168, 171, 173, 174, 177, 178, 190, 191, 198, 202, 203, 205, 206, 207, 209, 210, 211, 212, 214, 215, 219, 220, 223, 228, 235, 240, 243, | Compound No. 7, 62, 66, 82, 89, 90, 95, 97, 100, 102, 150, 153, 159, 176, 185, 201, 204, 208, 213, 227, 237, 251, 252, 267, 276, 277, 290, 292, 293 | Compound No. 101, 142, 155, 156, 157, 200, 253, 254, 255, 256, 257, 260, 262, 264, 268, 270, 272, 273, 278, 279, 287, 288, 289, 291, 320, 323, |

TABLE 3-continued

In Vitro IC$_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| | 216, 217, 218, 221, 222, 224, 238, 248, 259, 261, 263, 266, 271, 275, 280, 282, 283, 284, 285, 286, 294, 299, 304, 310, 311, 312, 315, 317, 321, 322, 325 | 244, 247, 249, 265, 269, 274, 281, 295, 296, 298, 300, 308, 316, 324 | | |
| B cell proliferation EC$_{50}$ (nM) | Compound No. 38, 162, 199 | Compound No. 1, 2, 5, 22, 26, 27, 39, 40, 43, 49, 57, 71, 87, 112, 197, 207, 235 | Compound No. 4, 8, 9, 10, 11, 14, 15, 18, 19, 20, 21, 24, 25, 28, 29, 30, 31, 32, 34, 35, 36, 41, 42, 45, 46, 47, 50, 51, 61, 69, 70, 76, 77, 78, 79, 80, 85, 86, 91, 98, 100, 103, 104, 105, 106, 107, 110, 111, 114, 119, 124, 133, 135, 145, 152, 161, 162, 163, 169, 195, 212, 243, 294, 312 | Compound No. 3, 6, 7, 12, 13, 16, 17, 23, 33, 37, 44, 48, 53, 54, 55, 62, 63, 66, 67, 68, 72, 73, 74, 75, 81, 82, 83, 84, 88, 89, 90, 93, 95, 96, 97, 99, 101, 102, 108, 109, 113, 115, 123, 125, 126, 128, 134, 136, 137, 138, 139, 141, 142, 144, 146, 147, 148, 149, 150, 151, 153, 154, 155, 156, 157, 158, 159, 160, 166, 167, 168, 170, 171, 173, 174, 176, 177, 178, 180, 187, 185, 188, 190, 191, 196, 198, 200, 201, 202, 203, 204, 205, 206, 208, 209, 210, 211, 213, 214, 215, 216, 219, 220, 221, 222, 223, 224, 227, 228, 229, 230, 231, 232, 233, 234, 237, 244, 245, 247, 248, 249, 251, 252, 253, 254, 255, 256, 257, 270, 276, 277, 278, 289, 290, 292, 295, 296, 298, 300, 301, 302, 303, 306, 308, 310, 311 |

TABLE 4

Structures of the Compounds for the IC50 results described in Table 3.

Structure

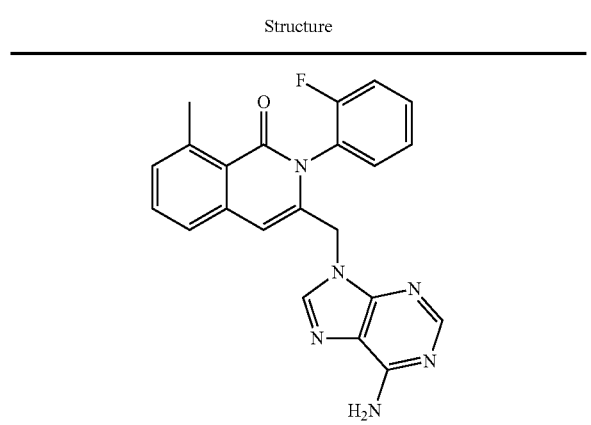

Compound 1

TABLE 4-continued

Structures of the Compounds for the IC50 results described in Table 3.

Structure

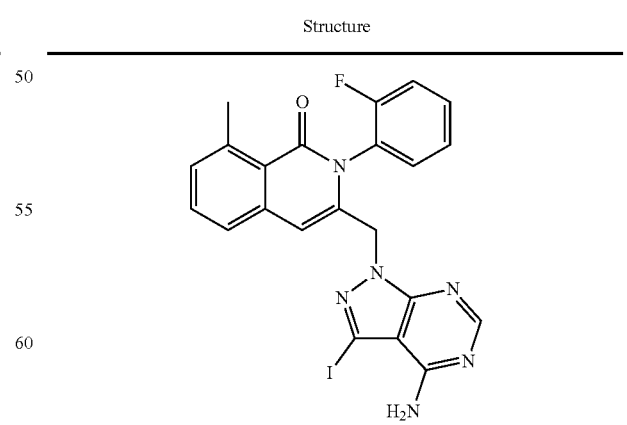

Compound 2

TABLE 4-continued
Structures of the Compounds for the IC50 results described in Table 3.
Structure
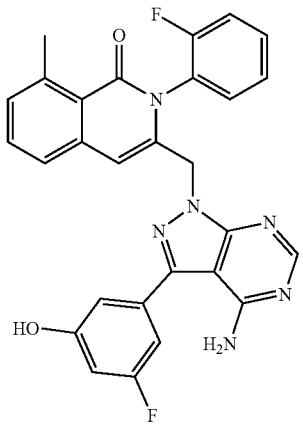 [SMILES: Cc1cccc2cc(Cn3nc(-c4cc(O)cc(F)c4)c4c(N)ncnc43)n(-c3ccccc3F)c(=O)c12]
Compound 3
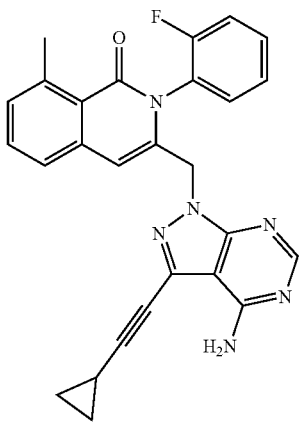 [SMILES: Cc1cccc2cc(Cn3nc(C#CC4CC4)c4c(N)ncnc43)n(-c3ccccc3F)c(=O)c12]
Compound 4
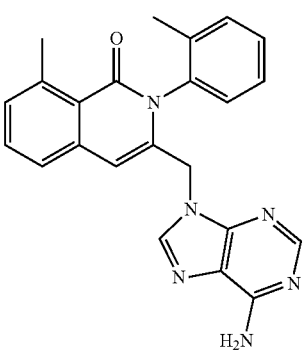 [SMILES: Cc1ccccc1-n1c(Cn2cnc3c(N)ncnc32)cc2cccc(C)c2c1=O]
Compound 5
TABLE 4-continued
Structures of the Compounds for the IC50 results described in Table 3.
Structure
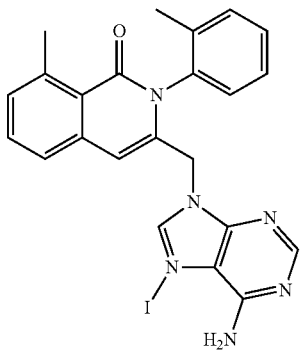
Compound 6
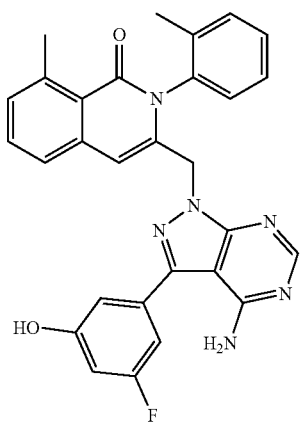 [SMILES: Cc1ccccc1-n1c(Cn2nc(-c3cc(O)cc(F)c3)c3c(N)ncnc32)cc2cccc(C)c2c1=O]
Compound 7
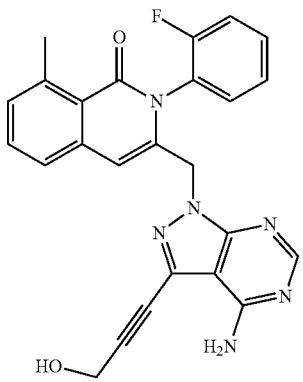 [SMILES: Cc1cccc2cc(Cn3nc(C#CCO)c4c(N)ncnc43)n(-c3ccccc3F)c(=O)c12]
Compound 8

TABLE 4-continued

Structures of the Compounds for the IC50 results described in Table 3.

| Structure |
|---|
| Compound 9 |
| Compound 10 |
| Compound 11 |
| Compound 12 |
| Compound 13 |
| Compound 14 |

TABLE 4-continued

Structures of the Compounds for the IC50 results described in Table 3.

Structure

Compound 15

Compound 16

Compound 17

TABLE 4-continued

Structures of the Compounds for the IC50 results described in Table 3.

Structure

Compound 18

Compound 19

Compound 20

TABLE 4-continued
Structures of the Compounds for the IC50 results described in Table 3.
Structure
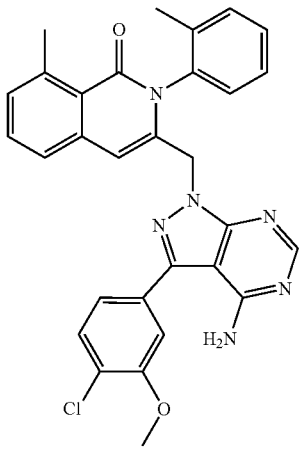 [SMILES: COc1cc(-c2nn(Cc3cc4cccc(C)c4c(=O)n3-c3ccccc3C)c3ncnc(N)c23)ccc1Cl]
Compound 21
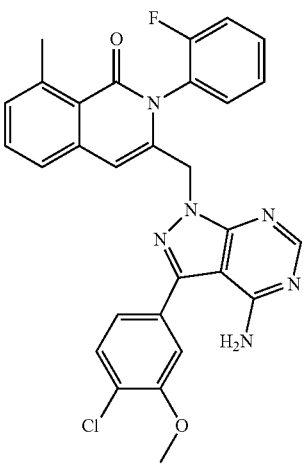 [SMILES: COc1cc(-c2nn(Cc3cc4cccc(C)c4c(=O)n3-c3ccccc3F)c3ncnc(N)c23)ccc1Cl]
Compound 22
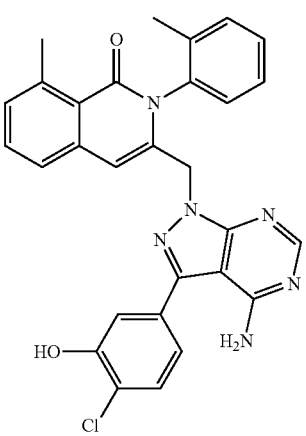 [SMILES: Cc1ccccc1-n1c(Cn2nc(-c3ccc(Cl)c(O)c3)c3c(N)ncnc32)cc2cccc(C)c2c1=O]
Compound 23
TABLE 4-continued
Structures of the Compounds for the IC50 results described in Table 3.
Structure
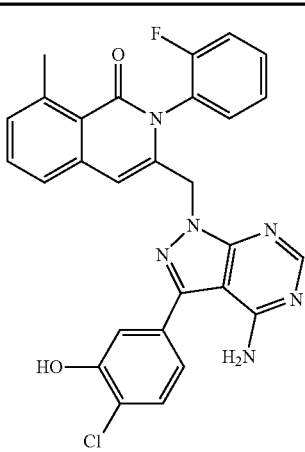
Compound 24
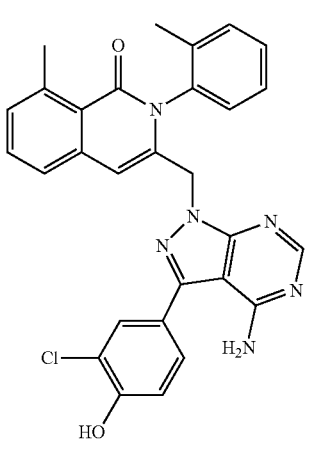 [SMILES: Cc1ccccc1-n1c(Cn2nc(-c3ccc(O)c(Cl)c3)c3c(N)ncnc32)cc2cccc(C)c2c1=O]
Compound 25
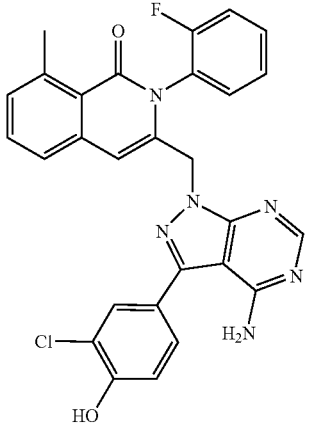 [SMILES: Cc1cccc2cc(Cn3nc(-c4ccc(O)c(Cl)c4)c4c(N)ncnc43)n(-c3ccccc3F)c(=O)c12]
Compound 26

TABLE 4-continued
Structures of the Compounds for the IC50 results described in Table 3.
Structure
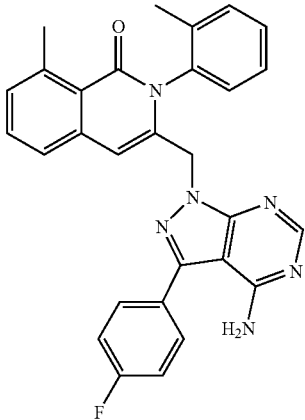 [SMILES: Cc1ccccc1-n1c(Cn2nc(-c3ccc(F)cc3)c3c(N)ncnc32)cc2cccc(C)c2c1=O]
Compound 27
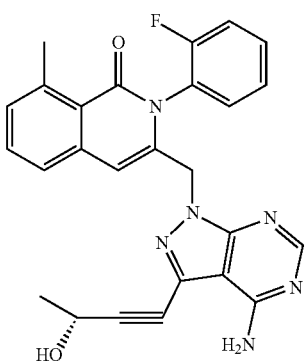 [SMILES: Cc1cccc2cc(Cn3nc(C#C[C@@H](C)O)c4c(N)ncnc43)n(-c3ccccc3F)c(=O)c12]
Compound 28
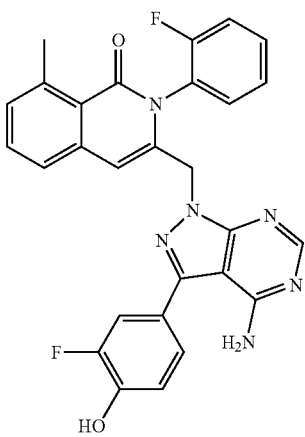 [SMILES: Cc1cccc2cc(Cn3nc(-c4ccc(O)c(F)c4)c4c(N)ncnc43)n(-c3ccccc3F)c(=O)c12]
Compound 29
TABLE 4-continued
Structures of the Compounds for the IC50 results described in Table 3.
Structure
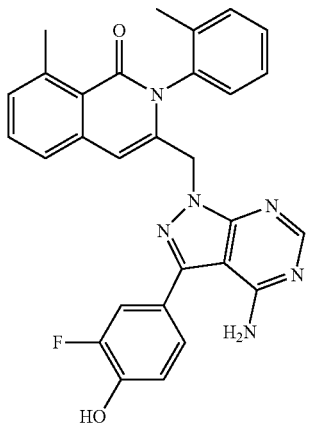
Compound 30
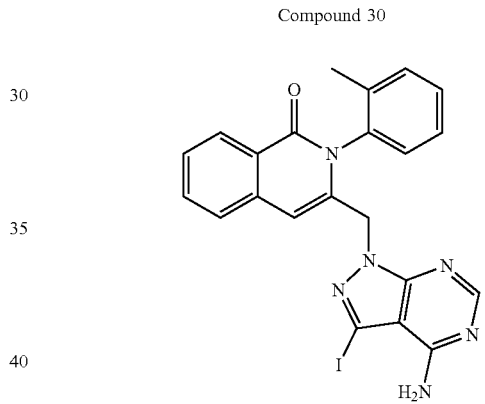
Compound 31
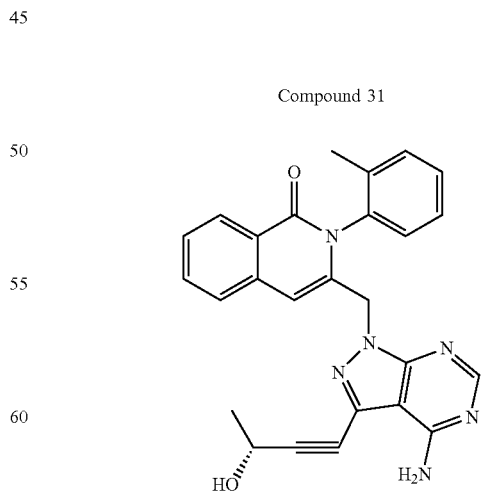
Compound 32

TABLE 4-continued
Structures of the Compounds for the IC50 results described in Table 3.
Structure
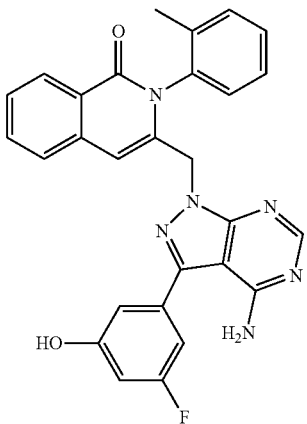 [SMILES: Cc1ccccc1-n1c(Cn2nc(-c3cc(O)cc(F)c3)c3c(N)ncnc32)cc2ccccc2c1=O]
Compound 33
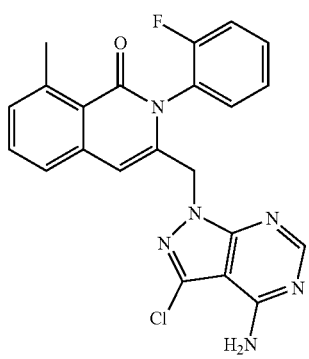 [SMILES: Cc1cccc2cc(Cn3nc(Cl)c4c(N)ncnc43)n(-c3ccccc3F)c(=O)c12]
Compound 34
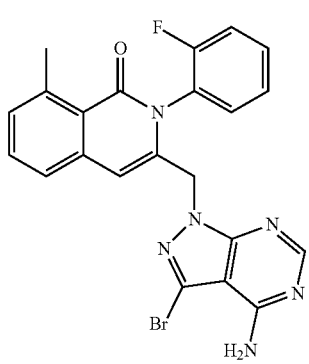
Compound 35
TABLE 4-continued
Structures of the Compounds for the IC50 results described in Table 3.
Structure
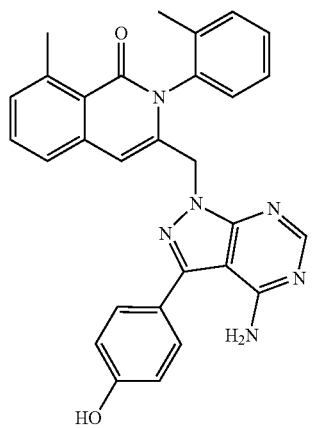 [SMILES: Cc1ccccc1-n1c(Cn2nc(-c3ccc(O)cc3)c3c(N)ncnc32)cc2cccc(C)c2c1=O]
Compound 36
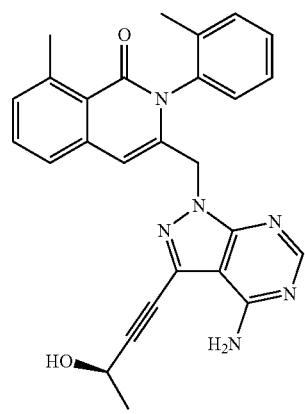 [SMILES: Cc1ccccc1-n1c(Cn2nc(C#C[C@@H](C)O)c3c(N)ncnc32)cc2cccc(C)c2c1=O]
Compound 37
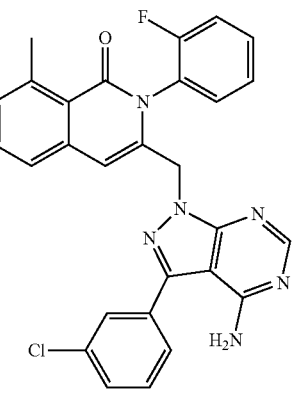
Compound 38

TABLE 4-continued

Structures of the Compounds for the IC50 results described in Table 3.

Structure

Compound 39

Compound 40

Compound 41

TABLE 4-continued

Structures of the Compounds for the IC50 results described in Table 3.

Structure

Compound 42

Compound 43

Compound 44

TABLE 4-continued

Structures of the Compounds for the IC50 results described in Table 3.

Structure

Compound 45

Compound 46

Compound 47

TABLE 4-continued

Structures of the Compounds for the IC50 results described in Table 3.

Structure

Compound 48

Compound 49

Compound 50

TABLE 4-continued

Structures of the Compounds for the IC50 results described in Table 3.

Structure

Compound 51

Compound 52

Compound 53

TABLE 4-continued

Structures of the Compounds for the IC50 results described in Table 3.

Structure

Compound 54

Compound 55

Compound 56

TABLE 4-continued
Structures of the Compounds for the IC50 results described in Table 3.
Structure
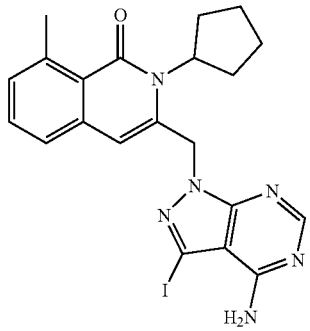 [SMILES: Cc1cccc2cc(Cn3nc(I)c4c(N)ncnc43)n(C3CCCC3)c(=O)c12]
Compound 57
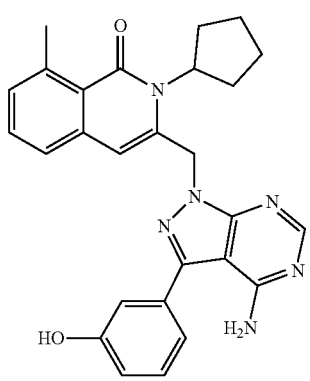 [SMILES: Cc1cccc2cc(Cn3nc(-c4cccc(O)c4)c4c(N)ncnc43)n(C3CCCC3)c(=O)c12]
Compound 58
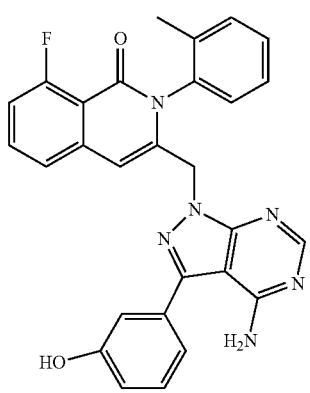 [SMILES: Cc1ccccc1-n1c(Cn2nc(-c3cccc(O)c3)c3c(N)ncnc32)cc2cccc(F)c2c1=O]
Compound 59
TABLE 4-continued
Structures of the Compounds for the IC50 results described in Table 3.
Structure
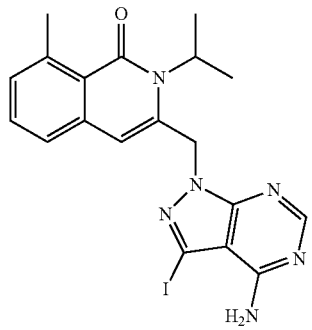
Compound 60
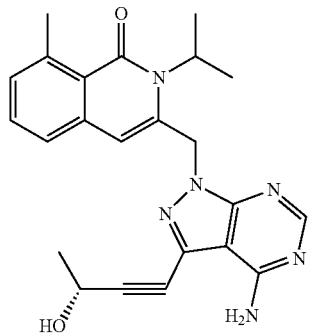 [SMILES: Cc1cccc2cc(Cn3nc(C#C[C@@H](C)O)c4c(N)ncnc43)n(C(C)C)c(=O)c12]
Compound 61
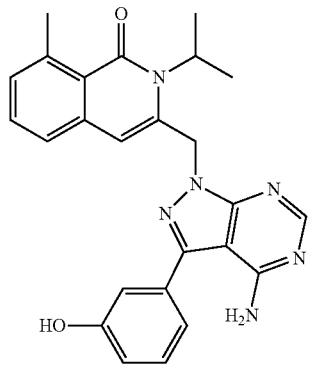 [SMILES: Cc1cccc2cc(Cn3nc(-c4cccc(O)c4)c4c(N)ncnc43)n(C(C)C)c(=O)c12]
Compound 62

TABLE 4-continued
Structures of the Compounds for the IC50 results described in Table 3.
| Structure |
| --- |
| 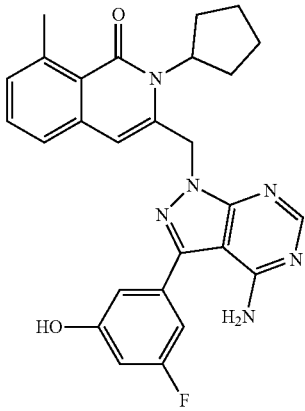 [SMILES: Cc1cccc2cc(Cn3nc(-c4cc(O)cc(F)c4)c4c(N)ncnc43)n(C3CCCC3)c(=O)c12] |
| Compound 63 |
| 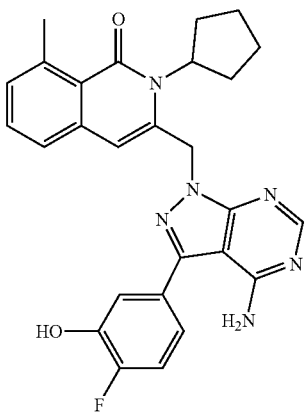 [SMILES: Cc1cccc2cc(Cn3nc(-c4ccc(F)c(O)c4)c4c(N)ncnc43)n(C3CCCC3)c(=O)c12] |
| Compound 64 |
| 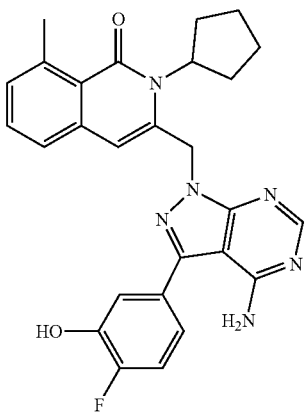 [SMILES: Cc1cccc2cc(Cn3nc(-c4ccc(F)c(O)c4)c4c(N)ncnc43)n(C3CCCC3)c(=O)c12] |
| Compound 65 |
TABLE 4-continued
Structures of the Compounds for the IC50 results described in Table 3.
| Structure |
| --- |
| 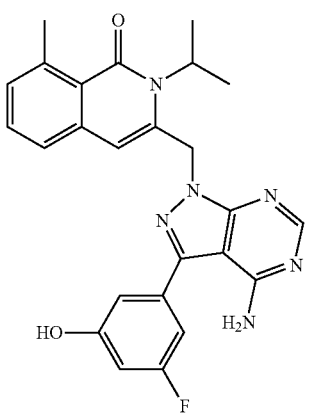 [SMILES: Cc1cccc2cc(Cn3nc(-c4cc(O)cc(F)c4)c4c(N)ncnc43)n(C(C)C)c(=O)c12] |
| Compound 66 |
| 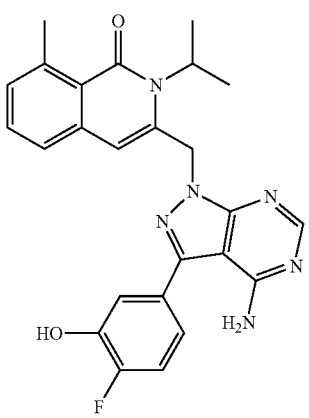 [SMILES: Cc1cccc2cc(Cn3nc(-c4ccc(F)c(O)c4)c4c(N)ncnc43)n(C(C)C)c(=O)c12] |
| Compound 67 |
| 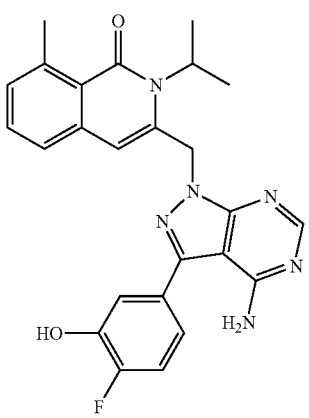 [SMILES: Cc1cccc2cc(Cn3nc(-c4ccc(F)c(O)c4)c4c(N)ncnc43)n(C(C)C)c(=O)c12] |
| Compound 68 |

TABLE 4-continued

Structures of the Compounds for the IC50 results described in Table 3.

Structure

Compound 69

Compound 70

Compound 71

TABLE 4-continued

Structures of the Compounds for the IC50 results described in Table 3.

Structure

Compound 72

Compound 73

Compound 74

TABLE 4-continued
Structures of the Compounds for the IC50 results described in Table 3.
Structure
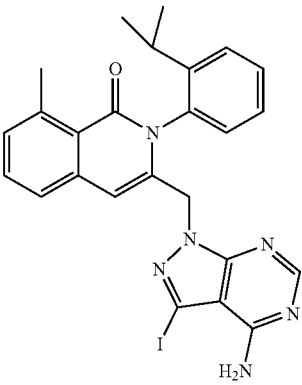 [SMILES: Cc1cccc2cc(Cn3nc(I)c4c(N)ncnc43)n(-c3ccccc3C(C)C)c(=O)c12]
Compound 75
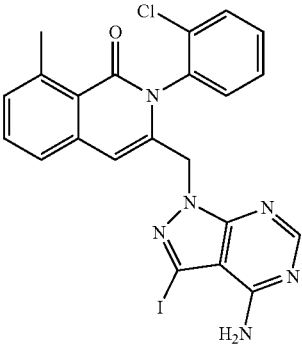 [SMILES: Cc1cccc2cc(Cn3nc(I)c4c(N)ncnc43)n(-c3ccccc3Cl)c(=O)c12]
Compound 76
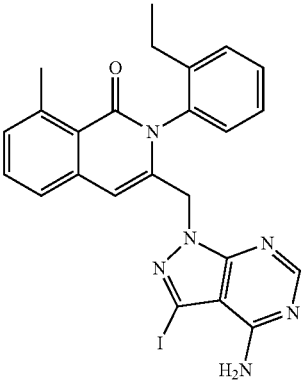 [SMILES: CCc1ccccc1-n1c(Cn2nc(I)c3c(N)ncnc32)cc2cccc(C)c2c1=O]
Compound 77
TABLE 4-continued
Structures of the Compounds for the IC50 results described in Table 3.
Structure
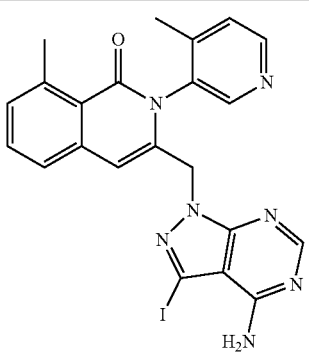 [SMILES: Cc1ccncc1-n1c(Cn2nc(I)c3c(N)ncnc32)cc2cccc(C)c2c1=O]
Compound 78
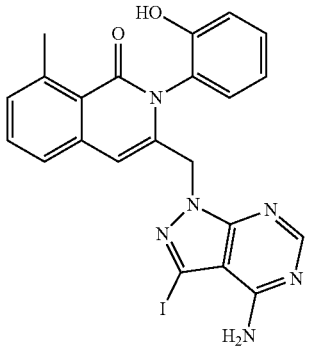 [SMILES: Cc1cccc2cc(Cn3nc(I)c4c(N)ncnc43)n(-c3ccccc3O)c(=O)c12]
Compound 79
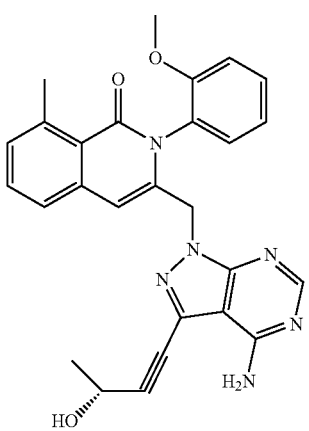 [SMILES: COc1ccccc1-n1c(Cn2nc(C#C[C@@H](C)O)c3c(N)ncnc32)cc2cccc(C)c2c1=O]
Compound 80

TABLE 4-continued

Structures of the Compounds for the IC50 results described in Table 3.

Structure

Compound 81

Compound 82

Compound 83

Compound 84

Compound 85

Compound 86

TABLE 4-continued

Structures of the Compounds for the IC50 results described in Table 3.

Structure

Compound 87

Compound 88

Compound 89

TABLE 4-continued

Structures of the Compounds for the IC50 results described in Table 3.

Structure

Compound 90

Compound 91

Compound 92

TABLE 4-continued
Structures of the Compounds for the IC50 results described in Table 3.
Structure
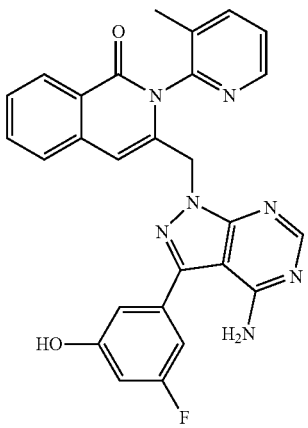 [SMILES: Cc1cccnc1-n1c(Cn2nc(-c3cc(O)cc(F)c3)c3c(N)ncnc32)cc2ccccc2c1=O]
Compound 93
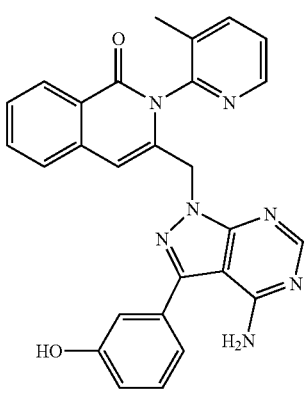 [SMILES: Cc1cccnc1-n1c(Cn2nc(-c3cccc(O)c3)c3c(N)ncnc32)cc2ccccc2c1=O]
Compound 94
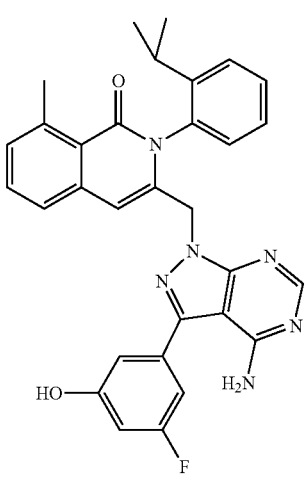 [SMILES: Cc1cccc2cc(Cn3nc(-c4cc(O)cc(F)c4)c4c(N)ncnc43)n(-c3ccccc3C(C)C)c(=O)c12]
Compound 95
TABLE 4-continued
Structures of the Compounds for the IC50 results described in Table 3.
Structure
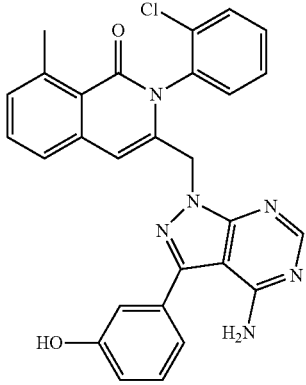
Compound 96
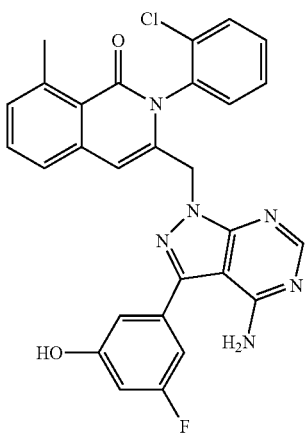 [SMILES: Cc1cccc2cc(Cn3nc(-c4cc(O)cc(F)c4)c4c(N)ncnc43)n(-c3ccccc3Cl)c(=O)c12]
Compound 97
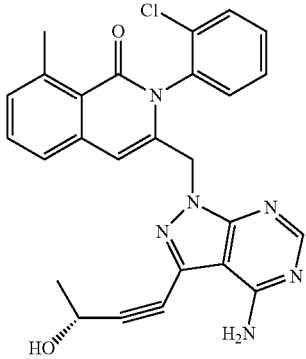 [SMILES: Cc1cccc2cc(Cn3nc(C#C[C@@H](C)O)c4c(N)ncnc43)n(-c3ccccc3Cl)c(=O)c12]
Compound 98

TABLE 4-continued
Structures of the Compounds for the IC50 results described in Table 3.
Structure
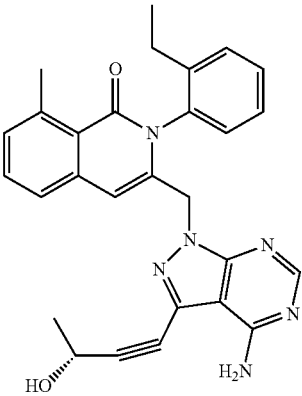 [SMILES: CCc1ccccc1-n1c(Cn2nc(C#C[C@@H](C)O)c3c(N)ncnc32)cc2cccc(C)c2c1=O]
Compound 99
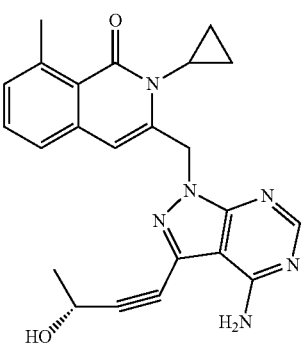 [SMILES: Cc1cccc2cc(Cn3nc(C#C[C@@H](C)O)c4c(N)ncnc43)n(C3CC3)c(=O)c12]
Compound 100
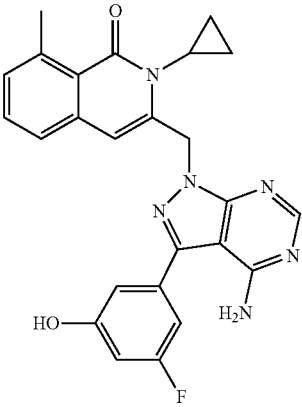 [SMILES: Cc1cccc2cc(Cn3nc(-c4cc(O)cc(F)c4)c4c(N)ncnc43)n(C3CC3)c(=O)c12]
Compound 101
TABLE 4-continued
Structures of the Compounds for the IC50 results described in Table 3.
Structure
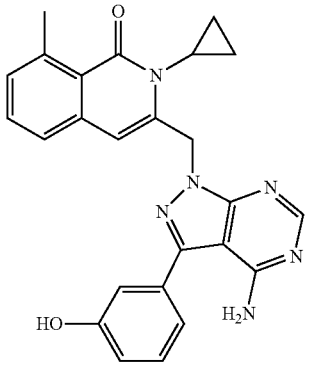 [SMILES: Cc1cccc2cc(Cn3nc(-c4cccc(O)c4)c4c(N)ncnc43)n(C3CC3)c(=O)c12]
Compound 102
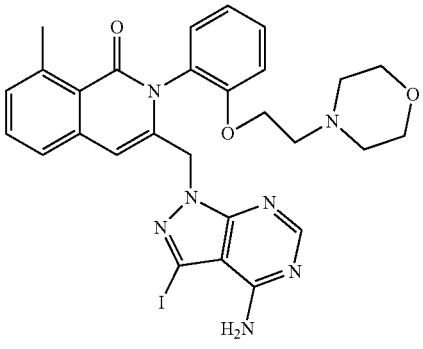 [SMILES: Cc1cccc2cc(Cn3nc(I)c4c(N)ncnc43)n(-c3ccccc3OCCN3CCOCC3)c(=O)c12]
Compound 103
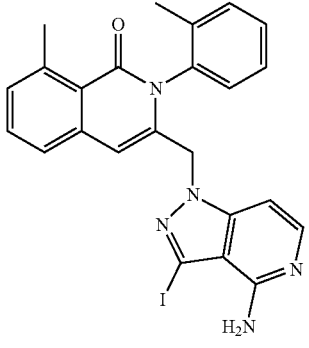 [SMILES: Cc1ccccc1-n1c(Cn2nc(I)c3c(N)nccc32)cc2cccc(C)c2c1=O]
Compound 104
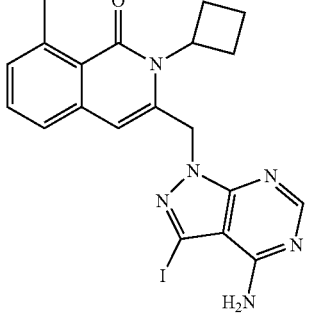
Compound 105

TABLE 4-continued
Structures of the Compounds for the IC50 results described in Table 3.
Structure
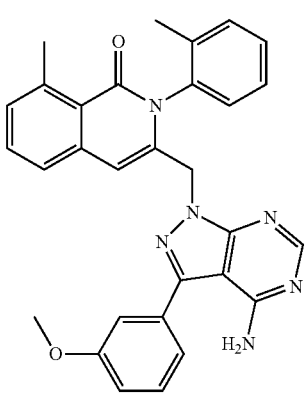 [SMILES: COc1cccc(-c2nn(Cc3cc4cccc(C)c4c(=O)n3-c3ccccc3C)c3ncnc(N)c23)c1]
Compound 106
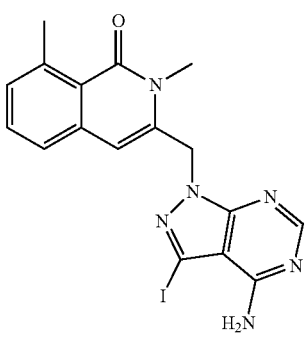 [SMILES: Cc1cccc2cc(Cn3nc(I)c4c(N)ncnc43)n(C)c(=O)c12]
Compound 107
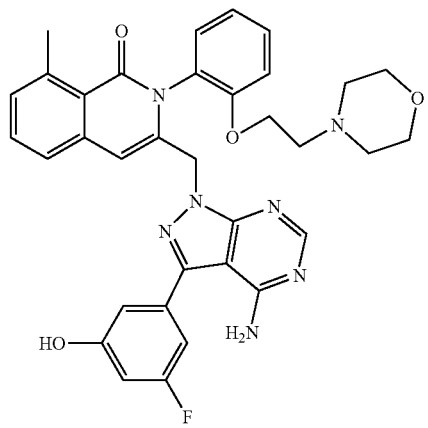 [SMILES: Cc1cccc2cc(Cn3nc(-c4cc(O)cc(F)c4)c4c(N)ncnc43)n(-c3ccccc3OCCN3CCOCC3)c(=O)c12]
Compound 108
TABLE 4-continued
Structures of the Compounds for the IC50 results described in Table 3.
Structure
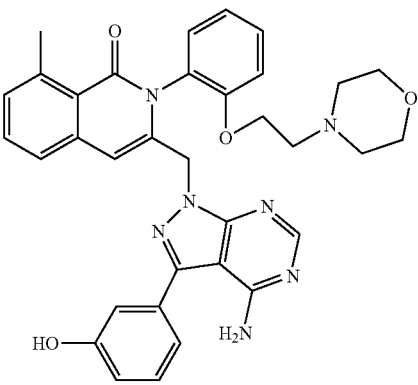 [SMILES: Cc1cccc2cc(Cn3nc(-c4cccc(O)c4)c4c(N)ncnc43)n(-c3ccccc3OCCN3CCOCC3)c(=O)c12]
Compound 109
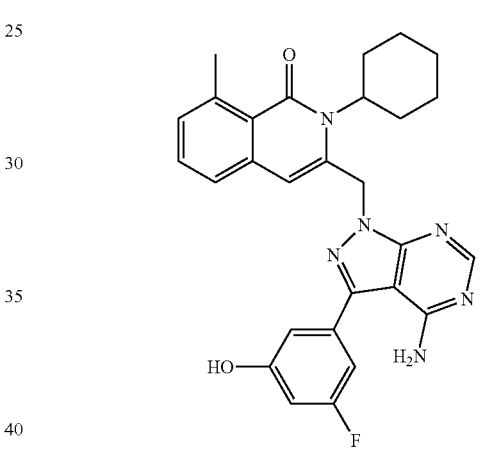
Compound 110
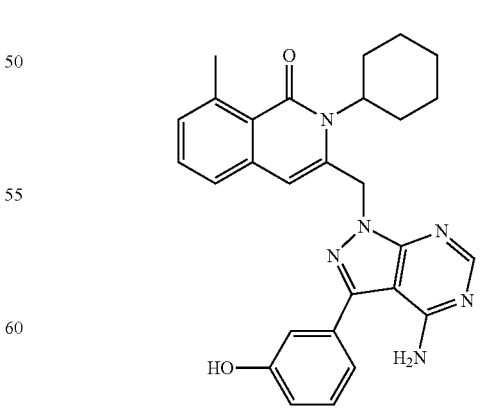
Compound 111

TABLE 4-continued
Structures of the Compounds for the IC50 results described in Table 3.
Structure
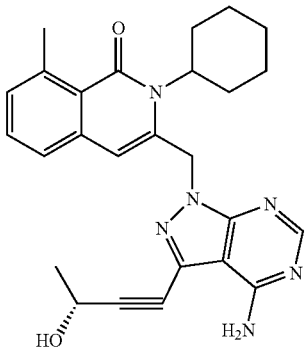 [SMILES: Cc1cccc2cc(Cn3nc(C#C[C@@H](C)O)c4c(N)ncnc43)n(C3CCCCC3)c(=O)c12]
Compound 112
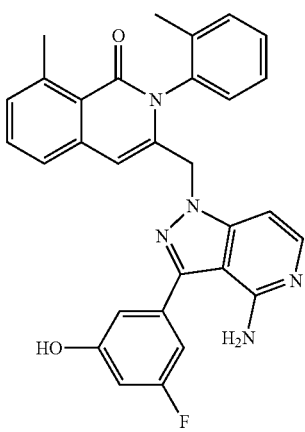 [SMILES: Cc1ccccc1-n1c(Cn2nc(-c3cc(O)cc(F)c3)c3c(N)nccc32)cc2cccc(C)c2c1=O]
Compound 113
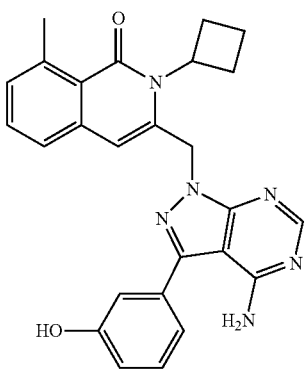 [SMILES: Cc1cccc2cc(Cn3nc(-c4cccc(O)c4)c4c(N)ncnc43)n(C3CCC3)c(=O)c12]
Compound 114
TABLE 4-continued
Structures of the Compounds for the IC50 results described in Table 3.
Structure
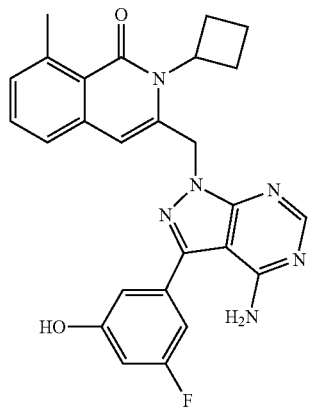 [SMILES: Cc1cccc2cc(Cn3nc(-c4cc(O)cc(F)c4)c4c(N)ncnc43)n(C3CCC3)c(=O)c12]
Compound 115
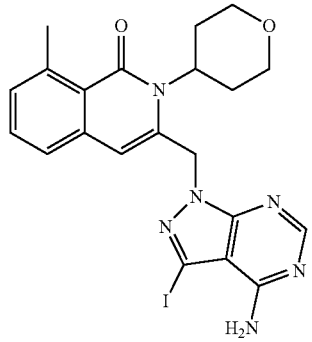 [SMILES: Cc1cccc2cc(Cn3nc(I)c4c(N)ncnc43)n(C3CCOCC3)c(=O)c12]
Compound 116
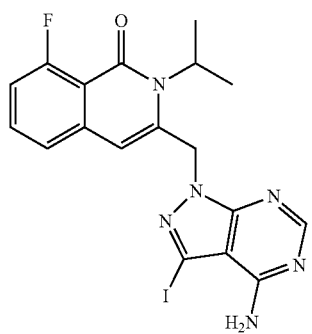 [SMILES: CC(C)n1c(Cn2nc(I)c3c(N)ncnc32)cc2cccc(F)c2c1=O]
Compound 117

TABLE 4-continued

Structures of the Compounds for the IC50 results described in Table 3.

Structure

Compound 118

Compound 119

Compound 120

TABLE 4-continued

Structures of the Compounds for the IC50 results described in Table 3.

Structure

Compound 121

Compound 122

Compound 123

TABLE 4-continued

Structures of the Compounds for the IC50 results described in Table 3.

Structure

Compound 124

Compound 125

Compound 126

TABLE 4-continued

Structures of the Compounds for the IC50 results described in Table 3.

Structure

Compound 127

Compound 128

Compound 129

TABLE 4-continued
Structures of the Compounds for the IC50 results described in Table 3.
Structure
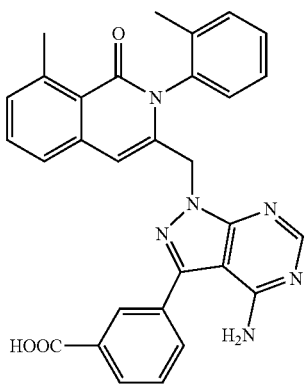 [SMILES: Cc1ccccc1-n1c(Cn2nc(-c3cccc(C(=O)O)c3)c3c(N)ncnc32)cc2cccc(C)c2c1=O]
Compound 130
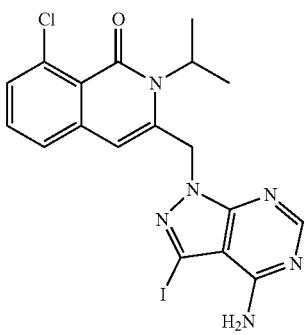 [SMILES: CC(C)n1c(Cn2nc(I)c3c(N)ncnc32)cc2cccc(Cl)c2c1=O]
Compound 131
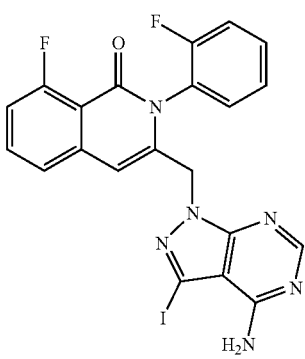 [SMILES: Nc1ncnc2c1c(I)nn2Cc1cc2cccc(F)c2c(=O)n1-c1ccccc1F]
Compound 132
TABLE 4-continued
Structures of the Compounds for the IC50 results described in Table 3.
Structure
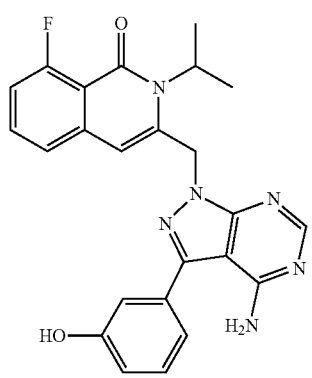 [SMILES: CC(C)n1c(Cn2nc(-c3cccc(O)c3)c3c(N)ncnc32)cc2cccc(F)c2c1=O]
Compound 133
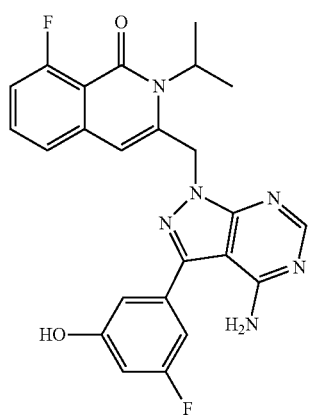 [SMILES: CC(C)n1c(Cn2nc(-c3cc(O)cc(F)c3)c3c(N)ncnc32)cc2cccc(F)c2c1=O]
Compound 134
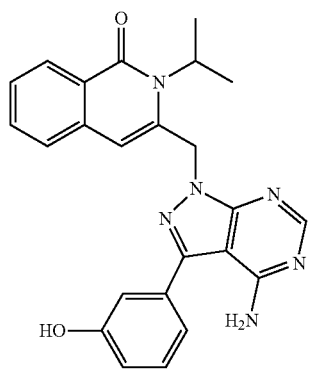 [SMILES: CC(C)n1c(Cn2nc(-c3cccc(O)c3)c3c(N)ncnc32)cc2ccccc2c1=O]
Compound 135

TABLE 4-continued

Structures of the Compounds for the IC50 results described in Table 3.

Structure

Compound 136

Compound 137

Compound 138

TABLE 4-continued

Structures of the Compounds for the IC50 results described in Table 3.

Structure

Compound 139

Compound 141

Compound 142

TABLE 4-continued

Structures of the Compounds for the IC50 results described in Table 3.

Structure

Compound 143

Compound 144

Compound 145

TABLE 4-continued

Structures of the Compounds for the IC50 results described in Table 3.

Structure

Compound 146

Compound 147

Compound 148

TABLE 4-continued
Structures of the Compounds for the IC50 results described in Table 3.
Structure
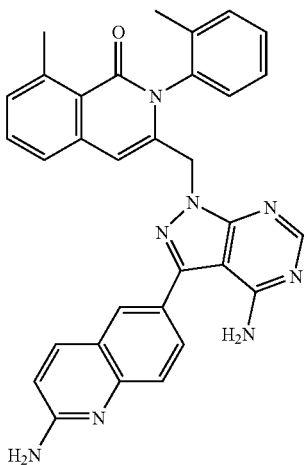 [SMILES: Cc1ccccc1-n1c(Cn2nc(-c3ccc4nc(N)ccc4c3)c3c(N)ncnc32)cc2cccc(C)c2c1=O]
Compound 149
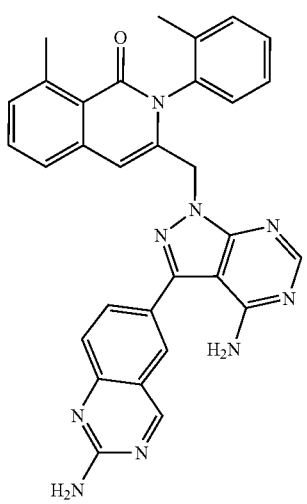 [SMILES: Cc1ccccc1-n1c(Cn2nc(-c3ccc4nc(N)ncc4c3)c3c(N)ncnc32)cc2cccc(C)c2c1=O]
Compound 150
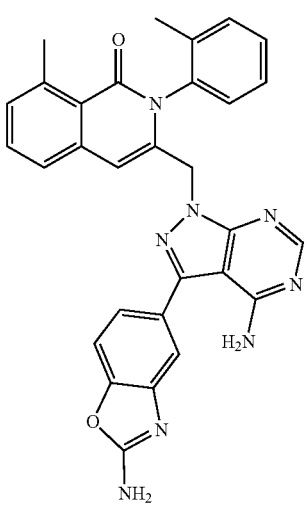 [SMILES: Cc1ccccc1-n1c(Cn2nc(-c3ccc4oc(N)nc4c3)c3c(N)ncnc32)cc2cccc(C)c2c1=O]
Compound 151
TABLE 4-continued
Structures of the Compounds for the IC50 results described in Table 3.
Structure
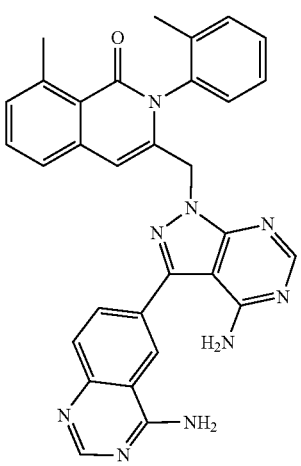 [SMILES: Cc1ccccc1-n1c(Cn2nc(-c3ccc4ncnc(N)c4c3)c3c(N)ncnc32)cc2cccc(C)c2c1=O]
Compound 152
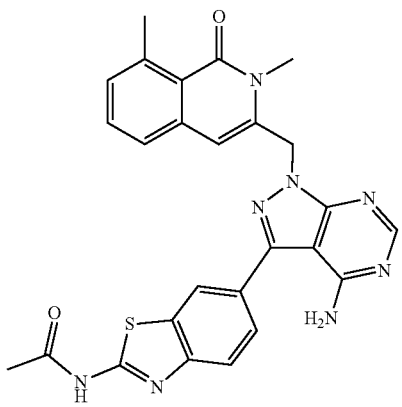 [SMILES: CC(=O)Nc1nc2ccc(-c3nn(Cc4cc5cccc(C)c5c(=O)n4C)c4ncnc(N)c34)cc2s1]
Compound 153
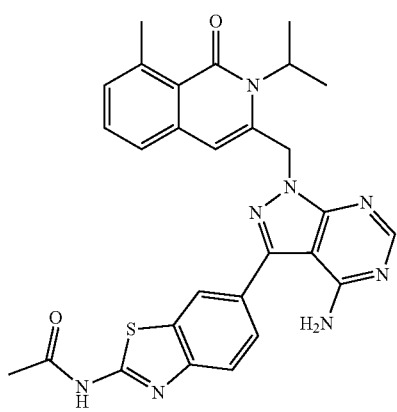 [SMILES: CC(=O)Nc1nc2ccc(-c3nn(Cc4cc5cccc(C)c5c(=O)n4C(C)C)c4ncnc(N)c34)cc2s1]
Compound 154

TABLE 4-continued
Structures of the Compounds for the IC50 results described in Table 3.
Structure
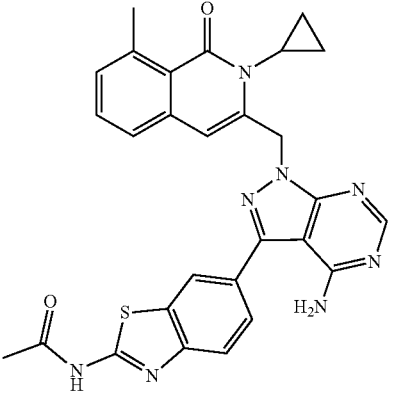 [SMILES: CC(=O)Nc1nc2ccc(-c3nn(Cc4cc5cccc(C)c5c(=O)n4C4CC4)c4ncnc(N)c34)cc2s1]
Compound 155
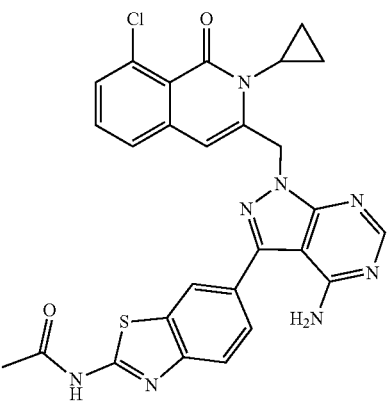 [SMILES: CC(=O)Nc1nc2ccc(-c3nn(Cc4cc5cccc(Cl)c5c(=O)n4C4CC4)c4ncnc(N)c34)cc2s1]
Compound 156
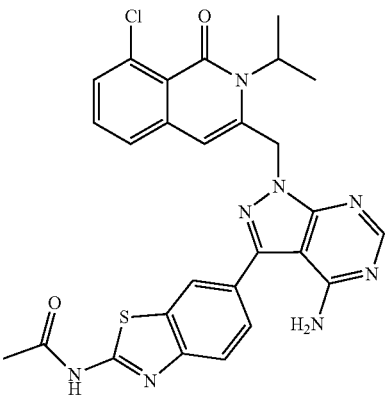 [SMILES: CC(=O)Nc1nc2ccc(-c3nn(Cc4cc5cccc(Cl)c5c(=O)n4C(C)C)c4ncnc(N)c34)cc2s1]
Compound 157
TABLE 4-continued
Structures of the Compounds for the IC50 results described in Table 3.
Structure
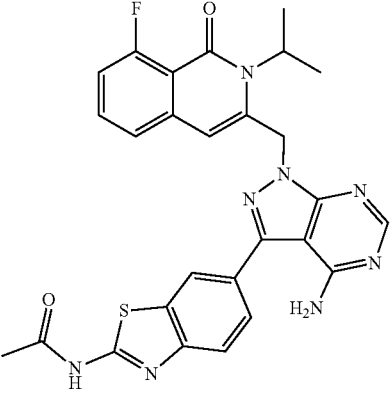 [SMILES: CC(=O)Nc1nc2ccc(-c3nn(Cc4cc5cccc(F)c5c(=O)n4C(C)C)c4ncnc(N)c34)cc2s1]
Compound 158
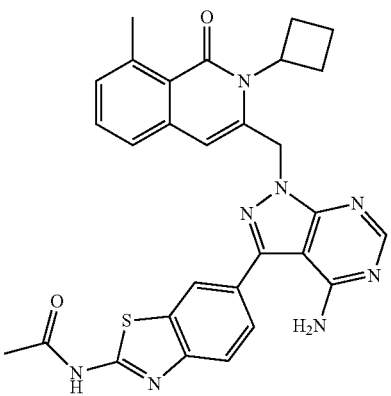 [SMILES: CC(=O)Nc1nc2ccc(-c3nn(Cc4cc5cccc(C)c5c(=O)n4C4CCC4)c4ncnc(N)c34)cc2s1]
Compound 159
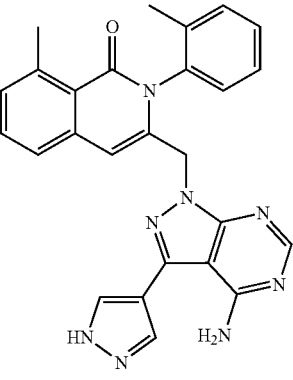 [SMILES: Cc1ccccc1-n1c(Cn2nc(-c3cn[nH]c3)c3c(N)ncnc32)cc2cccc(C)c2c1=O]
Compound 160

TABLE 4-continued
Structures of the Compounds for the IC50 results described in Table 3.
Structure
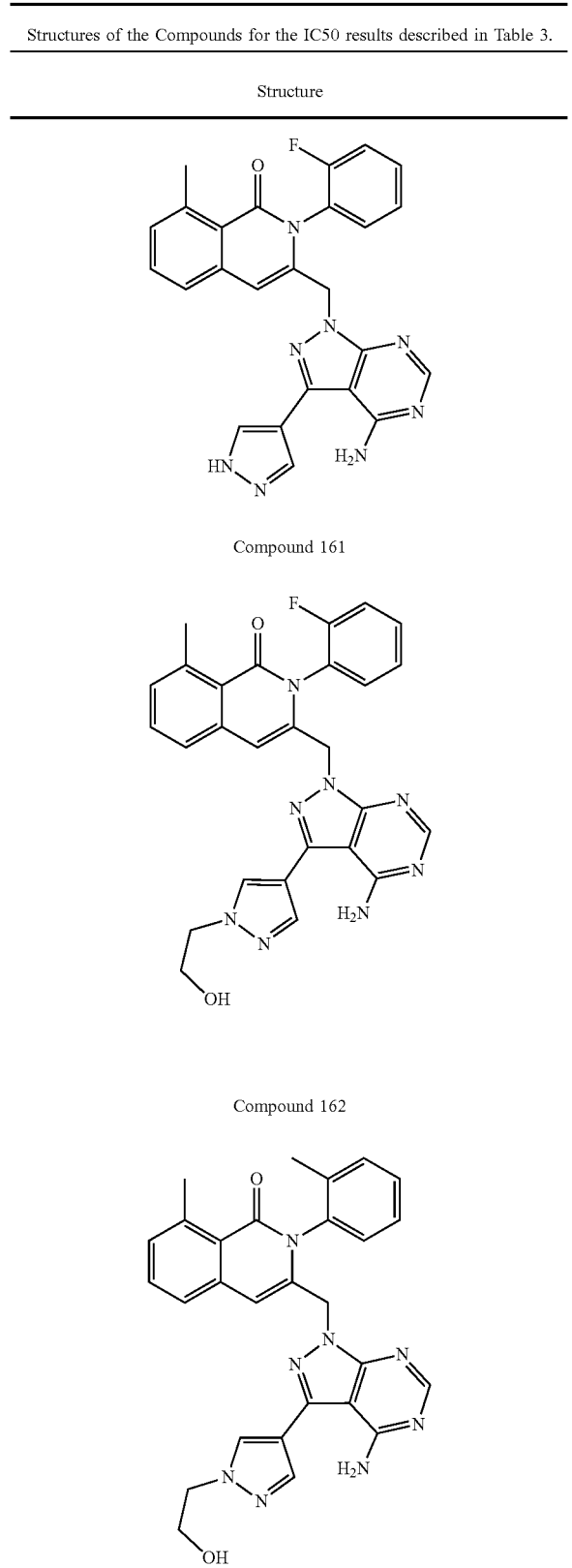
Compound 161
Compound 162
Compound 163
TABLE 4-continued
Structures of the Compounds for the IC50 results described in Table 3.
Structure
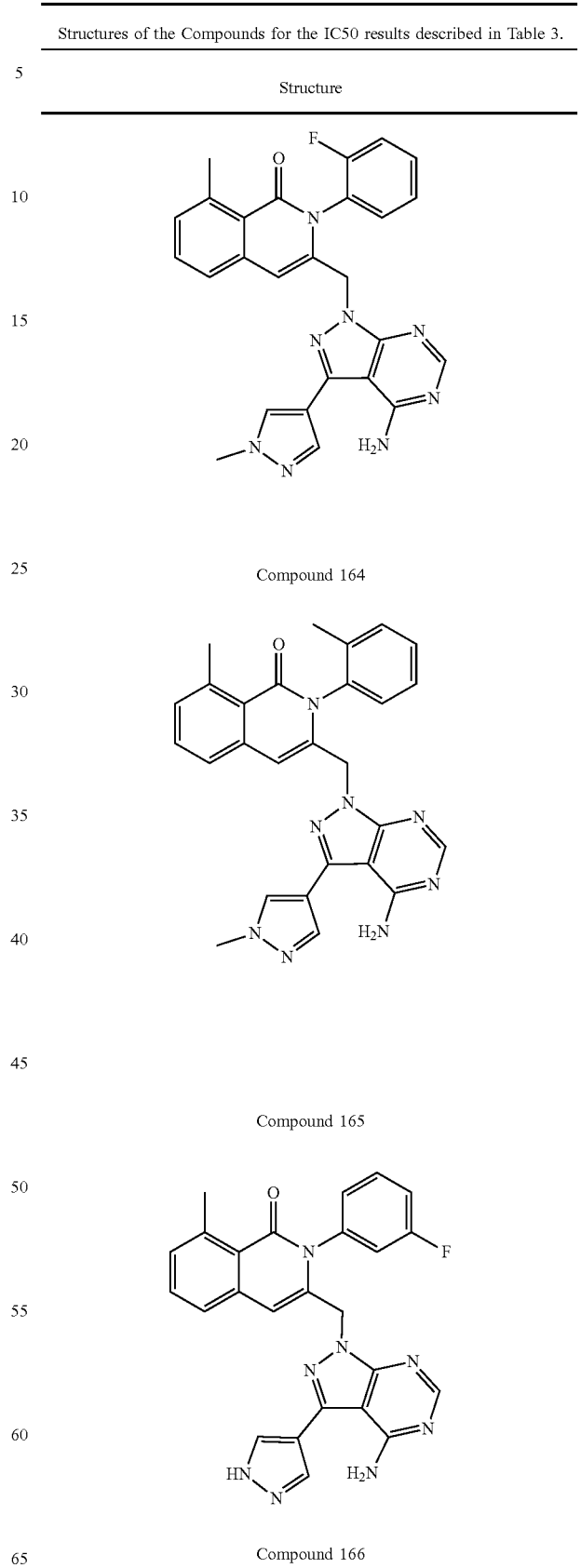
Compound 164
Compound 165
Compound 166

TABLE 4-continued
Structures of the Compounds for the IC50 results described in Table 3.
Structure
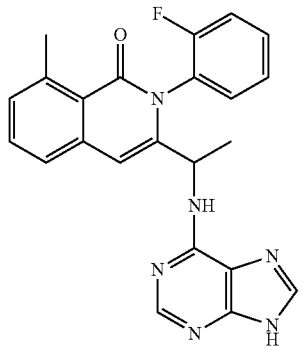 [SMILES: Cc1cccc2cc(C(C)Nc3ncnc4[nH]cnc34)n(-c3ccccc3F)c(=O)c12]
Compound 167
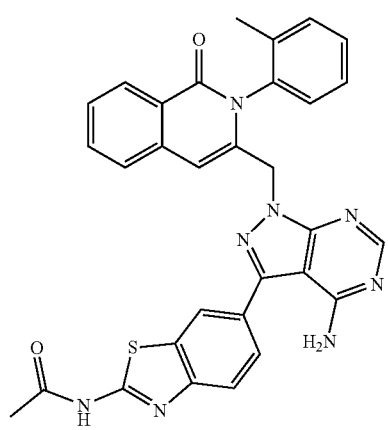 [SMILES: CC(=O)Nc1nc2ccc(-c3nn(Cc4cc5ccccc5c(=O)n4-c4ccccc4C)c4ncnc(N)c34)cc2s1]
Compound 168
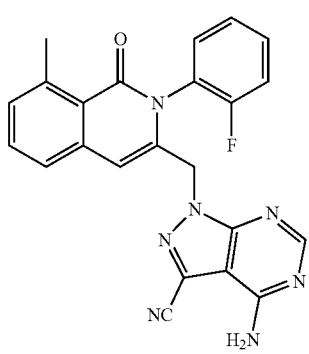 [SMILES: Cc1cccc2cc(Cn3nc(C#N)c4c(N)ncnc43)n(-c3ccccc3F)c(=O)c12]
Compound 169
TABLE 4-continued
Structures of the Compounds for the IC50 results described in Table 3.
Structure
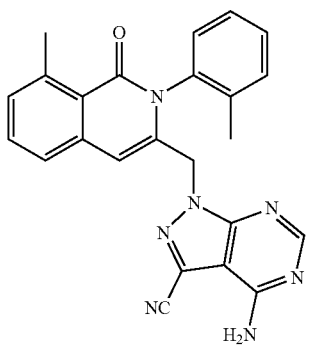 [SMILES: Cc1ccccc1-n1c(Cn2nc(C#N)c3c(N)ncnc32)cc2cccc(C)c2c1=O]
Compound 170
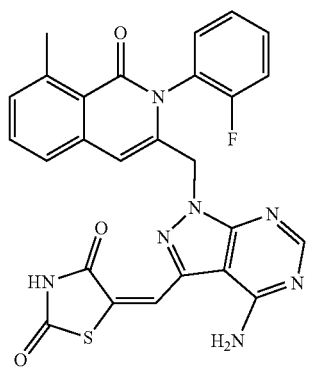 [SMILES: Cc1cccc2cc(Cn3nc(/C=C4/SC(=O)NC4=O)c4c(N)ncnc43)n(-c3ccccc3F)c(=O)c12]
Compound 171
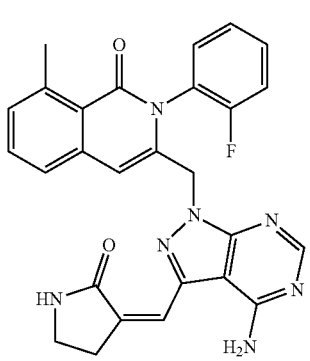 [SMILES: Cc1cccc2cc(Cn3nc(/C=C4/CCNC4=O)c4c(N)ncnc43)n(-c3ccccc3F)c(=O)c12]
Compound 172

TABLE 4-continued
Structures of the Compounds for the IC50 results described in Table 3.
Structure
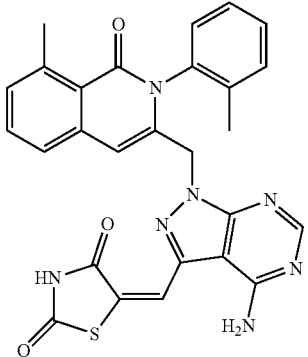 [SMILES: Cc1ccccc1-n1c(Cn2nc(/C=C3/SC(=O)NC3=O)c3c(N)ncnc32)cc2cccc(C)c2c1=O]
Compound 173
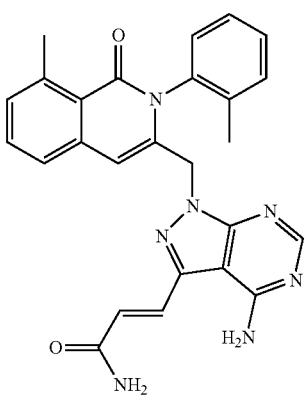 [SMILES: Cc1ccccc1-n1c(Cn2nc(/C=C/C(N)=O)c3c(N)ncnc32)cc2cccc(C)c2c1=O]
Compound 174
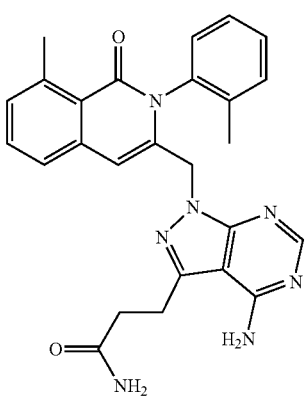 [SMILES: Cc1ccccc1-n1c(Cn2nc(CCC(N)=O)c3c(N)ncnc32)cc2cccc(C)c2c1=O]
Compound 175
TABLE 4-continued
Structures of the Compounds for the IC50 results described in Table 3.
Structure
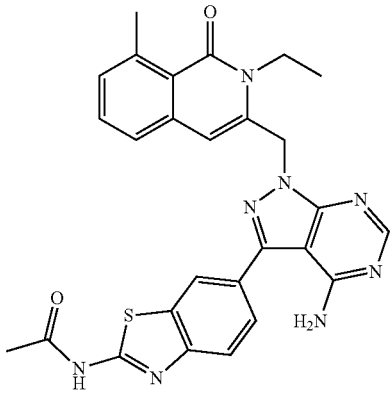 [SMILES: CCn1c(Cn2nc(-c3ccc4nc(NC(C)=O)sc4c3)c3c(N)ncnc32)cc2cccc(C)c2c1=O]
Compound 176
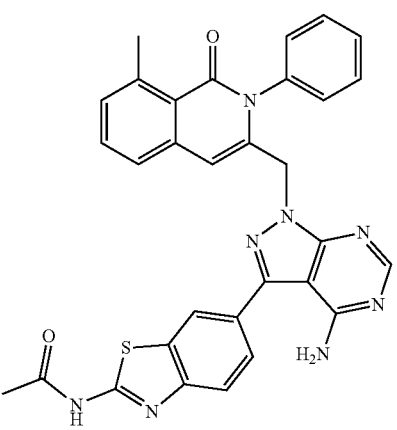 [SMILES: CC(=O)Nc1nc2ccc(-c3nn(Cc4cc5cccc(C)c5c(=O)n4-c4ccccc4)c4ncnc(N)c34)cc2s1]
Compound 177
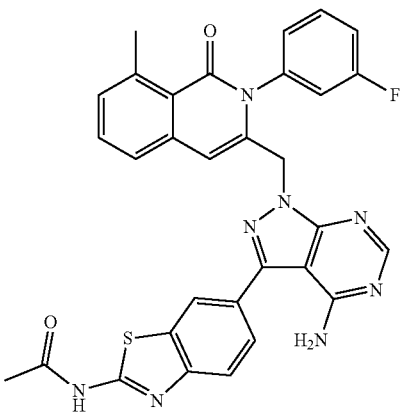 [SMILES: CC(=O)Nc1nc2ccc(-c3nn(Cc4cc5cccc(C)c5c(=O)n4-c4cccc(F)c4)c4ncnc(N)c34)cc2s1]
Compound 178

TABLE 4-continued
Structures of the Compounds for the IC50 results described in Table 3.
Structure
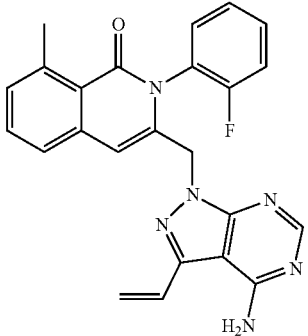 [SMILES: C=Cc1nn(Cc2cc3cccc(C)c3c(=O)n2-c2ccccc2F)c2ncnc(N)c12]
Compound 179
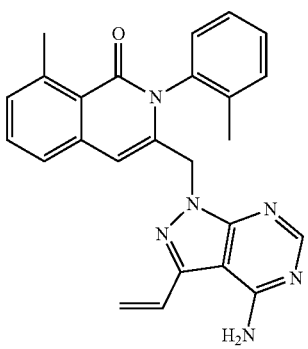
Compound 180
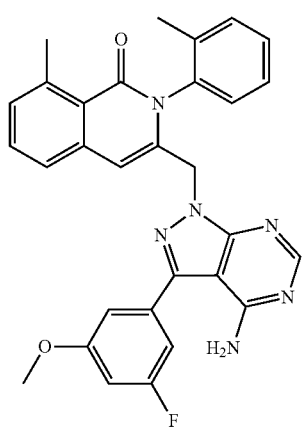 [SMILES: COc1cc(F)cc(-c2nn(Cc3cc4cccc(C)c4c(=O)n3-c3ccccc3C)c3ncnc(N)c23)c1]
Compound 181
TABLE 4-continued
Structures of the Compounds for the IC50 results described in Table 3.
Structure
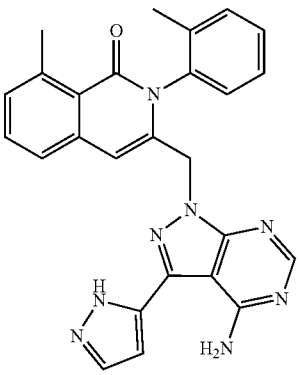 [SMILES: Cc1ccccc1-n1c(Cn2nc(-c3ccn[nH]3)c3c(N)ncnc32)cc2cccc(C)c2c1=O]
Compound 182
Compound 183
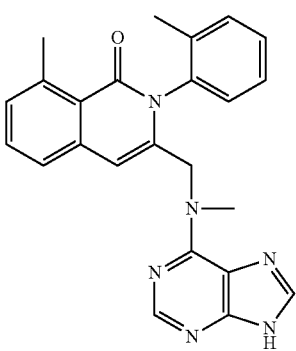 [SMILES: Cc1ccccc1-n1c(CN(C)c2ncnc3[nH]cnc23)cc2cccc(C)c2c1=O]
Compound 184

TABLE 4-continued
Structures of the Compounds for the IC50 results described in Table 3.
Structure
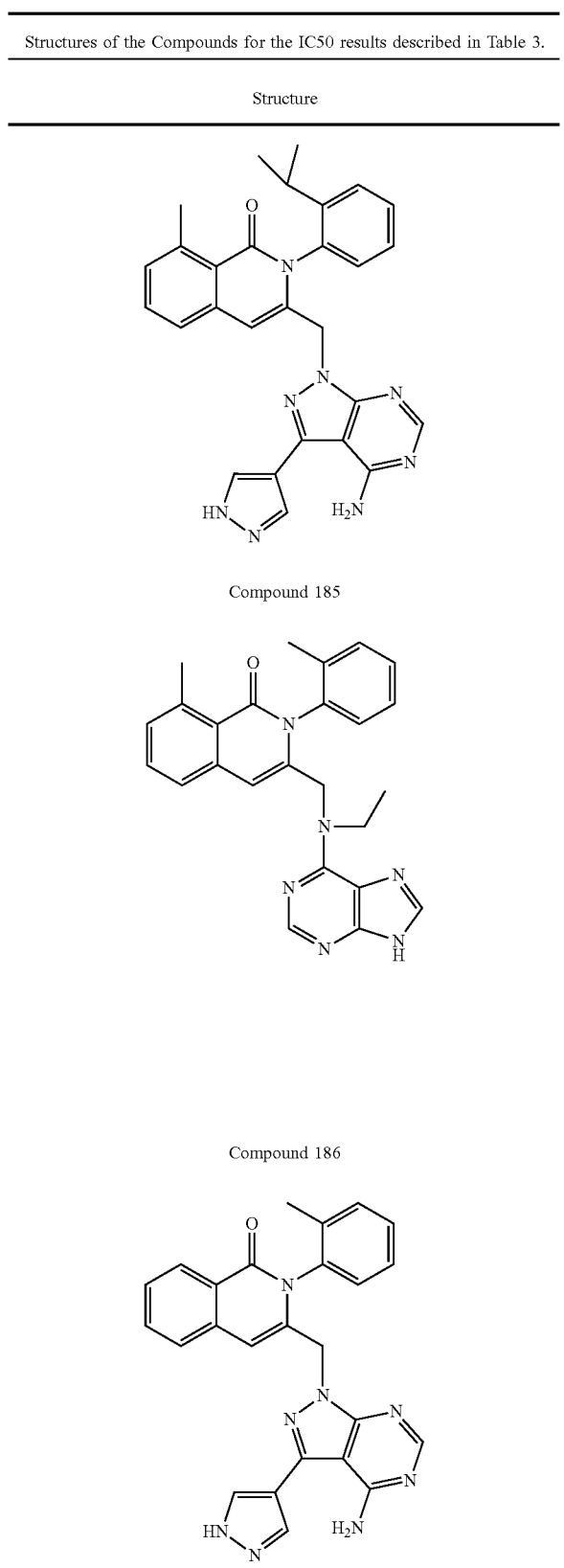
Compound 185
Compound 186
Compound 187
TABLE 4-continued
Structures of the Compounds for the IC50 results described in Table 3.
Structure
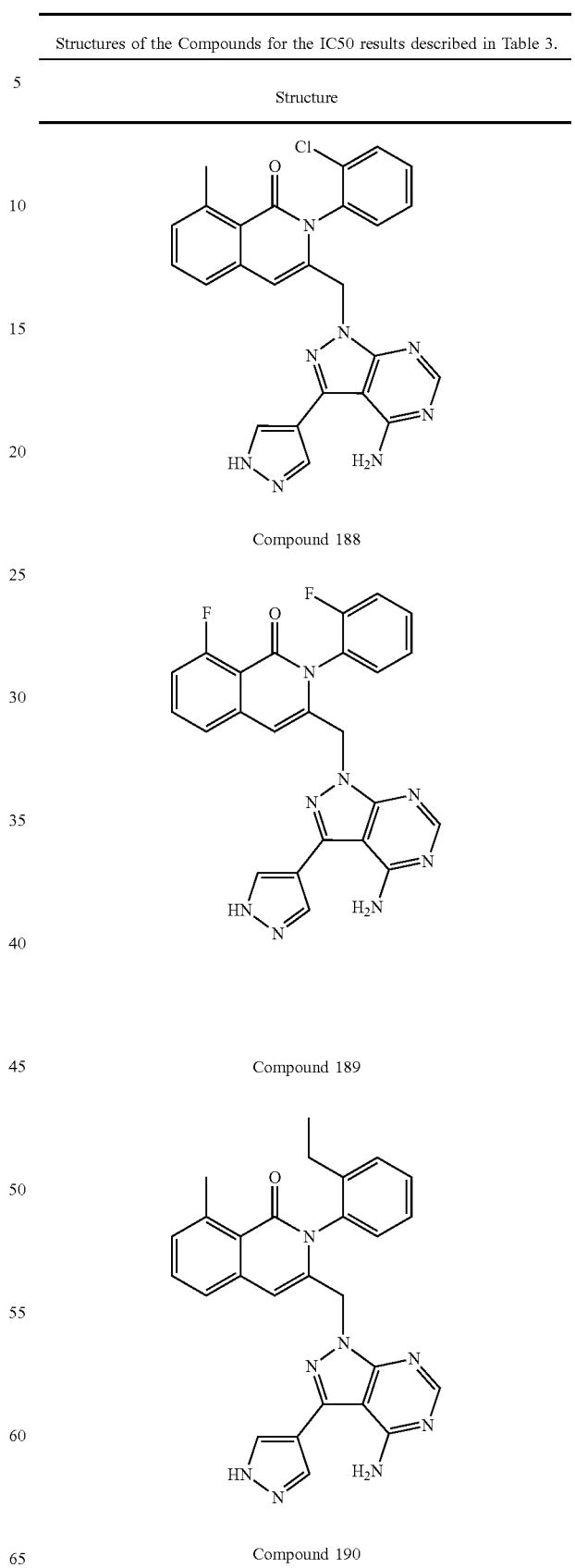
Compound 188
Compound 189
Compound 190

TABLE 4-continued
Structures of the Compounds for the IC50 results described in Table 3.
Structure
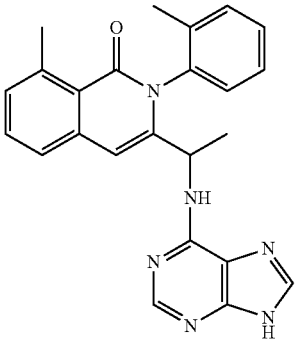 [SMILES: Cc1ccccc1-n1c(C(C)Nc2ncnc3[nH]cnc23)cc2cccc(C)c2c1=O]
Compound 191
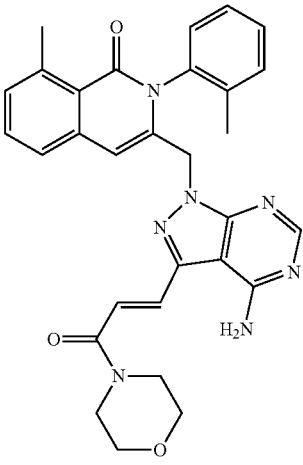 [SMILES: Cc1ccccc1-n1c(Cn2nc(/C=C/C(=O)N3CCOCC3)c3c(N)ncnc32)cc2cccc(C)c2c1=O]
Compound 192
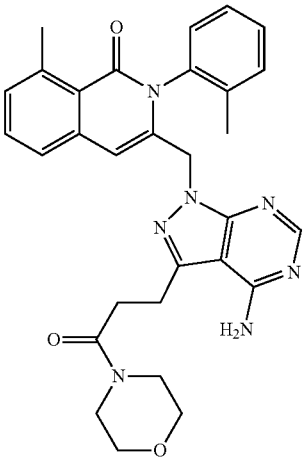 [SMILES: Cc1ccccc1-n1c(Cn2nc(CCC(=O)N3CCOCC3)c3c(N)ncnc32)cc2cccc(C)c2c1=O]
Compound 193
TABLE 4-continued
Structures of the Compounds for the IC50 results described in Table 3.
Structure
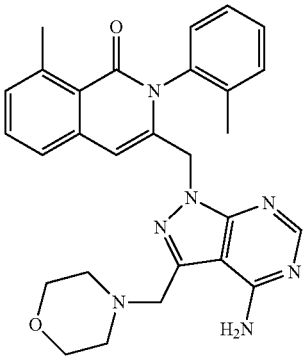 [SMILES: Cc1ccccc1-n1c(Cn2nc(CN3CCOCC3)c3c(N)ncnc32)cc2cccc(C)c2c1=O]
Compound 194
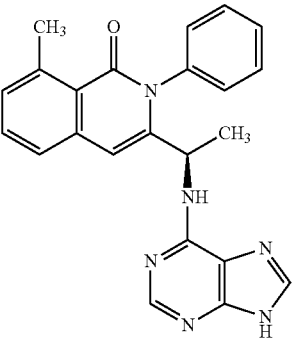 [SMILES: Cc1cccc2cc([C@@H](C)Nc3ncnc4[nH]cnc34)n(-c3ccccc3)c(=O)c12]
Compound 195
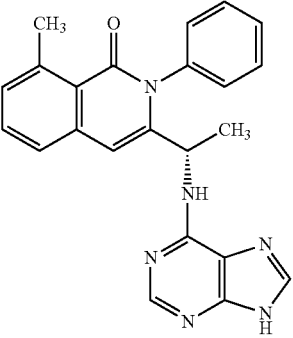 [SMILES: Cc1cccc2cc([C@H](C)Nc3ncnc4[nH]cnc34)n(-c3ccccc3)c(=O)c12]
Compound 196
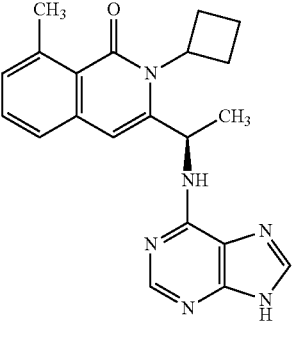 [SMILES: Cc1cccc2cc([C@@H](C)Nc3ncnc4[nH]cnc34)n(C3CCC3)c(=O)c12]
Compound 197

TABLE 4-continued

Structures of the Compounds for the IC50 results described in Table 3.

Structure

Compound 198

Compound 199

Compound 200

Compound 201

Compound 202

Compound 203

Compound 204

TABLE 4-continued

Structures of the Compounds for the IC50 results described in Table 3.

Structure

Compound 205

Compound 206

Compound 207

Compound 208

Compound 209

Compound 210

Compound 211

TABLE 4-continued

Structures of the Compounds for the IC50 results described in Table 3.

Structure

Compound 212

Compound 213

Compound 214

Compound 215

Compound 216

Compound 217

Compound 218

TABLE 4-continued

Structures of the Compounds for the IC50 results described in Table 3.

Structure

Compound 219

Compound 220

Compound 221

TABLE 4-continued

Structures of the Compounds for the IC50 results described in Table 3.

Structure

Compound 222

Compound 223

Compound 224

TABLE 4-continued

Structures of the Compounds for the IC50 results described in Table 3.

Structure

Compound 225

Compound 226

Compound 227

TABLE 4-continued

Structures of the Compounds for the IC50 results described in Table 3.

Structure

Compound 228

Compound 229

Compound 230

Compound 231

TABLE 4-continued

Structures of the Compounds for the IC50 results described in Table 3.

Structure

Compound 232

Compound 233

Compound 234

TABLE 4-continued

Structures of the Compounds for the IC50 results described in Table 3.

Structure

Compound 235

Compound 236

Compound 237

TABLE 4-continued
Structures of the Compounds for the IC50 results described in Table 3.
Structure
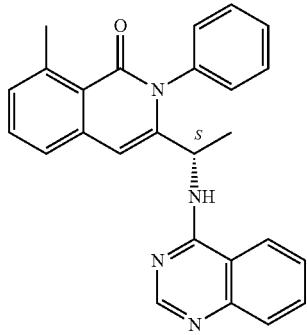
Compound 238
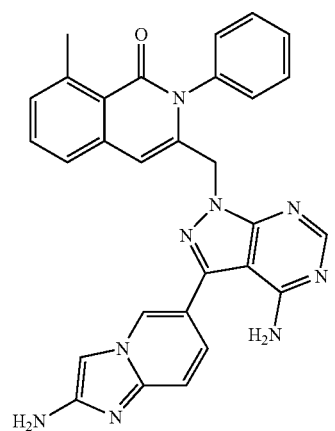 [SMILES: Cc1cccc2cc(Cn3nc(-c4ccc5nc(N)cn5c4)c4c(N)ncnc43)n(-c3ccccc3)c(=O)c12]
Compound 239
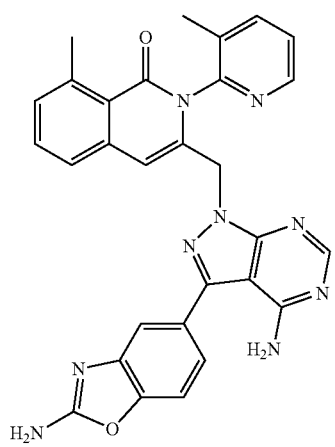 [SMILES: Cc1cccnc1-n1c(Cn2nc(-c3ccc4oc(N)nc4c3)c3c(N)ncnc32)cc2cccc(C)c2c1=O]
Compound 240
TABLE 4-continued
Structures of the Compounds for the IC50 results described in Table 3.
Structure
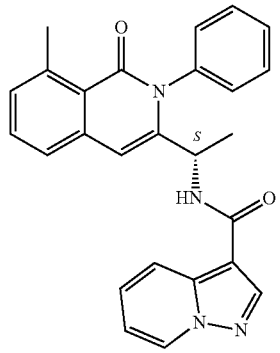
Compound 241
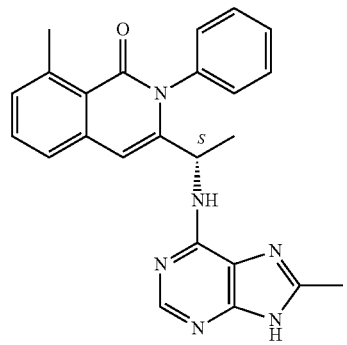
Compound 242
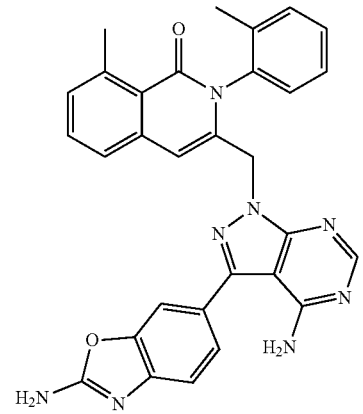 [SMILES: Cc1ccccc1-n1c(Cn2nc(-c3ccc4nc(N)oc4c3)c3c(N)ncnc32)cc2cccc(C)c2c1=O]
Compound 243

TABLE 4-continued
Structures of the Compounds for the IC50 results described in Table 3.
Structure
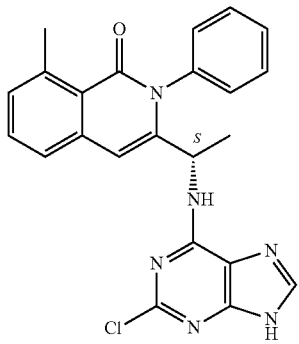
Compound 244
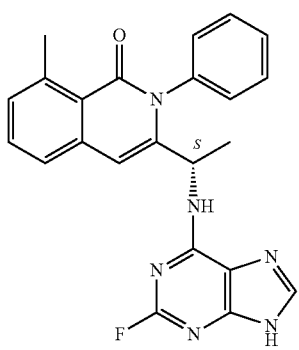
Compound 245
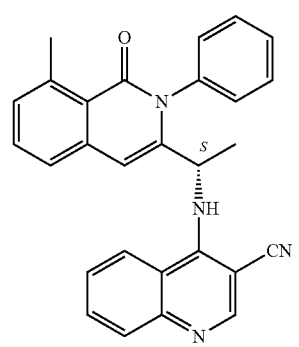
Compound 246
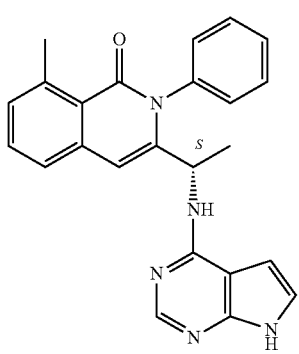
Compound 247
TABLE 4-continued
Structures of the Compounds for the IC50 results described in Table 3.
Structure
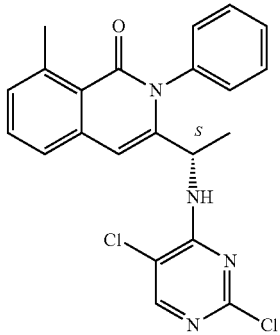
Compound 248
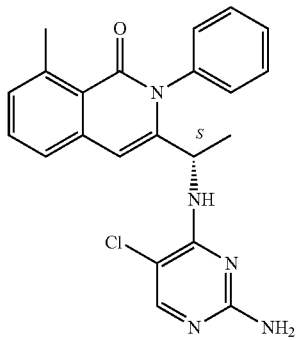
Compound 249
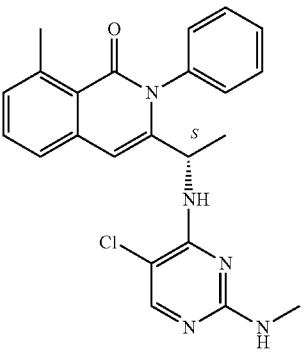
Compound 250

TABLE 4-continued

Structures of the Compounds for the IC50 results described in Table 3.

Structure

Compound 251

Compound 252

Compound 253

Compound 254

Compound 255

Compound 256

Compound 257

TABLE 4-continued

Structures of the Compounds for the IC50 results described in Table 3.

Structure

Compound 258

Compound 259

Compound 260

Compound 261

TABLE 4-continued

Structures of the Compounds for the IC50 results described in Table 3.

Structure

Compound 262

Compound 263

Compound 264

Compound 265

TABLE 4-continued
Structures of the Compounds for the IC50 results described in Table 3.
Structure
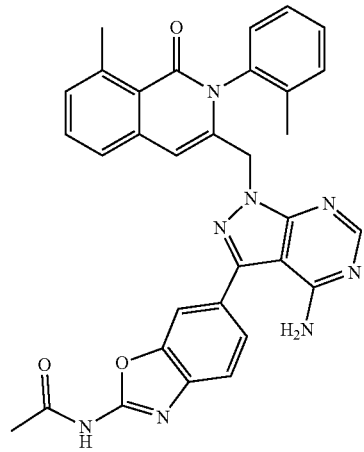 [SMILES: CC(=O)Nc1nc2ccc(-c3nn(Cc4cc5cccc(C)c5c(=O)n4-c4ccccc4C)c4ncnc(N)c34)cc2o1]
Compound 266
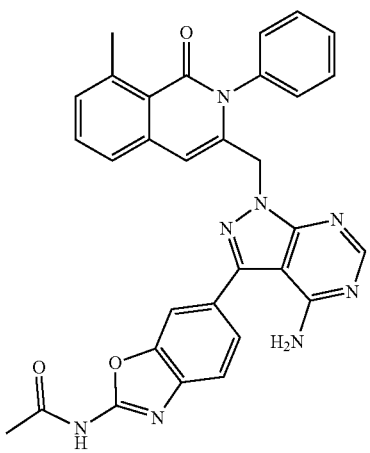 [SMILES: CC(=O)Nc1nc2ccc(-c3nn(Cc4cc5cccc(C)c5c(=O)n4-c4ccccc4)c4ncnc(N)c34)cc2o1]
Compound 269
Compound 267
Compound 270
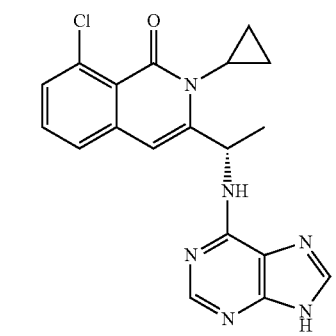 [SMILES: C[C@H](Nc1ncnc2[nH]cnc12)c1cc2cccc(Cl)c2c(=O)n1C1CC1]
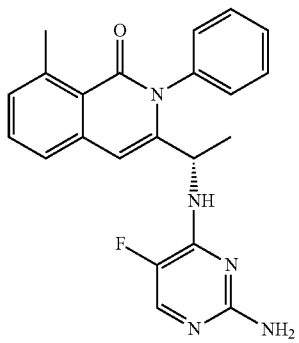
Compound 268
Compound 271

TABLE 4-continued
Structures of the Compounds for the IC50 results described in Table 3.
Structure
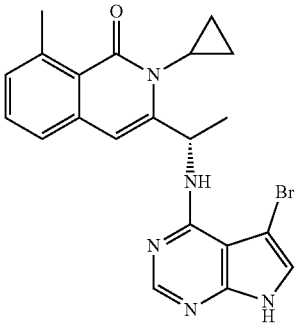 [SMILES: Cc1cccc2cc([C@H](C)Nc3ncnc4[nH]cc(Br)c34)n(C3CC3)c(=O)c12]
Compound 272
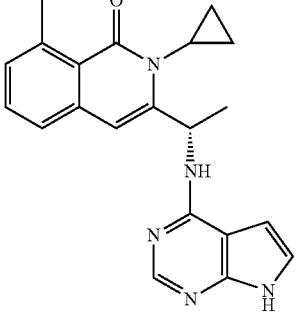
Compound 273
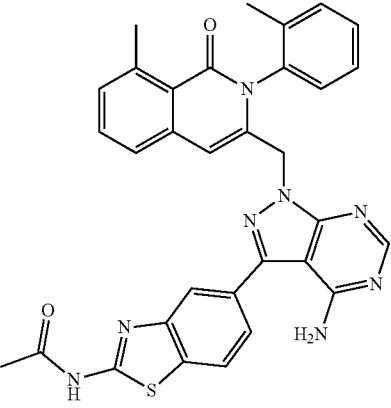 [SMILES: CC(=O)Nc1nc2cc(-c3nn(Cc4cc5cccc(C)c5c(=O)n4-c4ccccc4C)c4ncnc(N)c34)ccc2s1]
Compound 274
TABLE 4-continued
Structures of the Compounds for the IC50 results described in Table 3.
Structure
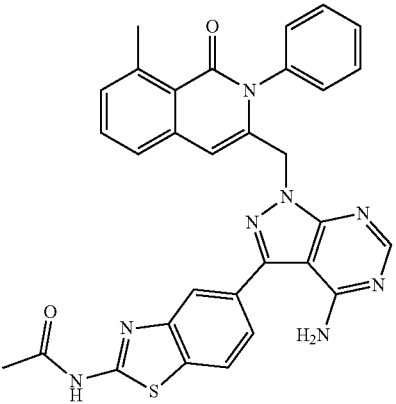 [SMILES: CC(=O)Nc1nc2cc(-c3nn(Cc4cc5cccc(C)c5c(=O)n4-c4ccccc4)c4ncnc(N)c34)ccc2s1]
Compound 275
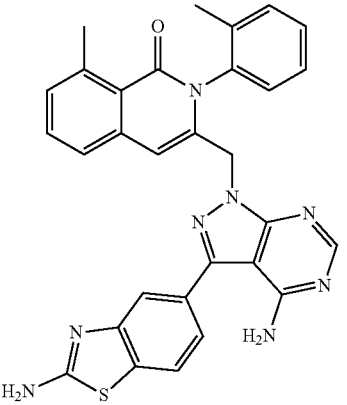 [SMILES: Cc1ccccc1-n1c(Cn2nc(-c3ccc4sc(N)nc4c3)c3c(N)ncnc32)cc2cccc(C)c2c1=O]
Compound 276
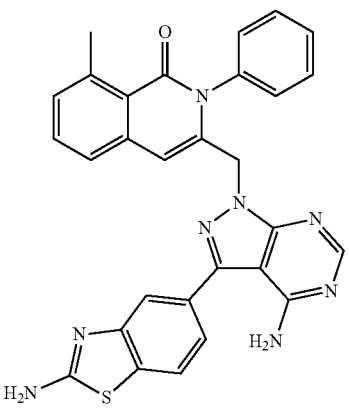 [SMILES: Cc1cccc2cc(Cn3nc(-c4ccc5sc(N)nc5c4)c4c(N)ncnc43)n(-c3ccccc3)c(=O)c12]
Compound 277

TABLE 4-continued

Structures of the Compounds for the IC50 results described in Table 3.

| Structure |
|---|
| Compound 278 |
| Compound 279 |
| Compound 280 |
| Compound 281 |
| Compound 282 |
| Compound 283 |
| Compound 284 |
| Compound 285 |

TABLE 4-continued
Structures of the Compounds for the IC50 results described in Table 3.
Structure
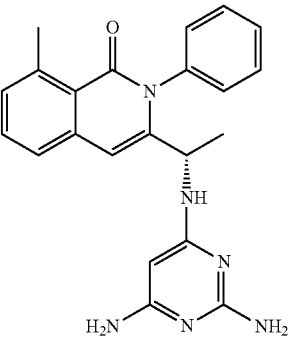 [SMILES: Cc1cccc2cc([C@H](C)Nc3cc(N)nc(N)n3)n(-c3ccccc3)c(=O)c12]
Compound 286
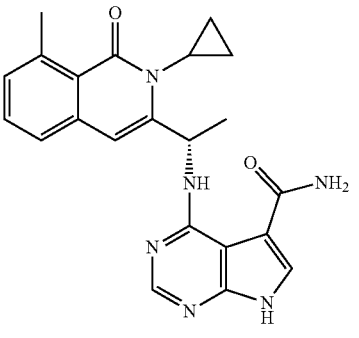 [SMILES: Cc1cccc2cc([C@H](C)Nc3ncnc4[nH]cc(C(N)=O)c34)n(C3CC3)c(=O)c12]
Compound 287
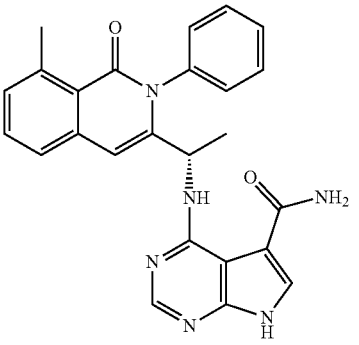 [SMILES: Cc1cccc2cc([C@H](C)Nc3ncnc4[nH]cc(C(N)=O)c34)n(-c3ccccc3)c(=O)c12]
Compound 288
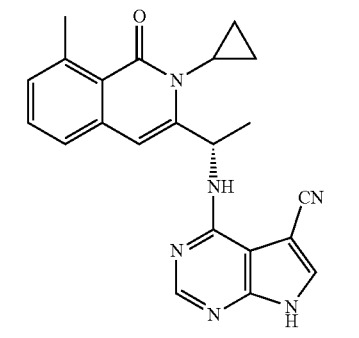 [SMILES: Cc1cccc2cc([C@H](C)Nc3ncnc4[nH]cc(C#N)c34)n(C3CC3)c(=O)c12]
Compound 289
TABLE 4-continued
Structures of the Compounds for the IC50 results described in Table 3.
Structure
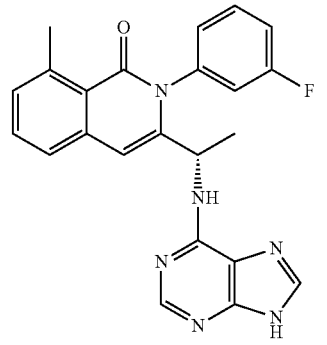 [SMILES: Cc1cccc2cc([C@H](C)Nc3ncnc4[nH]cnc34)n(-c3cccc(F)c3)c(=O)c12]
Compound 290
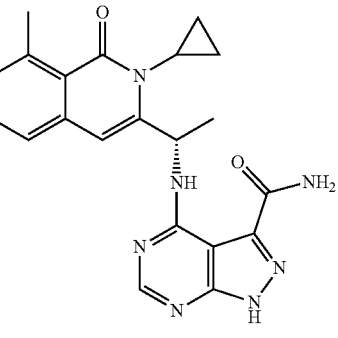
Compound 291
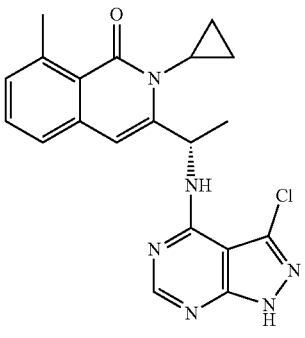 [SMILES: Cc1cccc2cc([C@H](C)Nc3ncnc4[nH]nc(Cl)c34)n(C3CC3)c(=O)c12]
Compound 292
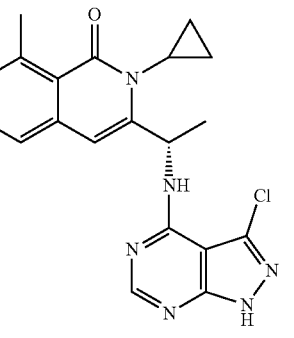
Compound 293

TABLE 4-continued
Structures of the Compounds for the IC50 results described in Table 3.
Structure
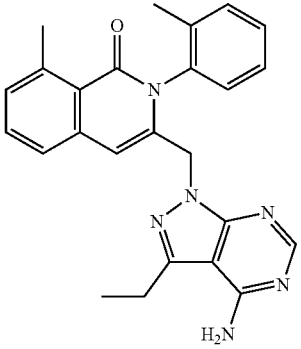 [SMILES: CCc1nn(Cc2cc3cccc(C)c3c(=O)n2-c2ccccc2C)c2ncnc(N)c12]
Compound 294
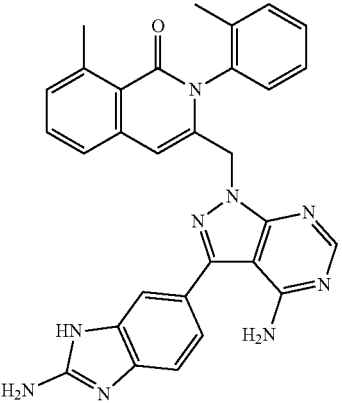 [SMILES: Cc1ccccc1-n1c(Cn2nc(-c3ccc4nc(N)[nH]c4c3)c3c(N)ncnc32)cc2cccc(C)c2c1=O]
Compound 295
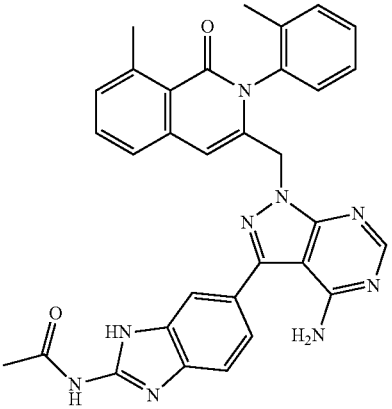 [SMILES: CC(=O)Nc1nc2ccc(-c3nn(Cc4cc5cccc(C)c5c(=O)n4-c4ccccc4C)c4ncnc(N)c34)cc2[nH]1]
Compound 296
TABLE 4-continued
Structures of the Compounds for the IC50 results described in Table 3.
Structure
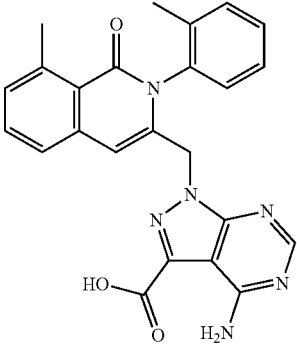 [SMILES: Cc1ccccc1-n1c(Cn2nc(C(=O)O)c3c(N)ncnc32)cc2cccc(C)c2c1=O]
Compound 297
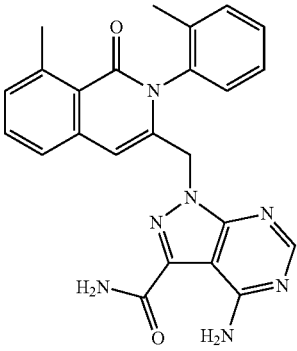 [SMILES: Cc1ccccc1-n1c(Cn2nc(C(N)=O)c3c(N)ncnc32)cc2cccc(C)c2c1=O]
Compound 298
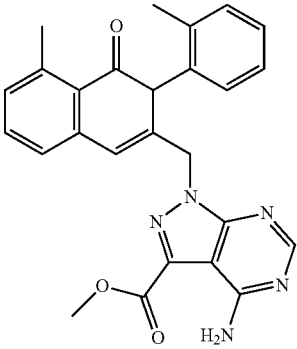 [SMILES: COC(=O)c1nn(CC2=Cc3cccc(C)c3C(=O)C2c2ccccc2C)c2ncnc(N)c12]
Compound 299

TABLE 4-continued
Structures of the Compounds for the IC50 results described in Table 3.
Structure
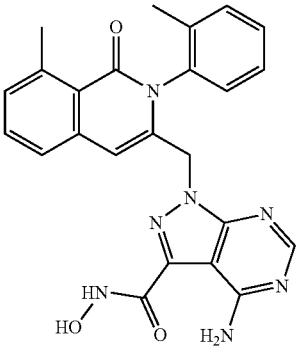 [SMILES: Cc1ccccc1-n1c(Cn2nc(C(=O)NO)c3c(N)ncnc32)cc2cccc(C)c2c1=O]
Compound 300
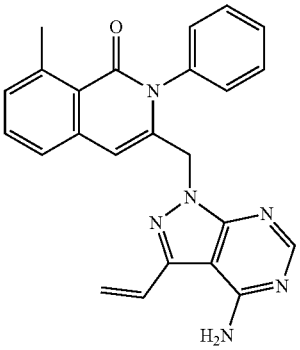 [SMILES: C=Cc1nn(Cc2cc3cccc(C)c3c(=O)n2-c2ccccc2)c2ncnc(N)c12]
Compound 301
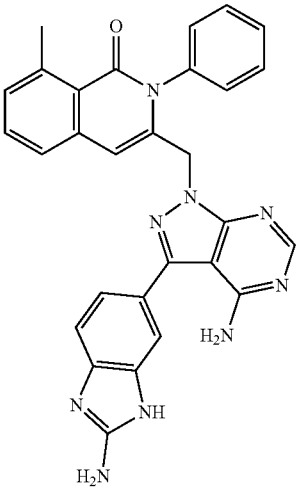 [SMILES: Cc1cccc2cc(Cn3nc(-c4ccc5nc(N)[nH]c5c4)c4c(N)ncnc43)n(-c3ccccc3)c(=O)c12]
Compound 302
TABLE 4-continued
Structures of the Compounds for the IC50 results described in Table 3.
Structure
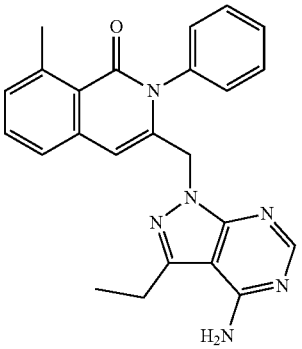 [SMILES: CCc1nn(Cc2cc3cccc(C)c3c(=O)n2-c2ccccc2)c2ncnc(N)c12]
Compound 303
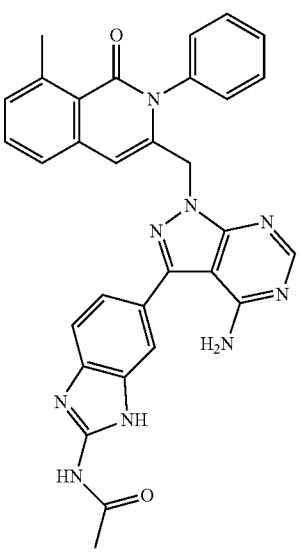 [SMILES: CC(=O)Nc1nc2ccc(-c3nn(Cc4cc5cccc(C)c5c(=O)n4-c4ccccc4)c4ncnc(N)c34)cc2[nH]1]
Compound 304
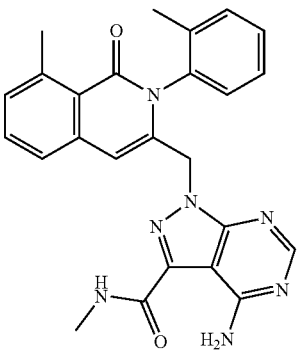 [SMILES: CNC(=O)c1nn(Cc2cc3cccc(C)c3c(=O)n2-c2ccccc2C)c2ncnc(N)c12]
Compound 305

TABLE 4-continued
Structures of the Compounds for the IC50 results described in Table 3.
Structure
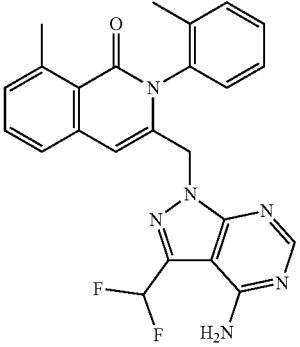 [SMILES: Cc1ccccc1-n1c(Cn2nc(C(F)F)c3c(N)ncnc32)cc2cccc(C)c2c1=O]
Compound 306
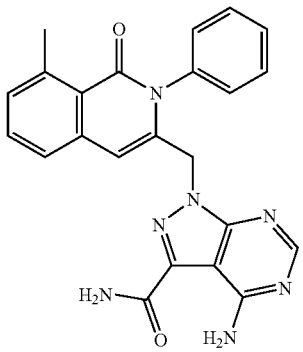 [SMILES: Cc1cccc2cc(Cn3nc(C(N)=O)c4c(N)ncnc43)n(-c3ccccc3)c(=O)c12]
Compound 307
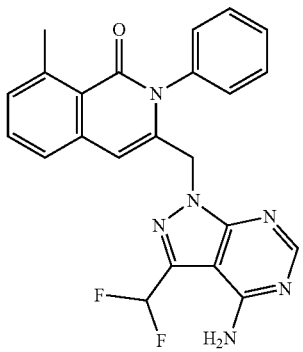 [SMILES: Cc1cccc2cc(Cn3nc(C(F)F)c4c(N)ncnc43)n(-c3ccccc3)c(=O)c12]
Compound 308
TABLE 4-continued
Structures of the Compounds for the IC50 results described in Table 3.
Structure
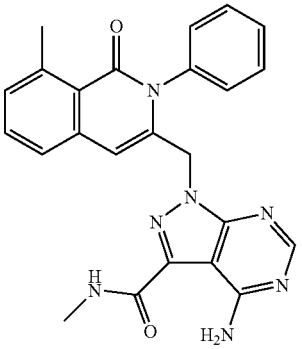 [SMILES: CNC(=O)c1nn(Cc2cc3cccc(C)c3c(=O)n2-c2ccccc2)c2ncnc(N)c12]
Compound 309
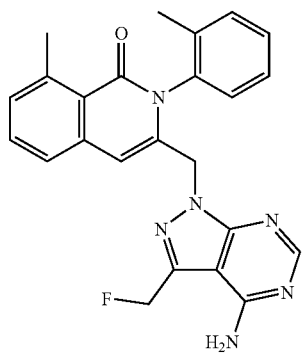 [SMILES: Cc1ccccc1-n1c(Cn2nc(CF)c3c(N)ncnc32)cc2cccc(C)c2c1=O]
Compound 310
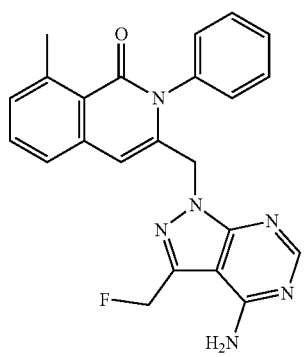 [SMILES: Cc1cccc2cc(Cn3nc(CF)c4c(N)ncnc43)n(-c3ccccc3)c(=O)c12]
Compound 311

TABLE 4-continued
Structures of the Compounds for the IC50 results described in Table 3.
| Structure |
|---|
| 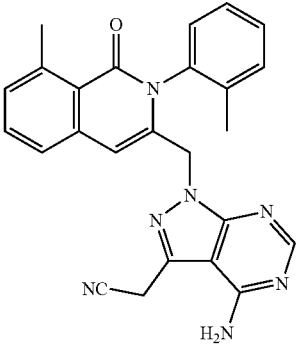 [SMILES: Cc1ccccc1-n1c(Cn2nc(CC#N)c3c(N)ncnc32)cc2cccc(C)c2c1=O] |
| Compound 312 |
| 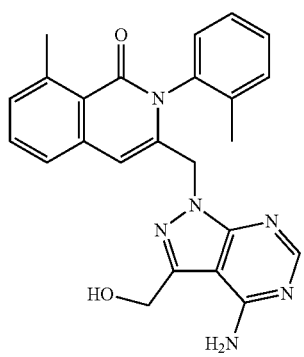 [SMILES: Cc1ccccc1-n1c(Cn2nc(CO)c3c(N)ncnc32)cc2cccc(C)c2c1=O] |
| Compound 313 |
| 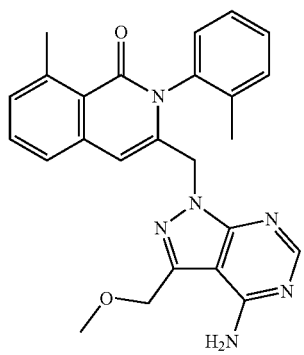 [SMILES: COCc1nn(Cc2cc3cccc(C)c3c(=O)n2-c2ccccc2C)c2ncnc(N)c12] |
| Compound 314 |
TABLE 4-continued
Structures of the Compounds for the IC50 results described in Table 3.
| Structure |
|---|
| 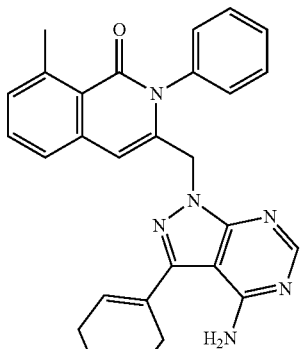 |
| Compound 315 |
| 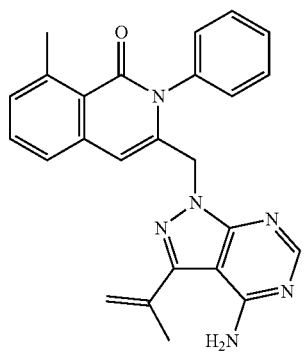 [SMILES: C=C(C)c1nn(Cc2cc3cccc(C)c3c(=O)n2-c2ccccc2)c2ncnc(N)c12] |
| Compound 316 |
| 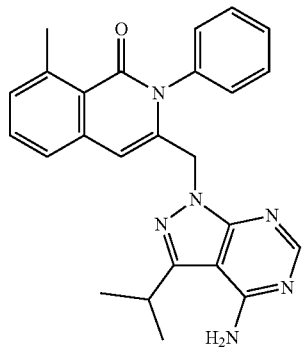 [SMILES: Cc1cccc2cc(Cn3nc(C(C)C)c4c(N)ncnc43)n(-c3ccccc3)c(=O)c12] |
| Compound 317 |

TABLE 4-continued
Structures of the Compounds for the IC50 results described in Table 3.
Structure
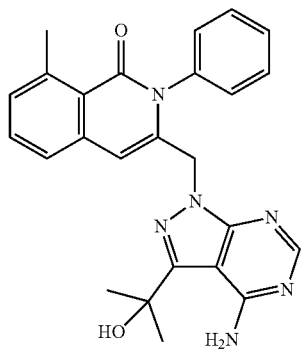 [SMILES: Cc1cccc2cc(Cn3nc(C(C)(C)O)c4c(N)ncnc43)n(-c3ccccc3)c(=O)c12]
Compound 318
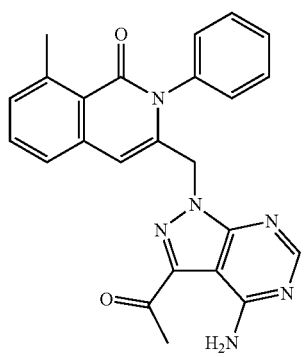 [SMILES: CC(=O)c1nn(Cc2cc3cccc(C)c3c(=O)n2-c2ccccc2)c2ncnc(N)c12]
Compound 319
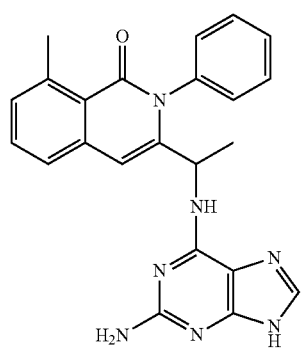
Compound 320
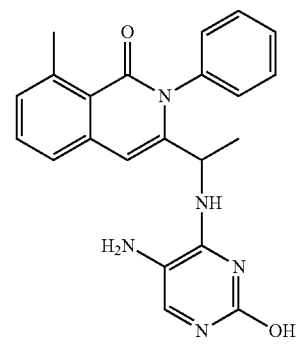 [SMILES: Cc1cccc2cc(C(C)Nc3nc(O)ncc3N)n(-c3ccccc3)c(=O)c12]
Compound 321
TABLE 4-continued
Structures of the Compounds for the IC50 results described in Table 3.
Structure
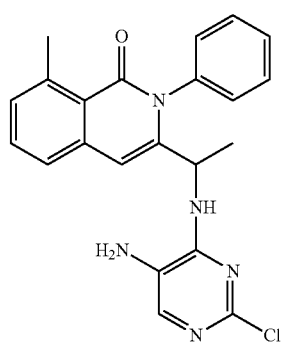 [SMILES: Cc1cccc2cc(C(C)Nc3nc(Cl)ncc3N)n(-c3ccccc3)c(=O)c12]
Compound 322
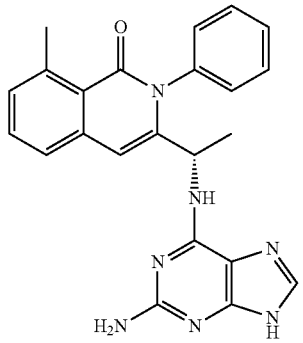
Compound 323
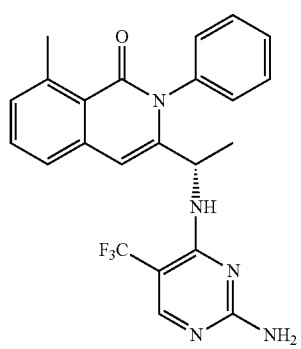 [SMILES: Cc1cccc2cc([C@H](C)Nc3nc(N)ncc3C(F)(F)F)n(-c3ccccc3)c(=O)c12]
Compound 324

TABLE 4-continued

Structures of the Compounds for the IC50 results described in Table 3.

Structure

Compound 325

Example 22

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl3:MeOH (1:1). The biphasic mixture is vortexed, briefly centrifuged, and the organic phase is transferred to a new tube using a gel loading pipette tip precoated with CHCl₃. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 23

Expression and Inhibition Assays of Abl

The cross-activity or lack thereof of one or more compounds of the present invention against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAPFAKKK (SEQ ID NO: 1) is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 24

Expression and Inhibition Assays of Hck

The cross-activity or lack thereof of one or more compounds of the present invention against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK (SEQ ID NO: 2) is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 25

Expression and Inhibition Assays of Insulin Receptor (IR)

The cross-activity or lack thereof of one or more compounds of the present invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl2, 10 mM MnCl2, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 26

Expression and Inhibition Assays of Src

The cross-activity or lack thereof of one or more compounds of the present invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK (SEQ ID NO: 2) is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 27

Expression and Inhibition Assays of DNA-PK (DNAK)

The cross-activity or lack thereof of one or more compounds of the present invention against DNAK kinase can be measured according to any procedures known in the art. DNA-PK can be purchased from Promega and assayed using the DNA-PK Assay System (Promega) according to the manufacturer's instructions.

Example 28

Expression and Inhibition Assays of mTOR

The cross-activity or lack thereof of one or more compounds of the present invention against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR—FRET buffer) for a final concentration of 1.3 nM antibody and 6.7 mM EDTA. The plate is sealed, incubated for 1 hour at room temperature, and then read on a plate reader set up for LanthaScreen™ TR—FRET. Data is analyzed and IC50s are generated using GraphPad Prism 5.

Example 29

Expression and Inhibition Assays of Vascular Endothelial Growth Receptor

The cross-activity or lack thereof of one or more compounds of the present invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 30

Expression and Inhibition Assays of Ephrin Receptor B4 (EphB4)

The cross-activity or lack thereof of one or more compounds of the present invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 31

Expression and Inhibition Assays of Epidermal Growth Factor Receptor (EGFR)

The cross-activity or lack thereof of one or more compounds of the present invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2

Example 32

Expression and Inhibition Assays of KIT Assay

The cross-activity or lack thereof of one or more compounds of the present invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl2, 1 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 33

Expression and Inhibition Assays of RET

The cross-activity or lack thereof of one or more compounds of the present invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK (SEQ ID NO: 1) is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 34

Expression and Inhibition Assays of Platelet Derived Growth Factor Receptor (PDGFR)

The cross-activity or lack thereof of one or more compounds of the present invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK (SEQ ID NO: 1) is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 35

Expression and Inhibition Assays of FMS-Related Tyrosine Kinase 3 (FLT-3)

The cross-activity or lack thereof of one or more compounds of the present invention against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK (SEQ ID NO: 1) is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 36

Expression and Inhibition Assays of TEK Receptor Tyrosine Kinase (TIE2)

The cross-activity or lack thereof of one or more compounds of the present invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 37

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37 C and 5% $CO_2$. Alamar Blue fluoresce is read at 560Ex/590Em, and IC50 or EC50 values are calculated using GraphPad Prism 5.

Example 38

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5.

Example 39

Antitumor Activity In Vivo

The compounds described herein can be evaluated in a panel of human and murine tumor models.
Paclitaxel-Refractory Tumor Models
1. Clinically-Derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/M46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days×5 schedule.
5. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.
One or more compounds of the invention can be used in combination other therapeutic agents in vivo in the multi-drug resistant human colon carcinoma xenografts HCT/VM46 or any other model known in the art including those described herein.

Example 40

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/ml NADPH; 75 μL of 20.0 mg/ml mouse, rat or human liver microsome; 0.4 μL of 0.2 M phosphate buffer, and 425 μL of dd$H_2O$. Negative control (without NADPH) tube contains 75 μL of 20.0 mg/ml mouse, rat or human liver microsome; 0.4 μL of 0.2 M phosphate buffer, and 525 μL of dd$H_2O$. The reaction is started by adding 1.0 μL of 10.0 mM tested compound. The reaction tubes are incubated at 37° C. 100 μL sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 41

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μL for half-life determination), containing 5 μM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 μL of the incubation mixture to 200 μL of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, Cl2, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 42

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 43

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, phillladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt 5473, phospho-Akt T308, Akt, and β-actin (Cell Signaling Technologies).

The results demonstrate that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and may be indicative of mTORC2 inhibitors or inhibitors of upstream kinases such as PI3K or Akt.

Example 44

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 45

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 46

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about 1×10$^6$ leukemic cells (e.g. Ph+human or murine cells, or p190 transduced bone marrow cells). These cells are administered together with a radioprotective dose of about 5×10$^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevec) alone under the conditions tested.

Example 47

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to demonstrate that the kinase inhibitors disclosed herein can suppress or delay the onset of lupus symptoms in lupus disease model mice.

Example 48

Murine Bone Marrow Transplant Assay

Female recipient mice are lethally irradiated from a γ ray source. About 1 hr after the radiation dose, mice are injected with about 1×106 leukemic cells from early passage p190 transduced cultures (e.g. as described in *Cancer Genet Cytogenet.* 2005 August; 161(1):51-6). These cells are administered together with a radioprotective dose of approximately 5×106 normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and 5473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 μl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to demonstrate that effective therapeutic doses of the compounds disclosed herein can be used for inhibiting the proliferation of leukemic cells.

Example 49

TNP-Ficoll T-Cell Independent B-Cell Activation Assay

To test the effects of the compounds of the present invention in suppressing T cell independent antibody production, the TNP-Ficoll B-cell activation assay was used as described herein. Compounds of the present invention were dissolved in an appropriate vehicle (e.g. 5% 1-methyl-2-pyrrolidinone, 85% polyethylene glycol 400, 10% Solutor). Compounds were administered orally approximately 1 hr before TNP-Ficoll treatment to 4-10 week old mice. To study the effects of the compounds on B-cell activation, one set of mice were grouped according to the following table:

| Group# | Mice/group treated | Comp group | Antigen injection at day-1 Group | TNP-F | Route | Compound Administration from day-1 to day-7 (mg/kg) | Route | Regimen |
|---|---|---|---|---|---|---|---|---|
| 1 | 4 | Vehicle | Antigen only | 200 uL (0.5 mg/ml) | ip | 0 | Po | BID for 7 days |
| 2 | 8 | — | Antigen only | | | 0 | | |
| 3 | 8 | Compound #7 | reference | | | 30 | | |
| 4 | 8 | Compound #53 | Antigen + cmp | | | 1 | | |
| 5 | 8 | | | | | 3 | | |
| 6 | 8 | | | | | 10 | | |
| 7 | 8 | | | | | 30 | | |
| 8 | 8 | | | | | 60 | | |

Four animals in group 1, and eight animals in groups 2 to 7 were euthanized in $CO_2$ 2 hours after the last compound administration on day 7. Blood was immediately collected by cardio-puncture and kept at 37° C. for 1 hr to clot followed by overnight incubation at 4° C. to allow the clot to contract. The following day, serum was collected by decanting and centrifugation at 3000 rpm for 10 min. The collected serum was then frozen at −80° C. for future analysis.

Serum samples were analyzed for anti-TNP antibody titers by ELISA as described herein. TNP-BSA was coated onto a Nunc Maxisorb microtiter plate with 100 µl/well at a concentration of 10 µg/ml in phosphate buffered saline (PBS). The Maxisorb plate was incubated for 1.5 hours at room temperature and the solution was removed. 200 µl/well of blocking buffer (e.g. 1% BSA in PBS) was added to each well and incubated 1 hr at room temperature. The plate was washed once with 200 µl/well of PBS 0.05% Tween-20 (wash buffer). A 1:2 dilution of serum from each mouse in blocking buffer was added to each well in the first column (1) of the microtiter plate. The serum in each well of column 1 was then diluted 3-fold in blocking buffer and added to column 2. The serum in each well of column 2 was diluted 3-fold in blocking buffer and added to column 3. The procedure was repeated across the twelve columns of the microtiter plate. The microtiter plate was incubated 1 hr at room temperature. Serum was removed from the plate and the plate was washed three times with wash buffer. 100 µl/well of goat anti-mouse IgG3-HRP diluted 1:250 in blocking buffer was added to each well and incubated 1 hr at room temperature. The anti-mouse IgG3-HRP was removed from the microtiter plate and the plate was washed six times with wash buffer. HRP substrate (200 µl ABTS solution+30% $H_2O_2$+10 ml citrate buffer) was added to each well at 100 µl/well, incubated 2-20 minutes in the dark and the amount of anti-TNP IgG3 was determined spectrophotometrically at 405 nm. Similarly, anti-TNP IgM and total anti-TNP Ab were determined using anti-mouse IgM-HRP and anti-mouse Ig-HRP respectively.

Figure 2:
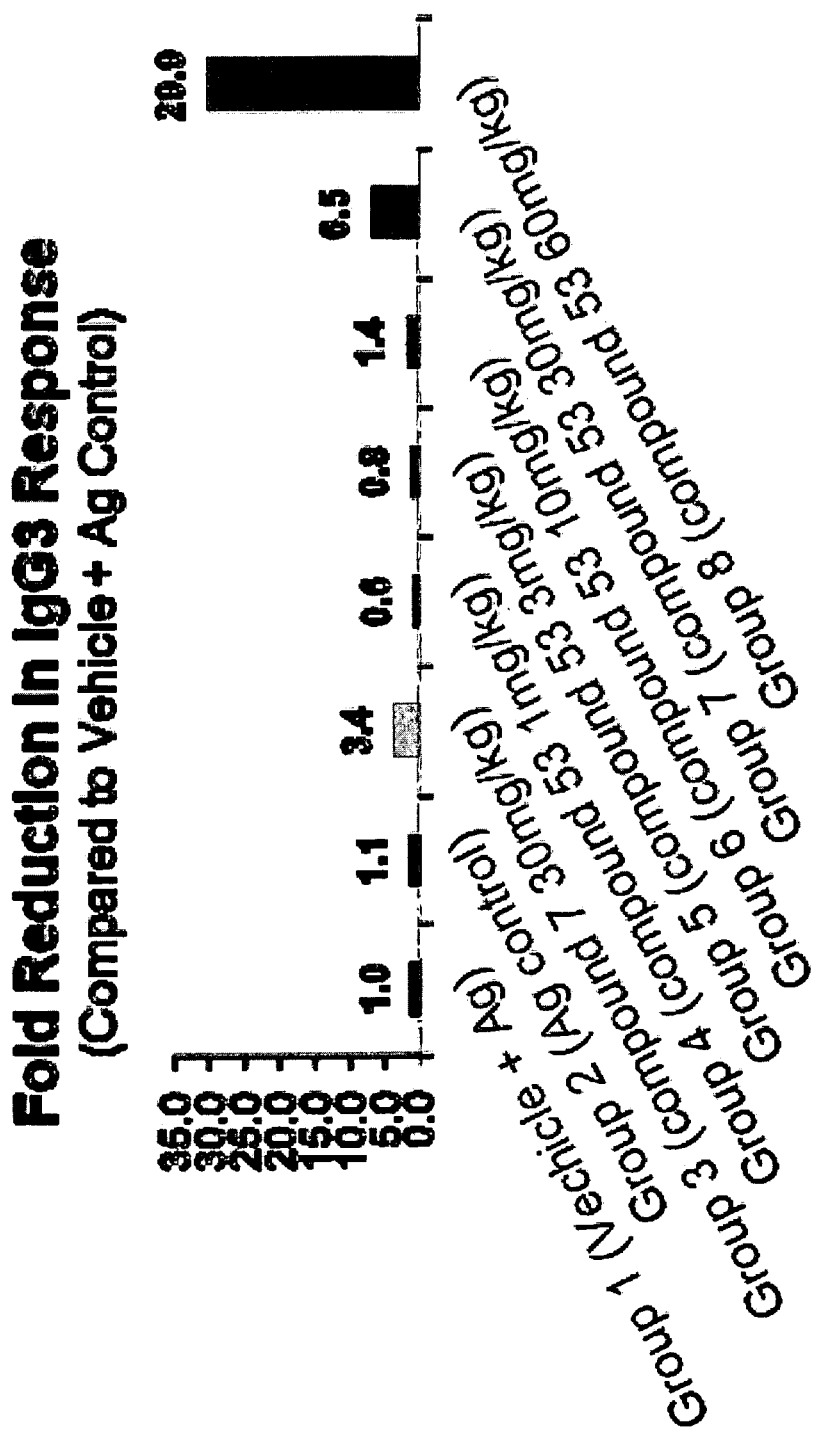
FIG. 2 depicts the fold reduction in TNP specific IgG3 response to antigens provided by compounds 7 and 53 of formula IV as compared to a vehicle control, when administered orally.

The results as shown in FIG. 2 further show that under the conditions tested compounds #7 and #53 exhibit 3.4 and 6.5-fold reductions respectively in IgG3 levels relative to vehicle control mice at a 30 mg/kg dose level. FIG. 2 further shows that compound #53 exhibits 29.9-fold reduction in IgG3 levels relative to vehicle control mice at a 60 mg/kg dose level under the conditions tested.

Example 50

Rat Developing Type II Collagen Induced Arthritis Assay

In order to study the effects of the compounds of the present invention on the autoimmune disease arthritis, a collagen induced developing arthritis model was used. Female Lewis rats were given collagen injections at day 0. Bovine type II collagen was prepared as a 4 mg/ml solution in 0.01N acetic acid. Equal volumes of collagen and Freund's incomplete adjuvant were emulsified by hand mixing until a bead of the emulsified material held its form in water. Each rodent received a 300 µl injection of the mixture at each injection time spread over three subcutaneous sites on the back.

Oral compound administration began on day 0 and continued through day 16 with vehicle (5% NMP, 85% PEG 400, 10% Solutol) or compounds of the present invention in vehicle or control (e.g. methotrexate) at 12 hour intervals daily. Rats were weighed on days 0, 3, 6, 9-17 and caliper measurements of ankles taken on days 9-17. Final body weights were taken, and then the animals were euthanized on day 17. After euthanization, blood was drawn and hind paws and knees were removed. Blood was further processed for pharmacokinetics experiments as well as an anti-type II collagen antibody ELISA assay. Hind paws were weighed and then with the knees preserved in 10% formalin. The paws and knees were subsequently processed for microscopy. Livers, spleen and thymus were also weighed. Sciatic nerves were prepared for histopathology.

Knee and ankle joints were fixed for 1-2 days and decalcified for 4-5 days. Ankle joints were cut in half longitudinally, knees were cut in half along the frontal plane. Joints were then processed, embedded, sectioned and stained with toluidine blue. Scoring of the joints was done according to the following criteria:

Knee and Ankle Inflammation
0=Normal
1=Minimal infiltration of inflammatory cells in synovium/periarticular tissue
2=Mild infiltration
3=Moderate infiltration with moderate edema
4=Marked infiltration with marked edema
5=Severe infiltration with severe edema.

Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)

Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, Emphasis on Small Tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, Emphasis on Femoral Condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving >½ but <¾ of tibial or femoral surface (medial or lateral)
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

A=Mean Disease Control−Mean Normal
B=Mean Treated−Mean Normal

Figure 3:
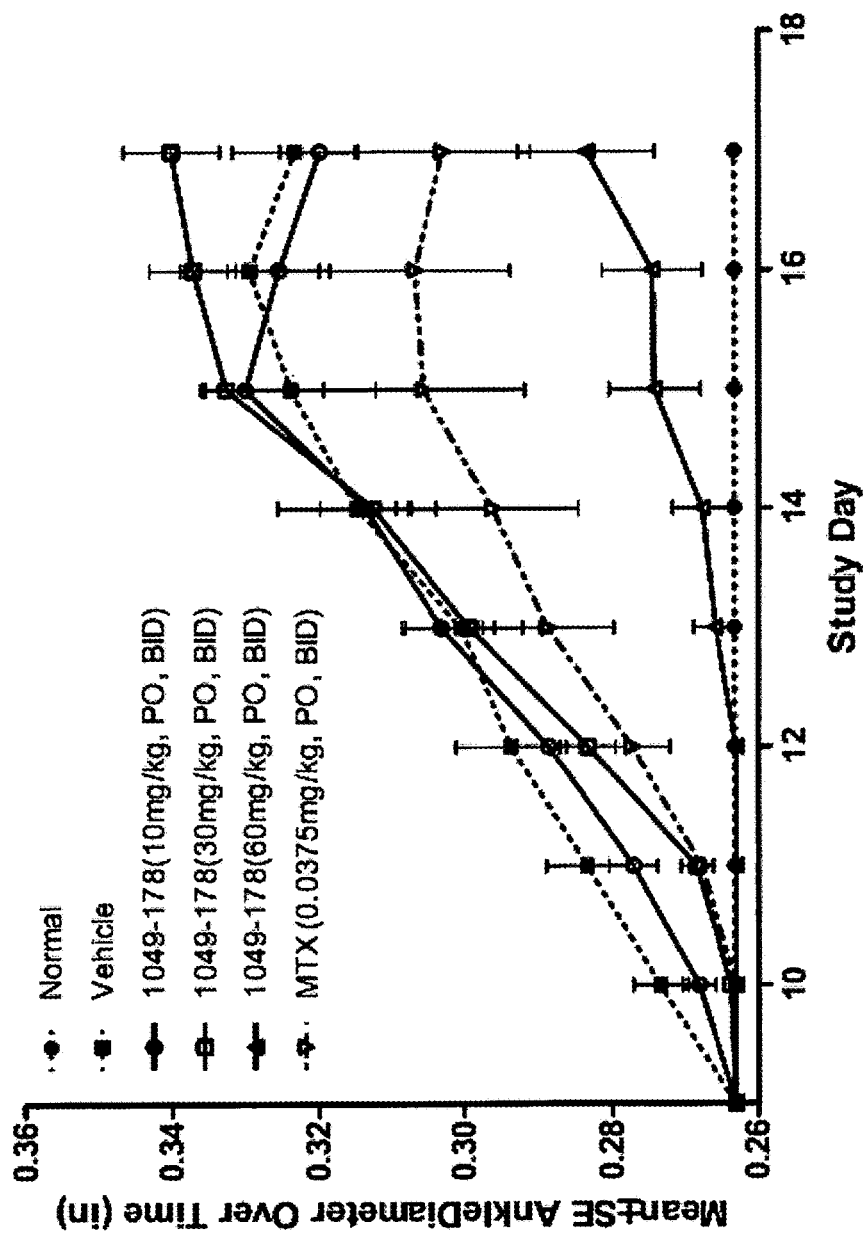
FIG. 3 depicts the dose-dependent effect of twice daily oral administration of compound 53 of formula IV in reducing the increase in ankle diameter over time in a collagen-induced developing arthritis model in rats. Also depicted are the results from non-arthritic control rats, arthritic control rats administered with a negative control vehicle, and arthritic control rats treated twice daily with methotrexate.

The results as shown in FIG. 3 demonstrate the effect of compound #53 at 10, 30, and 60 mg/kg dosages at 12 hour intervals on mean ankle diameter over time in a rat developing type II collagen induced arthritis model under the conditions tested. Relative to the vehicle alone control or to the methotrexate control, the compounds of the present invention exhibited a significant reduction in arthritis induced ankle diameter increase over time.

Figure 4:
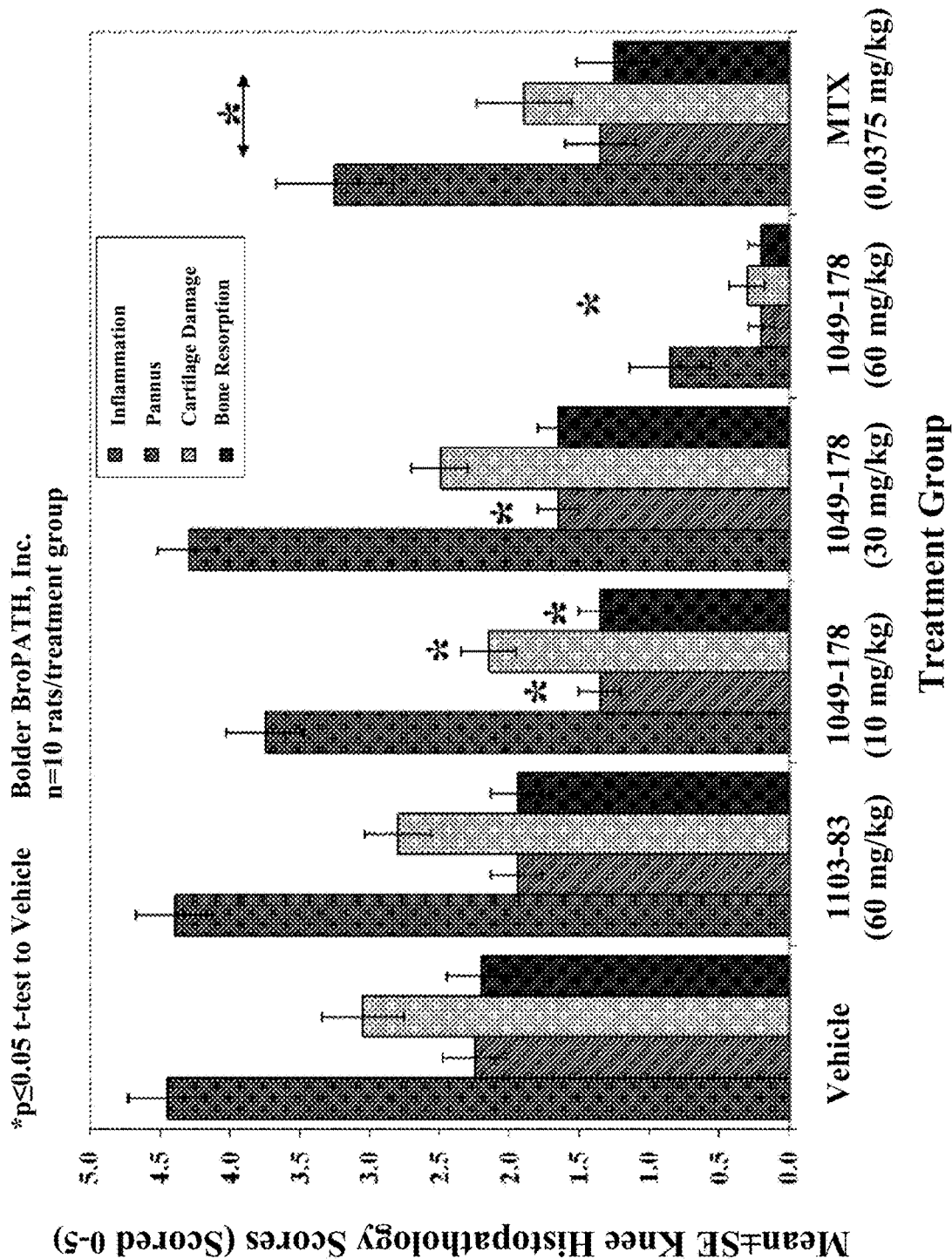
FIG. 4 depicts the dose-dependent effect of compounds 7 and 53 of formula IV in improving ankle histopathology when administered in a collagen-induced developing arthritis model in rats. Also depicted are the results from arthritic control rats administered with negative control vehicle or methotrexate.

The results as shown in FIG. 4 demonstrate the effect of compounds #7 and #53 on ankle histopathology in the categories of inflammation, pannus, cartilage damage, and bone resorption as previously described under the conditions tested. The results show a significant reduction in one or more categories by one of the compounds of the present invention (i.e. compound #53) under the conditions tested. FIG. 4 further shows that at 60 mg/kg, there is a statistically significant reduction in all categories of ankle histopathology for one of the compounds of the present invention (i.e. compound #53) under the conditions tested. This suggests that one or more compounds of the present invention may be useful for the treatment and reduction of arthritis disease symptoms.

Figure 5:
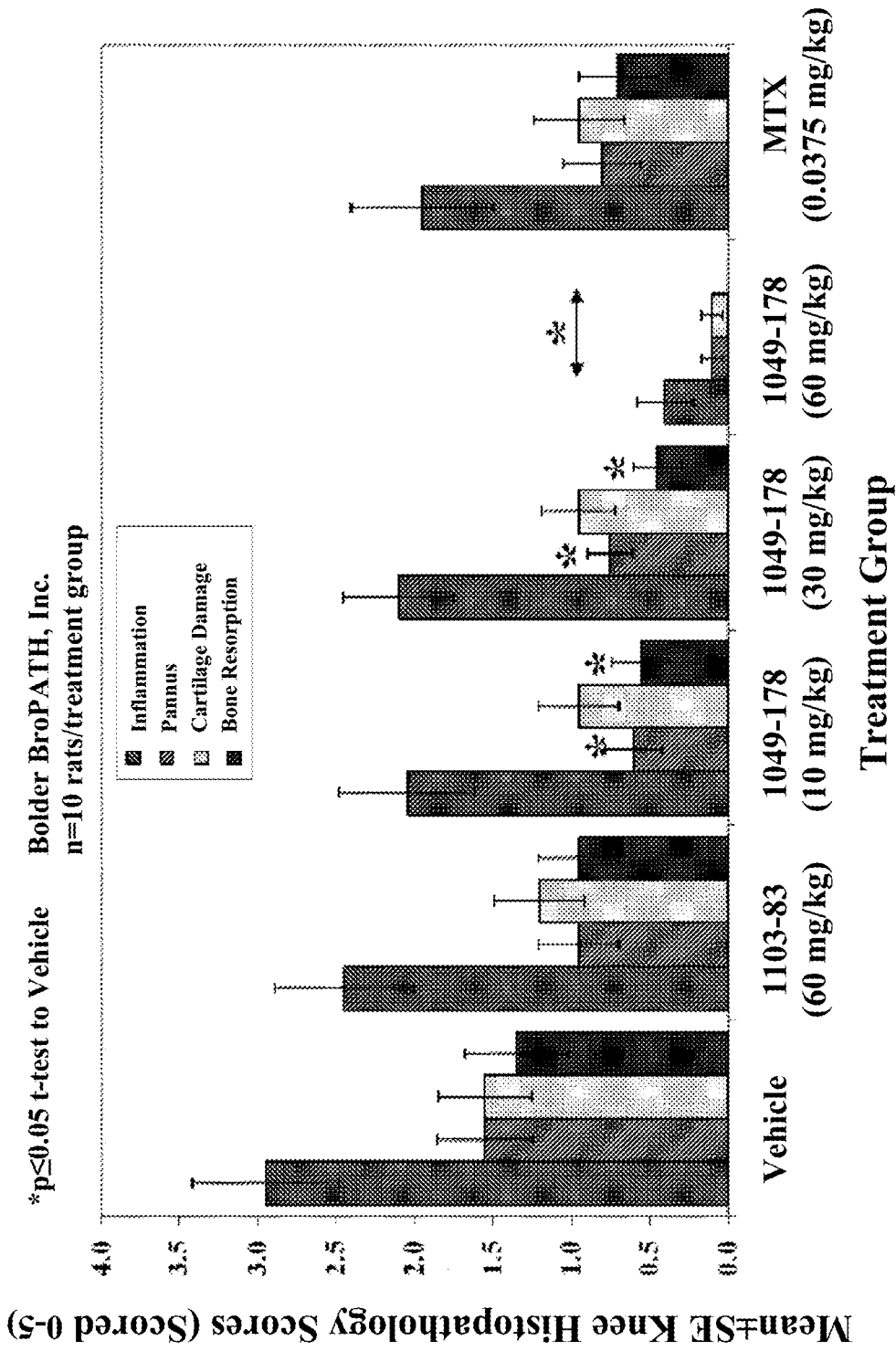
FIG. 5 depicts the dose-dependent effect of compounds 7 and 53 of formula IV in improving knee histopathology when administered in a collagen-induced developing arthritis model in rats. Also depicted are the results from arthritic control rats administered with negative control vehicle or positive control methotrexate.

The results as shown in FIG. 5 demonstrate the effect of compounds #7 and #53 on knee histopathology under the conditions tested. The results demonstrate a dose dependent reduction in knee histopathology. This suggests that one or more compounds of the present invention may be useful for the treatment and reduction of arthritis disease symptoms.

Figure 6:
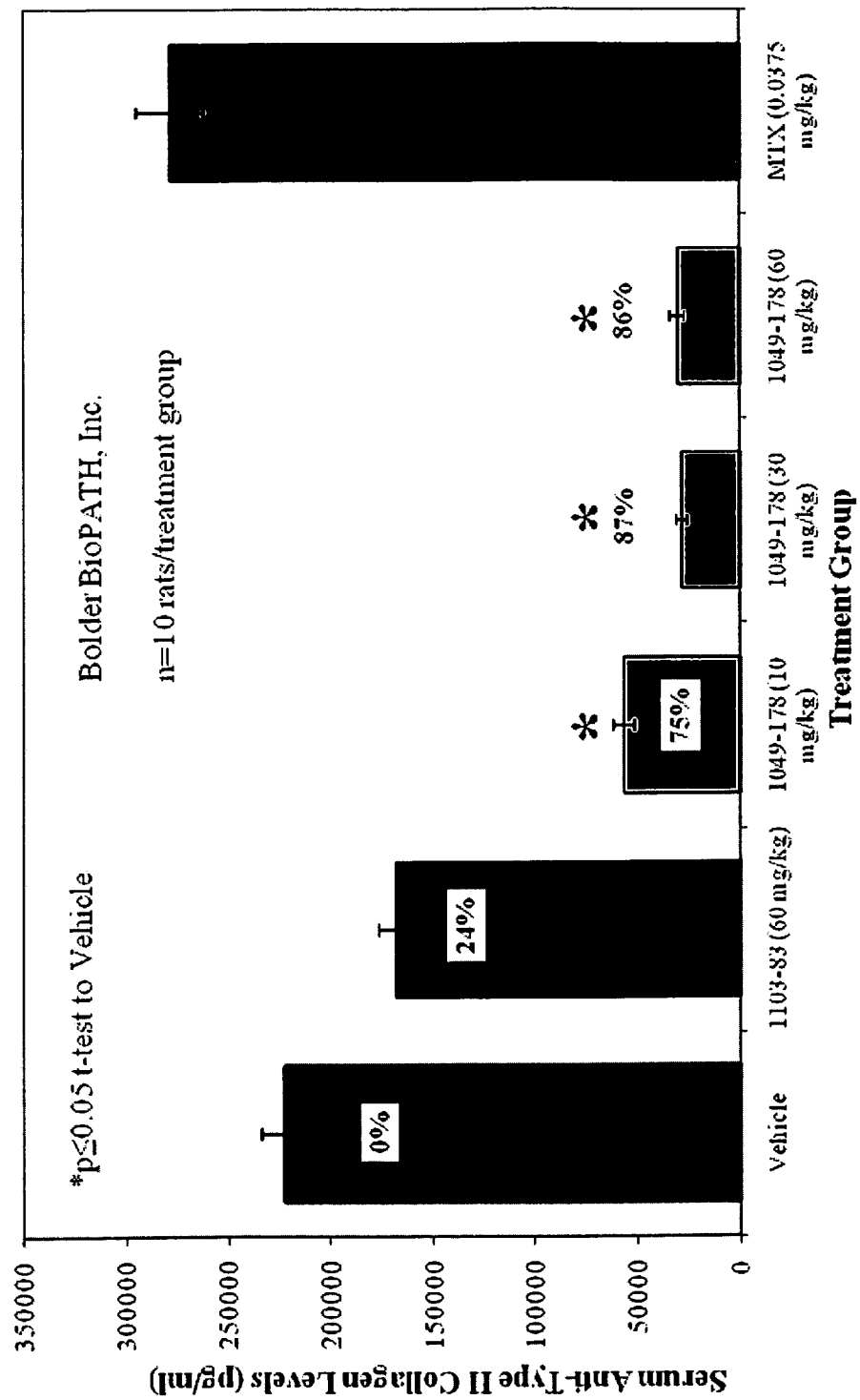
FIG. 6 depicts the dose-dependent effect of compounds 7 and 53 of formula IV in reducing the level of anti-type II collagen antibodies in vivo when administered to a collagen-induced developing arthritis rat model. Also depicted are the results from arthritic rats administered with negative control vehicle or methotrexate.

The results as shown in FIG. 6 demonstrate the effect of the compounds #7 and #53 on serum anti-type II collagen levels under the conditions tested. The results further show a significant reduction at 10, 20, and 60 mg/kg dosage levels of serum anti-type II collagen levels for compound #53, suggesting that one or more compounds of the present invention may not only be useful for the treatment and reduction of arthritis disease symptoms, but may also be useful for the inhibition of the autoimmune reaction itself.

Figure 7:
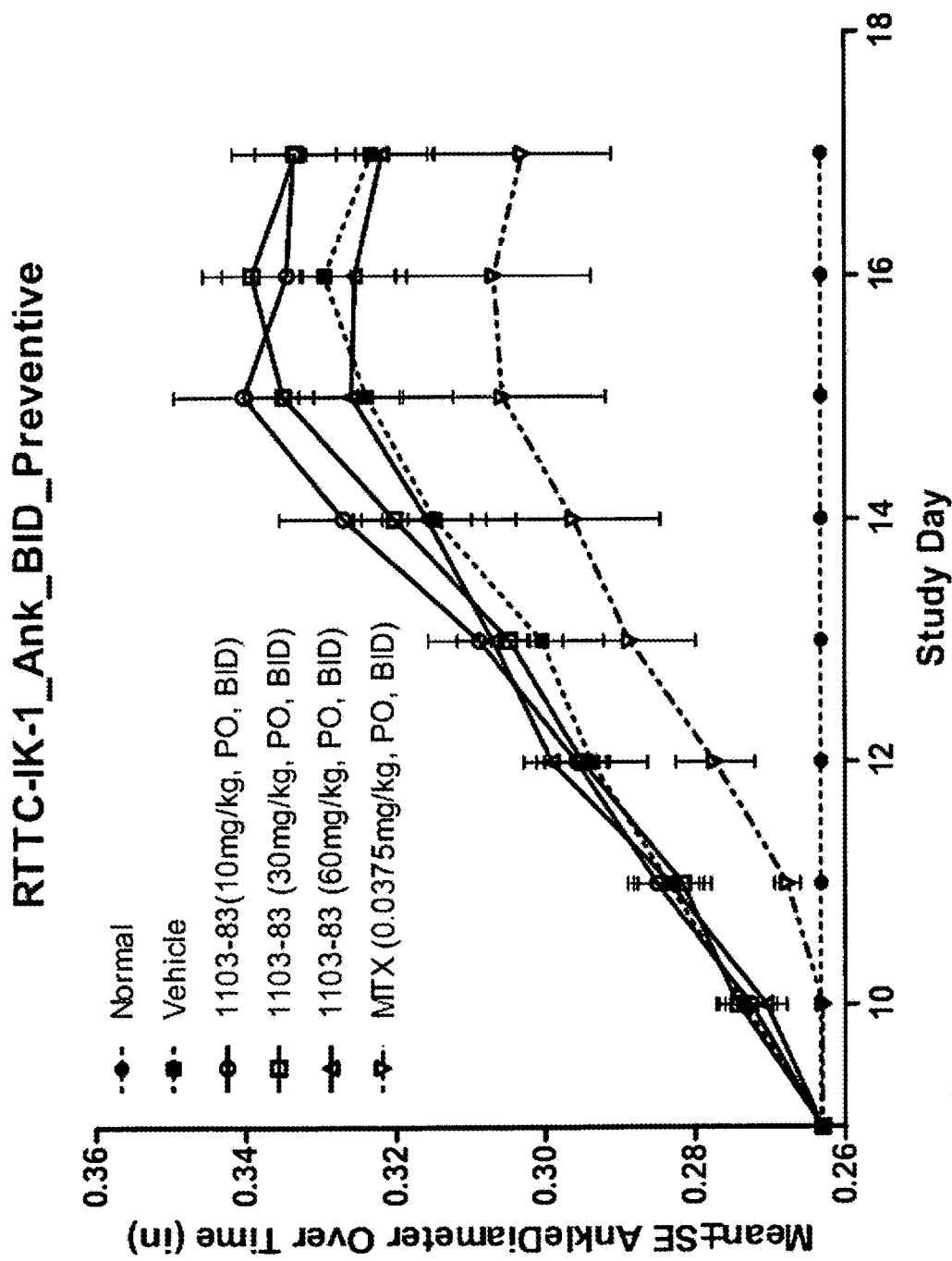
FIG. 7 depicts the dose-dependent effect of compound 7 of formula IV on improving ankle histopathology when administered in collagen-induced developing arthritis model in rats. Also depicted are the results from arthritic vehicle control rats and methotrexate-treated arthritic rats.

The results as shown in FIG. 7 demonstrate the effect of compound #7 at 10, 30, and 60 mg/kg dosages at 12 hour intervals on mean ankle diameter over time under the conditions tested. Relative to the vehicle alone control or to the methotrexate control, the compound exhibited a reduction in arthritis induced ankle diameter increase over time

Example 51

Rat Established Type II Collagen Induced Arthritis Assay

In order to examine the dose responsive efficacy of the compounds of the present invention in inhibiting the inflammation, cartilage destruction and bone resorption of 10 day established type II collagen induced arthritis in rats, compounds were administered orally daily or twice daily for 6 days.

Female Lewis rats were anesthetized and given collagen injections prepared and administered as described previously on day 0. On day 6, animals were anesthetized and given a second collagen injection. Caliper measurements of normal (pre-disease) right and left ankle joints were performed on day 9. On days 10-11, arthritis typically occurred and rats were randomized into treatment groups. Randomization was performed after ankle joint swelling was obviously established and there was good evidence of bilateral disease.

After an animal was selected for enrollment in the study, treatment was initiated by the oral route Animals were given vehicle, control (Enbrel) or compound doses, twice daily or once daily (BID or QD respectively). Dosing was administered on days 1-6 using a volume of 2.5 ml/kg (BID) or 5 ml/kg (QD) for oral solutions. Rats were weighed on days 1-7 following establishment of arthritis and caliper measurements f ankles taken every day. Final body weights were taken on day 7 and animals were euthanized.

Figure 8:
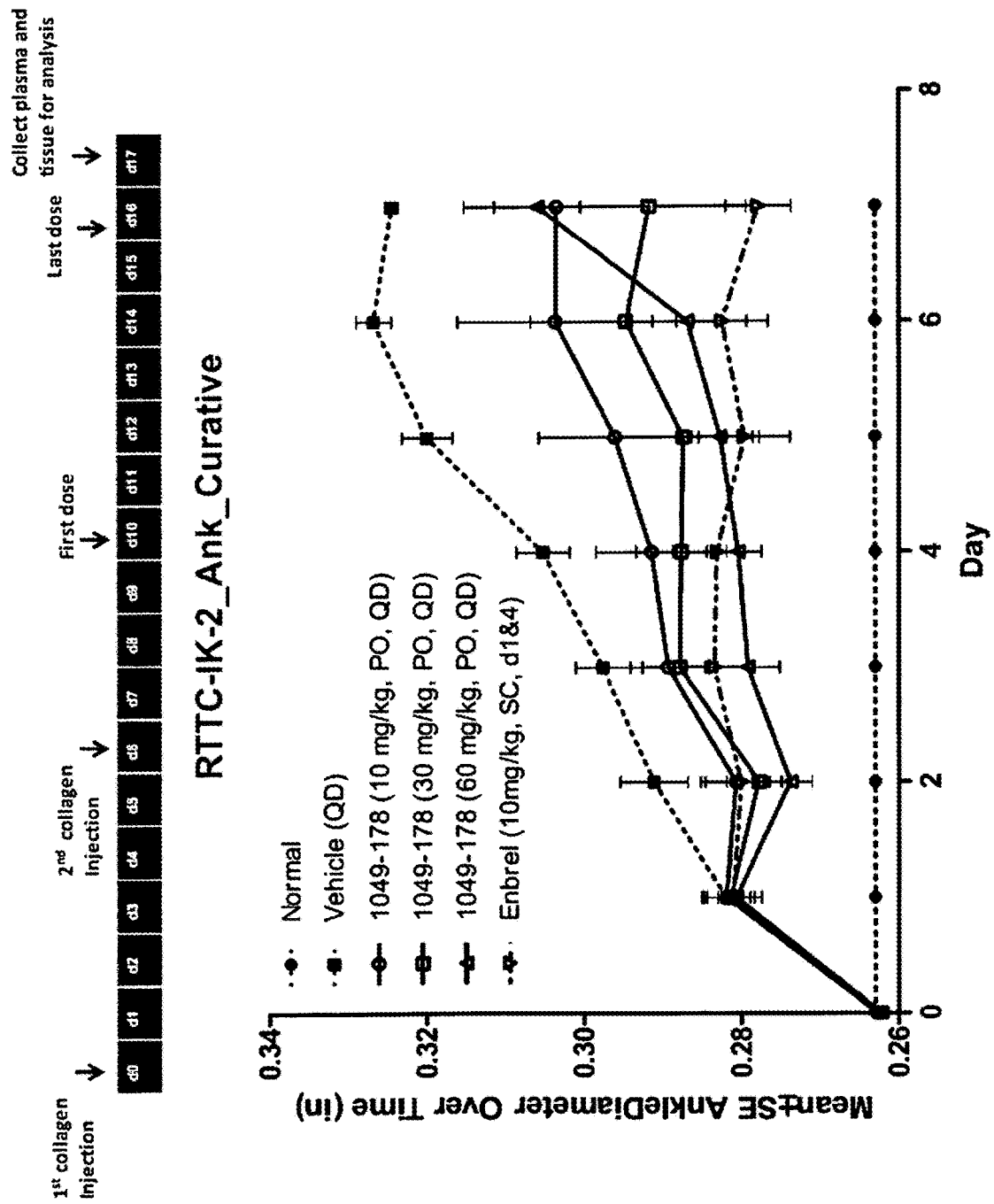
FIG. 8 depicts the dose-dependent effect of compound 53 of formula IV administered daily on ankle histopathology in a collagen-induced established arthritis model in rats. Also depicted are the results from arthritic arthritic vehicle control rats and Enbrel-treated arthritic rats.
Figure 9:
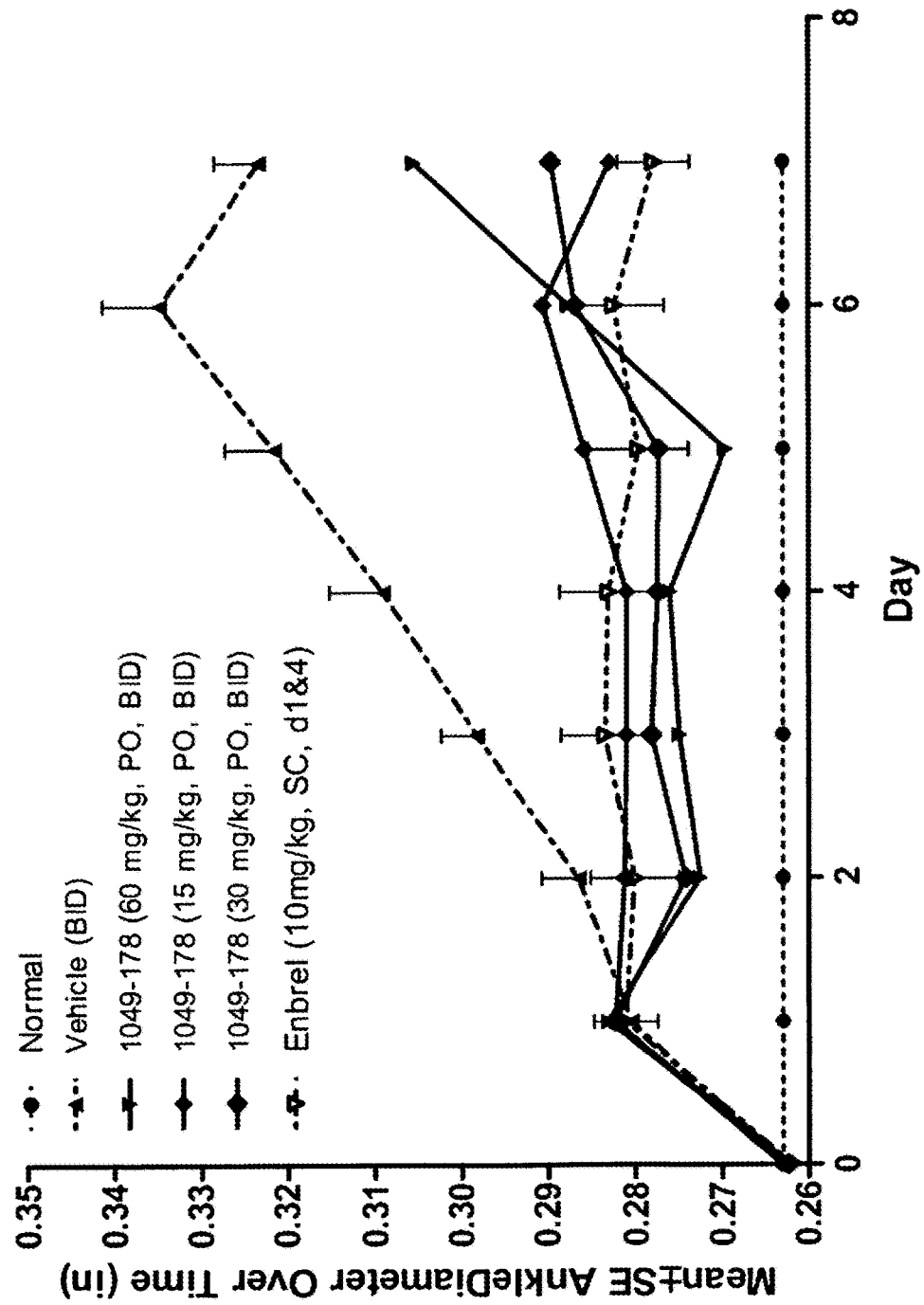
FIG. 9 depicts the dose-dependent effect of compound 53 of formula IV administered twice daily on ankle histopathology in a collagen-induced established arthritis model in rats. Also depicted are the results from arthritic vehicle control rats and Enbrel-treated arthritic rats.

The results as shown in FIG. 8 shows a significant reduction in mean ankle diameter increase over time for compound #53 with a once daily dosage under the conditions tested. The results in FIG. 9 further demonstrate a significant reduction in mean ankle diameter increase over time for compound #53 with a twice daily dosage under the conditions tested. This suggests that the compounds of the present invention can be useful for the treatment of autoimmune diseases such as arthritis. When tested in the same model, at least five other compounds of the present invention exhibit comparable or even higher efficacy as compared to compound #53.

Example 52

Adjuvant Induced Arthritis Assay

Intrathecal Catheterization of Rats

Isoflurane-anesthetized Lewis rats (200-250 g) were implanted with an intrathecal (IT) catheter. After a 6 d recovery period, all animals except those that appeared to have sensory or motor abnormalities (fewer than 5% of the total number) were used for experiments. For IT administration, 10 µl of drug or saline followed by 10 µl of isotonic saline was injected through the catheter.

Adjuvant Arthritis and Drug Treatment

Lewis rats were immunized at the base of the tail with 0.1 ml of complete Freund's adjuvant (CFA) on day 0 several days after catheter implantation (n=6/group). Drug (e.g. one or more compounds of the present invention or or vehicle) treatment was generally started on day 8 and continued daily until day 20. Clinical signs of arthritis generally begin on day 10, and paw swelling was determined every second day by water displacement plethysmometry.

The results as depicted in FIG. 10 by the average change in paw volume under the dosage regimes indicated show that under the conditions tested, compound #53 shows a dose dependent reduction in the average paw volume increase as measured in this adjuvant induced arthritis model system. These results suggest that one or more of the compounds of the present invention may be useful for the treatment of one or more of the diseases or conditions described herein.

The results as depicted in FIG. 11 show that compound #53 does not exhibit toxicity or other adverse reaction under the conditions tested as measured by a lack of weight loss.

Example 53

Rodent Pharmacokinetic Assay

In order to study the pharmacokinetics of the compounds of the present invention a set of 4-10 week old mice are grouped according to the following table:

| Group# | Mice/group | Compound Administration from day-1 to day-7 | | |
|--------|------------|---------|-------|---------|
|        |            | (mg/kg) | Route | Regimen |
| 1      | 3          | 1       | Po    | BID for 7 days |
| 2      | 3          | 3       |       |         |
| 3      | 3          | 10      |       |         |
| 4      | 3          | 30      |       |         |
| 5      | 3          | 60      |       |         |

Compounds of the present invention are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the present invention.

Example 54

Basotest Assay

The baseotest assay is performed using Orpegen Pharma Basotest reagent kit. Heparinized whole blood is pre-incubated with test compound or solvent at 37 C for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. Compounds 7 and 53 when tested in this assay inhibit allergen induced activation of basophilic granulocytes at sub micromolar range.

Example 55

Combination Use of PI3Kδ Inhibitors and Agents that Inhibit IgE Production or Activity The compounds of the present invention may present synergistic or additive efficacy when administered in combination with agents that inhibit IgE production or activity. Agents that inhibit IgE production include, for example, one or more of 1E1-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3Kδ are efficacious in treatment of autoimmune and inflammatory disorders (AIID) for example rheumatoid arthritis. If any of the compounds causes an undesired level of IgE production, one may choose to administer it in combination with an agent that inhibits IgE production or IgE activity. Additionally, the administration of PI3Kδ or PI3Kδ/γ inhibitors of the present invention in combination with inhibitors of mTOR may also exhibit synergy through enhanced inhibition of the PI3K pathway. Various in vivo and in vitro models may be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3Kδ inhibitors of the present invention such as compound 53 with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, for example, compound 53 of the present invention, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3Kδ inhibitor and mTOR inhibitor exhibit a reduction in antigen specific IgG3 response as compared to the mice treated with vehicle alone. Additionally, the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated Animals are given vehicle, PI3Kδ inhibitor, or PI3Kδ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

It is expected that the combination treatment using PI3Kδ inhibitor and rapamycin provides greater efficacy than treatment with PI3Kδ inhibitor alone.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of the Formula 406:

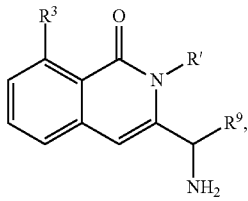

406 or an enantiomer or a mixture of enantiomers thereof, or a pharmaceutically acceptable salt thereof, wherein:

R' is a moiety of Formula II:

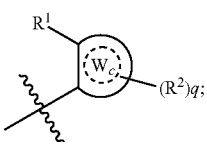

Formula II wherein $W_c$ is aryl, heteroaryl, heterocycloalkyl, or cycloalkyl;

q is an integer of 0, 1, 2, 3, or 4;

$R^1$ is hydrogen, alkyl, alkenyl, alkynyl, alkoxy, amido, alkoxycarbonyl, sulfonamido, halo, cyano, or nitro;

each instance of $R^2$ is independently alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl, sulfonamido, halo, cyano, hydroxyl, or nitro; and $R^9$ is hydrogen, $C_{1-10}$ alkyl, cycloalkyl, or hetercycloalkyl.

2. The compound of claim 1, wherein $R^3$ is hydrogen, alkyl, or halo.

3. The compound of claim 2, wherein $R^3$ is —H, —CH$_3$, —CH$_2$CH$_3$, —CF$_3$, —Cl or —F.

4. The compound of claim 3, wherein $R^3$ is methyl.

5. The compound of claim 3, wherein $R^3$ is chloro.

6. The compound of claim 1, wherein $W_c$ is aryl.

7. The compound of claim 1, wherein $R^9$ is $C_{1-10}$alkyl.

8. The compound of claim 1, wherein the compound is a compound of Formula 406A:

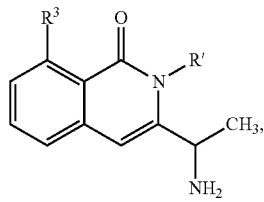

406A or an enantiomer or a mixture of enantiomers thereof, or a pharmaceutically acceptable salt thereof.

9. The compound of claim 8, wherein the compound is a compound of Formula 1304:

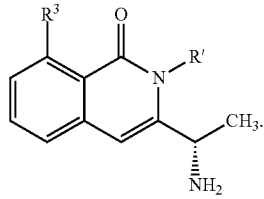

1304

10. The compound of claim 9, wherein R' is

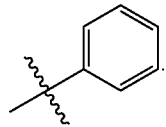 [SMILES: *c1ccccc1]

.

11. The compound of claim 10, wherein $R^3$ is chloro.

12. The compound of claim 1, which is Compound 4704:

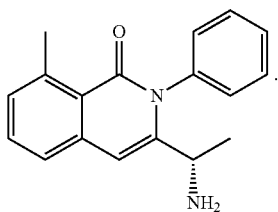

13. The compound of claim 1, which is Compound 5003:

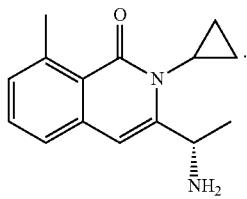

14. The compound of claim 1, which is Compound 5009:

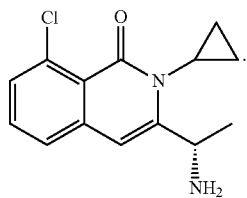

15. A compound of the Formula 405:

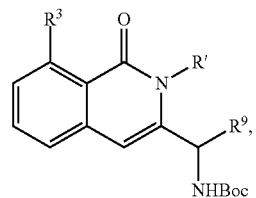

or an enantiomer or a mixture of enantiomers thereof, or a pharmaceutically acceptable salt thereof, wherein:

R' is a moiety of Formula II:

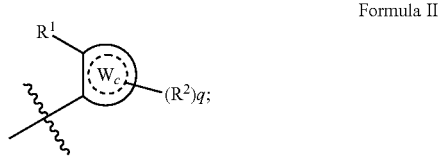

wherein $W_c$ is aryl, heteroaryl, heterocycloalkyl, or cycloalkyl;

q is an integer of 0, 1, 2, 3, or 4;

$R^1$ is hydrogen, alkyl, alkenyl, alkynyl, alkoxy, amido, alkoxycarbonyl, sulfonamido, halo, cyano, or nitro;

each instance of $R^2$ is independently alkyl, alkenyl, alkynyl, cycloalkyl, heterocycloalkyl, aryl, heteroaryl, heteroarylalkyl, alkoxy, amino, halo, cyano hydroxy or nitro;

$R^3$ is hydrogen, alkyl, alkenyl, alkynyl, cycloalkyl, heterocycloalkyl, alkoxy, amido, amino, alkoxycarbonyl, sulfonamido, halo, cyano, hydroxyl, or nitro; and $R^9$ is hydrogen, $C_{1-10}$alkyl, cycloalkyl, or hetercycloalkyl.

16. The compound of claim 15, wherein the compound is a compound of Formula 405A:

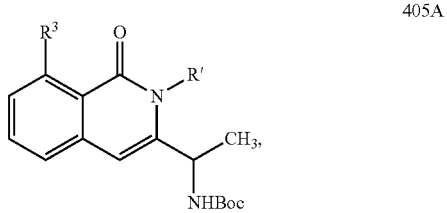

or an enantiomer or a mixture of enantiomers thereof, or a pharmaceutically acceptable salt thereof.

* * * * *